United States Patent
Wang

(10) Patent No.: US 7,136,173 B2
(45) Date of Patent: *Nov. 14, 2006

(54) METHOD AND APPARATUS FOR END-POINT DETECTION

(75) Inventor: Hui Wang, Fremont, CA (US)

(73) Assignee: ACM Research, Inc., Fremont, CA (US)

(*) Notice: Subject to any disclaimer, the term of this patent is extended or adjusted under 35 U.S.C. 154(b) by 200 days.

This patent is subject to a terminal disclaimer.

(21) Appl. No.: 10/276,286

(22) PCT Filed: May 3, 2001

(86) PCT No.: PCT/US01/14652

§ 371 (c)(1),
(2), (4) Date: Apr. 4, 2003

(87) PCT Pub. No.: WO01/88229

PCT Pub. Date: Nov. 22, 2001

(65) Prior Publication Data

Related U.S. Application Data

(63) Continuation of application No. 09/570,566, filed on May 12, 2000, now Pat. No. 6,447,668, which is a continuation-in-part of application No. 09/497,894, filed on Feb. 4, 2000, now Pat. No. 6,440,295, which is a continuation of application No. PCT/US99/15506, filed on Jul. 8, 1999.

(60) Provisional application No. 60/092,316, filed on Jul. 9, 1998.

(51) Int. Cl.
*G01B 11/04* (2006.01)

(52) U.S. Cl. .................................... 356/636; 356/630

(58) Field of Classification Search ............... 356/636, 356/630, 625; 204/212, 224 M, 237; 205/660, 205/771; 451/8

See application file for complete search history.

(56) References Cited

U.S. PATENT DOCUMENTS

| 2,751,344 | A | | 6/1956 | Kienberger et al. | |
|---|---|---|---|---|---|
| 4,021,278 | A | * | 5/1977 | Hood et al. | 438/8 |
| 4,078,980 | A | | 3/1978 | Harris et al. | |
| 4,304,641 | A | | 12/1981 | Grandia et al. | |
| 5,096,550 | A | * | 3/1992 | Mayer et al. | 205/642 |
| 5,217,586 | A | | 6/1993 | Datta et al. | |
| 5,284,554 | A | | 2/1994 | Datta et al. | |
| 5,335,681 | A | | 8/1994 | Schmid | |
| 5,421,987 | A | | 6/1995 | Tzanavaras et al. | |

(Continued)

FOREIGN PATENT DOCUMENTS

EP  0 257 670  3/1988

(Continued)

OTHER PUBLICATIONS

Aug. 25, 2003, Decision on Grant, SUX, Russian Version & English Translation.

(Continued)

*Primary Examiner*—Hwa (Andrew) Lee
*Assistant Examiner*—Roy M. Punnoose
(74) *Attorney, Agent, or Firm*—Morrison & Foerster LLP

(57) ABSTRACT

An apparatus for detecting the end-point of an electropolishing process of a metal layer formed on a wafer (1004) includes an end-point detector. The end-point detector is disposed adjacent the nozzle (1008) used to electropolish the wafer. In one embodiment, the end-point detector is configured to measure the optical reflectivity of the portion of the wafer being electropolished.

20 Claims, 73 Drawing Sheets

U.S. PATENT DOCUMENTS

| | | |
|---|---|---|
| 5,443,707 A | 8/1995 | Mori |
| 5,489,341 A | 2/1996 | Bergman et al. |
| 5,516,412 A | 5/1996 | Andricacos et al. |
| 5,567,300 A | 10/1996 | Datta et al. |
| 5,584,310 A | 12/1996 | Bergman et al. |
| 5,620,581 A | 4/1997 | Ang |
| 5,670,034 A | 9/1997 | Lowery |
| 5,678,320 A | 10/1997 | Thompson et al. |
| 5,722,875 A * | 3/1998 | Iwashita et al. ............... 451/8 |
| 5,744,019 A | 4/1998 | Ang |
| 5,865,984 A * | 2/1999 | Corbin et al. ............... 205/670 |
| 6,017,437 A | 1/2000 | Ting et al. |
| 6,056,869 A * | 5/2000 | Uzoh ......................... 205/771 |
| 6,440,295 B1 * | 8/2002 | Wang ......................... 205/640 |
| 6,447,668 B1 * | 9/2002 | Wang ......................... 205/645 |

FOREIGN PATENT DOCUMENTS

| | | |
|---|---|---|
| JP | 57171690 | 10/1982 |
| JP | 01234590 | 9/1989 |
| JP | 05243183 A | 9/1993 |
| SU | 463174 | 6/1975 |
| WO | 90/00476 | 1/1990 |
| WO | 95/20064 | 7/1995 |

OTHER PUBLICATIONS

Contolini et al., "Copper electroplating Process for Sub-Half-Micron ULSI Structures," VMIC Conference 1995, ISMIC-104/95/0322, (Jun. 27-29, 1995). pp. 322-328.

Devaraj et al., "Pulsed Electrodeposition of Copper," Plating & Surface Finishing (Aug. 1992) 72-78.

Dubin et al., "Copper Plating Techniques for ULSI Metalization," Advanced MicroDevices, (no date).

Dubin, "Electrochemical Deposition of Copper On-Chip Interconnects", Advanced MicroDevices.

Gauvin et al., "The Effect of Chloride Ions on Copper Deposition", J. of Electrochemical Society, (Feb. 1952) vol. 99, pp. 71-76.

Osero "An Overview of Pulse Plating", Plating and Surface finishing, (Mar. 1986).

Passal, "Copper Plating During the Last Fifty Years", Plating (Jun. 1959) 628-638.

Singer, "Copper Goes Mainstream: Low k to Follow", Semiconductor International (Nov. 1997) 67-69.

* cited by examiner

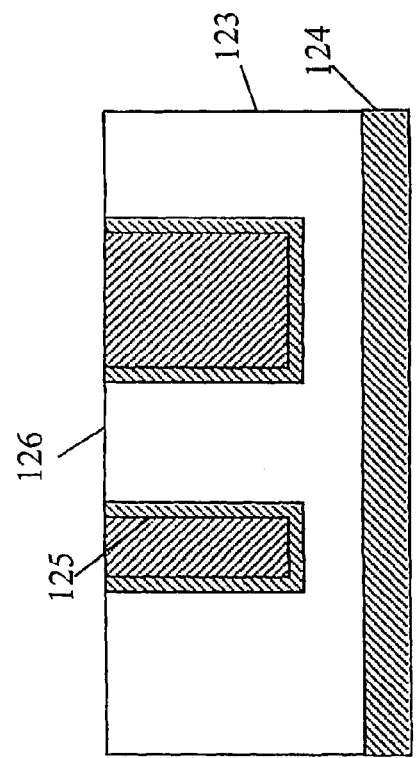
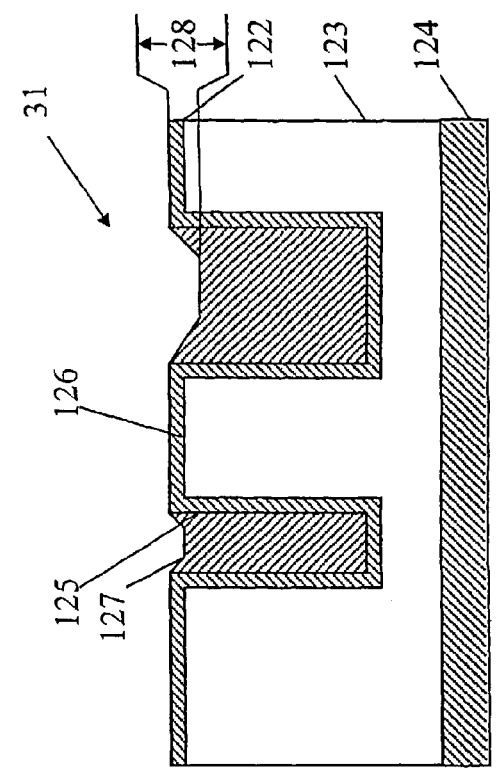
Fig. 1A
Fig. 1B
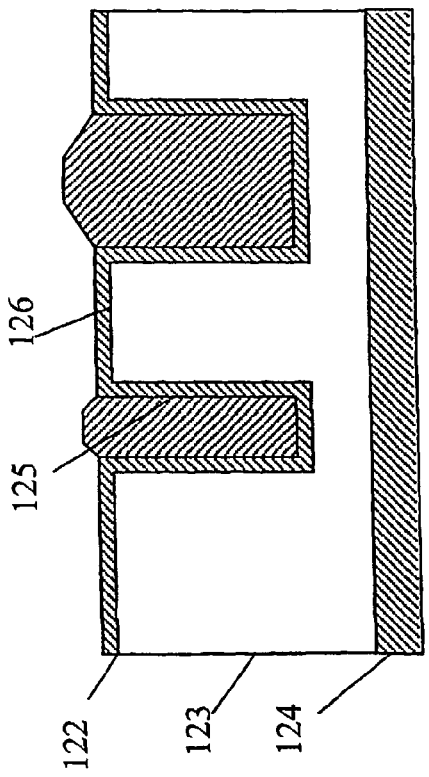
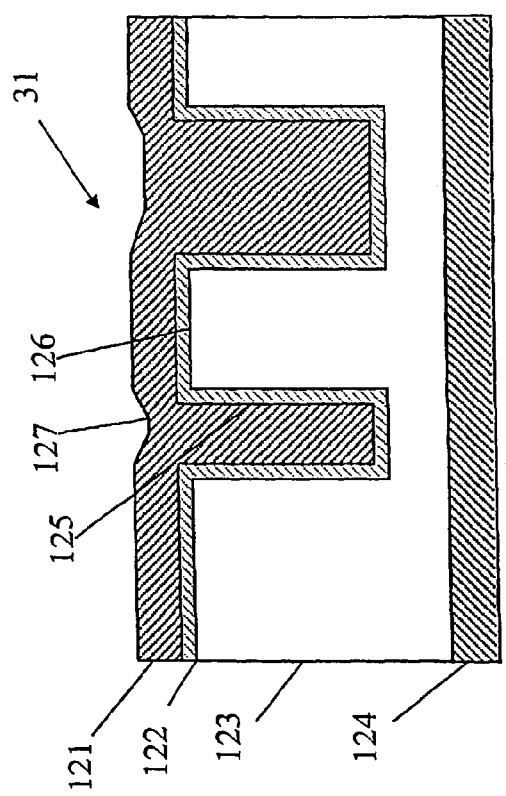
Fig. 1C
Fig. 1D

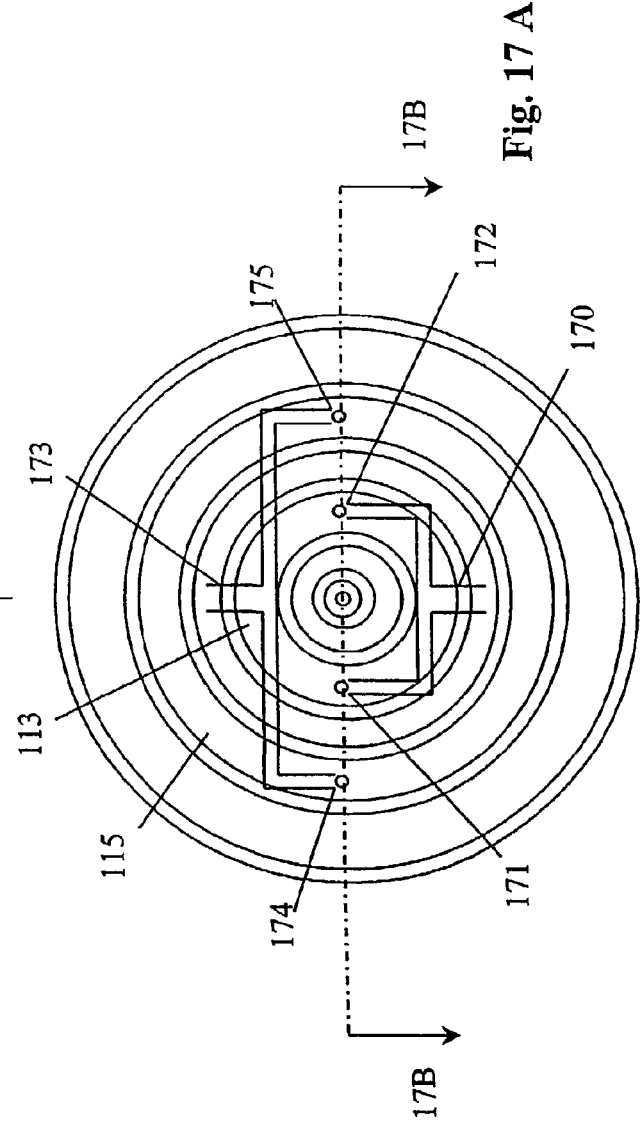
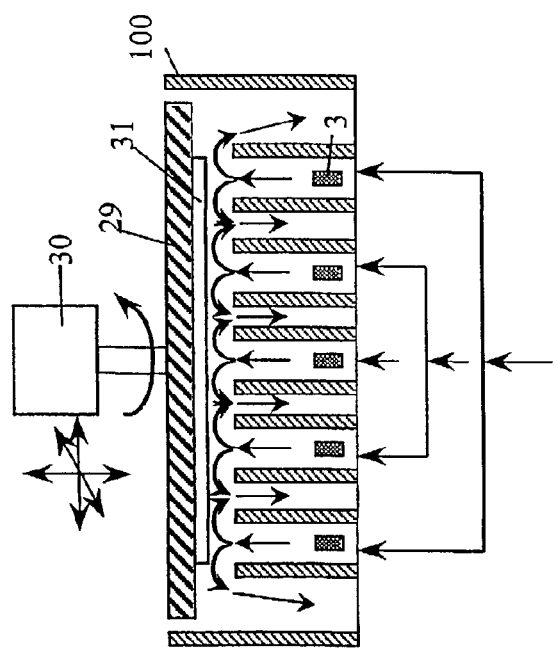
Fig. 17 B
Fig. 17 A

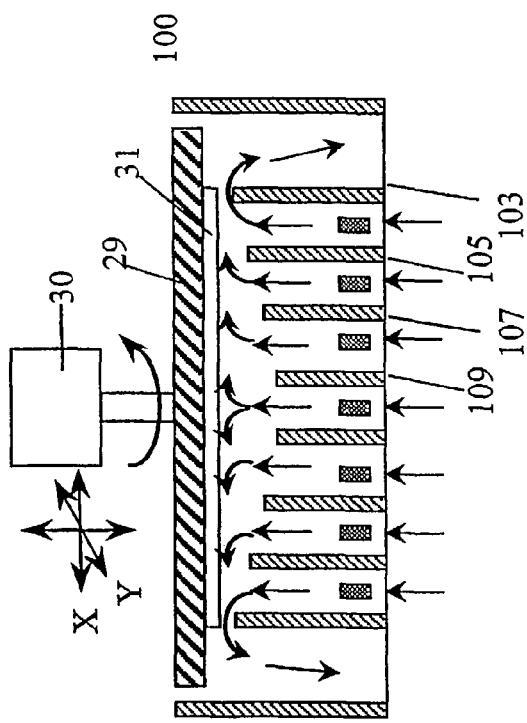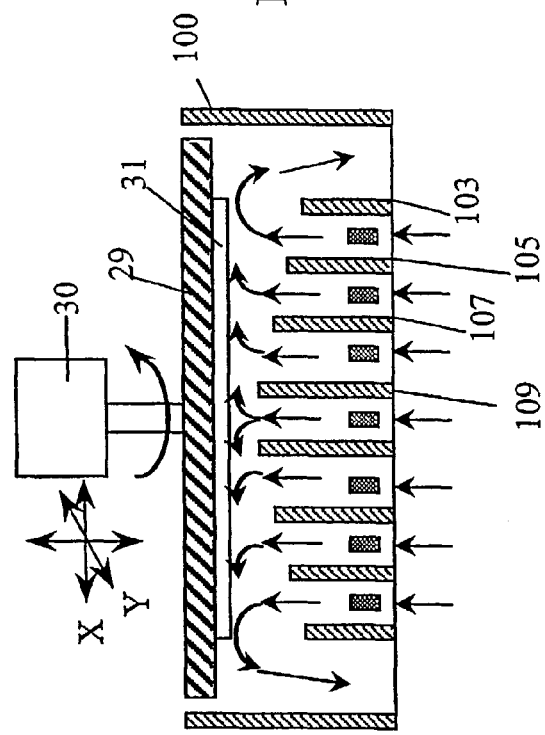

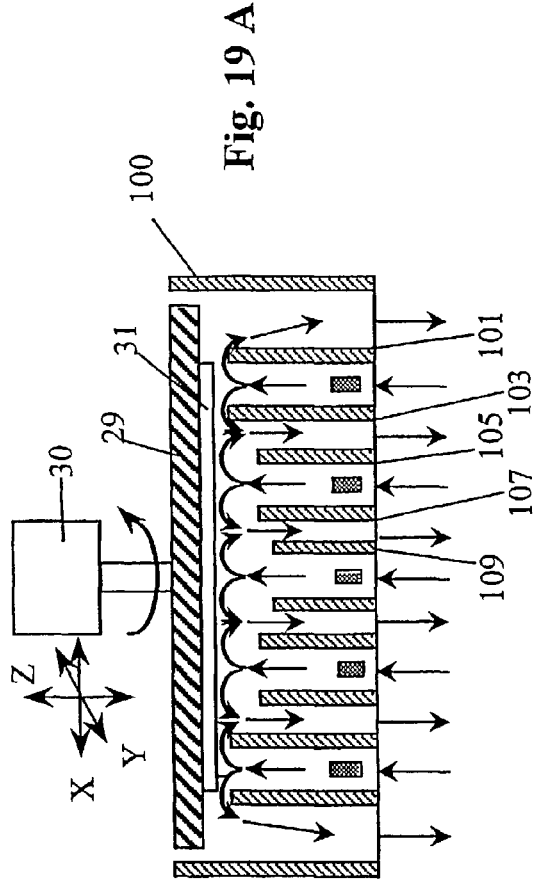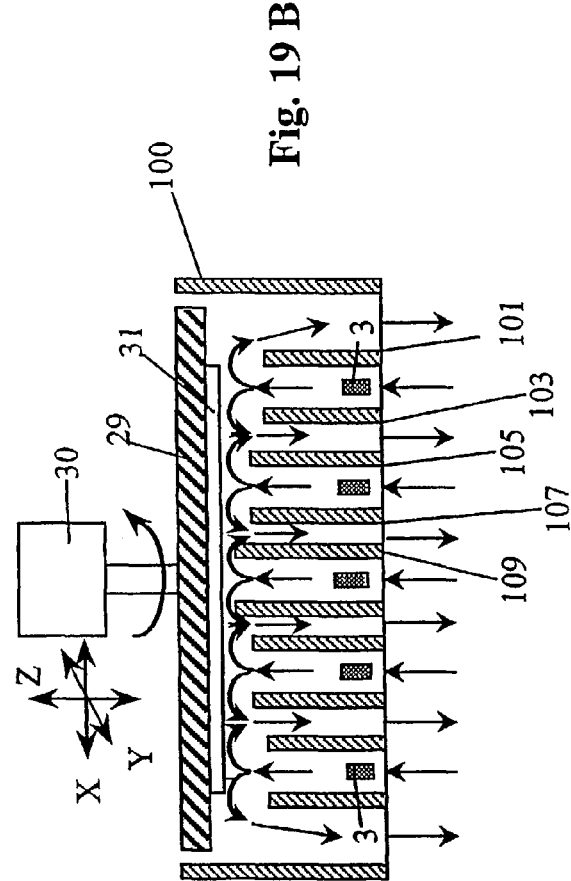

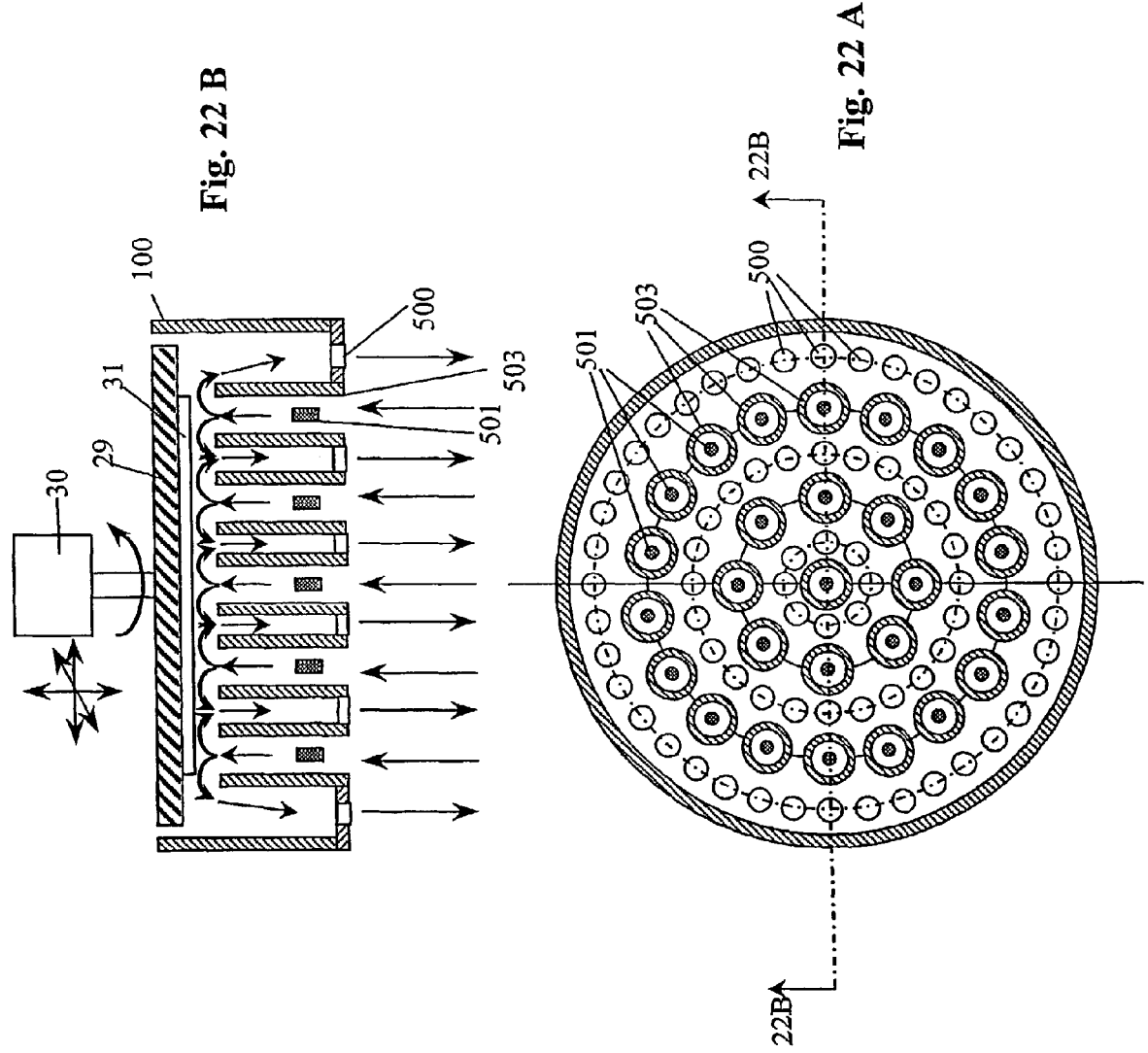

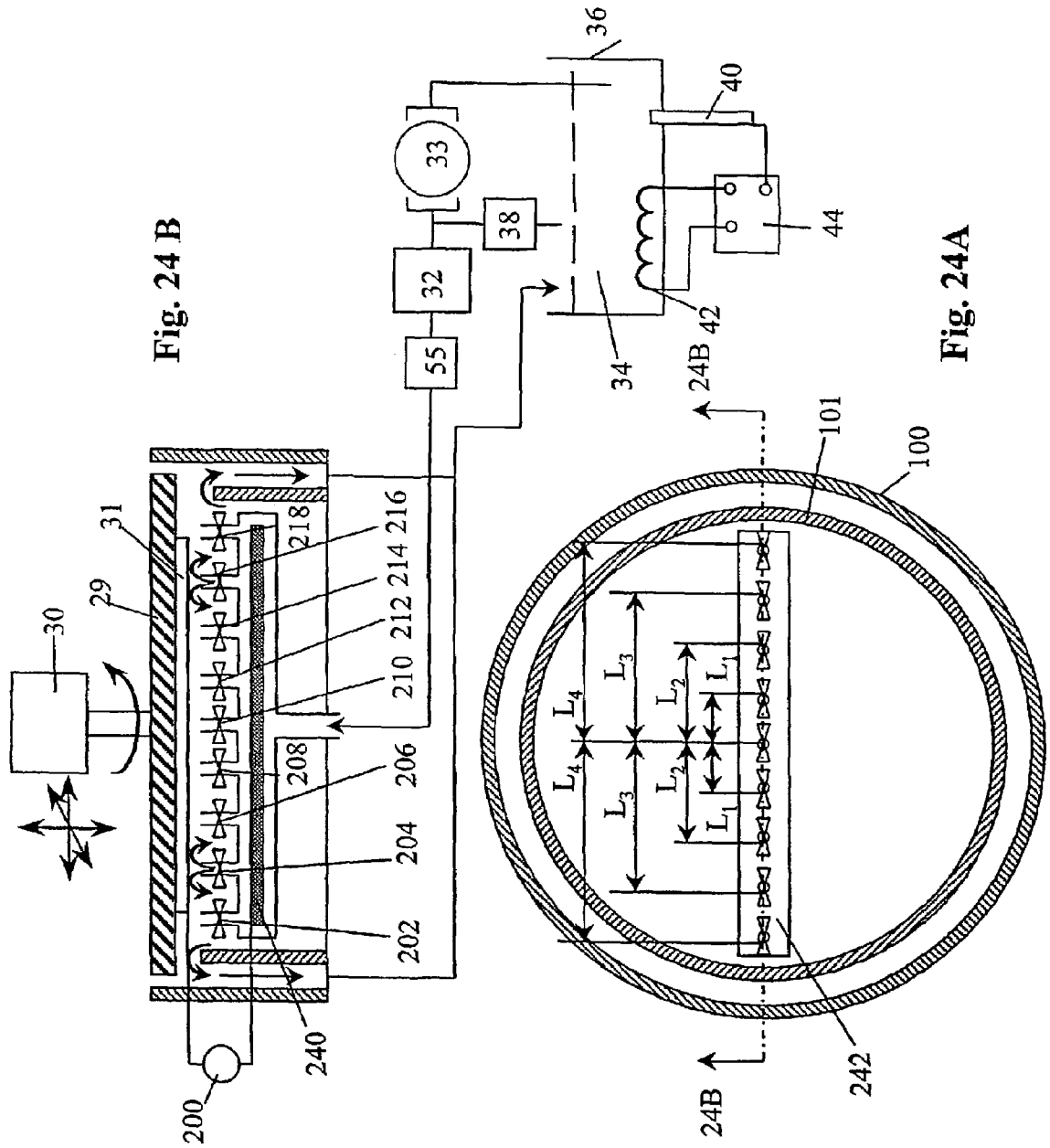

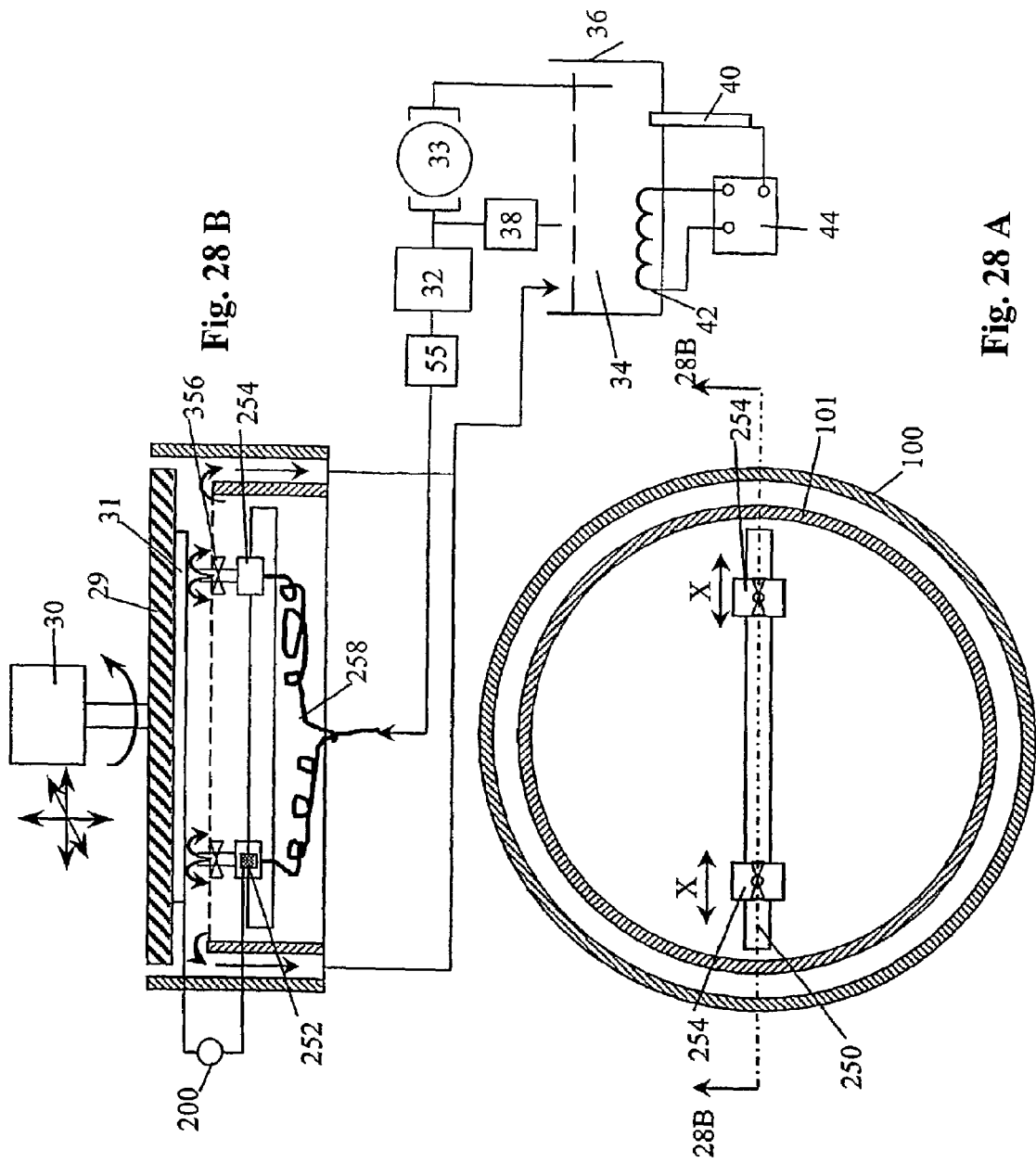

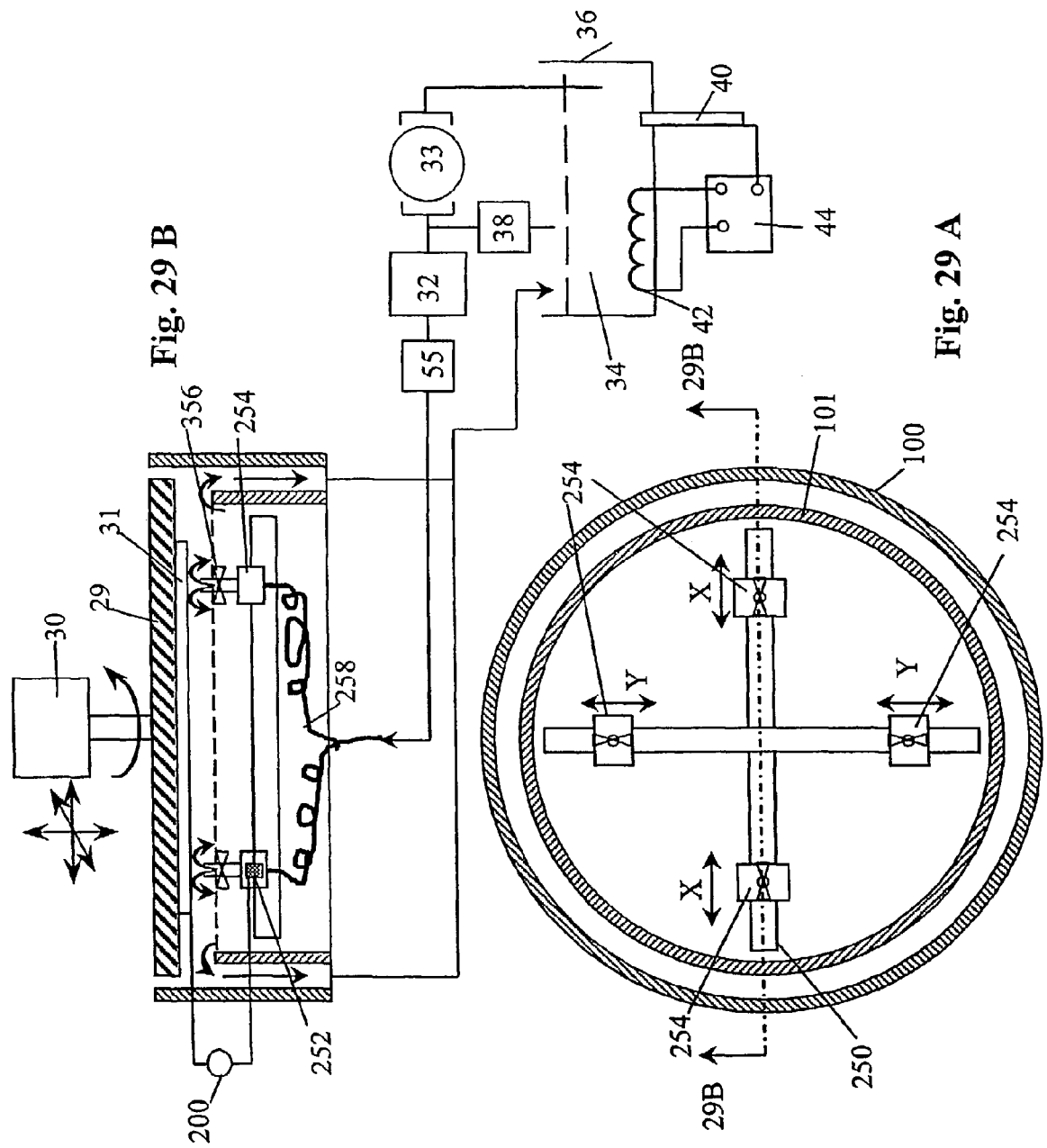

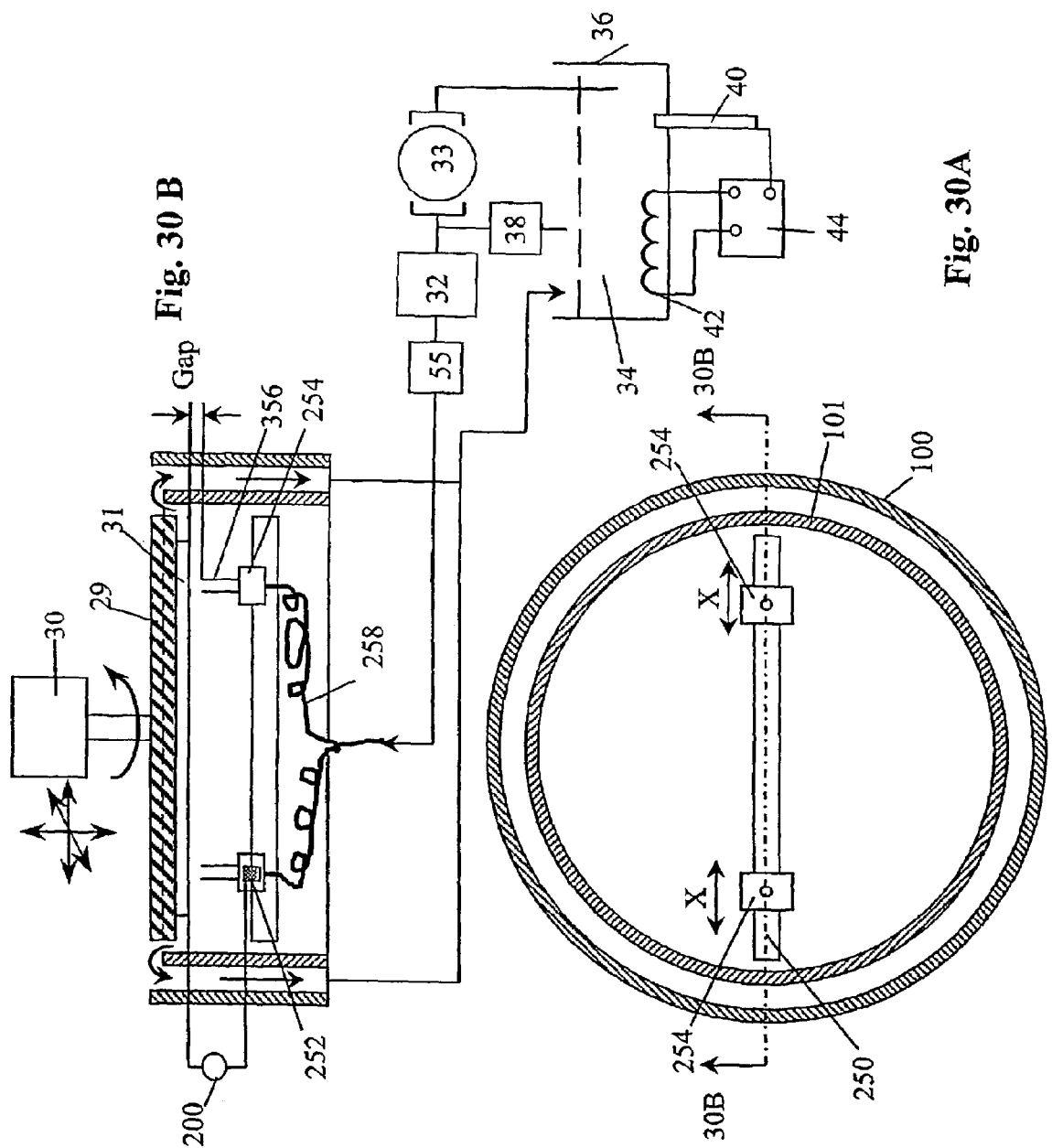

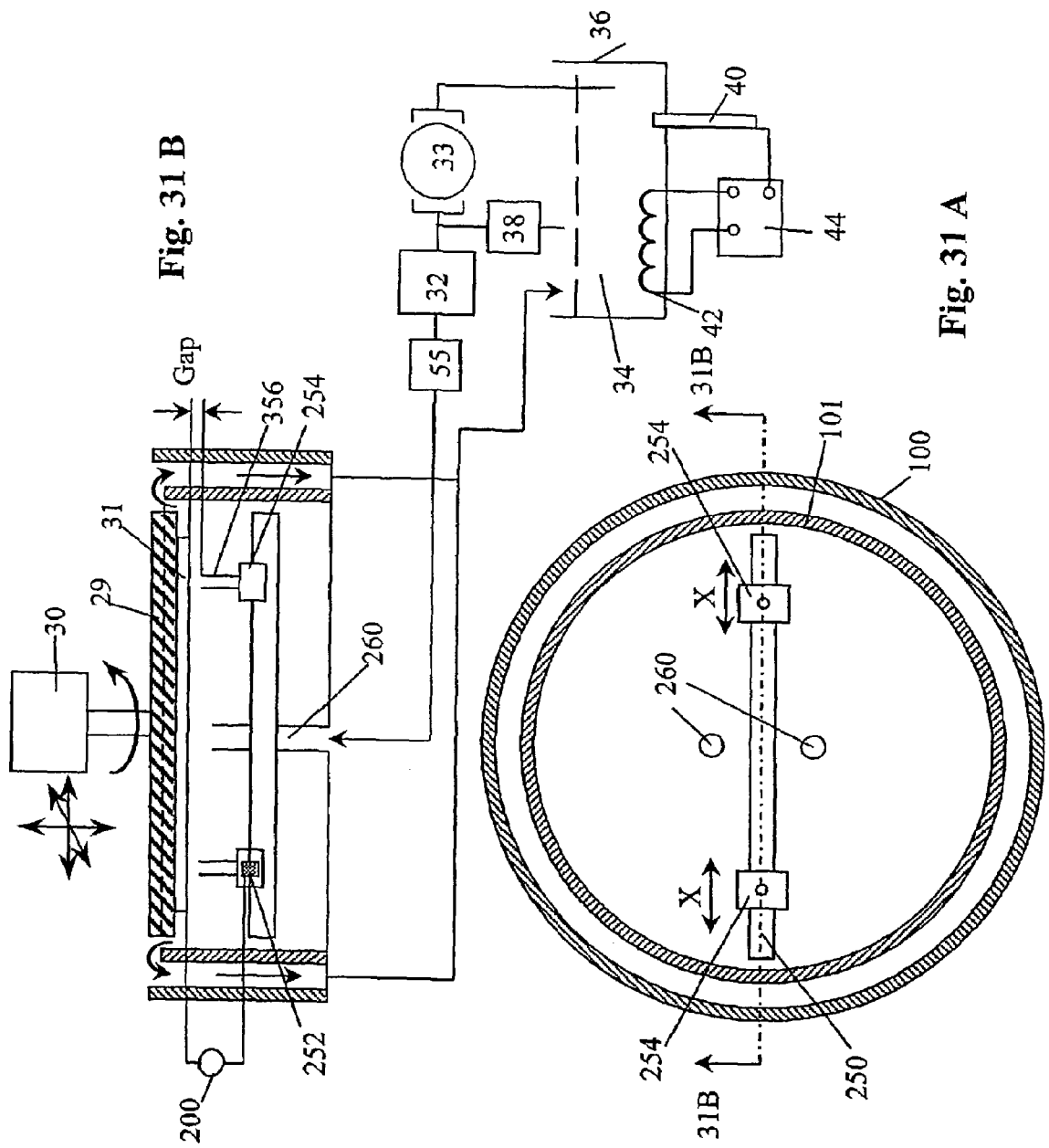

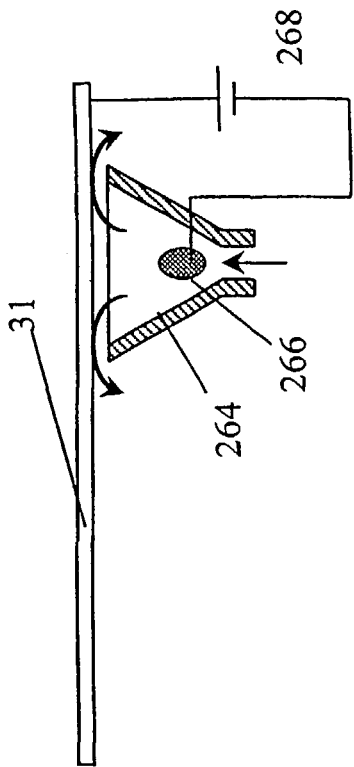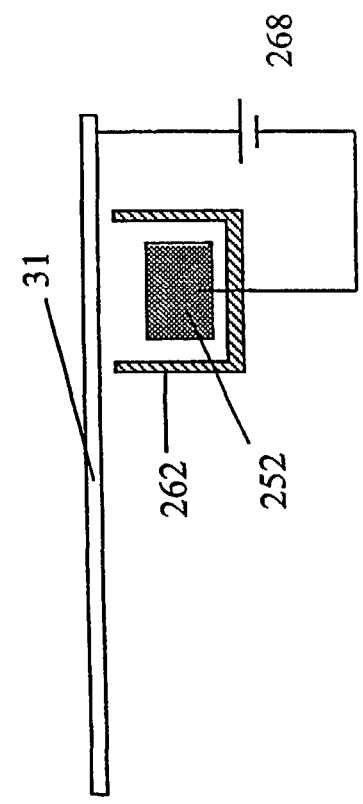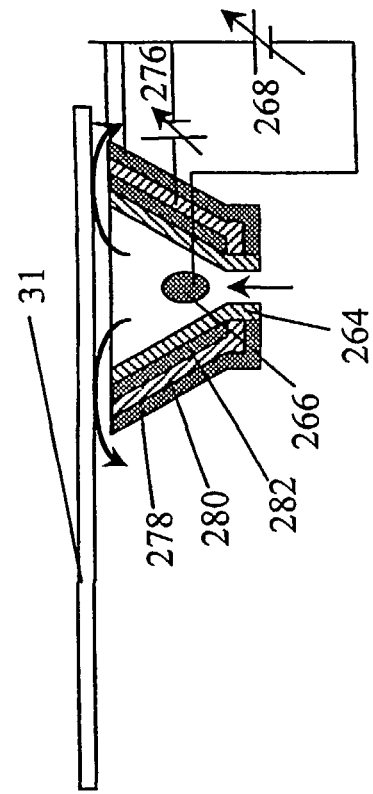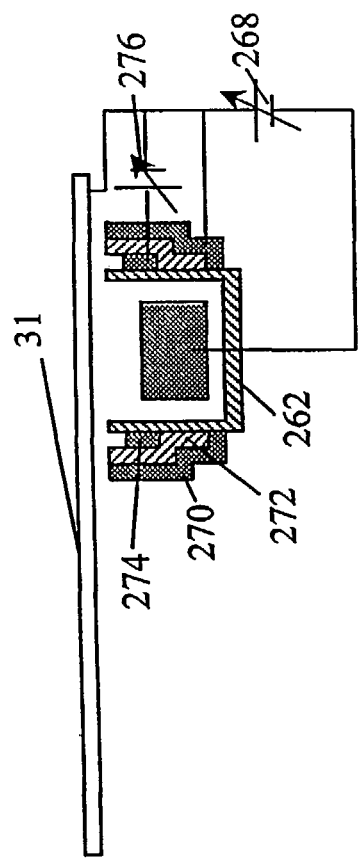

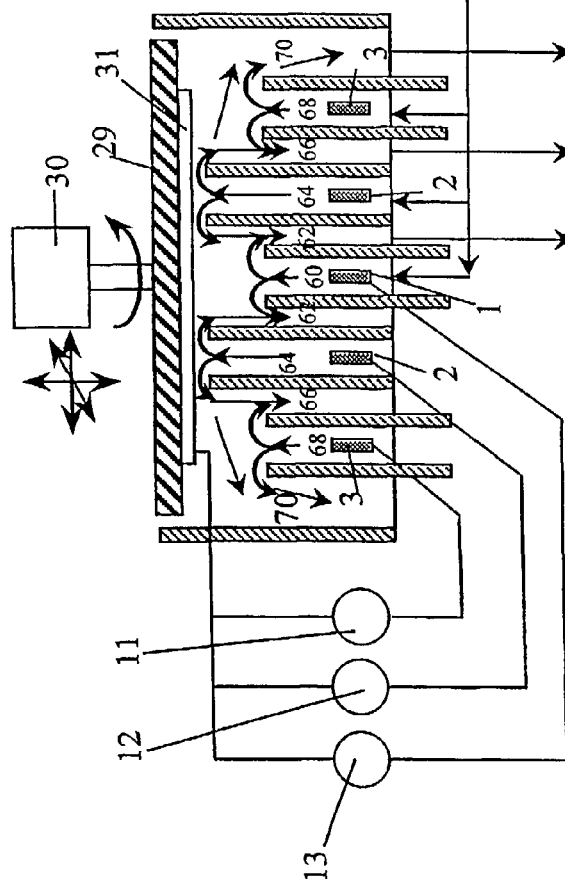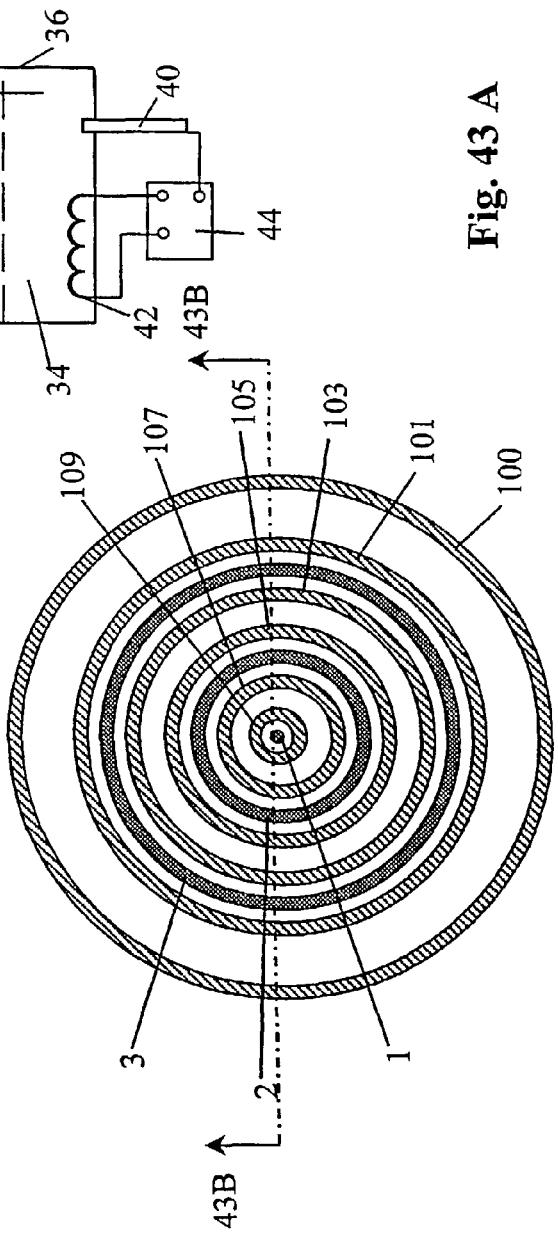
Fig. 43 B
Fig. 43 A

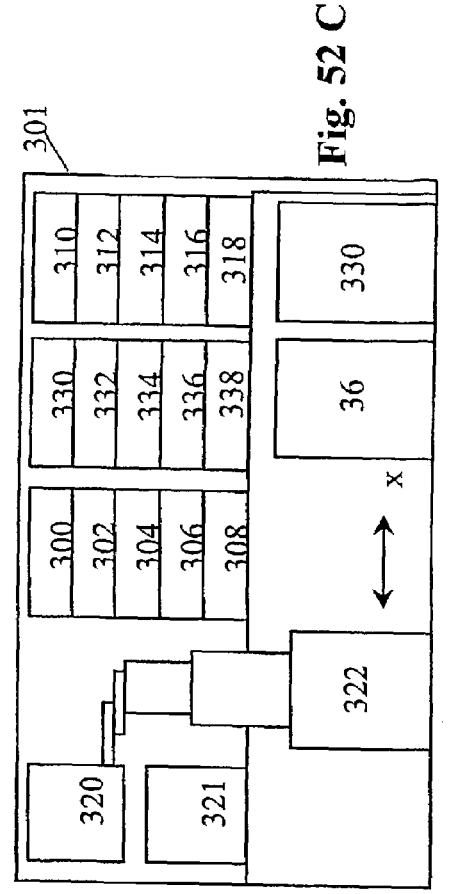
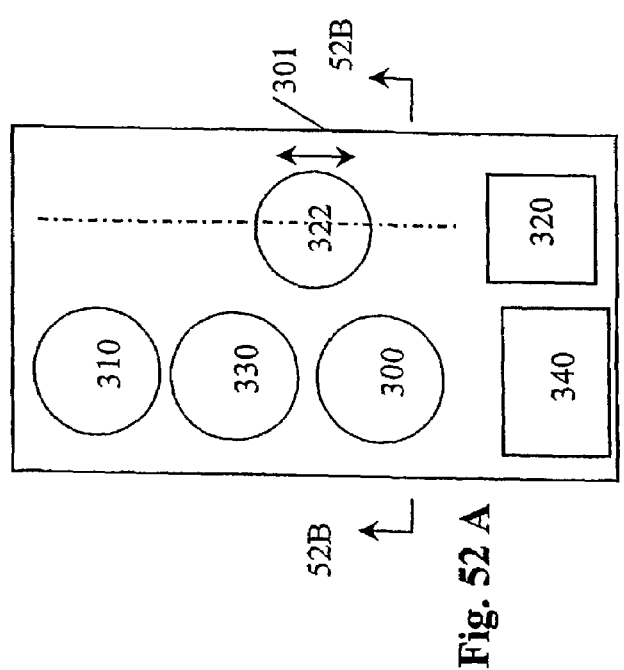
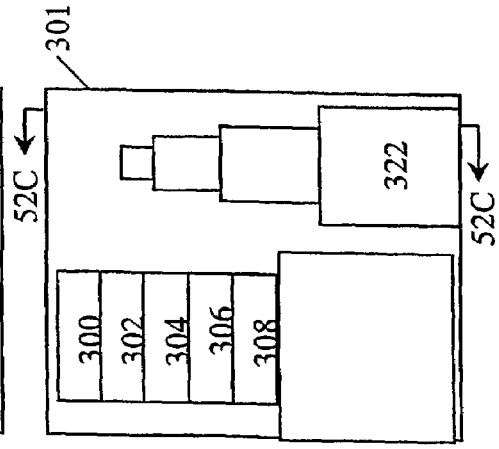

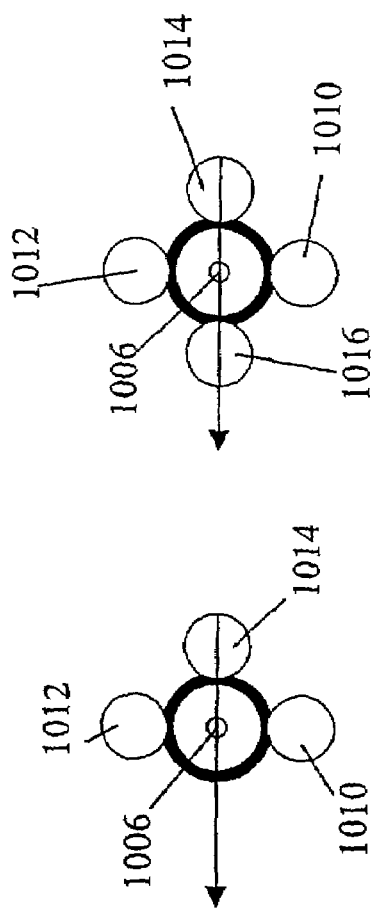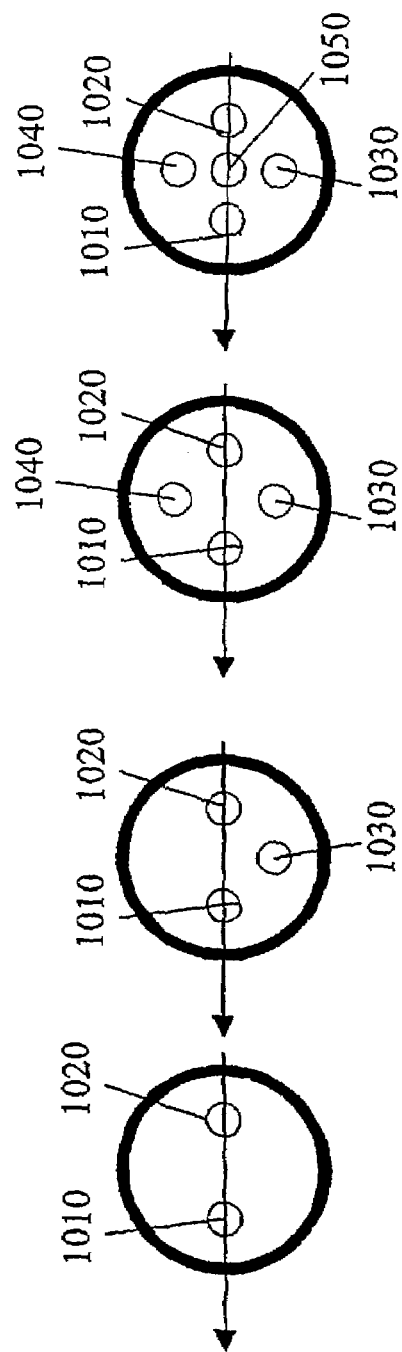
Fig. 63A  Fig. 63B
Fig. 64A  Fig. 64B  Fig. 64C  Fig. 64D

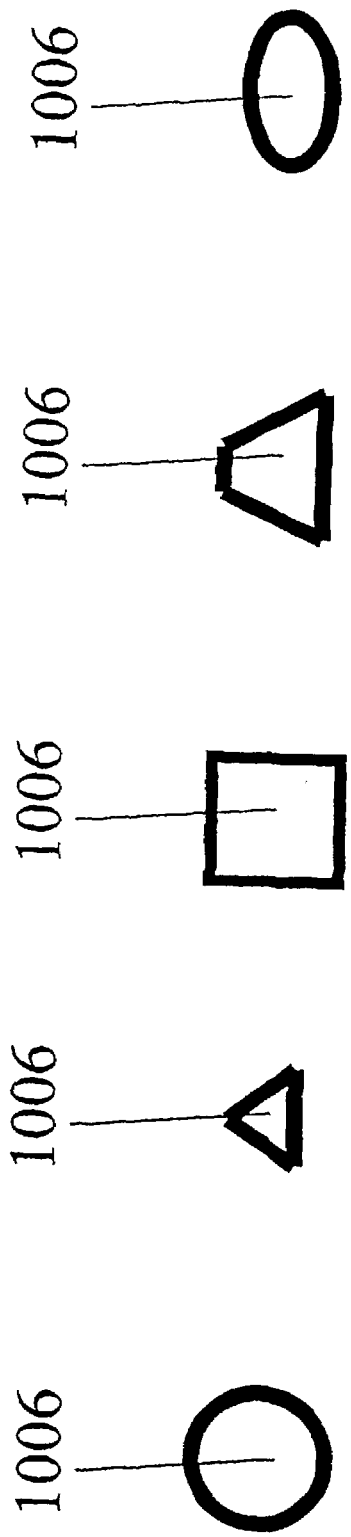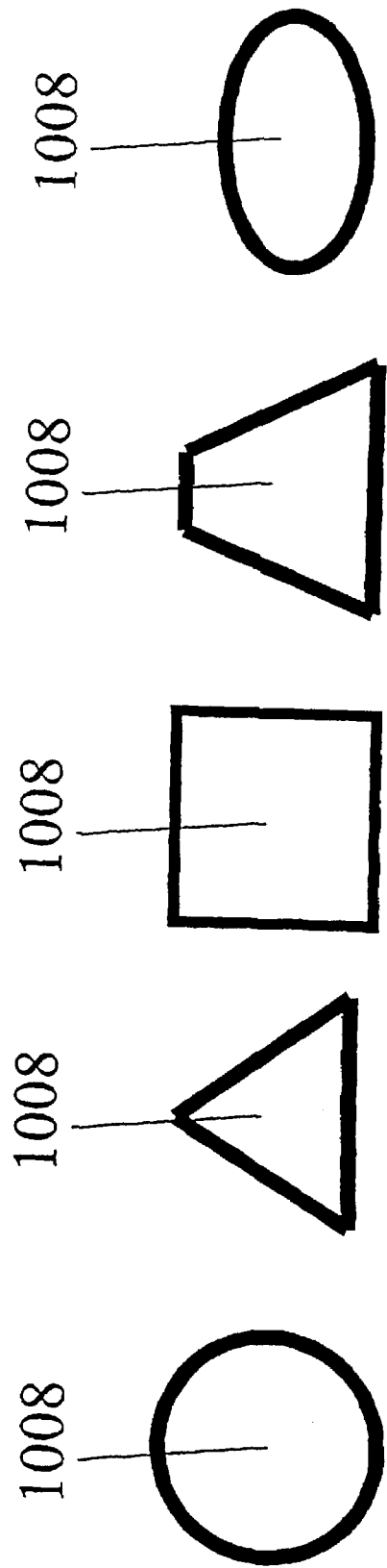

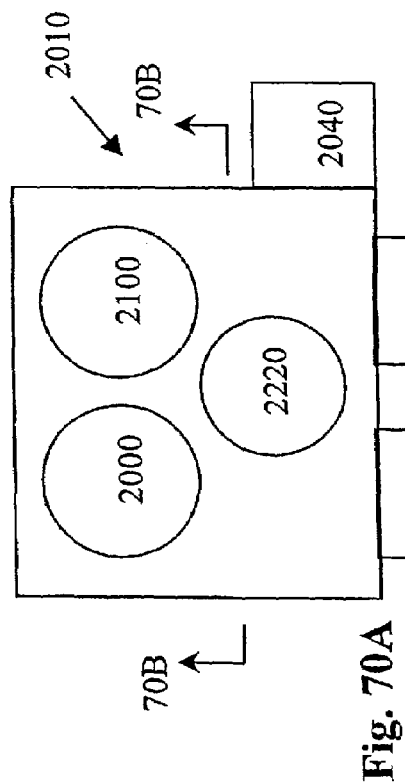
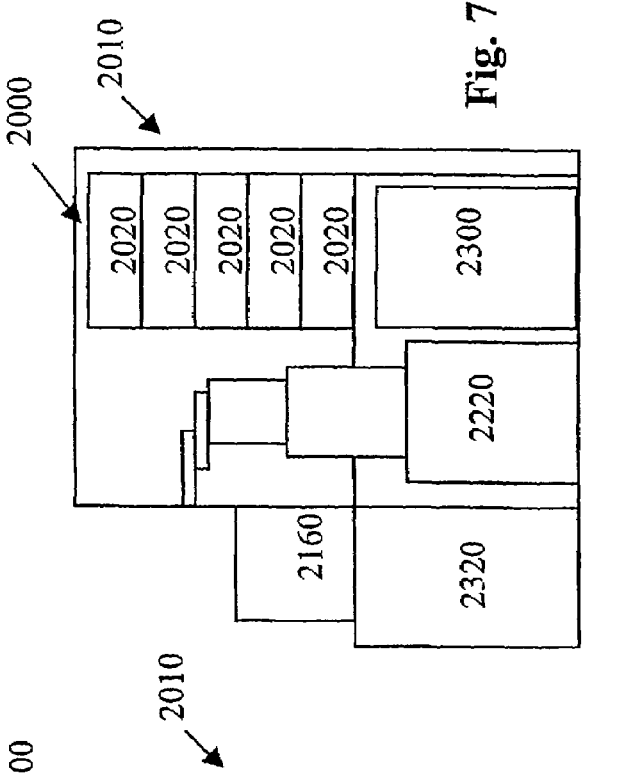
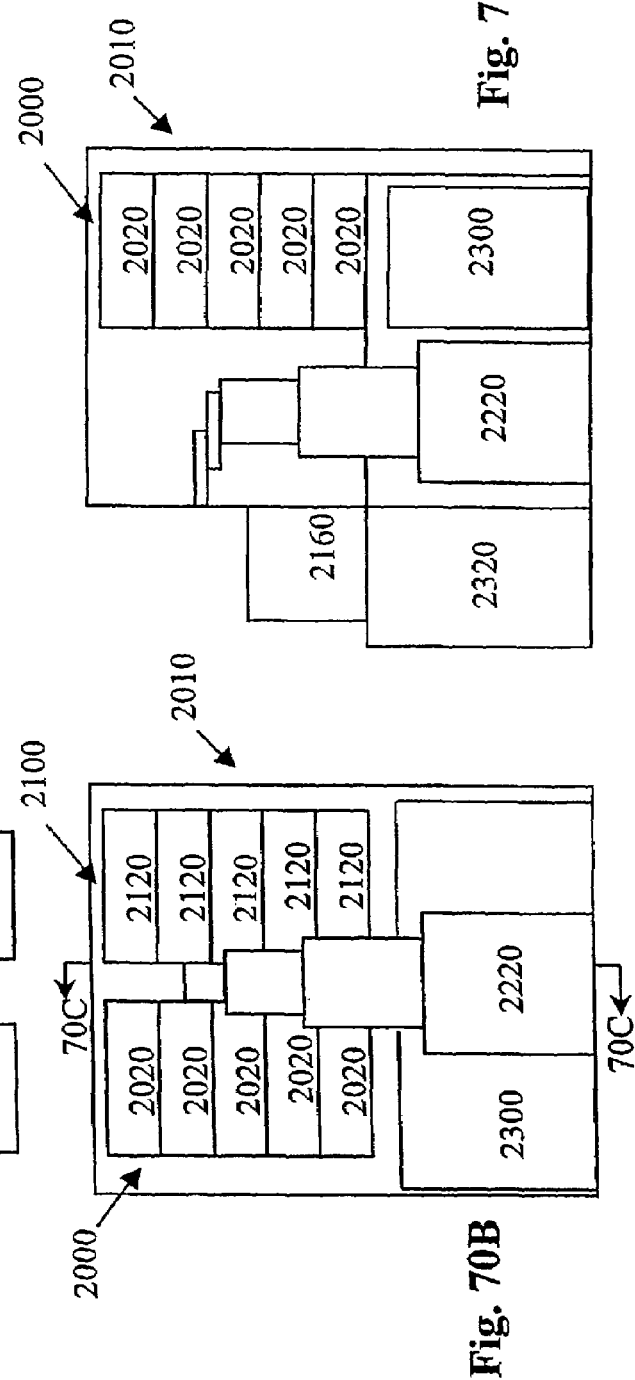

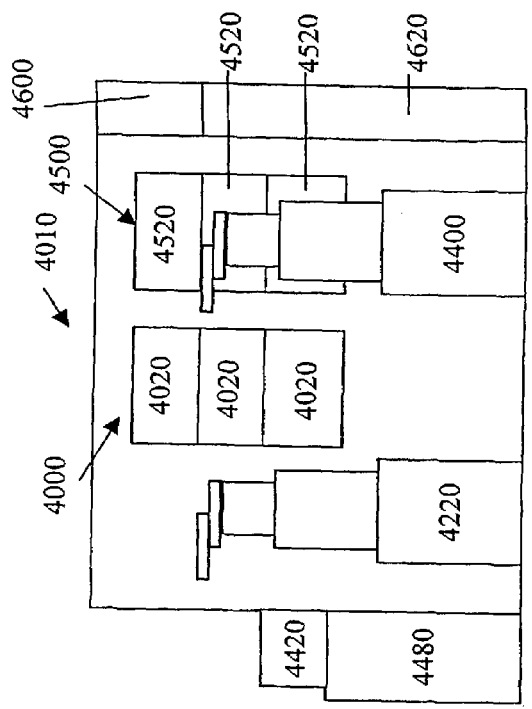
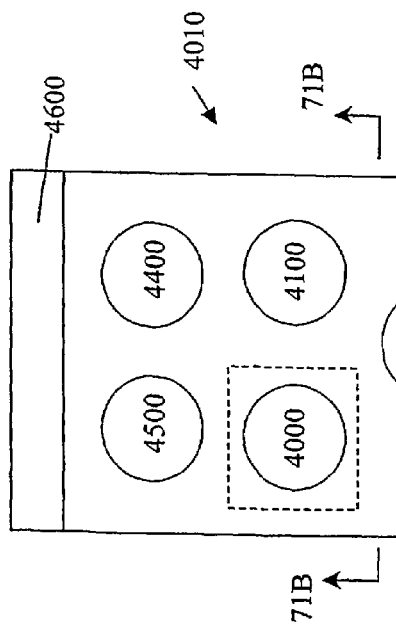
Fig. 71A
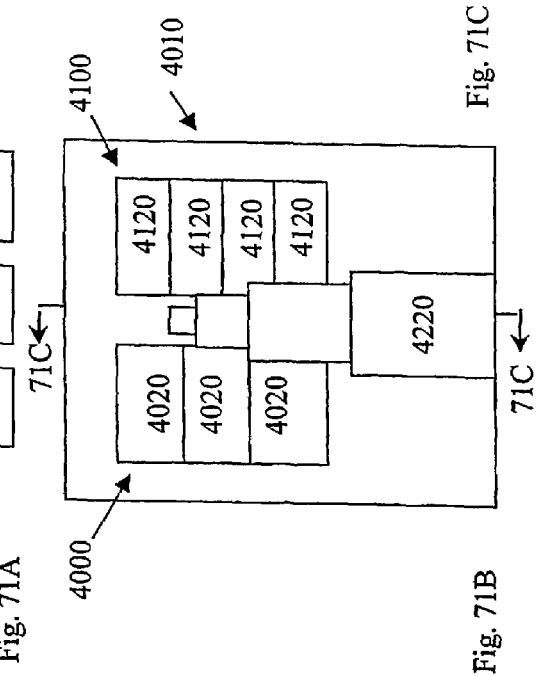
Fig. 71B
Fig. 71C

METHOD AND APPARATUS FOR END-POINT DETECTION

CROSS REFERENCE TO RELATED APPLICATIONS

This application is a 35 U.S.C. §371 National Stage of International Patent Application No. PCT/US01/14652, filed May 3, 2001, titled METHOD AND APPARATUS FOR END-POINT DETECTION, which is a continuation of U.S. application Ser. No. 09/570,566, filed May 12, 2000, titled METHOD AND APPARATUS FOR END-POINT DETECTION, now issued as U.S. Pat. No. 6,447,668, which is a continuation-in-part of U.S. application Ser. No. 09/497,894, filed Feb. 4, 2000, titled METHODS AND APPARATUS FOR ELECTROPOLISHNG METAL INTERCONNECTIONS ON SEMICONDUCTOR DEVICES, now issued as U.S. Pat. No. 6,440,295, which is a continuation of PCT/US99/15506, filed Jul. 8, 1999, titled METHODS AND APPARATUS FOR ELECTROPOLISHING METAL INTERCONNECTIONS ON SEMICONDUCTOR DEVICES, which claims benefit under 35 U.S.C. §119(e) of U.S. Provisional Application Ser. No. 60/092,316, filed Jul. 9, 1998, titled METHODS AND APPARATUS FOR ELECTROPOLISHING METAL INTERCONNECTIONS ON SEMICONDUCTOR DEVICES.

BACKGROUND OF THE INVENTION

1. Field of the Invention

The present invention generally relates to methods and apparatus for electropolishing metal layers on semiconductor wafers. More particularly, the present invention relates to a system for electropolishing interconnections in semiconductor devices formed on semiconductor wafers.

2. Description of the Related Art

In general, semiconductor devices are manufactured or fabricated on disks of semiconducting materials called wafers or slices. More particularly, wafers are initially sliced from a silicon ingot. The wafers then undergo multiple masking, etching, and deposition processes to form the electronic circuitry of semiconductor devices.

During the past decades, the semiconductor industry has increased the power of semiconductor devices in accordance with Moore's law, which predicts that the power of semiconductor devices will double every 18 months. This increase in the power of semiconductor devices has been achieved in part by decreasing the feature size (i.e., the smallest dimension present on a device) of these semiconductor devices. In fact, the feature size of semiconductor devices has quickly gone from 0.35 microns to 0.25 microns, and now to 0.18 microns. Undoubtedly, this trend toward smaller semiconductor devices is likely to proceed well beyond the sub-0.18 micron stage.

However, one potential limiting factor to developing more powerful semiconductor devices is the increasing signal delays at the interconnections (the lines of conductors, which connect elements of a single semiconductor device and/or connect any number of semiconductor devices together). As the feature size of semiconductor devices has decreased, the density of interconnections on the devices has increased. However, the closer proximity of interconnections increases the line-to-line capacitance of the interconnections, which results in greater signal delay at the interconnections. In general, interconnection delays have been found to increase with the square of the reduction in feature size. In contrast, gate delays (i.e., delay at the gates or mesas of semiconductor devices) have been found to increase linearly with the reduction in feature size.

One conventional approach to compensate for this increase in interconnection delay has been to add more layers of metal. However, this approach has the disadvantage of increasing production costs associated with forming the additional layers of metal. Furthermore, these additional layers of metal generate additional heat, which can be adverse to both chip performance and reliability.

Consequently, the semiconductor industry has started to use copper rather than aluminum to form the metal interconnections. One advantage of copper is that it has greater conductivity than aluminum. Also, copper is less resistant to electromigration (meaning that a line formed from copper will have less tendency to thin under current load) than aluminum. However, one significant disadvantage to using copper has been its tendency to bleed into the silicon substrate, thus contaminating the semiconductor device.

Additionally, before copper can be widely used for interconnections, new processing techniques are required. More particularly, in a conventional damascene process, metal is patterned within canal-like trenches and/or vias. The deposited metal is then polished back using chemical mechanical polishing ("CMP"). In general, depending on the interconnection structure design, anywhere from half a micron to 1.5 millimeters of metal needs to be polished. Polishing such a large quantity of metal using conventional CMP requires a long polishing time and consumes a large quantity of slurry, which leads to high manufacturing costs.

SUMMARY OF THE INVENTION

The present invention relates to an end-point detector for detecting the end-point of an electropolishing process of a metal layer formed on a wafer. The end-point detector is disposed adjacent the nozzle used to electropolish the wafer. In one embodiment, the end-point detector is configured to measure the optical reflectivity of the portion of the wafer being electropolished.

DESCRIPTION OF THE DRAWING FIGURES

The subject matter of the present invention is particularly pointed out and distinctly claimed in the concluding portion of the specification. The present invention, however, both as to organization and method of operation, may best be understood by reference to the following description taken in conjunction with the claims and the accompanying drawing figures, in which like parts may be referred to by like numerals:

FIGS. 1A–1D are cross-section views of a semiconductor wafer in accordance with various aspects of the present invention;

FIG. 17A is a top view of a portion of a seventh alternative embodiment in accordance with various aspects of the present invention;

FIG. 17B is a view, partly in cross section, taken along the line 17B—17B in FIG. 17A, and partly in block diagram form, of the alternative embodiment shown in FIG. 17A;

FIG. 18A is a cross section view of an eighth alternative embodiment in accordance with various aspects of the present invention;

FIG. 18B is a cross section view of a ninth alternative embodiment in accordance with various aspects of the present invention;

FIG. 19A is a cross section view of a tenth alternative embodiment in accordance with various aspects of the present invention;

FIG. 19B is a cross section view of an eleventh alternative embodiment in accordance with various aspects of the present invention;

FIG. 22A is a top view of a portion of a fifteenth alternative embodiment in accordance with various aspects of the present invention;

FIG. 22B is a view, partly in cross section, taken along the line 22B—22B in FIG. 22A, and partly in block diagram form, of the alternative embodiment shown in FIG. 22A;

FIG. 24A is a top view of a portion of a nineteenth alternative embodiment in accordance with various aspects of the present invention;

FIG. 24B is a view, partly in cross section, taken along the line 24B—24B in FIG. 24A, and partly in block diagram form, of the alternative embodiment shown in FIG. 24A;

FIG. 28A is a top view of a portion of a twenty-fifth alternative embodiment in accordance with various aspects of the present invention;

FIG. 28B is a view, partly in cross section, taken along the line 28B—28B in FIG. 28A, and partly in block diagram form, of the alternative embodiment shown in FIG. 28A;

FIG. 29A is a top view of a portion of a twenty-sixth alternative embodiment in accordance with various aspects of the present invention;

FIG. 29B is a view, partly in cross section, taken along the line 29B—29B in FIG. 29A, and partly in block diagram form, of the alternative embodiment shown in FIG. 29A;

FIG. 30A is a top view of a portion of a twenty-seventh alternative embodiment in accordance with various aspects of the present invention;

FIG. 30B is a view, partly in cross section, taken along the line 30B—30B in FIG. 30A, and partly in block diagram form, of the alternative embodiment shown in FIG. 30A;

FIG. 31A is a top view of a portion of a twenty-eighth alternative embodiment in accordance with various aspects of the present invention;

FIG. 31B is a view, partly in cross section, taken along the line 31B—31B in FIG. 31A, and partly in block diagram form, of the alternative embodiment shown in FIG. 31A;

FIG. 32A is a cross section view of a portion of a twenty-ninth alternative embodiment in accordance with various aspects of the present invention;

FIG. 32B is a cross section view of a portion of a thirtieth alternative embodiment in accordance with various aspects of the present invention;

FIG. 32C is a cross section view of a portion of a thirty-first alternative embodiment in accordance with various aspects of the present invention;

FIG. 32D is a cross section view of a portion of a thirty-second alternative embodiment in accordance with various aspects of the present invention;

FIG. 43A is a top view of a portion of a forty-third alternative embodiment in accordance with various aspects of the present invention;

FIG. 43B is a view, partly in cross section, taken along the line 43B—43B in FIG. 43A, and partly in block diagram form, of the alternative embodiment shown in FIG. 43A;

FIGS. 52A–52C are schematic top, cross section, and side views, respectively, of still another embodiment of a wafer processing tool in accordance with various aspects of the present invention;

FIGS. 63A and 64B are schematics of various configurations of end-point detectors;

FIGS. 64A through 64D are schematics of various configurations of end-point detectors;

FIGS. 65A through 65E are cross-sectional views of various end-point detectors;

FIGS. 66A through 66E are cross sectional views of various nozzles;

FIGS. 70A through 70C are top, front cross section, and side cross section views, respectively, of a wafer processing tool;

FIGS. 71A through 71C are top, front cross section, and side cross section views, respectively, of another wafer processing tool.

DETAILED DESCRIPTION OF EXEMPLARY EMBODIMENTS

Figure 2:
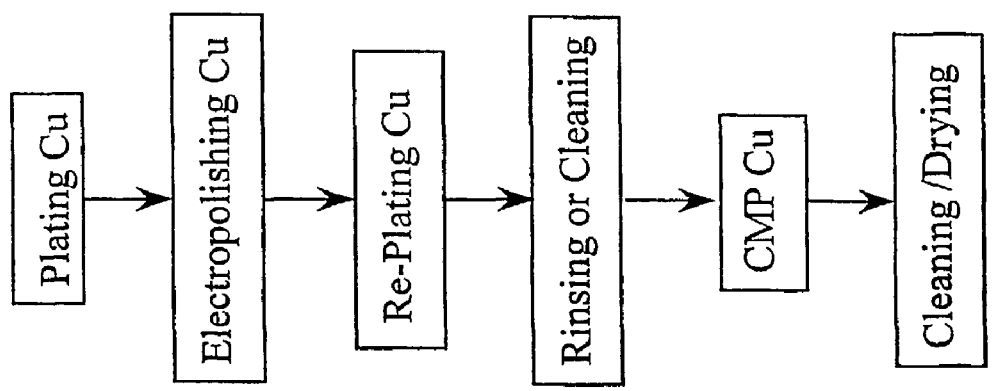
FIG. 2 is a flow chart for processing wafers in accordance with various aspects of the present invention.

In order to provide a more thorough understanding of the present invention, the following description sets forth numerous specific details, such as specific material, parameters, and the like. It should be recognized, however, that such description is not intended as a limitation on the scope of the present invention, but is instead provided to enable a full and complete description of the exemplary embodiments.

With reference to FIG. 1A, a semiconductor wafer 31, according to one aspect of the present invention, suitably includes a substrate layer 124. More particularly, in an exemplary embodiment of the present invention, substrate layer 124 preferably includes silicon. It should be recognized, however, that substrate layer 124 can include various semiconductor materials, such as gallium arsenide and the like, depending on the particular application.

Semiconductor wafer 31, according to another aspect of the present invention, suitably includes a dielectric layer 123 formed on top of substrate layer 124. In the present exemplary embodiment, dielectric layer 123 preferably includes silicon dioxide (SiO2). Dielectric layer 123 can be formed on substrate layer 124 using any convenient deposition method, such as chemical vapor deposition, evaporation, sputtering, and the like.

Additionally, dielectric layer 123 can include various materials having dielectric constant ("K") values lower than that of SiO2, these various materials being generally referred to as low-K materials, such as hydrogen-silsesquioxane (HSQ), Xerogel, polymer, aerogel, and the like. In comparison to SiO2, which has a dielectric constant of about 4.2, HSQ has a dielectric constant of about 3.0 to 2.5, and Xerogel has a dielectric constant of about 2.0. In general, a low-K material provides better electrical isolation. Therefore, the use of a low-K material as dielectric layer 123 can facilitate the formation of semiconductor devices with smaller feature sizes.

After dielectric layer 123 is suitably formed on substrate layer 124, the circuitry for semiconductor devices is suitably formed using any convenient process. In the present exemplary embodiment, a damascene process is preferably used. Accordingly, trenches (also known as gaps) 125 and gates (also known as mesas) 126 are formed in dielectric layer 123 using any convenient patterning method, such as photomasking, photolithography, microlithography, and the like.

Next, a barrier layer 122, according to still another aspect of the present invention, is suitably formed on top of dielectric layer 123. As depicted in FIG. 1A, barrier layer 122 also suitably lines the walls of trenches 125. As will be described below, when a metal layer 121, which includes copper, is formed on top of dielectric layer 123, barrier layer 122 suitably prevents the copper in metal layer 121 from diffusing into dielectric layer 123. Accordingly, in the present exemplary embodiment, barrier layer 122 preferably includes material resistant to the diffusion of copper, such as titanium, tantalum, tungsten, titanium-nitride, tantalum-nitride, tungsten-nitride, and the like. Barrier layer 122 can be deposited using any convenient deposition method, such as physical vapor deposition (PVD), chemical vapor deposition (CVD), and the like. It should be recognized, however, that barrier layer 122 can be omitted in some applications. For example, when dielectric layer 123 is formed from a material, which is resistant to diffusion of copper, or when the diffusion of copper into dielectric layer 123 will not adversely affect the performance of the semiconductor device.

As alluded to above, depending on the particular application, metal layer 121, according to yet another aspect of the present invention, can be suitably formed on top of barrier layer 122 or formed on top of dielectric layer 123. Additionally, metal layer 121 is suitably deposited within trench 125. In the present exemplary embodiment, metal layer 121 preferably includes copper. Accordingly, metal layer 121 is formed on top of barrier layer 122 to suitably prevent the diffusion of copper from metal layer 121 into dielectric layer 123. Although the present invention is particularly well suited for use with metal layer 121 including copper, it should be recognized that metal layer 121 can include various electrically conductive materials, such as nickel, chromium, zinc, cadmium, silver, gold, rhodium, palladium, platinum, tin, lead, iron, indium, and the like.

Metal layer 121 can be formed on barrier layer 122 or on dielectric layer 123 using any convenient method, such as PVD, CVD, and the like. Additionally, metal layer 121 can be formed using an electroplating processing, which is described in copending application Ser. No. 09/232,864, entitled PLATING APPARATUS AND METHOD, filed on Jan. 15, 1999, the entire content of which is incorporated herein by reference.

With reference now to FIG. 1B, metal layer 121, formed on top of mesas 126, according to another aspect of the present invention, is suitably electropolished. The present invention can be advantageously used in a damascene process, in which the circuitry of a semiconductor device is patterned into trenches or gaps. It should be recognized, however, that the present invention can be used in conjunction with various other processes without deviating from the spirit and/or scope of the present invention.

With reference now to FIGS. 7A and 7B, a wafer electropolisher 50, according to various aspects of the present invention, is shown. In an exemplary embodiment of the present invention, wafer electropolisher 50 preferably includes polishing receptacle 100, which is divided into six sections 111, 112, 113, 114, 115 and 116 by section walls 109, 107, 105, 103 and 101. As will be described in greater detail below, it should be recognized that polishing receptacle 100 can be divided into any number of sections by any suitable number of section walls.

Polishing receptacle 100 and section walls 109, 107, 105, 103 and 101 are suitably formed from any convenient material electrically insulated and resistant to acid and corrosion, such as polytetrafluoroethylene (commercially known as TEFLON), PolyVinyl Chloride (PVC), PolyVinylindene Fluoride (PVDF), Polypropylene, and the like. In the present exemplary embodiment, polishing receptacle 100 and section walls 109, 107, 105, 103 and 101 are preferably formed from PVDF. It should be recognized, however, that polishing receptacle and each section wall 109, 107, 105, 103 and 101 can be formed from different materials depending on the particular application.

As depicted in FIG. 7B, in the present exemplary embodiment, electrolyte 34 flows into polishing receptacle 100 through inlets 4, 6 and 8 suitably formed in sections 111, 113 and 115, respectively. More particularly, a pump 33 suitably pumps electrolyte 34 from an electrolyte reservoir 36 to a pass filter 32 and into Liquid Mass Flow Controllers (LMFCs) 21, 22 and 23. Pass filter 32 suitably filters contaminants from electrolyte 34. In this manner, contaminants are prevented from entering polishing receptacle 100 and from clogging LMFCs 21, 22 and 23. In the present exemplary embodiment, pass filter 32 suitably removes particles larger than about 0.05 micrometer but smaller than about 0.1 micrometers. It should be recognized, however, that various filtering systems can be used depending on the particular application. Additionally, although filtering contaminants is advantageous, pass filter 32 can be omitted from wafer polisher 50 without deviating from the spirit and/or scope of the present invention.

Electrolyte 34 can include any convenient electroplating fluid, such as phosphoric acid, and the like. In the present exemplary embodiment, electrolyte 34 preferably includes orthophosphoric acid (H2PO4) having a concentration between about 60 percent by weight and about 85 percent by weight, and preferably about 76 percent by weight. Additionally, electrolyte 34 preferably includes orthophosphoric acid having about 1 percent aluminum metal (against weight of the acid). It should be recognized, however, that the concentration and composition of electrolyte 34 can vary depending on the particular application.

Pump 33 can include any convenient hydraulic pump, such as a centrifugal pump, a diaphragm pump, a bellow pump, and the like. Additionally, pump 33 is suitably resistant to acid, corrosion, and contamination. In the present exemplary embodiment, pump 33 includes a diaphragm pump. It should be recognized, as will be depicted and described below in conjunction with alternative embodiments, that two or more pumps 33 can be used without deviating from the spirit and/or scope of the present invention. Additionally, it should be recognized that electrolyte 34 can be suitably delivered to polishing receptacle 100 through inlets 4, 6 and 8, without pump 34. For example, electrolyte 34 can be maintained at pressure within electrolyte reservoir 36. Alternatively, the supply lines between electrolyte reservoir 36 and inlets 4, 6 and 8 can be maintained at pressure.

LMFCs 21, 22 and 23 can include any convenient mass flow controller, preferably resistant to acid, corrosion, and contamination. Additionally, LMFCs 21, 22 and 23 deliver electrolyte 34 at set flow rates to sections 115, 113 and 111, respectively. Additionally, LMFCs 21, 22 and 23 can suitably deliver electrolyte 34 at flow rates proportionate to the volumes of sections 115, 113 and 111. For example, if section 115 is larger in volume than section 113, then it can be advantageous for LMFC 21 to deliver electrolyte 34 at a greater flow rate than LMFC 22. In the present exemplary embodiment, LMFCs 21, 22 and 23 are preferably configured to deliver electrolyte 34 at a flow rate between about 0.5 liters per minute and about 40 liters per minute.

Additionally, in the present exemplary embodiment, a separate LMFC delivers electrolyte into each section 115, 113 and 111. As will be described in greater detail below, this configuration facilitates electropolishing of discrete portions of wafer 31. It should be recognized, however, that any number of LMFCs can be used depending on the particular application. Additionally, as will be described and depicted below in conjunction with alternative embodiments, electrolyte 34 can be delivered into polishing receptacle 100 from pump 33 without using LMFCs 21, 22 and 23.

In accordance with various aspects of the present invention, wafer polisher 50 suitably includes cathodes 1, 2 and 3 disposed within sections 111, 113 and 115, respectively. As will be described in greater detail below, although the present exemplary embodiment includes three cathodes, any number of cathodes, whether fewer or greater than three, can be used without deviating from the present invention. In general, the more cathodes used, the better film uniformity can be expected. However, the more cathodes used, the greater the cost. Accordingly, considering the trade off between performance and cost, the preferred number of cathodes can be from about 7 to about 20 for electropolishing 200-millimeter wafers, and from about 10 to about 30 for electropolishing 300-millimeter wafers.

Additionally, cathodes 1, 2 and 3 can include any convenient electrically conducting material, such as copper, lead, platinum, and the like. During the electroplating period, some of the metal ions, which migrate out of metal layer 121, can accumulate on cathodes 1, 2 and 3. Accordingly, cathodes 1, 2 and 3 can be suitably replaced at any appropriate time. For example, cathodes 1, 2 and 3 can be suitably replaced after processing about 100 wafers.

Alternatively, a deplating process for cathodes 1, 2 and 3 can be suitably performed. For example, as will be described in greater detail below, in accordance with various aspects of the present invention, when cathodes 1, 2 and 3 are charged positively and wafer 31 is charged negatively, then wafer 31 is suitably electroplated rather than electropolished. In this manner, wafer 31 can be suitably electroplated with the buildup of metal on cathodes 1, 2 and 3 to suitably deplate cathodes 1, 2 and 3. Although under the conditions described above, cathodes 1, 2 and 3 would function as anodes, for the sake of consistency and convenience, they will continue to be referred to as cathodes.

In the present exemplary embodiment, metal layer 121 includes copper. Accordingly, as described above, during the electropolishing process, some of the copper ions from metal layer 121 migrate to electroplate cathodes 1, 2 and 3. In the deplating process described above, a wafer 31 can be suitably electroplated with the buildup of copper on cathodes 1, 2 and 3. However, when cathodes 1, 2 and 3 are formed from copper, cathodes 1, 2 and 3 can dissolve during the deplating process. In this manner, cathodes 1, 2 and 3 can become deformed during the deplating process. Accordingly, in accordance with various aspects of the present invention, cathodes 1, 2 and 3 can be suitably formed from materials, which are resistant to being dissolved during the deplating process. For example, cathodes 1, 2 and 3 can be suitably formed from platinum. Alternatively, cathodes 1, 2 and 3 can be suitably formed from titanium suitably coated with a layer of platinum, preferably with a coating thickness of about 50 microns to about 400 microns.

In the present exemplary embodiment, a wafer chuck 29 suitably holds and positions wafer 31 within polishing receptacle 100. More particularly, wafer 31 is suitably positioned above the tops of section walls 101, 103, 105, 107 and 109 to form a gap to facilitate the flow of electrolyte 34 between the bottom surface of wafer 31 and the tops of section walls 101, 103, 105, 107 and 109. In the present exemplary embodiment, wafer 31 is suitably positioned above the tops of section walls 101, 103, 105, 107 and 109 to form a gap of about 2 millimeters to about 20 millimeters.

After wafer 31 is suitably positioned within polishing receptacle 100, cathodes 1, 2 and 3 are electrically connected to power supplies 13, 12 and 11, respectively. Additionally, wafer 31 is electrically connected to power supplies 13, 12 and 11. In this manner, when electrolyte 34 flows between the bottom surface of wafer 31 and the tops of section walls 101, 103, 105, 107 and 109, an electrical circuit is formed. More particularly, cathodes 1, 2 and 3 are electrically charged to have negative electric potential in comparison to wafer 31. In response to this negative electric potential at cathodes 1, 2 and 3, metal ions then migrate away from wafer 31, thus electropolishing wafer 31. However, when the polarity of the circuit is reversed (i.e., cathodes 1, 2 and 3 become anodes), metal ions migrate toward wafer 31, thus electroplating wafer 31.

Figure 33:
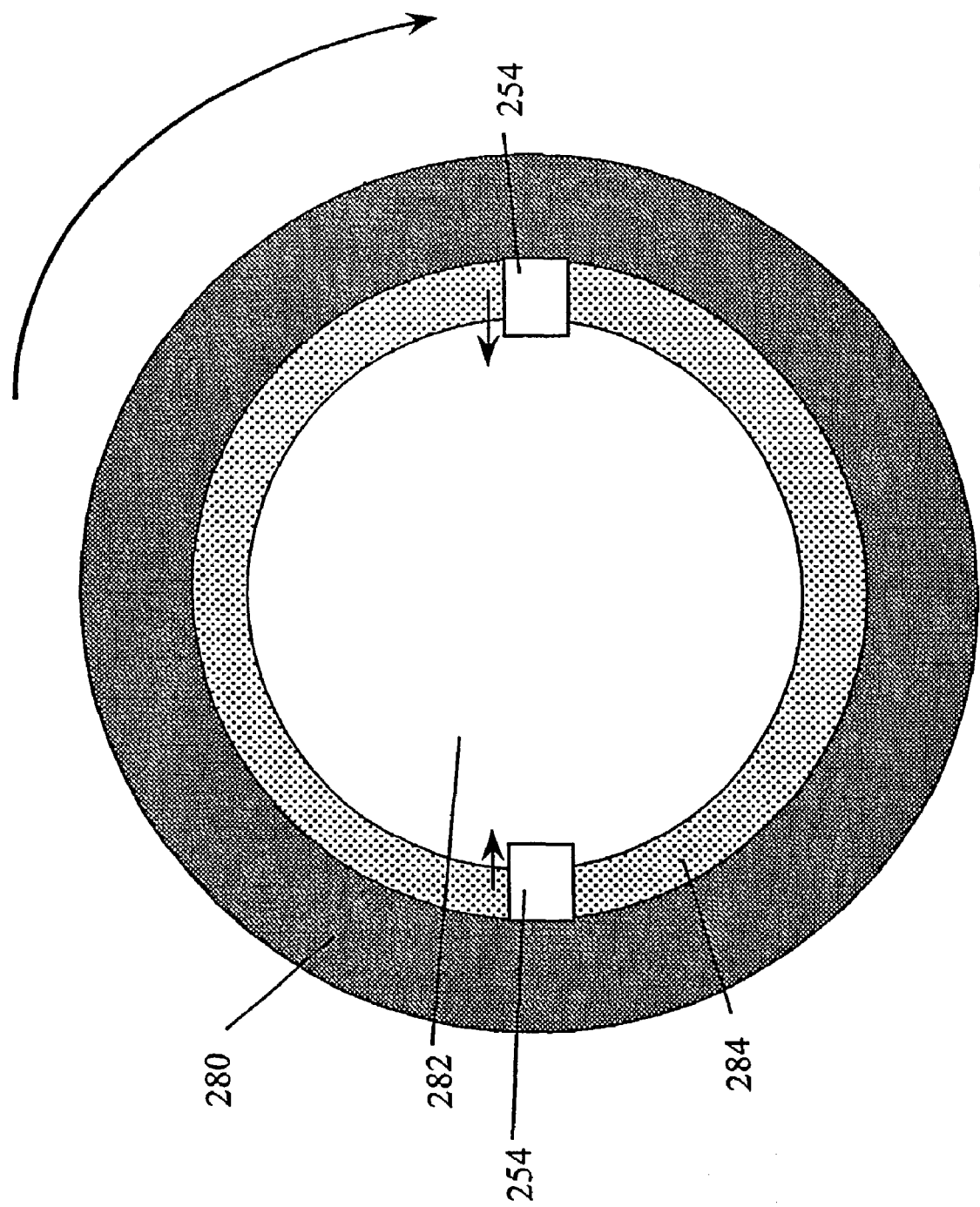
FIG. 33 is a top view of a wafer undergoing electropolishing in accordance with various aspects of the present invention.

In this manner, selective portions of wafer 31 can be suitably electropolished and electroplated by controlling the polarity of cathodes 1, 2 and 3, and by controlling the portions of wafer 31 contacted by electrolyte 34. FIG. 33 depicts the selective electropolishing of wafer 31 in accordance with various aspects of the present invention. With reference to FIG. 33, wafer area 280 has been electropolished, area 284 is being electropolished, and wafer area 282 has not been polished.

With reference again to FIGS. 7A and 7B, in general, the polishing current density determines the rate at which metal ions migrate to or from wafer 31. Accordingly, the higher the polishing current density, the greater the electropolishing or electroplating rate. In the present exemplary embodiment, a current density of about 0.1 amperes per decimeter-squared (A/dm$^2$) to about 40 amperes per decimeter-squared (A/dm$^2$), and preferably about 10 amperes per decimeter-squared (A/dm$^2$), can be used. It should be recognized, however, that various current densities can be used depending on the particular application.

Furthermore, power supplies 13, 12 and 11 can apply different current densities to cathodes 1, 2 and 3. For example, the current applied by power supplies 13, 12 and 11 can be set proportional to the surface area of wafer 31 that is covered by the corresponding cathodes. Accordingly, if the surface area of wafer 31 covered by cathode 3 is larger than that covered cathode 2, power supply 11 can be set to apply more current than power supply 12. In this manner, the rate of electropolishing can be controlled to facilitate a more uniform etching of the surface of wafer 31. It should be recognized that the same principle can also be used to facilitate a more uniform electroplating of the surface of wafer 31.

In accordance with another aspect of the present invention, power supplies 13, 12 and 11 can be operated in DC (i.e., direct current) mode. Alternatively, power supplies 13, 12 and 11 can be operated in a variety of pulse modes. For example, with reference to FIG. 8, power supplies 13, 12 and 11 can be operated using a bipolar pulse, a modified sine-wave, unipolar pulse, pulse reverse, pulse-on-pulse, duplex pulse, and the like. Power supplies 13, 12 and 11 can also be operated in constant current mode, constant voltage mode, and a combination of constant current mode and constant voltage mode.

With reference again to FIG. 7B, a drive mechanism 30 suitably rotates wafer 31 about the z-axis. In this manner, a more uniform electropolish can be achieved across the surface of wafer 31. In the present exemplary embodiment, drive mechanism 30 rotates wafer 31 about the z-axis at approximately 10 revolutions per minute to approximately 100 revolutions per minute, and preferably at about 20 revolutions per minute.

As depicted in FIG. 7A, cathodes 1, 2 and 3 are substantially circular in shape. Accordingly, with reference to FIG. 7B, the areas of wafer 31 above sections 112 and 114 are likely to be exposed to lower current density than the areas of wafer 31 above sections 111, 113 and 115 (i.e., those sections containing a cathode). In order to compensate, drive mechanism 30 suitably oscillates wafer 31 in the x and y directions. Alternatively or in addition to oscillating wafer 31, as depicted in FIGS. 9A to 9D, polishing receptacle 100, section walls 109, 107, 105, 103 and 101, and cathodes 1, 2 and 3 can be formed into non-circular shapes, such as triangles, squares, rectangles, pentagons, polygons, ellipses, and the like. In this manner, the polishing current distribution can be averaged out across the surface of wafer 31 as wafer 31 is rotated about the z-axis.

Electrolyte 34 returns to electrolyte reservoir 36 through outlets 5, 7 and 9, suitably formed in sections 112, 114 and 116, respectively. A pressure leak valve 38 is suitably placed between the outlet of pump 33 and electrolyte reservoir 36 to allow electrolyte 34 to leak back to electrolyte reservoir 36 when LMFCs 21, 22, and 23 are closed. Additionally, a heater 42, a temperature sensor 40, and a heater controller 44 suitably control the temperature of electrolyte 34 in electrolyte reservoir 36. In the present exemplary embodiment, wafer polisher 50 and electrolyte 34 are preferably operated at an operating temperature of about 15 degrees Celsius to about 60 degrees Celsius, and preferably at about 45 degrees Celsius.

Figure 10:
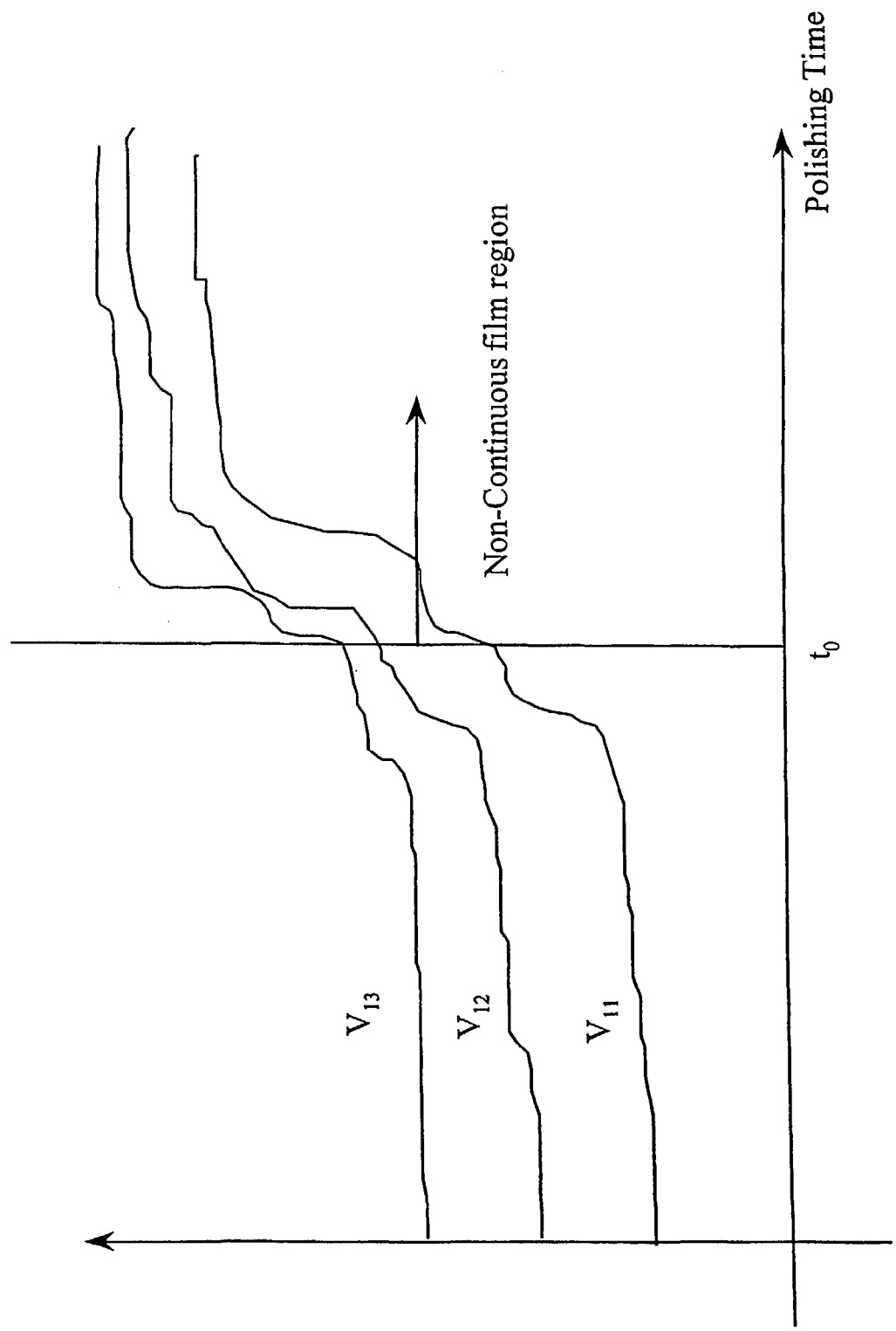
FIG. 10 is a plot of various waveforms depicting a portion of an electropolishing process in accordance with various aspects of the present invention.

With reference to FIG. 1A, wafer 31 is suitably electropolished for a period of time (i.e., an electropolishing time period), until metal layer 121 is removed from barrier layer 122, while metal layer 121 remains within trenches 125 (as depicted in FIG. 1B). With reference now to FIG. 7B, the requisite electropolishing time period can be determined by measuring the output voltage and current of power supplies 11, 12 and 13. More particularly, the resistance of barrier layer 122 is typically significantly greater than metal layer 121. For example, when barrier layer 122 includes titanium, titanium-nitride, tantalum, tantalum-nitride, tungsten, or tungsten-nitride and metal layer 121 includes copper, the resistance of barrier layer 122 is typically about 50 to about 100 times greater than the resistance of metal layer 121. Accordingly, the potential measured from edge to center of wafer 31 after polishing metal layer 121 away from the non-trench portions of wafer 31 is larger than that before polishing. As such, as detailed in the table below with reference to FIGS. 7A, 7B and 10, by comparing the output voltages of power supplies 11, 12 and 13, the portions of metal layer 121 above wafer 31 which have been removed can be suitably determined:

TABLE 1

1. If $V_{11}$ (Voltage of power supply 11) and $V_{12}$ (Voltage of power supply 12) are small in value, and $V_{13}$ (Voltage of power supply 13) is large in value, then metal layer 121 on wafer 31 above cathode 1 has been removed;
2. If $V_{11}$ is small in value, and $V_{12}$ and $V_{13}$ are large in value, then metal
   layer 121 on wafer 31 above cathode 3 has not been removed.
   Additionally, metal layer 121 above cathode 2 has been removed.
   However, the condition of metal layer 121 on wafer 31 above cathode 1 is unknown. Therefore, the following additional conditions can be consulted to determine the condition of metal layer 121 on wafer 31 above cathode 1:
   a. If $V_{12}$ and $V_{13}$ are close to each other in value, then metal layer 121 on wafer 31 above cathode 1 has not been removed; or
   b. If $V_{12}$ and $V_{13}$ are apart each other in value, then metal layer 121 on wafer 31 above cathode 1 has been removed;
3. If $V_{11}$, $V_{12}$ and $V_{13}$ are large in value, then metal layer 121 on wafer 31 above cathode 3 has been removed. However, the condition of metal layer 121 on wafer 31 above cathodes 2 and 1 is unknown. Therefore, the following additional conditions can be consulted to determine the condition of metal layer 121 on wafer 31 above cathodes 2 and 1:
   a. If $V_{11}$, $V_{12}$, $V_{13}$ are apart from each other in value, then metal layer 121 on wafer 31 above cathode 2 and cathode 1 have been removed;
   b. If $V_{11}$ and $V_{12}$ are apart each other in value, and $V_{12}$ and $V_{13}$ are close each other in value, then metal layer 121 on wafer 31 above cathode 2 has been removed. Additionally, metal layer 121 on wafer 31 above cathode 1 has not been removed;
   c. If $V_{11}$ and $V_{12}$ are close each other in value, and $V_{12}$ and $V_{13}$ are apart each other in value, then metal layer 121 on wafer 31 above cathode has not been removed. Additionally, metal layer 121 on wafer 31 above cathode 1 has been removed; or
   d. If $V_{12}$ and $V_{13}$ are close to $V_{11}$ in value, then metal layer 121 on wafer 31 above cathode 1 and 2 are has not been removed.

In the table described above, $V_{11}$, $V_{12}$ and $V_{13}$ were described as being large and/or small. It should be recognized, however, that the terms large and small are relative and not meant to relate to any particular voltages. For example, when $V_{11}$ and $V_{12}$ are described above as being small, $V_{11}$ and $V_{12}$ are small in comparison to $V_{13}$. As alluded to above, $V_{11}$ and $V_{12}$ could be as much as about 50 to about 100 times smaller than $V_{13}$.

In this manner, by referring to the above table, the areas of wafer 31, which require additional electropolishing, can be suitably determined. As will be described later in conjunction with an alternative embodiment of the present invention, monitors can be suitably configured to measure the voltage and current provided by each one of power supplies 11, 12 and 13. This data can be suitably transmitted to a control system, which can include the above logic table in electronic format. For example, the above table can be encoded and stored in an appropriate electronic storage medium, such as on magnetic tape, magnetic disk, compact disk, and the like, or in an appropriate electronic device, such as on an integrated circuit, memory chip, and the like. The control system can then execute appropriate commands to continue or to stop the electropolishing of a particular portion of wafer 31. It should be recognized that the control system described above can be integrated into an appropriate computer system, which can be a component of a wafer electropolishing tool, an example of which is described below.

Figure 55:
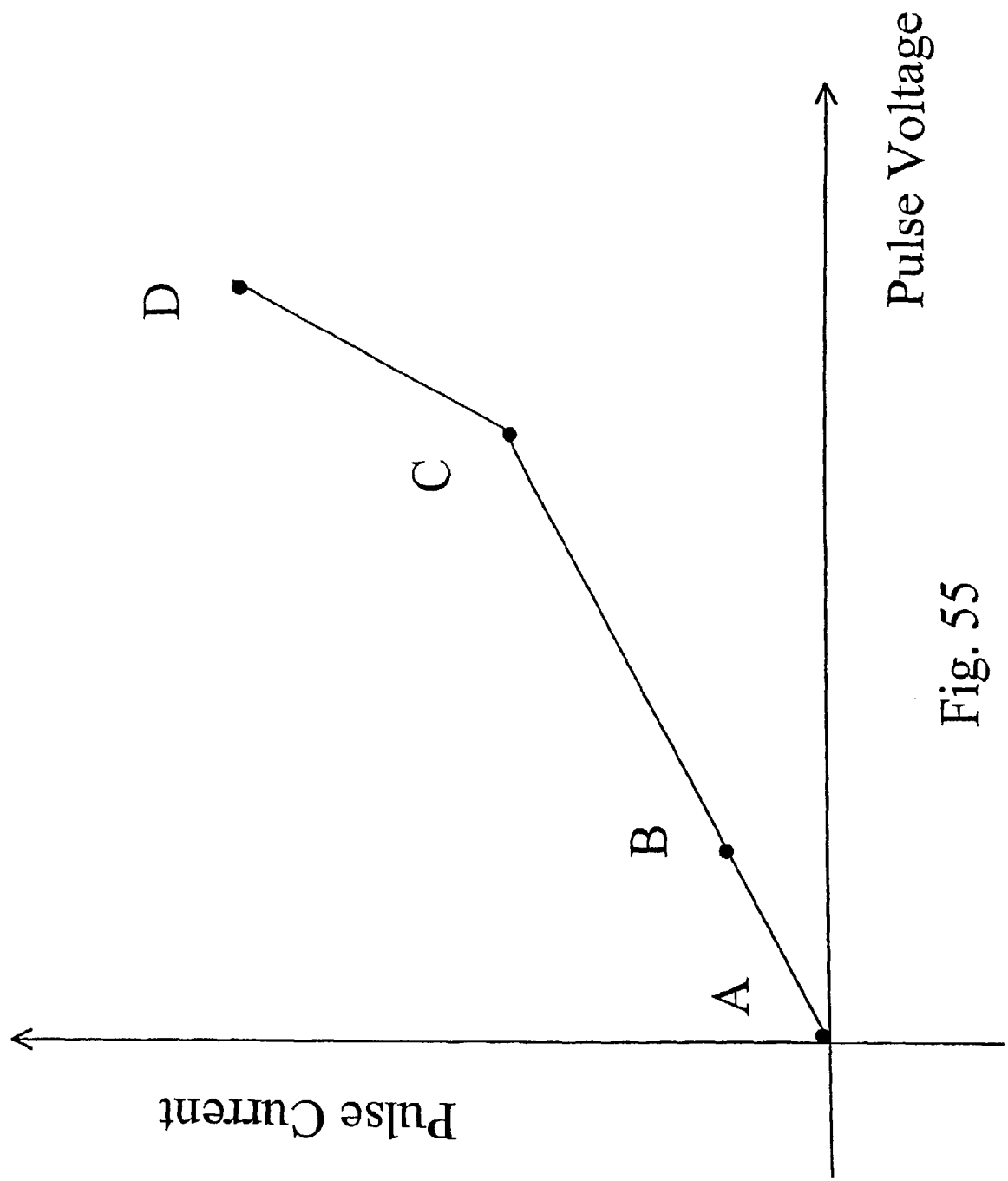
FIG. 55 is a graph depicting the relationship between current and voltage in a pulsed power supply.
Figure 56:
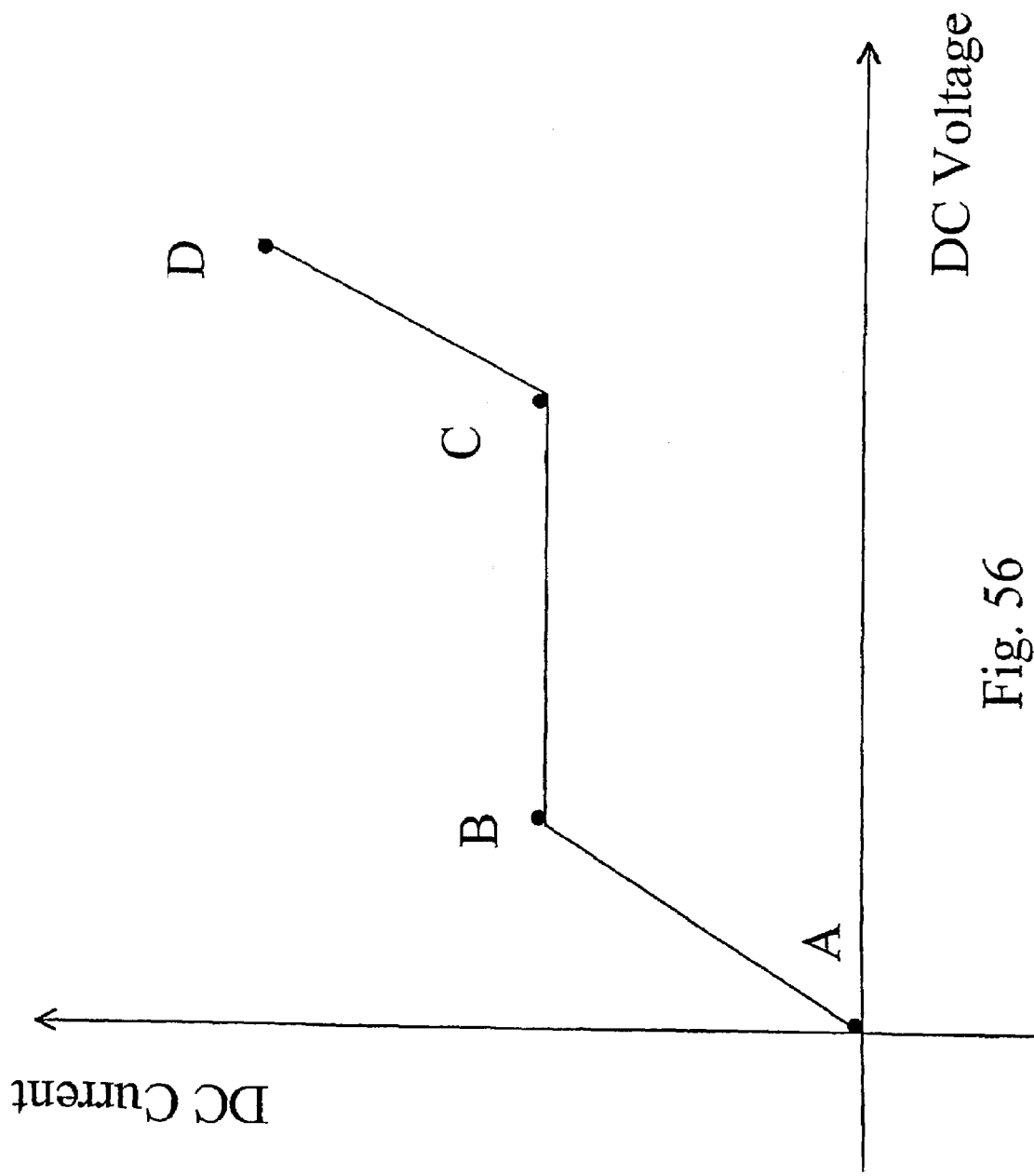
FIG. 56 is a graph depicting the relationship between current and voltage in a DC power supply.

As described above, power supplies 13, 12 and 11 can be operated in DC mode or in a variety of pulse modes. Additionally, they can be operated in constant current mode, constant voltage mode, or combination of these two modes. In FIG. 55, a graph is shown depicting the relationship between current and voltage during electropolishing using a pulsed power supply. In FIG. 56, a graph is shown depicting the relationship between current and voltage during electropolishing using a DC power supply.

In both FIGS. 55 and 56, three regions are depicted. These regions are characterized by different electropolishing rates (the rate at which the metal layer is removed) and different wafer surface profiles. In the region between points A and B (the etching region), the electropolishing rate is slower than the other two regions. In this region, a rough surface can result on the wafer, similar to the results obtained from a chemical etching process. In the region between C and D (the over-voltage polishing region), the electropolishing rate is faster than the other two regions. In this region, a rough surface can result on the wafer. In the region between points B and C (the polishing region), the electropolishing rate is faster than the etching region but slower than the over-voltage polishing region. In this region, a fine surface can result on the wafer.

Accordingly, the voltage and current of the power supply can be varied to control the electropolishing process. For example, when the metal layer to be removed is thick, the power supply can be maintained in the over-voltage polishing region to remove a greater amount of the metal layer. Once an initial layer is removed, the power supply can be maintained in the polishing region to obtain a smoother surface on the wafer. The power supply can then be maintained in the etching region to slow the rate of electropolishing. As described above, the current and voltage can be monitored to determine when to stop electropolishing (i.e., determining the end point). This end-point determination can be performed in all three regions depicted in FIGS. 55 and 56. But performing end-point detection in the etching region has the advantage that a small amount of the metal layer is removed in this region.

More particularly, when using a DC power supply in a constant voltage mode, the polishing voltage V can be controlled using the following formula:

$$V = \begin{cases} V_{polishing}, & \text{when } R < R_{02} \\ V_{monitor}, & \text{when } R > R_{01} \end{cases}$$

Where, $V_{polishing}$ is the voltage applied during normal electropolishing, such as the voltages in the polishing regions depicted in FIGS. 55 and 56. $V_{monitor}$ is the voltage applied during end-point detection, such as the voltages in the etching regions depicted in FIGS. 55 and 56. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I). $R_{01}$ is the predetermined resistance at which the applied voltage is reduced from $V_{polishing}$ to $V_{monitor}$. $R_{02}$ is the predetermined resistance at which the applied voltage is increased from $V_{monitor}$ to $V_{polishing}$.

Thus, the applied voltage can be switched between $V_{monitor}$ and $V_{polishing}$ to produce a smooth, planar, and non-recessed (i.e., recess 127 depicted in FIG. 1B is reduced or eliminated) surface on the wafer. By way of example, assume that a wafer is being electropolished. As such, $V_{polishing}$ is applied to remove the metal layer from the wafer. During this time, the electropolishing resistance R is monitored. As described above, as the metal layer is removed from the wafer, the electropolishing resistance R increases.

More particularly, as the metal layer is removed, the barrier layer underneath the metal layer becomes exposed. As described above, the barrier layer typically has a significantly greater electrical resistance than the metal layer. Consequently, as more of the barrier layer is exposed, the more the increase in electropolishing resistance R. When the electropolishing resistance R rises above the preset resistance $R_{01}$, then the applied voltage V is reduced to $V_{monitor}$. As described above, $V_{monitor}$ is sufficiently low that the electropolishing resistance R can be monitored while removing only a small amount of the metal layer from the wafer. By continuing to monitor the electropolishing resistance R, patches or sections of metal layers remaining on the wafer can be detected. More particularly, the electropolishing resistance R will decrease in these regions. If electropolishing resistance R falls below $R_{02}$, then the applied voltage V is increased to $V_{polishing}$. By adjusting $R_{01}$ and $R_{02}$, the electropolishing process can be tuned to produce a smooth, planar, and non-recessed surface on the wafer.

When using a DC power supply in a constant current mode, the polishing current I can be controlled using the following formula:

$$I = \begin{cases} I_{polishing}, \text{ when } R < R_{02} \\ I_{monitor}, \text{ when } R > R_{01} \end{cases}$$

Where, $I_{polishing}$ is the current applied during normal electropolishing, such as the currents in the polishing regions depicted in FIGS. 55 and 56. $I_{monitor}$ is the current applied during end-point detection, such as the currents in the etching regions depicted in FIGS. 55 and 56. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I). $R_{01}$ is the predetermined resistance at which the applied current is reduced from $I_{polishing}$ to $I_{monitor}$. $R_{02}$ is the predetermined resistance at which the applied current is increased from $I_{monitor}$ to $I_{polishing}$.

Thus, the applied current can be switched between $I_{monitor}$ and $I_{polishing}$ to produce a smooth, planar, and non-recessed surface on the wafer. By way of example, assume that a wafer is being electropolished. As such, $I_{polishing}$ is applied to remove the metal layer from the wafer. During this time, the electropolishing resistance R is monitored. As described above, as the metal layer is removed from the wafer, the electropolishing resistance R increases. More particularly, as the metal layer is removed, the barrier layer underneath the metal layer becomes exposed. As described above, the barrier layer typically has a significantly greater electrical resistance than the metal layer. Consequently, as more of the barrier layer is exposed, the more the increase in electropolishing resistance R. When the electropolishing resistance R rises above the preset resistance $R_{01}$, then the applied current I is reduced to $I_{monitor}$. As described above, $I_{monitor}$ is sufficiently low that the electropolishing resistance R can be monitored while removing only a small amount of the metal layer from the wafer. By continuing to monitor the electropolishing resistance R, patches or sections of metal layers remaining on the wafer can be detected. More particularly, the electropolishing resistance R will decrease in these regions. If electropolishing resistance R falls below $R_{02}$, then the applied current I is increased to $I_{polishing}$. By adjusting $R_{01}$ and $R_{02}$, the electropolishing process can be tuned to produce a smooth, planar, and non-recessed surface on the wafer.

When using a pulsed power supply in a constant voltage mode (meaning that the height of each pulse is approximately the same) with a constant duty cycle, the polishing voltage V can be controlled using the following formula:

$$V = \begin{cases} V_{polishing}, \text{ when } R < R_{02} \\ V_{monitor}, \text{ when } R > R_{01} \end{cases}$$

Where, $V_{polishing}$ is the voltage applied during normal electropolishing, such as the voltages in the polishing regions depicted in FIGS. 55 and 56. $V_{monitor}$ is the voltage applied during end-point detection, such as the voltages in the etching regions depicted in FIGS. 55 and 56. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I), where the applied current I is measured when the pulse is on or high. $R_{01}$ is the predetermined resistance at which the applied voltage is reduced from $V_{polishing}$ to $V_{monitor}$. $R_{02}$ is the predetermined resistance at which the applied voltage is increased from $V_{monitor}$ to $V_{polishing}$.

Thus, the applied voltage can be switched between $V_{monitor}$ and $V_{polishing}$ to produce a smooth, planar, and non-recessed surface on the wafer. By way of example, assume that a wafer is being electropolished. As such, $V_{polishing}$ is applied to remove the metal layer from the wafer. During this time, the electropolishing resistance R is monitored. As described above, as the metal layer is removed from the wafer, the electropolishing resistance R increases. More particularly, as the metal layer is removed, the barrier layer underneath the metal layer becomes exposed. As described above, the barrier layer typically has a significantly greater electrical resistance than the metal layer. Consequently, as more of the barrier layer is exposed, the more the increase in electropolishing resistance R. When the electropolishing resistance R rises above the preset resistance $R_{01}$, then the applied voltage V is reduced to $V_{monitor}$. As described above, $V_{monitor}$ is sufficiently low that the electropolishing resistance R can be monitored while removing only a small amount of the metal layer from the wafer. By continuing to monitor the electropolishing resistance R, patches or sections of metal layers remaining on the wafer can be detected. More particularly, the electropolishing resistance R will decrease in these regions. If electropolishing resistance R falls below $R_{02}$, then the applied voltage V is increased to $V_{polishing}$. By adjusting $R_{01}$ and $R_{02}$, the electropolishing process can be tuned to produce a smooth, planar, and non-recessed surface on the wafer.

When using a pulse power supply in a constant current mode with a constant duty cycle, the polishing current I can be controlled using the following formula:

$$I = \begin{cases} I_{polishing}, \text{ when } R < R_{02} \\ I_{monitor}, \text{ when } R > R_{01} \end{cases}$$

Where, $I_{polishing}$ is the current applied during normal electropolishing, such as the currents in the polishing regions depicted in FIGS. 55 and 56. $I_{monitor}$ is the current applied during end-point detection, such as the currents in the etching regions depicted in FIGS. 55 and 56. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I), where the applied voltage V is measured when the pulse is on or high. $R_{01}$ is the predetermined resistance at which the applied current is reduced from $I_{polishing}$ to $I_{monitor}$. $R_{02}$ is the predetermined resistance at which the applied current is increased from $I_{monitor}$ to $I_{polishing}$.

Thus, the applied current can be switched between $I_{monitor}$ and $I_{polishing}$ to produce a smooth, planar, and non-recessed surface on the wafer. By way of example, assume that a wafer is being electropolished. As such, $I_{polishing}$ is applied to remove the metal layer from the wafer. During this time, the electropolishing resistance R is monitored. As described above, as the metal layer is removed from the wafer, the electropolishing resistance R increases. More particularly, as the metal layer is removed, the barrier layer underneath the metal layer becomes exposed. As described above, the barrier layer typically has a significantly greater electrical resistance than the metal layer. Consequently, as more of the barrier layer is exposed, the more the increase in electropolishing resistance R. When the electropolishing resistance R rises above the preset resistance $R_{01}$, then the applied current I is reduced to $I_{monitor}$. As described above, $I_{monitor}$ is sufficiently low that the electropolishing resistance R can be monitored while removing only a small amount of the metal layer from the wafer. By continuing to monitor the electropolishing resistance R, patches or sections of metal layers remaining on the wafer can be detected. More particularly, the electropolishing resistance R will decrease in these regions. If electropolishing resistance R falls below $R_{02}$, then the applied current I is increased to $I_{polishing}$. By adjusting $R_{01}$ and $R_{02}$, the electropolishing process can be tuned to produce a smooth, planar, and non-recessed surface on the wafer.

When using a pulsed power supply in a constant voltage mode with variable duty cycle, the applied duty cycle D can be controlled using the following formula:

$$D = \begin{cases} D_{polishing}, & \text{when } R < R_{02} \\ D_{monitor}, & \text{when } R > R_{01} \end{cases}$$

Where $D_{polishing}$ is the duty cycle used during the electropolishing process. In one embodiment, $D_{polishing}$ is in the range between about 10 percent to about 100 percent, and preferably about 80 percent. $D_{monitor}$ is the duty cycle used during end-point detection. In one embodiment, $D_{monitor}$ is in the range between about 0.1 percent to about 10 percent, and preferably about 1 percent. The frequency of the pulse can be in the range of about 1 Herz to about 100 kiloHerz, and preferably about 100 Herz. The value of R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I), where the applied current I is measured when the pulse is on or high. $R_{01}$ is the predetermined resistance at which the applied duty cycle D is reduced from $D_{polishing}$ to $D_{monitor}$. $R_{02}$ is the predetermined resistance at which the applied duty cycle D is increased from $D_{monitor}$ to $D_{polishing}$.

Thus, the applied duty cycle D can be switched between $D_{monitor}$ and $D_{polishing}$ to produce a smooth, planar, and non-recessed surface on the wafer. By way of example, assume that a wafer is being electropolished. As such, $D_{polishing}$ is applied to remove the metal layer from the wafer. During this time, the electropolishing resistance R is monitored. As described above, as the metal layer is removed from the wafer, the electropolishing resistance R increases. More particularly, as the metal layer is removed, the barrier layer underneath the metal layer becomes exposed. As described above, the barrier layer typically has a significantly greater electrical resistance than the metal layer. Consequently, as more of the barrier layer is exposed, the more the increase in electropolishing resistance R. When the electropolishing resistance R rises above the preset resistance $R_{01}$, then the applied duty cycle D is reduced to $D_{monitor}$. As described above, $D_{monitor}$ is sufficiently low that the electropolishing resistance R can be monitored while removing only a small amount of the metal layer from the wafer. By continuing to monitor the electropolishing resistance R, patches or sections of metal layers remaining on the wafer can be detected. More particularly, the electropolishing resistance R will decrease in these regions. If electropolishing resistance R falls below $R_{02}$, then the applied duty cycle D is increased to $D_{polishing}$. By adjusting $R_{01}$ and $R_{02}$, the electropolishing process can be tuned to produce a smooth, planar, and non-recessed surface on the wafer.

When using a pulsed power supply in a constant current mode with variable duty cycle, the applied duty cycle D can be controlled using the following formula:

$$D = \begin{cases} D_{polishing}, & \text{when } R < R_{02} \\ D_{monitor}, & \text{when } R > R_{01} \end{cases}$$

Where $D_{polishing}$ is the duty cycle used during the electropolishing process. In one embodiment, $D_{polishing}$ is in the range between about 10 percent to about 100 percent, and preferably about 80 percent. $D_{monitor}$ is the duty cycle used during end-point detection. In one embodiment, $D_{monitor}$ is in the range between about 0.1 percent to about 10 percent, and preferably about 1 percent. The frequency of the pulse can be in the range of about 1 Herz to about 100 kiloHerz, and preferably about 100 Herz. The value of R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I), where the applied voltage V is measured when the pulse is on or high. $R_{01}$ is the predetermined resistance at which the applied duty cycle D is reduced from $D_{polishing}$ to $D_{monitor}$. $R_{02}$ is the predetermined resistance at which the applied duty cycle D is increased from $D_{monitor}$ to $D_{polishing}$.

Thus, the applied duty cycle D can be switched between $D_{monitor}$ and $D_{polishing}$ to produce a smooth, planar, and non-recessed surface on the wafer. By way of example, assume that a wafer is being electropolished. As such, $D_{polishing}$ is applied to remove the metal layer from the wafer. During this time, the electropolishing resistance R is monitored. As described above, as the metal layer is removed from the wafer, the electropolishing resistance R increases. When the electropolishing resistance R rises above the preset resistance $R_{01}$, then the applied duty cycle D is reduced to $D_{monitor}$. As described above, $D_{monitor}$ is sufficiently low that the electropolishing resistance R can be monitored while removing only a small amount of the metal layer from the wafer. By continuing to monitor the electropolishing resistance R, patches or sections of metal layers remaining on the wafer can be detected. More particularly, the electropolishing resistance R will decrease in these regions. If electropolishing resistance R falls below $R_{02}$, then the applied duty cycle D is increased to $D_{polishing}$. By adjusting $R_{01}$ and $R_{02}$, the electropolishing process can be tuned to produce a smooth, planar, and non-recessed surface on the wafer.

In the description above, the electropolishing voltage, current, or duty cycle have been described as being varied between two discrete levels (i.e., a polishing and a monitoring level). It should be recognized, however, that the electropolishing voltage, current, or duty cycle can be varied adaptively within a continuum.

More particularly, when using a DC power supply in a constant voltage mode, the polishing voltage V can be controlled using the following formula:

$$V = V_{polishing} - \left\{\frac{R - R_{\min}}{R_{\max} - R_{\min}}\right\}^N (V_{polishing} - V_{monitor})$$

Where, $V_{polishing}$ is the voltage applied during normal electropolishing, such as the voltages in the polishing regions depicted in FIGS. 55 and 56. $V_{monitor}$ is the voltage applied during end-point detection, such as the voltages in the etching regions depicted in FIGS. 55 and 56. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I). $R_{max}$ is the predetermined resistance at which the metal layer has been removed from the wafer surface, such as depicted in FIG. 1B. $R_{min}$ is the predetermined resistance at which the metal layer cover the wafer surface, such as depicted in FIG. 1A. N is a scaling factor that can be determined experimentally to tune the electropolishing process. As such, it can be any number, such as integer, rational and irrational fraction, and the like.

Thus, as the electropolishing resistance R approaches $R_{max}$, the applied voltage V approaches $V_{monitor}$. As the electropolishing resistance R approaches $R_{min}$, the applied voltage V approaches $V_{polishing}$. In this manner, the applied voltage V is adaptively controlled based on the electropolishing resistance R.

When using a DC power supply in a constant current mode, the polishing current I can be controlled using the following formula:

$$I = I_{polishing} - \left\{\frac{R - R_{\min}}{R_{\max} - R_{\min}}\right\}^N (I_{polishing} - I_{monitor})$$

Where, $I_{polishing}$ is the current applied during normal electropolishing, such as the currents in the polishing regions depicted in FIGS. 55 and 56. $I_{monitor}$ is the current applied during end-point detection, such as the currents in the etching regions depicted in FIGS. 55 and 56. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I). $R_{max}$ is the predetermined resistance at which the metal layer has been removed from the wafer surface, such as depicted in FIG. 1B. $R_{min}$ is the predetermined resistance at which the metal layer cover the wafer surface, such as depicted in FIG. 1A. N is a scaling factor that can be determined experimentally to tune the electropolishing process. As such, it can be any number, such as integer, rational and irrational fraction, and the like.

Thus, as the electropolishing resistance R approaches $R_{max}$, the applied current I approaches $I_{monitor}$. As the electropolishing resistance R approaches $R_{min}$, the applied current I approaches $I_{polishing}$. In this manner, the applied current I is adaptively controlled based on the electropolishing resistance R.

When using a pulsed power supply in a constant voltage mode with a constant duty cycle, the polishing voltage V can be controlled using the following formula:

$$V = V_{polishing} - \left\{\frac{R - R_{\min}}{R_{\max} - R_{\min}}\right\}^N (V_{polishing} - V_{monitor})$$

Where, $V_{polishing}$ is the voltage applied during normal electropolishing, such as the voltages in the polishing regions depicted in FIGS. 55 and 56. $V_{monitor}$ is the voltage applied during end-point detection, such as the voltages in the etching regions depicted in FIGS. 55 and 56. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I), where the applied current I is measured when the pulse is on or high. $R_{max}$ is the predetermined resistance at which the metal layer has been removed from the wafer surface, such as depicted in FIG. 1B. $R_{min}$ is the predetermined resistance at which the metal layer cover the wafer surface, such as depicted in FIG. 1A. N is a scaling factor that can be determined experimentally to tune the electropolishing process. As such, it can be any number, such as integer, rational and irrational fraction, and the like.

Thus, as the electropolishing resistance R approaches $R_{max}$, the applied voltage V approaches $V_{monitor}$. As the electropolishing resistance R approaches $R_{min}$, the applied voltage V approaches $V_{polishing}$. In this manner, the applied voltage V is adaptively controlled based on the electropolishing resistance R.

When using a pulsed power supply in a constant current mode with a constant duty cycle, the polishing current I can be controlled using the following formula:

$$I = I_{polishing} - \left\{\frac{R - R_{\min}}{R_{\max} - R_{\min}}\right\}^N (I_{polishing} - I_{monitor})$$

Where, $I_{polishing}$ is the current applied during normal electropolishing, such as the currents in the polishing regions depicted in FIGS. 55 and 56. $I_{monitor}$ is the current applied during end-point detection, such as the currents in the etching regions depicted in FIGS. 55 and 56. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I), where the applied voltage V is measured when the pulse is on or high. $R_{max}$ is the predetermined resistance at which the metal layer has been removed from the wafer surface, such as depicted in FIG. 1B. $R_{min}$ is the predetermined resistance at which the metal layer cover the wafer surface, such as depicted in FIG. 1A. N is a scaling factor that can be determined experimentally to tune the electropolishing process. As such, it can be any number, such as integer, rational and irrational fraction, and the like.

Thus, as the electropolishing resistance R approaches $R_{max}$, the applied current I approaches $I_{monitor}$. As the electropolishing resistance R approaches $R_{min}$, the applied current I approaches $I_{polishing}$. In this manner, the applied current I is adaptively controlled based on the electropolishing resistance R.

When using a pulsed power supply in a constant voltage mode with variable duty cycle, the applied duty cycle D can be controlled using the following formula:

$$D = D_{polishing} - \left\{ \frac{R - R_{min}}{R_{max} - R_{min}} \right\}^N (D_{polishing} - D_{monitor})$$

Where $D_{polishing}$ is the duty cycle used during the electropolishing process. In one embodiment, $D_{polishing}$ is in the range between about 10 percent to about 100 percent, and preferably about 80 percent. $D_{monitor}$ is the duty cycle used during end-point detection. In one embodiment, $D_{monitor}$ is in the range between about 0.1 percent to about 10 percent, and preferably about 1 percent. The frequency of the pulse can be in the range of about 1 Herz to about 100 kiloHerz, and preferably about 100 Herz. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I), where the applied current I is measured when the pulse is on or high. $R_{max}$ is the predetermined resistance at which the metal layer has been removed from the wafer surface, such as depicted in FIG. 1B. $R_{min}$ is the predetermined resistance at which the metal layer cover the wafer surface, such as depicted in FIG. 1A. N is a scaling factor that can be determined experimentally to tune the electropolishing process. As such, it can be any number, such as integer, rational and irrational fraction, and the like.

Thus, as the electropolishing resistance R approaches $R_{max}$, the applied duty cycle D approaches $D_{monitor}$. As the electropolishing resistance R approaches $R_{min}$, the applied duty cycle D approaches $D_{polishing}$. In this manner, the applied duty cycle D is adaptively controlled based on the electropolishing resistance R.

When using a pulsed power supply in a constant current mode with variable duty cycle, the applied duty cycle D can be controlled using the following formula:

$$D = D_{polishing} - \left\{ \frac{R - R_{min}}{R_{max} - R_{min}} \right\}^N (D_{polishing} - D_{monitor})$$

Where $D_{polishing}$ is the duty cycle used during the electropolishing process. In one embodiment, $D_{polishing}$ is in the range between about 10 percent to about 100 percent, and preferably about 80 percent. $D_{monitor}$ is the duty cycle used during end-point detection. In one embodiment, $D_{monitor}$ is in the range between about 0.1 percent to about 10 percent, and preferably about 1 percent. The frequency of the pulse can be in the range of about 1 Herz to about 100 kiloHerz, and preferably about 100 Herz. R is the electrical resistance monitored during end-point detection. As described above, the electropolishing resistance R can be determined by monitoring the applied voltage V and current I. More particularly, the electropolishing resistance R can be determined by dividing the applied voltage by the applied current (i.e., V/I), where the applied voltage V is measured when the pulse is on or high. $R_{max}$ is the predetermined resistance at which the metal layer has been removed from the wafer surface, such as depicted in FIG. 1B. $R_{min}$ is the predetermined resistance at which the metal layer cover the wafer surface, such as depicted in FIG. 1A. N is a scaling factor that can be determined experimentally to tune the electropolishing process. As such, it can be any number, such as integer, rational and irrational fraction, and the like.

Thus, as the electropolishing resistance R approaches $R_{max}$, the applied duty cycle D approaches $D_{monitor}$. As the electropolishing resistance R approaches $R_{min}$, the applied duty cycle D approaches $D_{polishing}$. In this manner, the applied duty cycle D is adaptively controlled based on the electropolishing resistance R.

In one exemplary embodiment, where the electrolyte used for the electropolishing process is 85% (wt.) H2PO4, $V_{polishing}$ can be in the range of about 0.5 volts to about 3 volts. $V_{monitor}$ can be in the range of about 0.1 volts to about 0.5 volts. $I_{polishing}$ can be in the range of about 5 mA/cm$^2$ to about 50 mA/cm$^2$. $I_{monitor}$ can be in the range of about 0.01 mA/cm$^2$ to about 5 mA/cm$^2$. For pulsed power supplies, the peak-to-peak voltage can be about 1 volt and the peak-to-peak current density can be about 30 mA/cm$^2$. It should be recognized, however, that these values are only exemplary and that they can vary depending on the particular application.

As described above, the appropriate electropolishing time period can be determined by measuring changes in the electropolishing resistance R. More particularly, during electropolishing where electrical power is applied through an electrode in contact with the edges of the wafer, the electropolishing resistance R can be expressed as follows:

$$R = R_{interface} + \frac{R_{ML} \times R_{barrier}}{R_{ML} + R_{barrier}} + R_{contact} + R_{cathode} \quad (1)$$

$$R = U / I$$

Where, R, U, and I are the electropolishing resistance, voltage, and current, respectively. $R_{interface}$ is the resistance between the interface of the wafer and the electrolyte. $R_{ML}$ is the resistance of the metal film from the edge of the wafer in contact with the electrode (i.e., the electrode that provides the electrical charge to the wafer) to the area of the wafer in contact with the electrolyte. $R_{barrier}$ is the resistance of the barrier layer from the edge of the wafer in contact with the electrode to the area of the wafer in contact with the electrolyte. $R_{contact}$ is the resistance where the wafer contacts the electrode. $R_{cathode}$ is the resistance between the cathode and the electrolyte.

Figure 57:
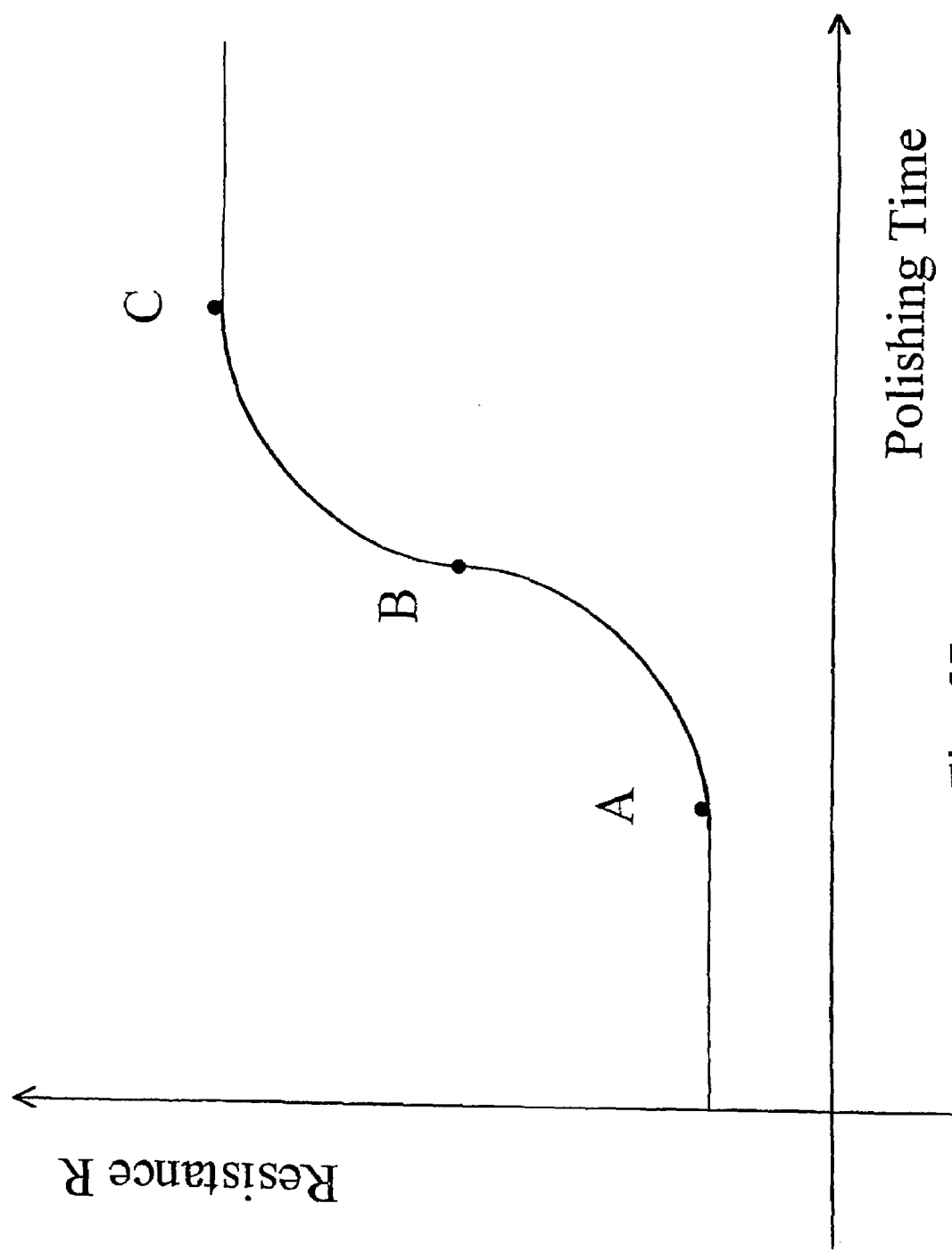
FIG. 57 is a graph depicting the relationship between resistance and polishing time.

With reference to FIG. 57, a graph is shown depicting changes in electropolishing resistance, R over time. The electropolishing process begins at about point A when the metal layer begins to be removed from the wafer surface, such as depicted in FIG. 1A. At about point C, the metal layer as be removed from the wafer surface, such as depicted in FIG. 1B. Thus, the electropolishing process is performed between endpoints A and B. The amount and profile of the metal layer remaining on the wafer surface being determined by where along the curve between these two endpoints the electropolishing process is stopped. It should be recognized, however, that the shape of the graph depicted in FIG. 57 can vary depending on the particular application.

With reference to equation (1) above, during the electropolishing process, changes in $R_{ML}$, $R_{barrier}$, $R_{contact}$, and $R_{cathode}$ can be assumed to be relatively constant compared to the changes in $R_{interface}$. Thus, when the derivative of equation (1) is taken with respect to time, the following results:

$$d(U/I)/dt = dR/dt = dR_{interface}/dt \qquad (2)$$

Figure 8:
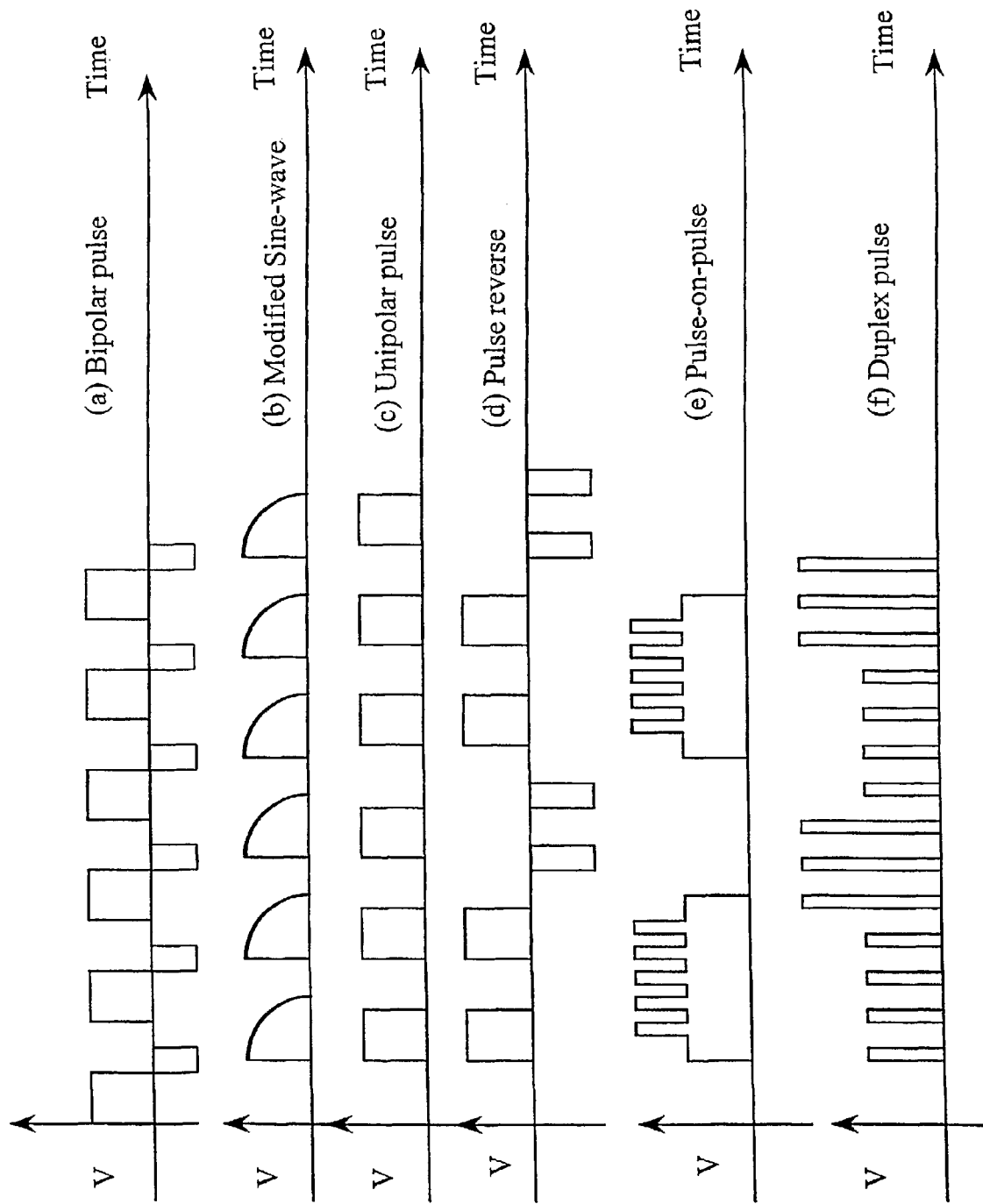
FIG. 8 is a plot of various waveforms, which may be used in conjunction with the electropolishing apparatus shown in FIG. 7A.
Figure 9:
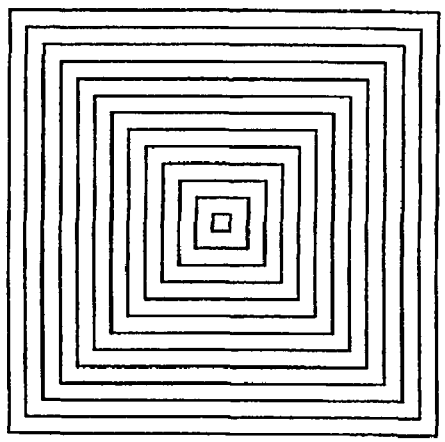
FIG. 9A–9D are top views of a portion of alternative embodiments of electropolishing apparatus in accordance with various aspects of the present invention.
Figure 9:
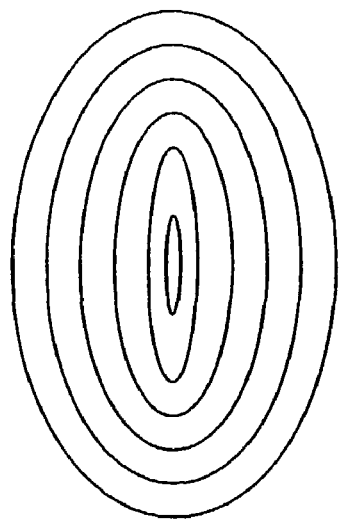
Figure 9:
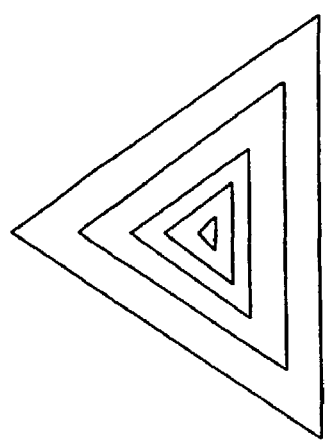
Figure 9:
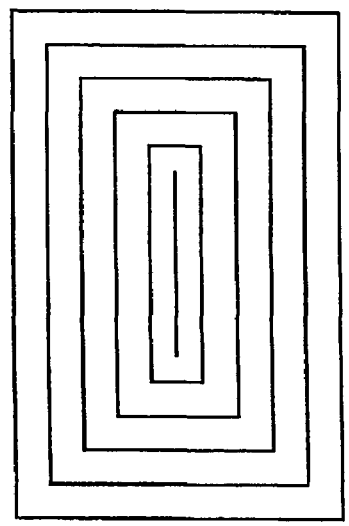

Thus equation (2) would represent tangent lines along the curve depicted FIG. 8 But as can be seen in FIG. 57, an inflection point exists at point B. Thus, based solely on equation (2), a point lying between points A and B can not be distinguished from a point lying between points B and C. But a second derivative of equation (1) can be taken to distinguish between points lying between points A and B from points lying between points B and C. In this manner, the amount and profile of the metal layer remaining on the wafer surface can be determined by stopping the electropolishing process at the desired endpoint along the curve depicted in FIG. 57.

For example, the electropolishing process can be stopped between points A and B by using the following formula to determine the endpoint:

$$\begin{cases} dR/dt = C_0, \\ d^2R/dt^2 > 0 \end{cases} \qquad (3)$$

Where, $C_0$ is a predetermined constant at which the electropolishing process is to be stopped.

The electropolishing process can be stopped at point B by using the following formula to determine the endpoint:

$$\begin{cases} dR/dt = C_{maximum}, \\ d^2R/dt^2 = 0 \end{cases} \qquad (4)$$

Where, $C_{maximum}$ is a predetermined constant at which the electropolishing process is to be stopped.

The electropolishing process can be stopped between points B and C by using the following formula to determine the endpoint:

$$\begin{cases} dR/dt = C_1, \\ d^2R/dt^2 < 0 \end{cases} \qquad (5)$$

Where, $C_1$ is a predetermined constant at which the electropolishing process is to be stopped.

The electropolishing process can be stopped entirely (for example, by turning off the power supply). Alternatively, as described above, the electropolishing rate can be reduced to continue to monitor the electropolishing resistance R. If the electropolishing resistance R sufficiently decreases (for example, as in unpolished patches or areas of the wafer), then the electropolishing rate can be increased.

The values of $C_0$, $C_{maximum}$, and $C_1$ can be determined experimentally. For example, wafers can be processed at various $C_0$ settings to determine the value that produces the desired wafer surface profile. Once this value is determined, they can be used to process additional wafers.

In one exemplary embodiment, $C_0$ can range between about 0.01 ohms/second to about 100 ohms/second. $C_{maximum}$ can range between about 10 ohms/second to about 100 ohms/second. $C_1$ can range between about 0.01 ohms/second to about 100 ohms/second. It should be recognized, however, that these values can vary depending on the particular application.

As described above, power supply 200 can be operated in DC mode or in a variety of pulse modes. Additionally, it can be operated in constant current mode, constant voltage mode, or combination of these modes. Further, when a pulsed power supply is used, the duty cycle can be constant or varied.

When using a DC or a pulsed power supply in a constant voltage mode, the electropolishing endpoint can be determined using the following formula:

$$dR/dt = U(-1/I^2)(dI/dt)$$

$$d^2R/dt^2 = U(2/I^3)(dI/dt)^2 + U(-1/I^2)(d^2I/dt^2) \qquad (6)$$

Where, U is the applied voltage and I is the applied current. When a pulsed power supply is used, the applied current I is measured when the pulse is on or high.

When using a DC or a pulsed power supply in a constant current mode, the electropolishing endpoint can be determined using the following formula:

$$dR/dt = (dU/dt)/I$$

$$d^2R/dt^2 = (d^2U/dt^2)/I \qquad (7)$$

Where, U is the applied voltage and I is the applied current. When a pulsed power supply is used, the applied voltage U is measured when the pulse is on or high.

Thus, when the values for $dR/dt$ and $d^2R/dt^2$ using formulas (6) or (7) meet the conditions setforth in equations (3), (4), or (5), the electropolishing process is stopped. The electropolishing process can be stopped entirely (for example, by turning off the power supply). Alternatively, as described above, the electropolishing rate can be reduced to continue to monitor the electropolishing resistance R. If the electropolishing resistance R sufficiently decreases (for example, as in unpolished patches or areas of the wafer), then the electropolishing rate can be increased. Additionally, when a pulsed power supply is used, the duty cycle can be altered to alter the electropolishing rate.

In the description above, the electropolishing resistance R was described as increasing when the metal layer is removed to expose the barrier layer. As alluded to earlier, in some applications, the barrier layer can be omitted from the wafer. When the wafer does not include a barrier layer, the dielectric layer is exposed when the metal layer is removed. Dielectric layers typically have a greater electrical resistance characteristic than the metal layer. Accordingly, the electropolishing resistance R will increase when the metal layer is removed to expose the dielectric layer.

Additionally, it should be appreciated, however, that various techniques can be used to determine the appropriate electropolishing time period. For example, as will be described in greater detail below in conjunction with an alternative embodiment, sensors can be used to measure the thickness of metal layer 121 (FIG. 1A) on wafer 31 (FIG. 1A and FIG. 7B).

Figure 53:
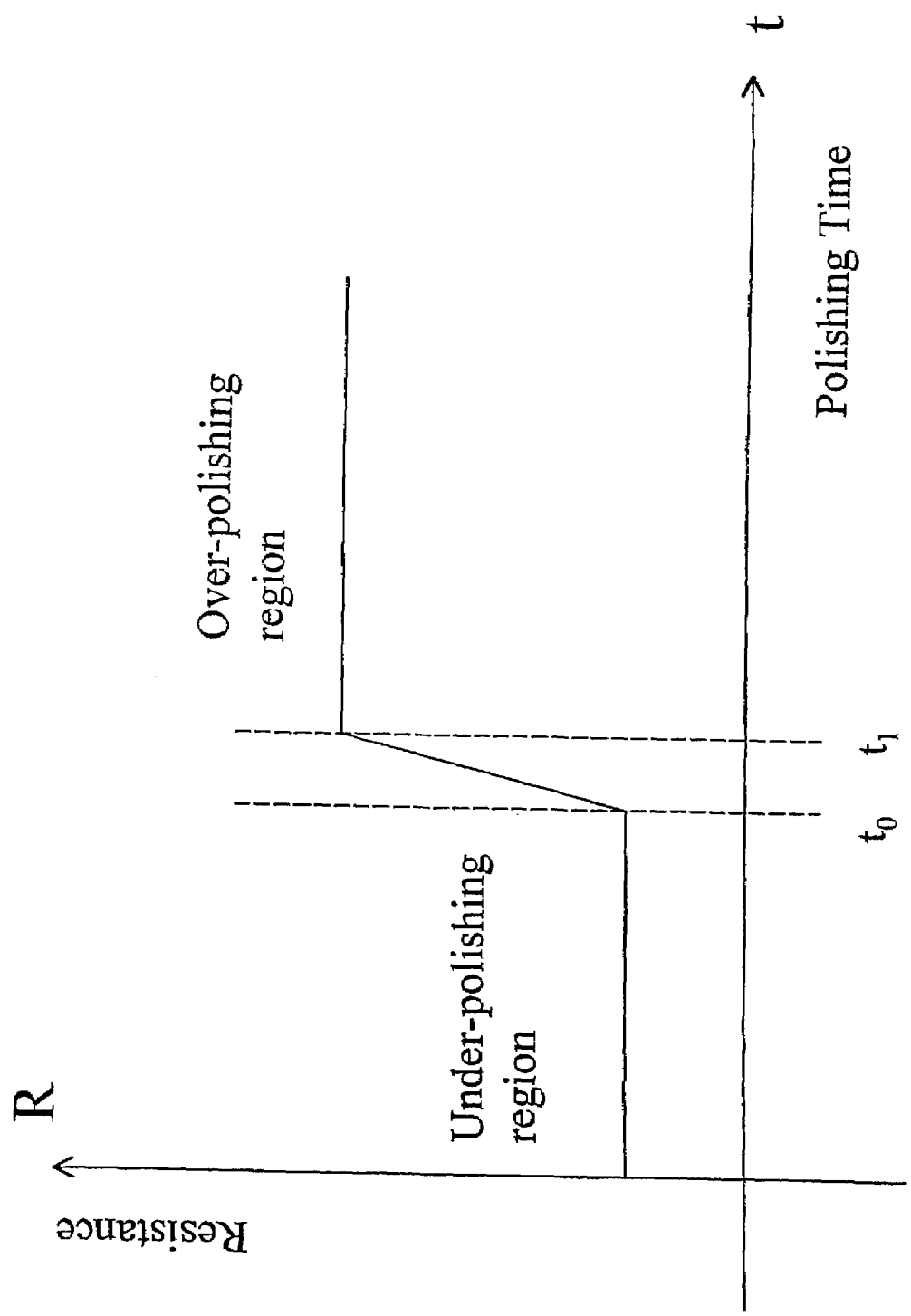
FIG. 53 is a waveform depicting a portion of a wafer processing operation in accordance with various aspects of the present invention.

Alternatively, with reference to FIG. 53, an end-point detector system can be suitably employed to determine the appropriate electropolishing time period. In accordance with an exemplary embodiment, the measured electrical resistance from edge to edge of wafer 31 (FIG. 1A) is monitored using appropriate measurement tools. As depicted in FIG. 53, as the surface area of metal layer 121 (FIG. 1A) on wafer 31 (FIG. 1A) is reduced due to electropolishing, the electrical resistance measured from edge to edge of wafer 31 (FIG. 1A) increases. Accordingly, the appropriate time at which to stop electropolishing is preferably around the time at which the measured electrical resistance from edge to edge of wafer 31 changes rapidly. With specific reference to FIG. 53, this would be at or near t0 and t1. The region beyond t1 is called the over-polishing region, meaning that wafer 31 (FIG. 1B) has been polished such that the level of metal layer 121 (FIG. 1B) within trench 125 (FIG. 1B) extends below the level of barrier layer 122 (FIG. 1B). The region before t0 is called the under-polishing region, meaning that metal layer 121 (FIG. 1A) has not been entirely removed from dielectric layer 122 (FIG. 1A) on gates 126 (FIG. 1A). The resistance signal can be sent to a computer, which can then send the appropriate signal to stop the polishing process.

With reference to FIGS. 7A and 7B, using the exemplary embodiment of the present invention described above, the following process steps can be employed to selectively electropolish portions of wafer 31:

Step 1: Turn on power supply 13;

Step 2: Turn on LMFC 23 only, such that electrolyte 34 only contacts the portion of wafer 31 above cathode 1 to electropolish metal layer 121 (FIG. 1A) above cathode 1;

Step 3: Turn off power supply 13 and turn off LMFC 23, when the thickness of metal layer 121 (FIG. 1A) reaches a set value or thickness;

Step 4: Repeat steps 1 to 3 for cathode 2, using LMFC 22 and power supply 12; and Step 5: Repeat steps 1 to 3 for cathode 3, using LMFC 21 and power supply 11.

In addition to the above described electropolishing sequence of cathode 1, then cathode 2, and then cathode 3, the electropolishing sequence can also be as follows:

1) cathode 3, then cathode 2, and then cathode 1;
2) cathode 2, then cathode 1, and then cathode 3;
3) cathode 2, then cathode 3, and then cathode 1;
4) cathode 3, then cathode 1, and then cathode 2; or
5) cathode 1, then cathode 3, and then cathode 2.

By selectively polishing portions of wafer 31, metal layer 121 (FIG. 1A) can be electropolished more uniformly from wafer 31, even when wafer 31 is a large diameter wafer. For example, the present invention can be used with a wafer 31 having a diameter of 300 millimeters or greater. In the present context, a uniform electropolish refers to electropolishing wafer 31 such that metal layer 121 is removed to an approximately even thickness across substantially all of the surface area of wafer 31. In general, in conventional electropolishing systems, the greater the diameter of wafer 31, the greater the nonuniformity of the electropolish. For example, the areas of wafer 31 near the center can be overpolished while the areas of wafer 31 near the edges of wafer 31 can be underpolished. This can be due in part to the varying charge densities applied across wafer 31 by conventional electropolishing systems.

In addition to selectively polishing portions of wafer 31, using the exemplary embodiment of the present invention described above, the following process steps can be employed to electropolish the entire surface of wafer 31 substantially at one time:

Step 1: Turn on all power supplies 11, 12 and 13. As described above, the current of each power supply 11, 12 and 13 can be suitably set proportionate to the surface area of wafer 31 covered by the corresponding cathode;

Step 2: Turn on LMFCs 21, 22 and 23. As also described above, the flow rate of electrolyte 34 from each LMFC 21, 22 and 23 can be suitably set proportionate to the surface area of wafer 31 covered by the corresponding cathode; and Step 3: Turn off power supplies 11, 12 and 13 at the same time when the thickness uniformity of metal layer 121 (FIG. 1A) reaches a set value or thickness. Also, power supplies 11, 12 and 13 can be turned off at different times to adjust the thickness uniformity of metal layer 121 (FIG. 1A).

In this manner, the rate of removal of metal layer 121 from different portions of wafer 31 can be suitably controlled to more uniformly electropolish metal layer 121 on wafer 31.

Having thus described the structure and operation of an exemplary embodiment, an application of the present invention in the context of a damascene process will be described below. It should be recognized, however, that such description is not intended as a limitation on the use or applicability of the present invention, but is instead provided to enable a full and complete description of the present exemplary embodiment.

With reference again to FIG. 1A, in general, when metal layer 121 is suitably formed on wafer 31, recesses 127 can form over trenches 125. As depicted in FIG. 1A, even after electropolishing, recesses 127 can remain in the metal layer 121 formed within trenches 125. This can be due in part to the original uneven topology of metal layer 121 depicted in FIG. 1A. Additionally, overpolishing can contribute to the formation of recesses 127 within trenches 125. The existence of recesses 127 can adversely affect the performance of the semiconductor device. Accordingly, recesses 127 having a recess depth 128 greater than about 500 Angstroms are typically considered undesirable. It should be recognized, however, that the amount of recess depth 128, which is acceptable, can vary depending on the particular application. For example, for a high precision semiconductor device, a recess depth 128 of no more than a few Angstroms can be acceptable. However, for a low cost semiconductor device, a recess depth 128 greater than 500 Angstroms can be acceptable.

In accordance with one aspect of the present invention, the electropolishing time period can be suitably controlled to prevent the formation of recesses 127 with recess depth 128 of greater than about 500 Angstroms. However, this can increase processing cost and reduce processing throughput. Accordingly, in accordance with another aspect of the present invention, an electropolishing and electroplating process can be suitably combined with a chemical mechanical polishing (CMP) process to remove recesses 127. In general, CMP processes can suitably produce a planar surface on wafer 31 with recesses 127 having a recess depth 128 between about 100 and about 500 Angstroms.

With reference to FIG. 1B, as described above, metal layer 121 is suitably electropolished from barrier layer 122 formed on mesas 126. With reference to FIG. 1C, wafer 31 then undergoes a replating process to replate a sufficient amount of metal to fix recesses 127 (FIG. 1B), meaning that metal is plated onto metal layer 121, which is formed in trenches 125 (FIG. 1B), without replating over barrier layer 122 on mesas 126. With reference to FIG. 7B, as alluded to earlier, wafer 31 can be suitably replated by reversing the polarity of power supplies 11, 12 and 13. In this manner, as also described in greater detail below, wafer 31 can be suitably replated without necessarily having to transfer wafer 31 to another station.

Next, in accordance with another aspect of the present invention, the metal layer 123 within trenches 125, which has been replated, is suitably planarized, and the barrier layer 122 is suitably removed. In the present exemplary embodiment, wafer 31 is preferably planarized using a CMP process. By having removed the majority of metal layer 123 using the above described electropolishing process, only a small amount of metal layer 123 now needs to be removed using CMP, which reduces overall processing time and cost.

Figure 3:
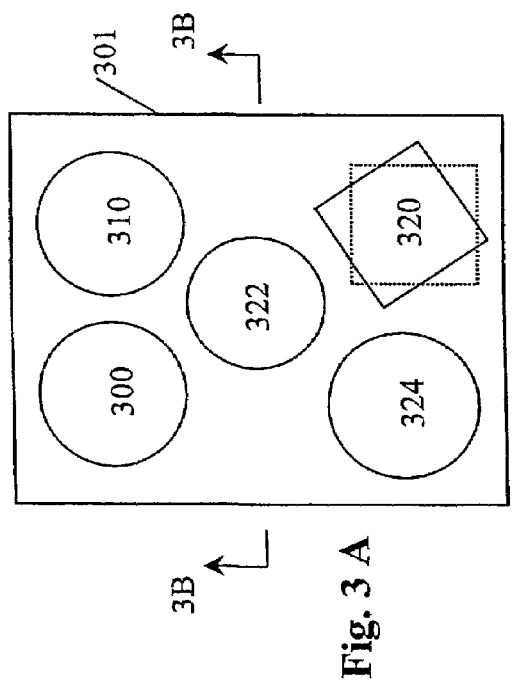
FIGS. 3A–3C are schematic top, cross section, and side views, respectively, of a wafer processing tool in accordance with various aspects of the present invention.
Figure 3:
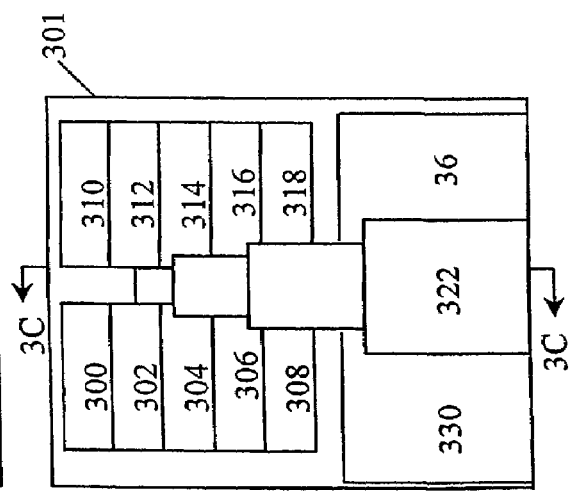
Figure 3:
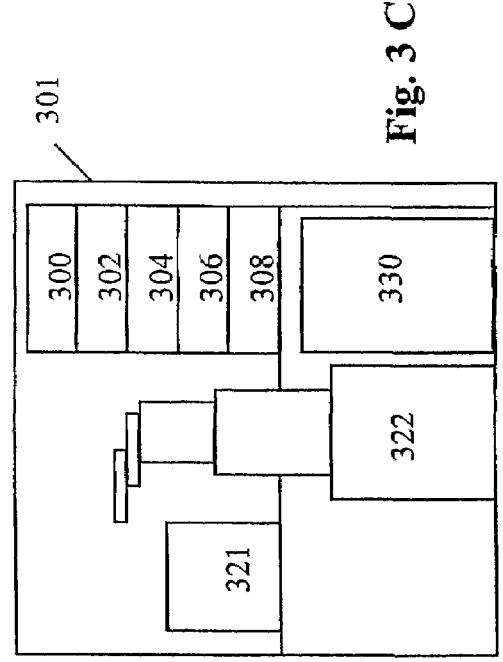
Figure 4A:
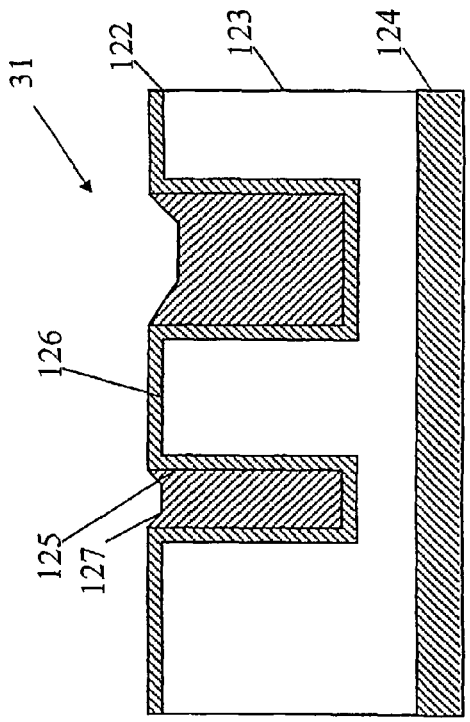
FIGS. 4A–4D are cross-section views of another wafer in accordance with various aspects of the present invention.
Figure 4B:
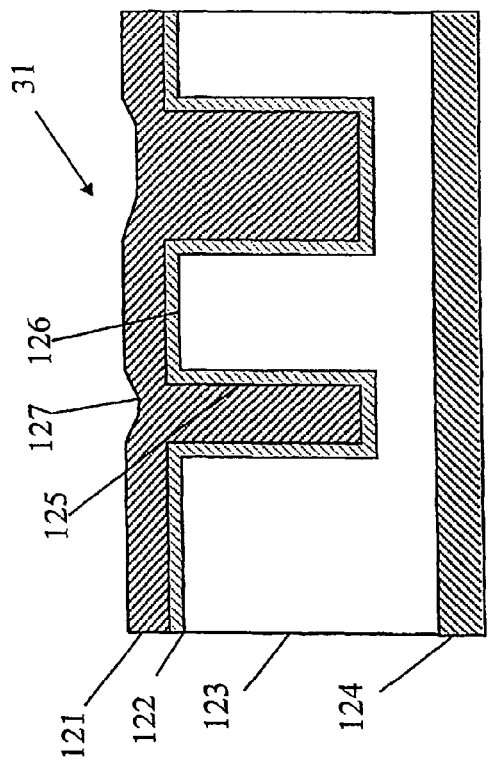
Figure 4C:
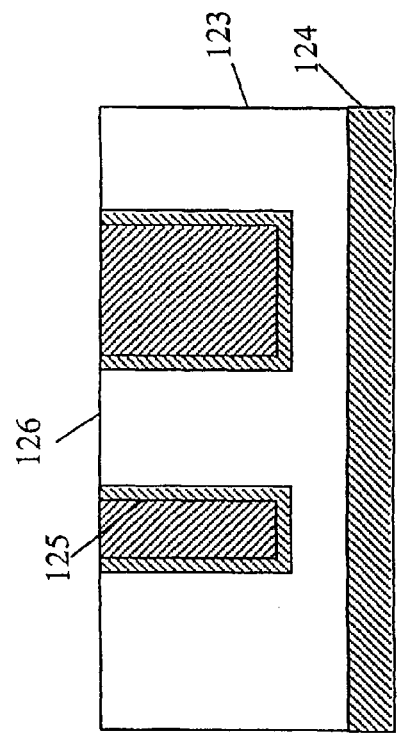
Figure 4D:
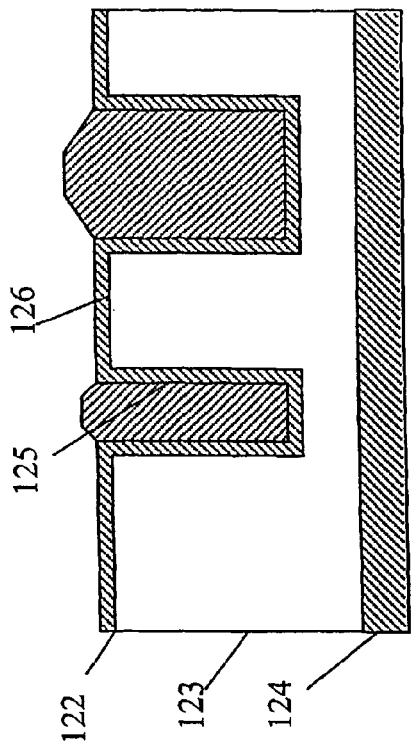

With reference now to FIGS. 3A to 3C, a wafer-processing tool 301, according to various aspects of the present invention, is shown. In an exemplary embodiment of the present invention, wafer processing tool 301 preferably includes electroplating/electropolishing cells 300, 302, 304, 306 and 308, cleaning cells 310, 312, 314, 316 and 318, a CMP cell 324, wafer cassette 320, and a robot 322.

Robot 322 begins by transferring a wafer from wafer cassette 320 to any one of electroplating/electropolishing cells 300, 302, 304, 306, or 308. The wafer is suitably electroplated with a metal layer 121 (FIG. 1A). Next, the wafer is suitably electropolished to remove metal layer 121 from barrier layer 122 (FIG. 1B). Next, the wafer is suitably replated to fix recesses 127 (FIGS. 1B and 1C). Robot 322 then transfers the wafer to any one of cleaning cells 310, 312, 314, 316, or 318. After the wafer is cleaned, robot 322 transfers the wafer to CMP cell 324, where the metal layer 121 is planarized and barrier layer 122 is removed (FIG. 1D). Robot 322 then transfers the wafer to any one of cleaning cells 300, 302, 304, 306, or 308 for the wafer to be cleaned and dried. Finally, robot 322 transfers the wafer to wafer cassette 320 and begins again with another wafer.

It should be recognized, however, that various modifications can be made to the configuration of wafer processing tool 301 without deviating from the spirit and/or scope of the present invention. For example, the initial electroplating and electropolishing of the wafer can be performed in separate cells. In general, different electrolytes are used for electroplating and electropolishing. For electroplating, a sulfuric acid is typically used. For electropolishing, a phosphoric acid is typically used. Although sulfuric acid can be used for electropolishing, the resulting surface can be non-uniform. Similarly, although phosphoric acid can be used for electroplating, the resulting surface can be non-uniform. A non-uniform surface can be acceptable for the replating process described above. However, a non-uniform surface can be unacceptable for the initial plating of metal layer 121.

Accordingly, when a uniform surface is preferred, the electroplating and electropolishing of the wafer can be performed in separate cells with different chemistries. Alternatively, when electroplating and electropolishing is performed in the same cell, the chemistry of the electrolyte solution within the cell can be varied. For example, for the replating process described above, a sulfuric acid solution can be added to facilitate a better electroplating process.

With reference to FIG. 2, the processing steps performed by wafer processing tool 301 are set forth in a flow chart format. It should be recognized, however, that various modifications can be made to the steps depicted in the flow chart in FIG. 2. For example, the wafers may be queued after the re-plating step, then rinsed and cleaned in a batch process.

Figure 5:
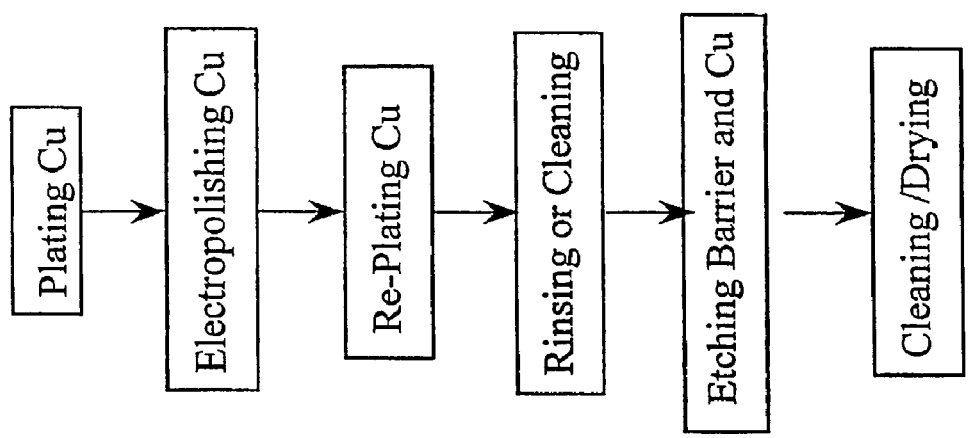
FIG. 5 is another flow chart for processing wafers in accordance with various aspects of the present invention.
Figure 6:
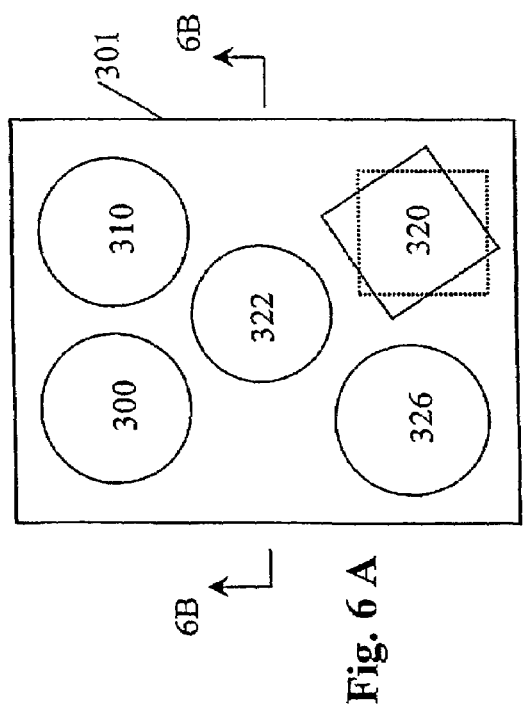
FIGS. 6A–6C are schematic top, cross section, and side views, respectively, of another wafer processing tool in accordance with various aspects of the present invention.
Figure 6:
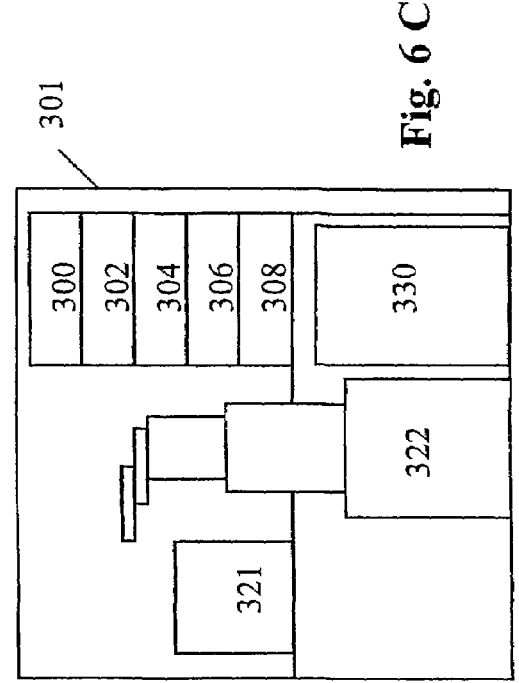
Figure 6:
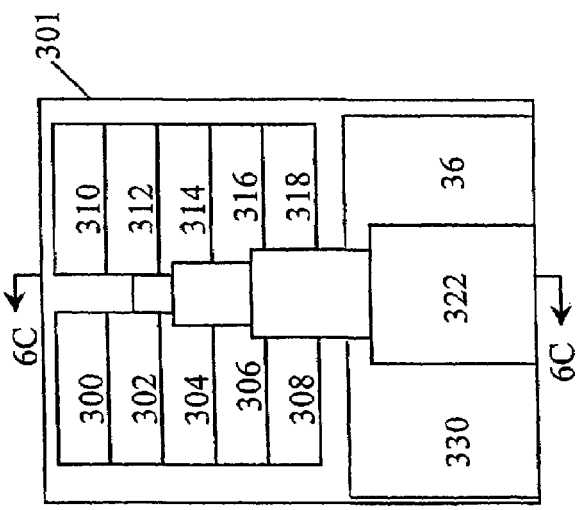

With reference to FIGS. 4A to 4D, one alternative to polishing wafer 31 using CMP after replating wafer 31 is to etch metal layer 121 and barrier layer 122 from wafer 31 using any convenient etching process. Accordingly, with reference to FIGS. 6A to 6C, wafer-processing tool 301 can be modified to include an etching cell 326. Similarly, with reference to FIG. 5, the processing steps performed by wafer processing tool 301 can be modified to include an etching step.

In the following description and associated drawing figures, various alternative embodiments in accordance with various aspects of the present invention will be described and depicted. It should be recognized, however, that these alternative embodiments are not intended to demonstrate all of the various modifications, which can be made to the present invention. Rather, these alternative embodiments are provided to demonstrate only some of the many modifications which are possible without deviating from the spirit and/or scope of the present invention.

Figure 11:
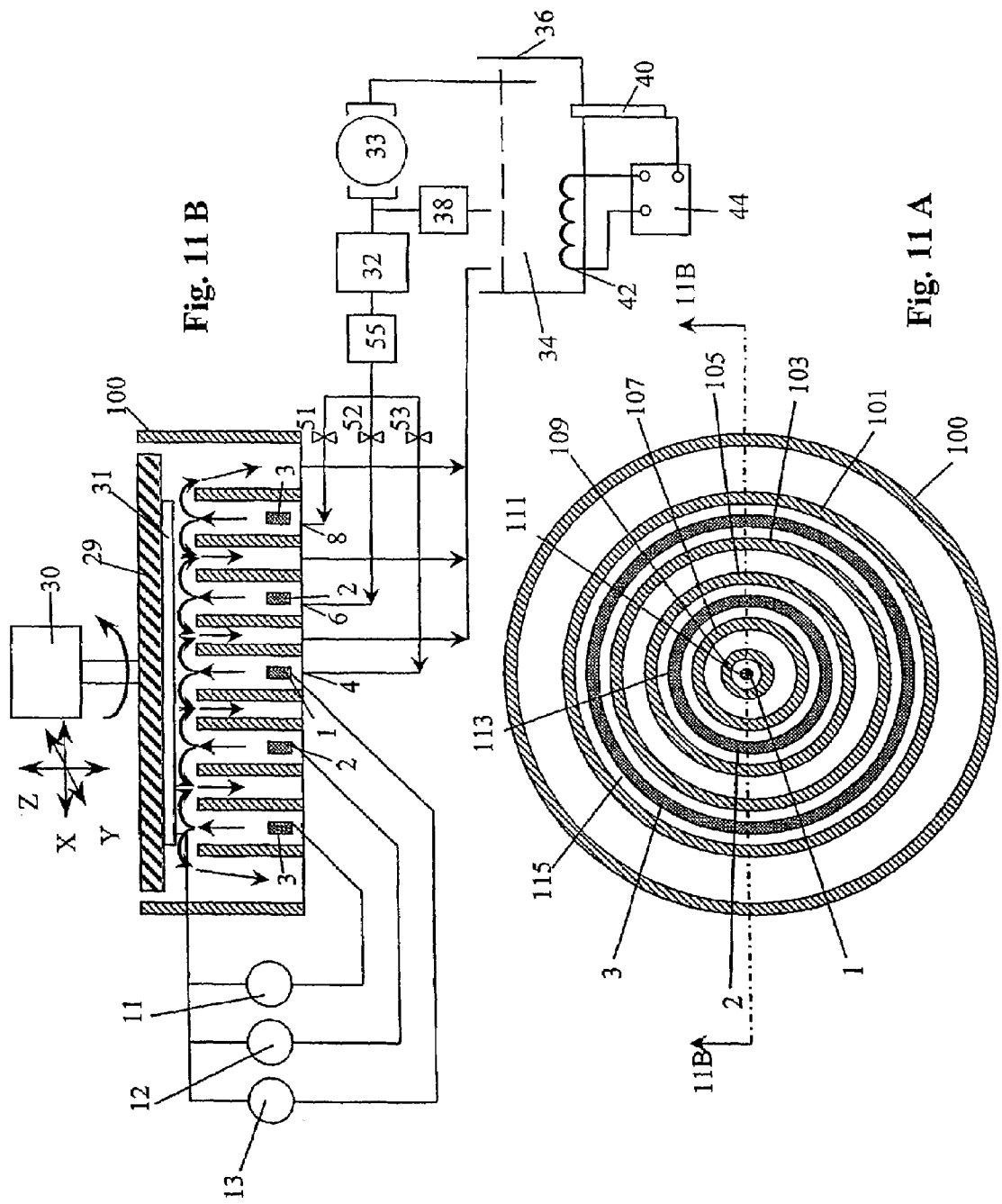
FIG. 11A is a top view of a portion of another alternative embodiment in accordance with various aspects of the present invention.
FIG. 11B is a view, partly in cross section, taken along the line 11B—11B in FIG. 11A, and partly in block diagram form, of the alternative embodiment shown in FIG. 11A.

With reference now to FIGS. 11A and 11B, an alternative embodiment of the present invention, according to various aspects of the present invention, is shown. The embodiment of FIGS. 11A and 11B is similar to that of FIGS. 7A and 7B except that LMFCs 21, 22 and 23 (FIGS. 7A and 7B) have been replaced by LMFC 55 and valves 51, 52 and 53. In the present alternative embodiment, valves 51, 52 and 53 are preferably on/off valves. The flow rate set of LMFC 55 can be preferably determined based on the status of each valve as follows:

$$\text{Flow rate set of LMFC } 55 = F.R.\,3 \times f(\text{valve } 51) +$$
$$F.R.\,2 \times f(\text{valve } 52) + -$$
$$F.R.\,1 \times f(\text{valve } 53)$$

Where, F.R. 3 is the set point of flow rate to inlet 4, F.R. 2 is the set point of flow rate to inlet 6, F.R. 3 is the set point of flow rate to inlet 8, and f (valve #) is a valve status function defined as follows:

$$f(\text{valve } \#) = 1, \text{ when valve } \# \text{ is turned on;}$$
$$0, \text{ when valve } \# \text{ is turned off.}$$

As alluded to above, the flow rates can be set proportionate to the volumes of section 15, 113 and 111.

Figure 12:
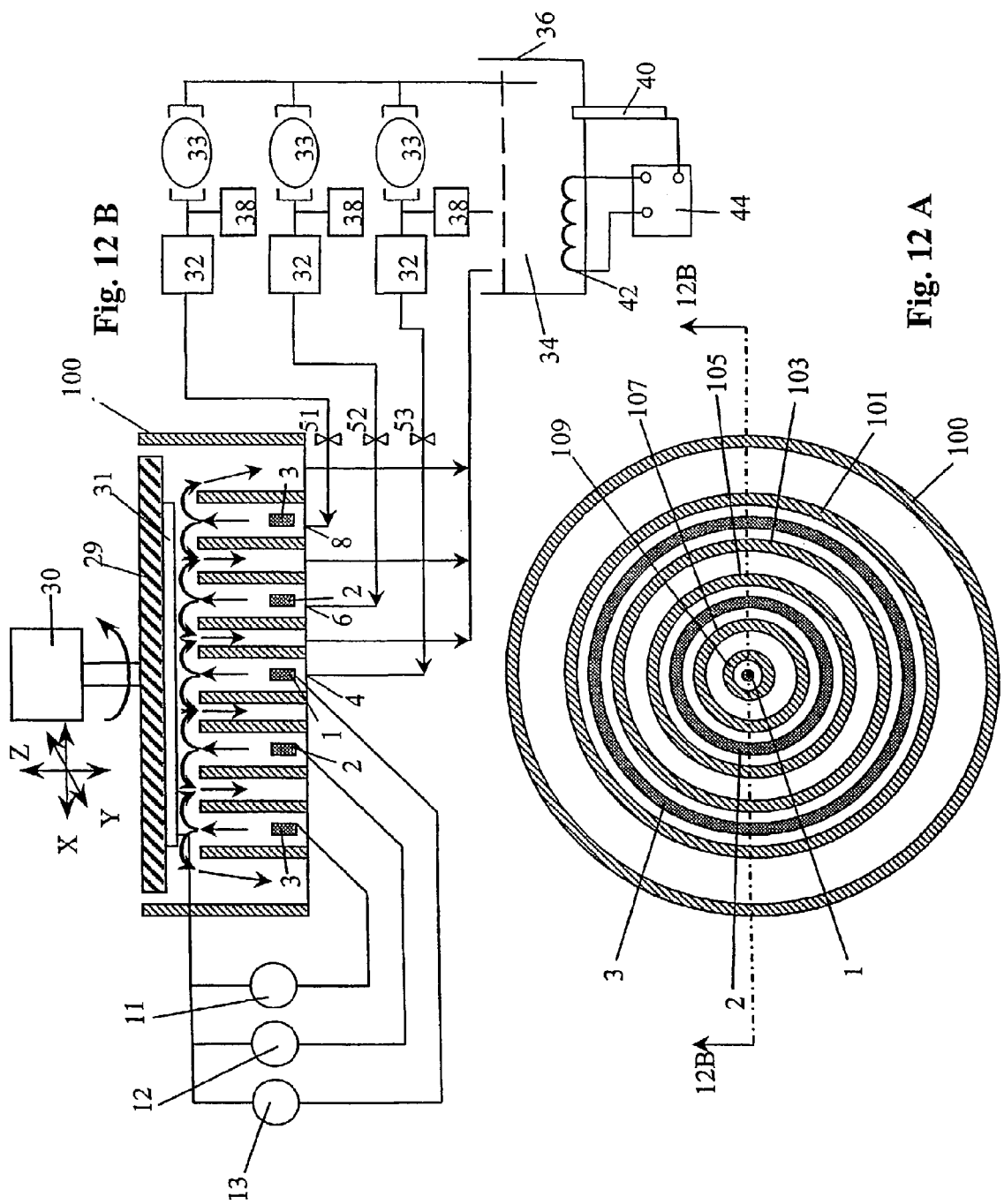
FIG. 12A is a top view of a portion of a second alternative embodiment in accordance with various aspects of the present invention.
FIG. 12B is a view, partly in cross section, taken along the line 12B—12B in FIG. 12A, and partly in block diagram form, of the alternative embodiment shown in FIG. 12A.

With reference now to FIGS. 12A and 12B, another alternative embodiment of the present invention, according to various aspects of the present invention, is shown. The embodiment of FIGS. 12A and 12B is similar to that of FIGS. 7A and 7B except that LMFCs 21, 22 and 23 (FIGS. 7A and 7B) have been replaced by three pumps 33 and on/off valves 51, 52 and 53. In the present alternative embodiment, the delivery of electrolyte 34 into polishing receptacle 100 through inlets 4, 6 and 8 can be preferably controlled independently by each one of three pumps 33 and one on/off valve 51, 52, or 53.

Figure 13:
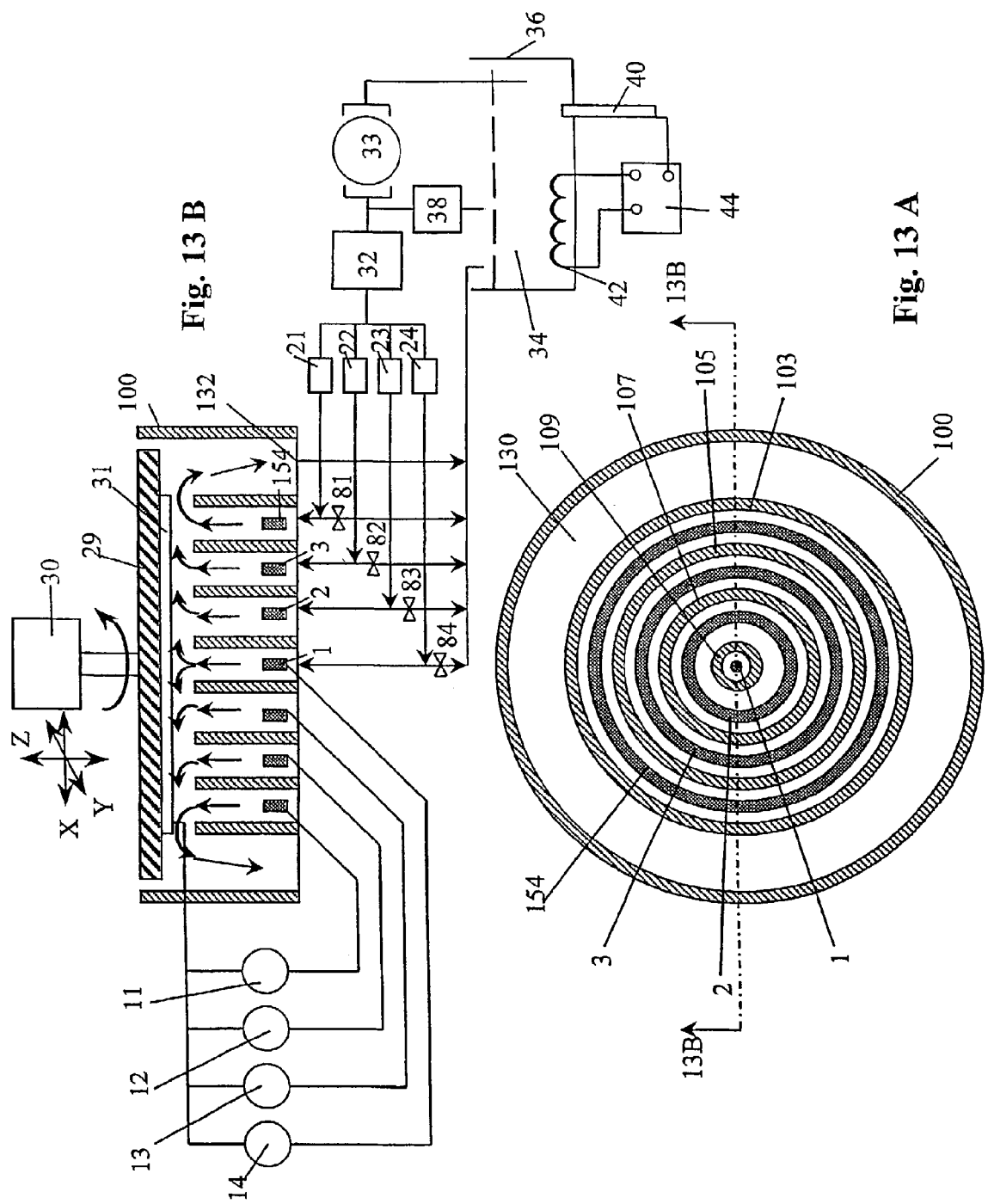
FIG. 13A is a top view of a portion of a third alternative embodiment in accordance with various aspects of the present invention.
FIG. 13B is a view, partly in cross section, taken along the line 13B—13B in FIG. 13A, and partly in block diagram form, of the alternative embodiment shown in FIG. 13A.

With reference now to FIGS. 13A and 13B, still another alternative embodiment of the present invention, according to various aspects of the present invention, is shown. In contrast to the exemplary embodiment shown in FIGS. 7A and 7B, in the present alternative embodiment, a cathode is preferably disposed in every section of polishing receptacle 100 except section 132. For example, additional cathode 154 is suitably disposed between section walls 103 and 105. Additionally, on/off valves 81, 82, 83 and 84 are suitably disposed between the electrolyte reservoir 36 and the outlets of LMFCs 21, 22, 23 and 24. Accordingly, when an on/off valve 81, 82, 83 or 84 is in an open position, electrolyte 34 can suitably flow back into electrolyte reservoir 36 through the open valve from polishing receptacle 100.

Using the present alternative embodiment described above, the following process steps can be suitably employed to selectively electropolish portions of wafer 31:

Step 1: Turn on power supply 14;

Step 2: Turn on LMFC 24 and open valves 81, 82, and 83. Turn off LMFCs 21, 22, and 23 and close valve 84, such that electrolyte 34 only contacts the portion of wafer 31 above cathode 1. Electrolyte 34 then returns to electrolyte reservoir 36 through outlet 132 suitably formed in section 130. Electrolyte 34 also returns to electrolyte reservoir 34 through open valves 81, 82 and 83;

Step 3: When the thickness of metal layer 121 (FIG. 1A) reaches a set value or thickness, turn off power supply 14 and turn off LMFC 24;

Step 4: Repeat steps 1 to 3 for cathode 2 (Turn on LMFC 23. Open valves 81, 82 and 84. Turn on power supply 13. Turn off LMFCs 21, 22 and 24. Close valve 83. Turn off power supplies 11, 12 and 14);

Step 5: Repeat steps 1 to 3 for cathode 3 (Turn on LMFC 22. Open valves 81, 83 and 84. Turn on power supply 12. Turn off LMFCs 21, 23 and 24. Close valve 82. Turn off power supplies 11, 13 and 14); and Step 6: Repeat steps 1 to 3 for cathode 4 (Turn on LMFC 21. Open valves 82, 83 and 84. Turn on power supply 11. Turn off LMFCs 22, 23 and 24. Close valve 81. Turn off power supplies 12, 13, and 14).

It should be recognized that rather than polishing from periphery of the wafer to center of the wafer, polishing also can be performed from center to periphery, or can be performed by randomly choosing a cathode sequence.

In addition to selectively electropolishing portions of wafer 31, using the present alternative embodiment described above, the following process steps can be employed to electropolish the entire surface of wafer 31 at one time:

Step 1: Turn on power supplies 11, 12, 13 and 14. As described earlier, the current of each power supply 11, 12, 13 and 14 can be suitably set proportionate to the surface area of wafer 31 covered by the corresponding cathode.

Step 2: Turn on LMFCs 21, 22, 23 and 24 and turn off valves 81, 82, 83, 84. As also described earlier, the flow rate of electrolyte 34 from LMFCs 21, 22, 23 and 24 can be suitably set proportionate to the surface area of wafer 31 covered by the corresponding cathode; and Step 3: Turn off power supplies 11, 12, 13 and 14 at the same time when metal layer 121 (FIG. 1A) reaches a set value or thickness. Also, power supplies 11, 12, 13 and 14 can be turned off at different times to adjust the thickness uniformity of metal layer 121 (FIG. 1A).

Figure 14:
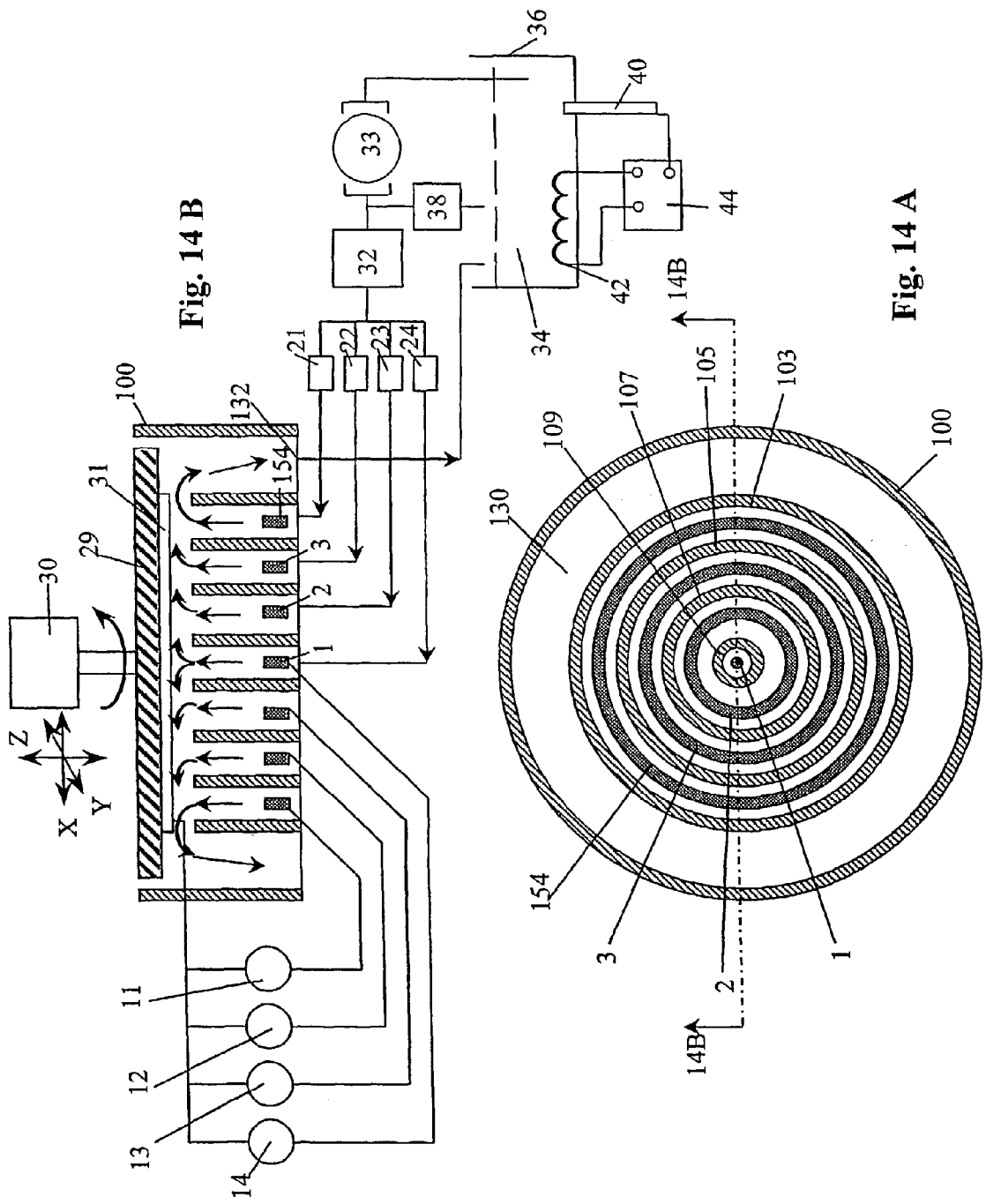
FIG. 14A is a top view of a portion of a fourth alternative embodiment in accordance with various aspects of the present invention.
FIG. 14B is a view, partly in cross section, taken along the line 14B—14B in FIG. 14A, and partly in block diagram form, of the alternative embodiment shown in FIG. 14A.

With reference now to FIGS. 14A and 14B, yet another alternative embodiment of the present invention, according to various aspects of the present invention, is shown. The embodiment of FIGS. 14A and 14B is similar to that of FIGS. 13A and 13B except that on/off valves 81, 82, 83 and 84 (FIGS. 13A and 13B) have been removed. Accordingly, electrolyte 34 returns to electrolyte reservoir 36 only through section 130.

Using the present alternative embodiment described above, the following process steps can be suitably employed to selectively electropolish portions of wafer 31:

Step 1: Turn on power supply 14 to output negative potential to electrode 1 (cathode 1). Turn on power supplies 11, 12 and 13 to output positive potential to electrode 4, 3 and 2 (anodes 4, 3 and 2), respectively;

Step 2: Turn on LMFC 24 only and turn off LMFCs 21 22, and 23. Wafer 31 is steeped in electrolyte 34, however, only the portion of wafer 31 above cathode 1 contacts electrolyte 34 from LMFC 24 and negative potential from cathode 1. Therefore, only the portion of metal layer 121 (FIG. 1A) on wafer 31 above cathode 1 is suitably electropolished;

Step 3: When metal layer 121 (FIG. 1A) reaches a set-value or thickness, turn off power supply 14 and turn off LMFC 24;

Step 4: Repeat steps 1 to 3 for cathode 2 (Turn on power supply 13 to output negative potential to cathode 2, and power supplies 11, 12, and 14 to output positive potential to anodes 4, 3, and 1, respectively. Turn on LMFC 23 and turn off LMFCs 21, 22 and 24);

Step 5: Repeat steps 1 to 3 for cathode 3 (Turn on power supply 12 to output negative potential to cathode 3. Turn on power supplies 11, 13 and 14 to output positive potential to anodes 4, 2 and 1, respectively. Turn on LMFC 22 and turn off LMFCs 21, 23 and 24); and Step 6: Repeat steps 1 to 3 for cathode 4 (Turn on power supply 11 to output negative potential to cathode 4. Turn on power supplies 12, 13 and 14 to output positive potential to anodes 1, 2 and 3, respectively. Turn on LMFC 21 and turn off LMFCs 22, 23 and 24).

In the above selective polishing process, instead of polishing from the center of wafer 31 to the periphery of wafer 31, the polishing also can be performed from the periphery to the center, or can be performed randomly depending on the cathode sequence.

In addition to selectively electropolishing portions of wafer 31, using the present alternative embodiment described above, the following process steps can be employed to electropolish the entire surface of wafer 31 at one time:

Step 1: Turn on power supplies 11, 12, 13 and 14. As described earlier, the current of each power supply 11, 12, 13 and 14 can be suitably set proportionate to the surface area of wafer 31 covered by the corresponding cathode;

Step 2: Turn on LMFCs 21, 22, 23 and 24. As also described earlier, the flow rate of electrolyte 34 from LMFCs 21, 22, 23 and 24 can be suitably set proportionate to the surface area of wafer 31 covered by the corresponding cathode; and Step 3: Turn off power supplies 11, 12, 13 and 14 at the same time when metal layer 121 (FIG. 1A) reaches a set value or thickness. Also, power supplies 11, 12, 13 and 14 can be turned off at different times to adjust the thickness uniformity of metal layer 121 (FIG. 1A).

Figure 15:
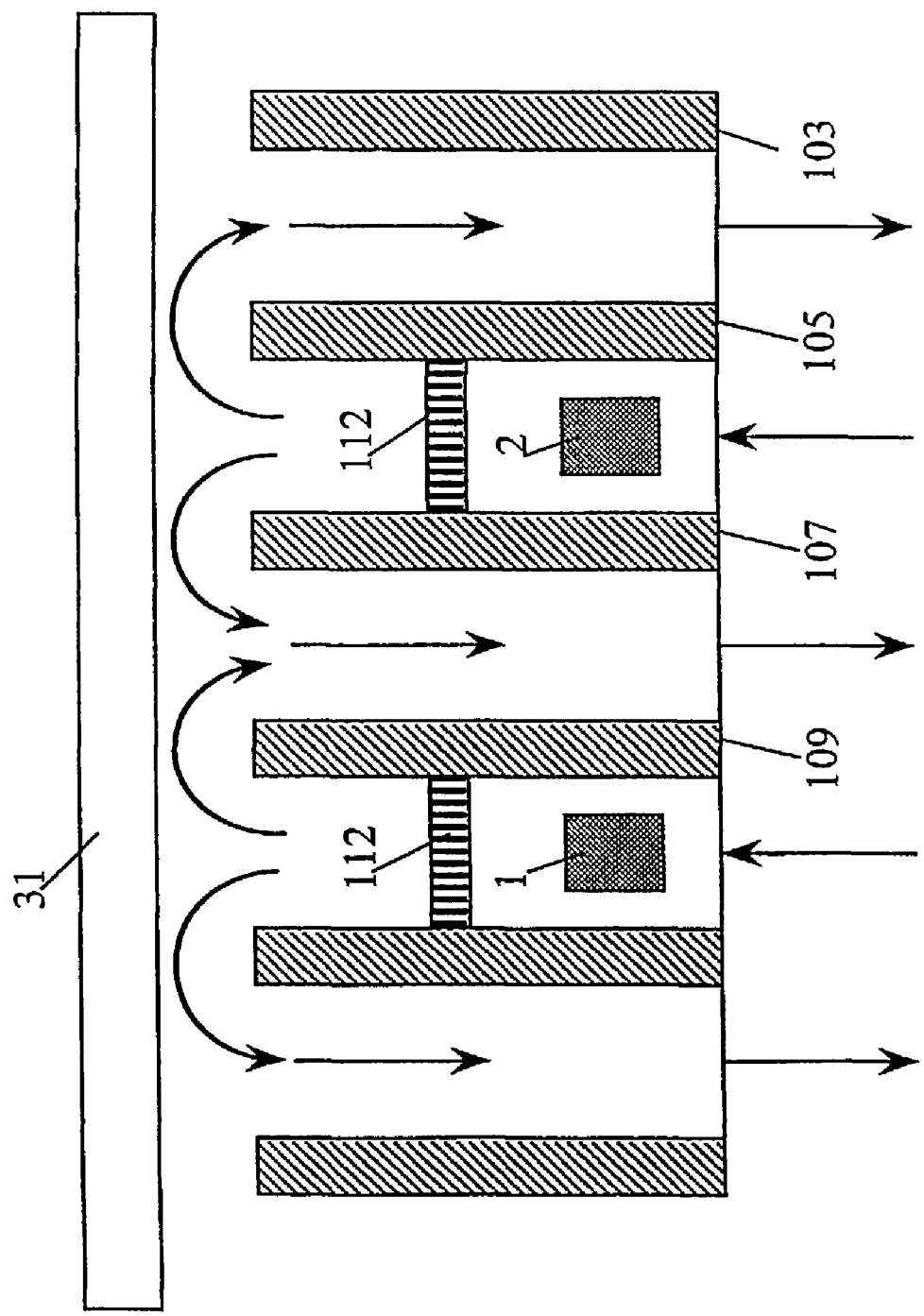
FIG. 15 is a cross section view of a fifth alternative embodiment in accordance with various aspects of the present invention.

With reference now to FIG. 15, another alternative embodiment of the present invention, according to various aspects of the present invention, is shown. The embodiment of FIG. 15 is similar to that of FIGS. 7A and 7B except that a diffuser ring 112 has been added above each cathode. In accordance with one aspect of the present invention, diffuser ring 112 preferably facilitates a more uniform flow of electrolyte 34 along section walls 109, 107, 105 and 103. As such, metal layer 121 (FIG. 1A) can be suitably electropolished more uniformly from wafer 31.

Additionally, diffuser ring 112 can be suitably formed using any convenient method. For example, diffuser ring 112 can be machined to have a number of holes. Alternatively, diffuser ring 112 can include any suitable porous material having porosity preferably in the range of about 10% to about 90%. Additionally, in the present alternative embodiment, diffuser ring 112 is preferably formed from anti-acid, anti-corrosion, particle and contamination free materials.

Figure 16:
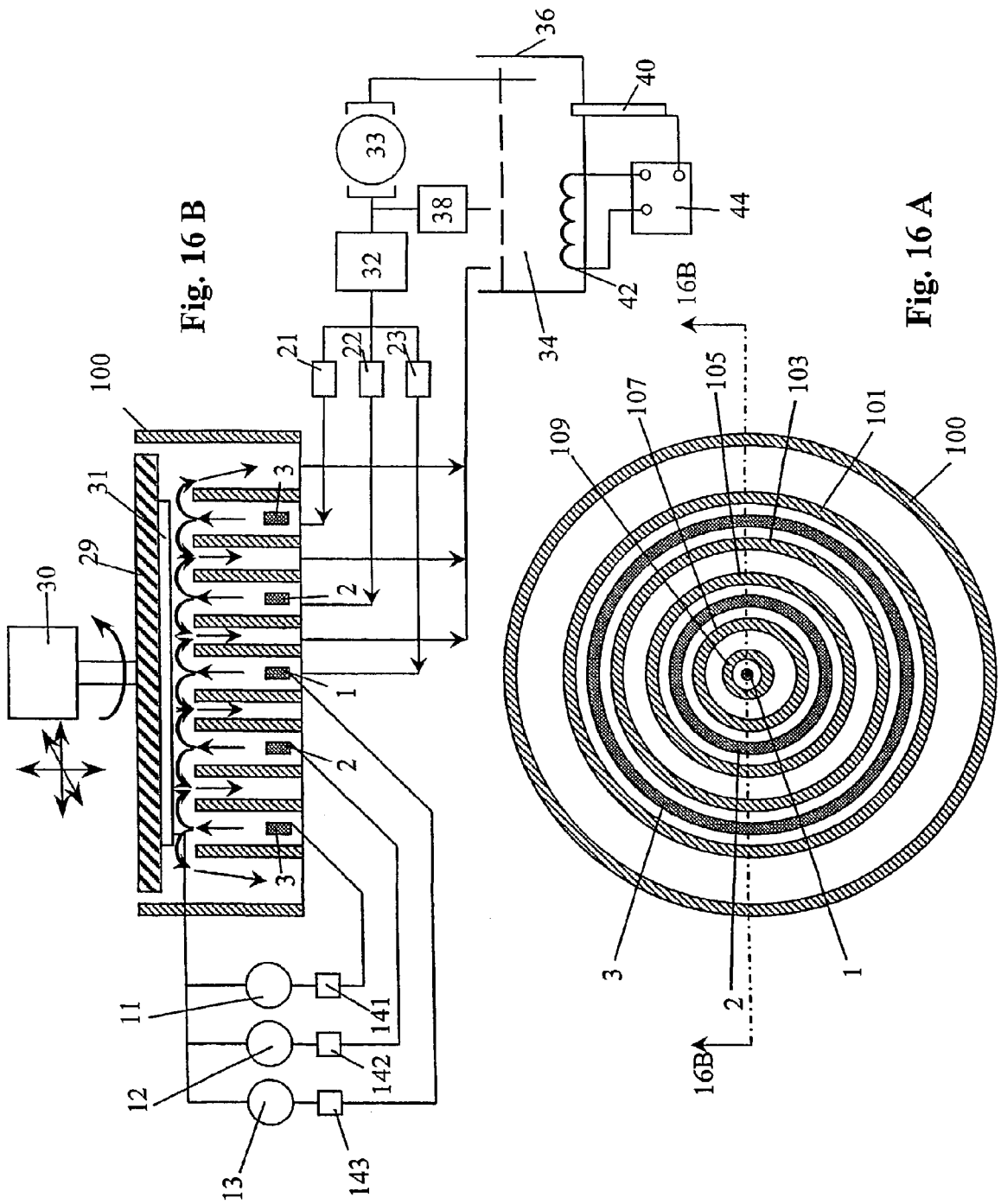
FIG. 16A is a top view of a portion of a sixth alternative embodiment in accordance with various aspects of the present invention.
FIG. 16B is a view, partly in cross section, taken along the line 16B—16B in FIG. 16A, and partly in block diagram form, of the alternative embodiment shown in FIG. 16A.

With reference now to FIGS. 16A and 16B, still another alternative embodiment of the present invention, according to various aspects of the present invention, is shown. The embodiment of FIGS. 16A and 16B is similar to that of FIGS. 7A and 7B except that charge accumulator meters 141, 142 and 143 have been added to power supplies 11, 12 and 13, respectively. In accordance with one aspect of the present invention, charge accumulator meters 141, 142 and 143 preferably measure the charge each power supply 11, 12 and 13 provides during the electropolishing process. The total number of atoms of copper removed can be calculated by dividing the accumulated charge by two. The total number of atoms of copper removed can then be used to determine how much copper remains to be electropolished.

With reference now to FIGS. 17A and 17B, yet another alternative embodiment of the present invention, according to various aspects of the present invention, is shown. The embodiment of FIGS. 17A and 17B is similar to that of FIGS. 7A and 7B except that polishing receptacle 100 suitably includes a plurality of inlets 171, 172, 174 and 175 suitably disposed in sections 113 and 115 for delivery of electrolyte 34. More particularly, in the present alternative embodiment, electrolyte 34 is preferably delivered into section 113 through feed line 170 and inlets 171 and 172. Electrolyte 34 is preferably delivered into section 115 through electrolyte feed line 173 and inlets 174 and 175. By delivering electrolyte 34 into plating receptacle 10 using a plurality of inlets 171, 172, 174 and 175, a more uniform flow profile can be preferably obtained. Furthermore, it should be recognized that sections 113 and 115 can include any number of additional inlets.

With reference now to FIGS. 18A and 18B, two additional alternative embodiments of the present invention, according to various aspects of the present invention, are shown. The embodiment of FIG. 18A is similar to that of FIGS. 13A and 13B and FIGS. 14A and 14B except that the height of section walls 109, 107, 105 and 103 increases outward along the radial direction. In contrast, in the embodiment of FIG. 18B, the height of section walls 109, 107, 105 and 103 decreases outward along the radial direction. In this manner, the flow pattern of electrolyte 34 can be further controlled to enhance the electropolishing process.

With reference now to FIGS. 19A and 19B, two additional alternative embodiments of the present invention, according to various aspects of the present invention, are shown. The embodiment of FIG. 19A is similar to that of FIGS. 7A and 7B except that the height of section walls 109, 107, 105, 103 and 101 increases outward along the radial direction. In contrast, in the embodiment of FIG. 19B, the height of section walls 109, 107, 105, 103 and 101 decreases outward along the radial direction. In this manner, the flow pattern of electrolyte 34 can be further controlled to enhance the electropolishing process.

Figure 20:
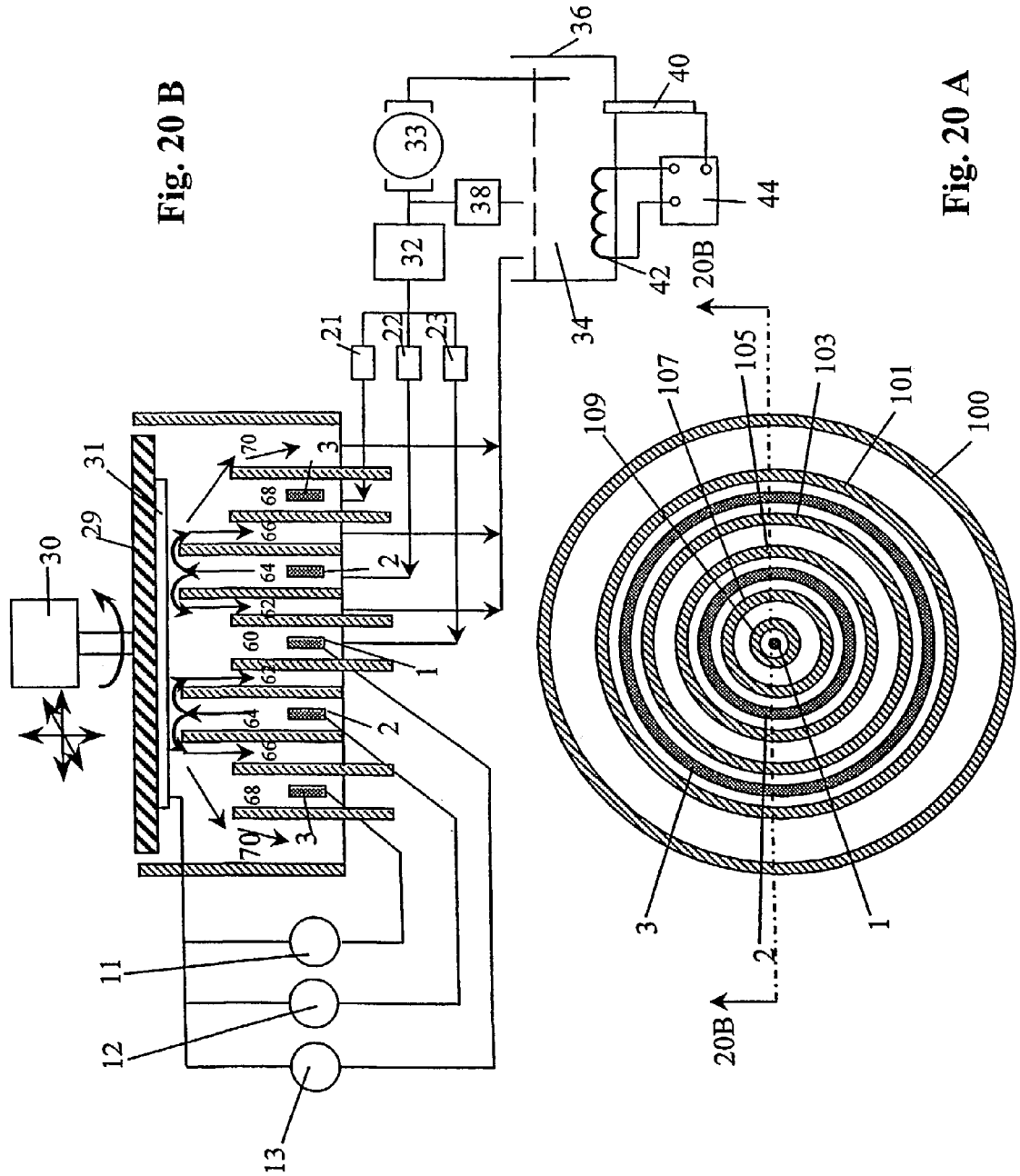
FIG. 20A is a top view of a portion of a twelfth alternative embodiment in accordance with various aspects of the present invention.
FIG. 20B is a view, partly in cross section, taken along the line 20B—20B in FIG. 20A, and partly in block diagram form, of the alternative embodiment shown in FIG. 20A.

With reference now to FIGS. 20A and 20B, yet another alternative embodiment of the present invention, according to various aspects of the present invention, is shown. The embodiment of FIGS. 20A and 20B is similar to that of FIGS. 7A and 7B, except that section walls 109, 107 105, 103 and 101 are configured to move up and down to adjust the flow pattern of electrolyte 34. As shown in FIG. 20B, section walls 105 and 107 can move up, such that electrolyte 34 flows toward the portion of wafer 31 above section walls 105 and 107.

Using the present alternative embodiment described above, the following process steps can be suitably employed to selectively electropolish portions of wafer 31:

Step 1: Turn on power supply 13;

Step 2: Turn on LMFC 23 only and move section wall 109 close to wafer 31, such that electrolyte 34 only contacts the portion of wafer 31 above section wall 109. In this manner, metal layer 121 (FIG. 1A) on the portion of wafer 31 above section wall 109 is suitably electropolished;

Step 3: When metal layer 121 (FIG. 1A) reaches a set value or thickness, turn off power supply 13, turn off LMFC 23, and move section wall 109 to a lower position;

Step 4: Repeat steps 1 to 3 for section walls 105 and 107 using LMFC 22, section walls 105 and 107, and power supply 12; and Step 5: Repeat steps 1 to 3 for section walls 101 and 103 using LMFC 21, section walls 101 and 103, and power supply 11.

In addition to selectively electropolishing portions of wafer 31, using the present alternative embodiment described above, the following process steps can be employed to electropolish the entire surface of wafer 31 at one time:

Step 1: Turn on power supplies 11, 12 and 13. As described earlier, the current of each power supply 11, 12 and 13 can be suitably set proportionate to the surface area of wafer 31 covered by the corresponding cathode.

Step 2: Turn on LMFCs 21, 22 and 23, and move all section walls 101, 103, 105, 107 and 109 adjacent to wafer 31. As also described earlier, the flow rate of electrolyte 34 from LMFCs 21, 22 and 23 can be suitably set proportionate to the surface area of wafer 31 covered by the corresponding cathode; and Step 3: Turn off power supplies 11, 12, and 13 at the same time when metal layer 121 (FIG. 1A) reaches a set value or thickness. Also, power supplies 11, 12 and 13 can be turned off at different times to adjust the thickness uniformity of metal layer 121 (FIG. 1A).

Figure 21A:
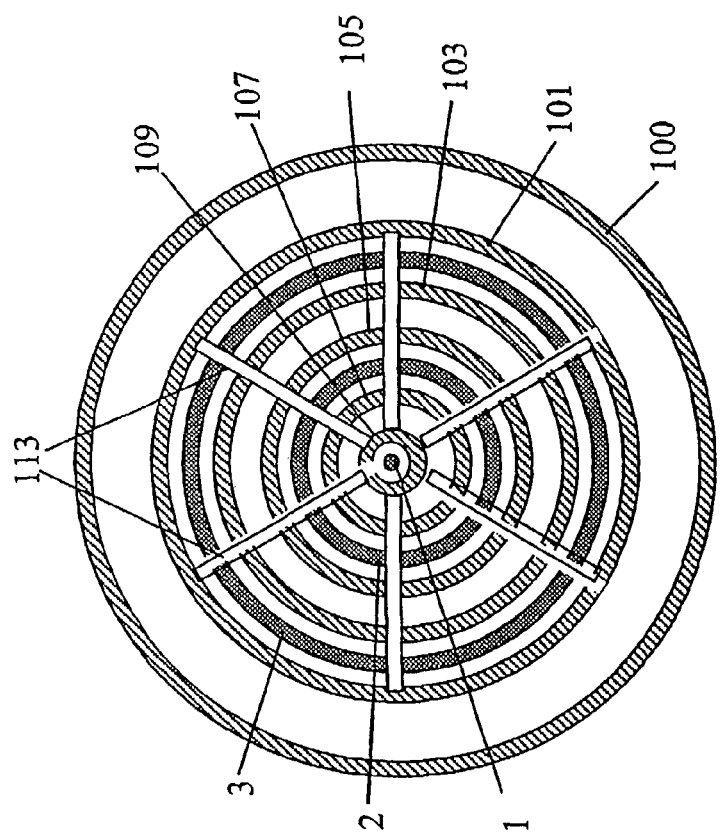
FIG. 21A is a top view of a portion of a thirteenth alternative embodiment in accordance with various aspects of the present invention.
Figure 21B:
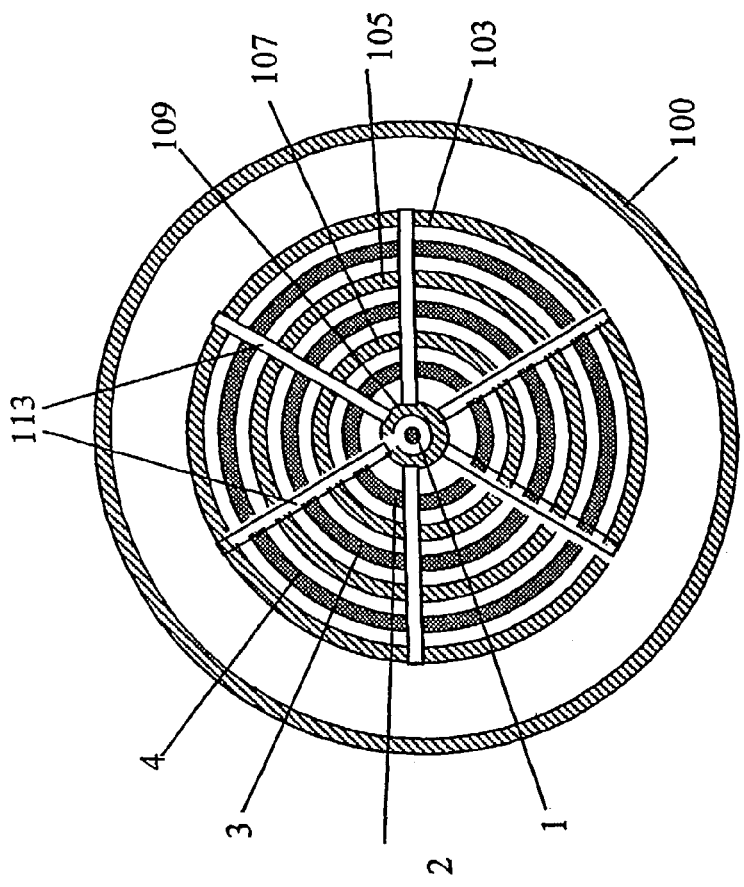
FIG. 21B is a top view of a portion of a fourteenth alternative embodiment in accordance with various aspects of the present invention.

With reference now to FIGS. 21A and 21B, two additional alternative embodiments of the present invention, according to various aspects of the present invention, are shown. The embodiment of FIG. 21A is similar to that of FIGS. 7A and 7B, except that, in the present alternative embodiment, cathodes 1, 2, 3 and 4 and section walls 109, 107, 105 and 103 are divided into six sections. The embodiment of FIG. 21B is similar to FIGS. 13A and 13B, except that, in the present alternative embodiment, cathodes 1, 2 and 3 and section walls 109, 107, 105, 103 and 101 are divided into six sections. It should be recognized, however, that with regard to both embodiments in FIGS. 21A and 21B, any number of sections can be used without deviating from the spirit and/or scope of the present invention.

Additionally, as described in the table below, the cathodes can be connected to one or more power supplies and the sections can be connected to one or more LMFCs in various combinations:

TABLE 2

| Combination No. | Various ways to connect the cathodes to one or more power supplies | Various ways to connect one or more sectors to one or more LMFCs |
|---|---|---|
| 1 | Each cathode is connected to an independent power supply | Each sector is connected to an independent LMFC |
| 2 | Each cathode is connected to an independent power supply | Sectors on the same radius are connected to an independent LMFC |
| 3 | Each cathode is connected to an independent power supply | All sectors are connected to an independent LMFC |
| 4 | Cathodes on the same radius are connected to an independent power supply | Each sector is connected to an independent LMFC |
| 5 | Cathodes on the same radius are connected to an independent power supply | Sectors on the same radius are connected to an independent LMFC |
| 6 | Cathodes on the same radius are connected to an independent power supply | All sectors are connected to an independent LMFC |
| 7 | All cathodes are connected to an independent power supply | Each sector is connected to an independent LMFC |
| 8 | All cathodes are connected to an independent power supply | Sectors on the same radius are connected to an independent LMFC |
| 9 | All cathodes are connected to an independent power supply | All sectors are connected to an independent LMFC |

In the above table, the operation of combination numbers 1, 2, 4 and 5 are the same as described earlier in conjunction with various alternative embodiments. The operation of combination numbers 3, 6, 7, 8 and 9 will be described in greater detail below in conjunction with various other alternative embodiments.

Figure 23:
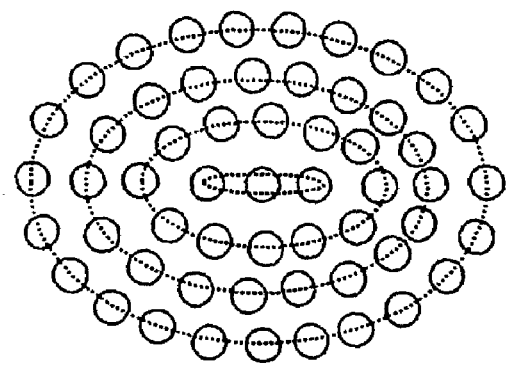
FIG. 23A is a top view of a portion of a sixteenth alternative embodiment in accordance with various aspects of the present invention.
FIG. 23B is a top view of a portion of a seventeenth alternative embodiment in accordance with various aspects of the present invention.
FIG. 23C is a top view of a portion of an eighteenth alternative embodiment in accordance with various aspects of the present invention.
Figure 23:
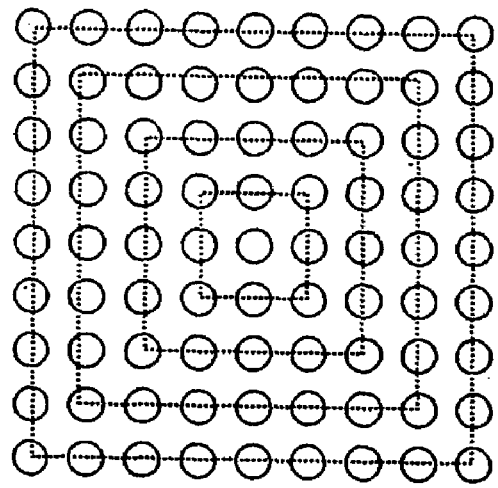
Figure 23:
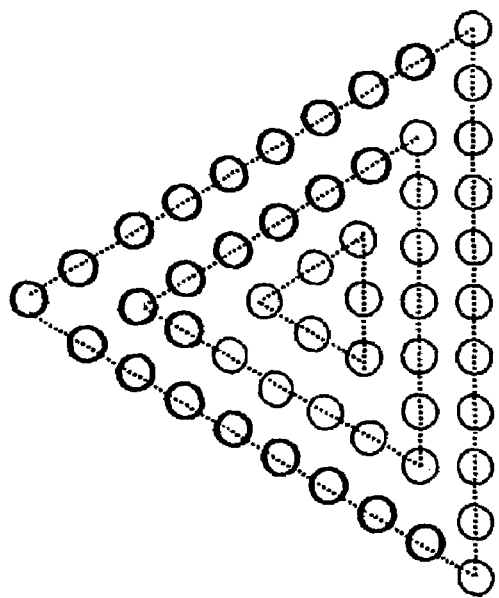

With reference now to FIGS. 22A and 22B, still another alternative embodiment of the present invention, according to various aspects of the present invention, is shown. The embodiment of FIGS. 22A and 22B is similar to that of FIGS. 7A and 7B, except that cathodes 1, 2 and 3 (FIGS. 7A and 7B) and section walls 109, 107, 105, 103 and 101 (FIGS. 7A and 7B) have been replaced by a plurality of rod-type cathodes 501 suitably disposed within a plurality of tubes 503. In the present alternative embodiment, electrolyte 34 (FIG. 7B) is preferably delivered to electropolishing receptacle 100 through plurality of tubes 503, contacts the surface of wafer 31, then drains out of electropolishing receptacle 100 through a plurality of drainage holes 500. As depicted in FIG. 22A, in the present alternative embodiment, cathodes 501, plurality of tubes 503, and plurality of drainage holes 500 are preferably arranged in a circular pattern. However, with reference to FIGS. 23A to 23C, cathodes 501, plurality of tubes 503, and plurality of drainage holes 500 can also be configured in various other patterns, such as a triangle (FIG. 23A), a square (FIG. 23B), an ellipse (FIG. 23C), and the like.

Additionally, as described in the table below, cathodes 501 and plurality of tubes 503 can be connected to power supplies 11, 12 and 13 (FIG. 7B) and LMFCs 21, 22 and 23 (FIG. 7B), respectively, in various combinations:

TABLE 3

| Combination No. | Various ways to connect cathodes 501 to one or more power supplies | Various ways to connect plurality of tubes 503 to one or more LMFCs |
|---|---|---|
| 1 | Each cathode is connected to an independent power supply | Each tube is connected to an independent LMFC |
| 2 | Each cathode is connected to an independent power supply | Tubes on the same radius are connected to an independent LMFC |
| 3 | Each cathode is connected. to an independent power supply | All tubes are connected to an independent LMFC |
| 4 | Cathodes on the same radius are connected to an independent power supply | Each tube is connected to an independent LMFC |
| 5 | Cathodes on the same radius are connected to an independent power supply | Tubes on the same radius are connected to an independent LMFC |
| 6 | Cathodes on the same radius are connected to an independent power supply | All tubes are connected to an independent LMFC |
| 7 | All cathodes are connected to an independent power supply | Each tube is connected to an independent LMFC |
| 8 | All cathodes are connected to an independent power supply | Tubes on the same radius are connected to an independent LMFC |
| 9 | All cathodes are connected to an independent power supply | All tubes are connected to an independent LMFC |

In the above table, the operation of combination numbers 1, 2, 4 and 5 are the same as described earlier in conjunction with various alternative embodiments. The operation of combination numbers 3, 6, 7, 8 and 9 will be described in greater detail below in conjunction with various other alternative embodiments.

With reference now to FIGS. 24A and 24B, another alternative embodiment of the present invention, according to various aspects of the present invention, is shown. The embodiment of FIGS. 24A and 24B is similar to that of FIGS. 7A and 7B, except that cathodes 1, 2 and 3 (FIGS. 7A and 7B) and section walls 109, 107, 105, 103 and 101 (FIGS. 7A and 7B) have been replaced with cathode 240, bar 242, and valves 202, 204, 206, 208, 210, 212, 214, 216 and 218. In the present alternative embodiment, the number of power supplies has been reduced to power supply 200. Additionally, valves 202, 204, 206, 208, 210, 212, 214, 216 and 218 are preferably on/off valves used to control the flow of electrolyte 34 onto wafer 31. Furthermore, valves 202, 204, 206, 208, 210, 212, 214, 216 and 218 are disposed symmetrically on bar 242 to facilitate a more uniform electropolishing process.

Using the present alternative embodiment described above, the following process steps can be suitably employed to selectively electropolish portions of wafer 31:

Step 1: Turn on power supply 200;

Step 2: Turn on pump 33, LMFC 55, and drive mechanism 30. Turn on valves 202 and 218, such that electrolyte 34 only contacts the portion of wafer 31 above valves 202 and 218. In this manner, metal layer 121 (FIG. 1A) on the portion of wafer 31 above valves 202 and 218 is electropolished;

Step 3: When metal layer 121 (FIG. 1A) reaches a set value or thickness, turn off power supply 200, LMFC 55, and valves 202 and 218;

Step 4: Repeat steps 1 to 3 for valves 204 and 216;

Step 5: Repeat steps 1 to 3 for valves 206 and 214;

Step 6: Repeat steps 1 to 3 for valves 208 and 212; and

Step 7: Repeat steps 1 to 3 for valves 210.

During the above described polishing process, power supply 200 can be operated in DC mode, or in a variety of pulse modes, as shown in FIG. 8. Also, the power supply can be turned on after turning on pump 33 and valves 202 and 216, or 204 and 214, or 206 and 212, or 210.

In addition to selectively electropolishing portions of wafer 31, using the present alternative embodiment described above, the following process steps can be employed to electropolish the entire surface of wafer 31 at one time:

Step 1: Turn on power supply 200;
Step 2: Turn on LMFC 55 and all valves 202, 204, 206, 208, 210, 212, 214, 216 and 218, such that electrolyte 34 contacts substantially the entire surface area of wafer 31; and
Step 3: Turn off power supply 200 and all valves when the film thickness reaches a set value. Also, valves 202, 204, 206, 208, 210, 212, 214, 216 and 218 can be turned off at different times to adjust the thickness uniformity of metal layer 121 (FIG. 1A) on wafer 31.

Figure 25:
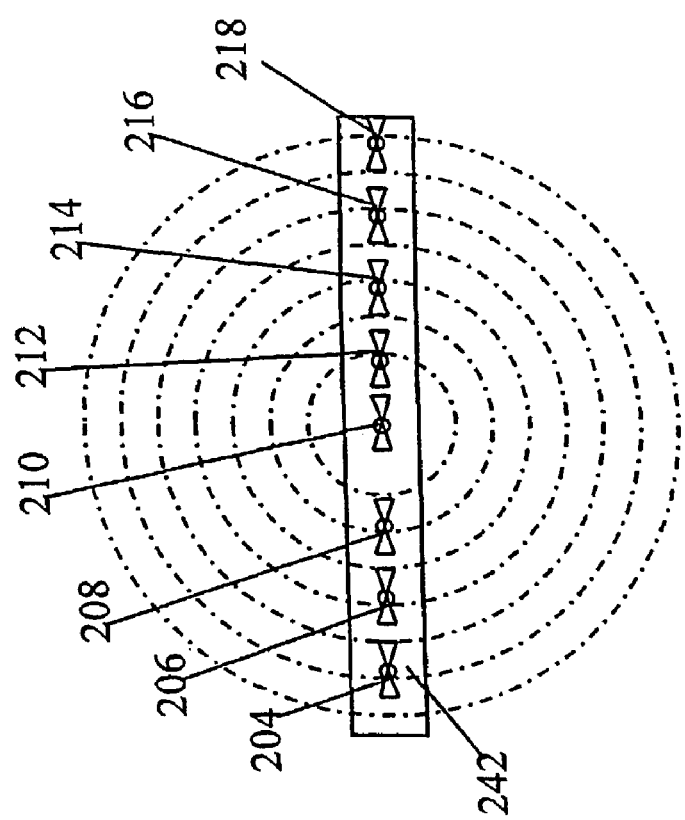
FIG. 25 is a top view of a portion of a twentieth alternative embodiment in accordance with various aspects of the present invention.

With reference now to FIG. 25, still another alternative embodiment of the present invention, according to various aspects of the present invention, is shown. The embodiment of FIG. 25 is similar to that of FIGS. 24A and 24B, except that all valves are disposed on bar 242 at different radii on bar 242 to facilitate a more uniform electropolish.

Using the present alternative embodiment described above, the following process steps can be suitably employed to selectively electropolish portions of wafer 31:

Step 1: Turn on power supply 200 (FIG. 24B);
Step 2: Turn on pump 33 (FIG. 24B), LMFC 55 (FIG. 24B), and drive mechanism 30 (FIG. 24B). Turn on valve 218, such that electrolyte 34 only contacts the portion of wafer 31 above valve 218. In this manner, metal layer 121 (FIG. 1A) on the portion of wafer 31 above valve 218 is electropolished;
Step 3: When metal layer 121 (FIG. 1A) reaches a set value or thickness, turn off power supply 200 (FIG. 24B), LMFC 55 (FIG. 24B), and valves 218;
Step 4: Repeat steps 1 to 3 for valve 204;
Step 5: Repeat steps 1 to 3 for valve 216;
Step 6: Repeat steps 1 to 3 for valve 206; and
Step 7: Repeat steps 1 to 3 for valves 214, 208, 212, and 210, respectively.

During the above described polishing process, power supply 200 (FIG. 24B) can be operated in DC mode, or in a variety of pulse modes, as shown in FIG. 8. Additionally, the electroplating sequence can be started from the center of wafer 31 to the edge of wafer 31 without deviating from the spirit and/or scope of the present invention.

In addition to selectively electropolishing portions of wafer 31, using the present alternative embodiment described above, the following process steps can be employed to electropolish the entire surface of wafer 31 at one time:

Step 1: Turn on power supply 200 (FIG. 24B);
Step 2: Turn on LMFC 55 (FIG. 24B) and all valves 204, 206, 208, 210, 212, 214, 216 and 218, such that electrolyte 34 contacts substantially the entire surface area of wafer 31; and
Step 3: Turn off power supplies 200 (FIG. 24B) and all valves when the film thickness reaches a set value. Also, valves 202, 204, 206, 208, 210, 212, 214, 216 and 218 can be turned off at different times to adjust the thickness uniformity of metal layer 121 (FIG. 1A) on wafer 31 (FIG. 24B).

Figure 26:
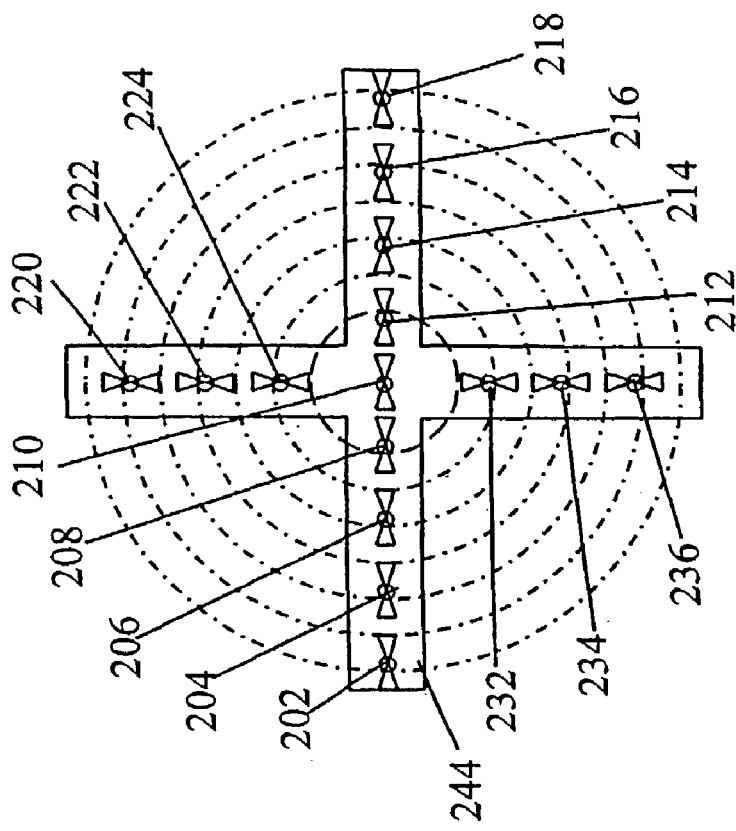
FIG. 26 is a top view of a portion of a twenty-first alternative embodiment in accordance with various aspects of the present invention.

With reference now to FIG. 26, yet another alternative embodiment of the present invention, according to various aspects of the present invention, is shown. The embodiment of FIG. 26 is similar to that of FIG. 25 except that an additional bar has been added to form a cross-shaped bar 244. Valves 202 and 218, 204 and 216, 206 and 214, 208 and 212 are placed symmetrically on the horizontal portion of bar 244 (as depicted in FIG. 26). Similarly, valves 220 and 236, 222 and 234, 224 and 232 are placed symmetrically on vertical portion of bar 244 (as depicted in FIG. 26). Additionally, as depicted in FIG. 26, the valves on horizontal portion of bar 244 are disposed at different radii than the valves on the vertical portion of bar 244.

Using the present alternative embodiment described above, the following process steps can be suitably employed to selectively electropolish portions of wafer 31:

Step 1: Turn on power supply 200 (FIG. 24B);
Step 2: Turn on pump 33 (FIG. 24B), LMFC 55 (FIG. 24B), and drive mechanism 30 (FIG. 24B). Turn on valves 218 and 202, such that electrolyte 34 contacts the portion of wafer 31 above valves 218 and 202. In this manner, metal layer 121 (FIG. 1A) on the portion of wafer 31 above valves 218 and 202 is electropolished.
Step 3: When metal layer 121 (FIG. 1A) reaches a set value or thickness, turn off power supply 200 (FIG. 24B), LMFC 55 (FIG. 24B), valves 218 and 202;
Step 4: Repeat steps 1 to 3 for valves 220 and 236;
Step 5: Repeat steps 1 to 3 for valves 204 and 216;
Step 6: Repeat steps 1 to 3 for valves 222 and 234; and
Step 7: Repeat steps 1 to 3 for valves 206 and 214, 224 and 232, 208 and 212, and 210 only, respectively.

During the above described polishing process, power supply 200 (FIG. 24B) can be operated in DC mode, or in a variety of pulse modes, as shown in FIG. 8.

In addition to selectively electropolishing portions of wafer 31, using the present alternative embodiment described above, the following process steps can be employed to electropolish the entire surface of wafer 31 at one time:

Step 1: Turn on power supply 200 (FIG. 24B);
Step 2: Turn on pump 33 (FIG. 24B), LMFC 55 (FIG. 24B), and all valves 204, 206, 208, 210, 212, 214, 216, 218, 220, 222, 224, 232, 234 and 236, such that electrolyte 34 only contacts substantially the entire surface area of wafer 31; and
Step 3: Turn off power supply 200 (FIG. 24B) and all valves when the thickness of metal layer 121 (FIG. 1A) reaches a set value. All valves 204, 206, 208, 210, 212, 214, 216, 218, 220, 222, 224, 232, 234 and 236 can be turned off at different times to adjust the thickness uniformity of metal layer 121 (FIG. 1A) on wafer 31 (FIG. 24B).

Figure 27C:
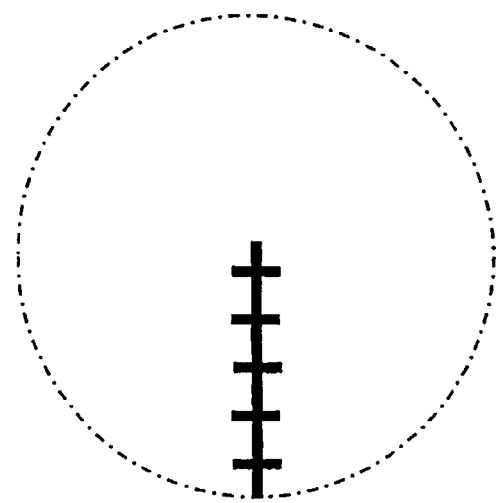
FIG. 27C is a top view of a portion of a twenty-fourth alternative embodiment in accordance with various aspects of the present invention.
Figure 27B:
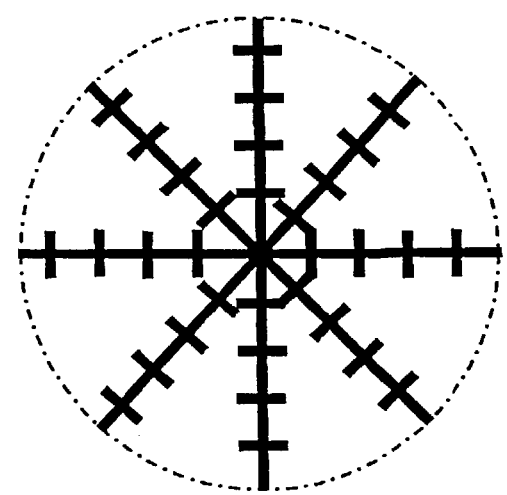
FIG. 27B is a top view of a portion of a twenty-third alternative embodiment in accordance with various aspects of the present invention.
Figure 27A:
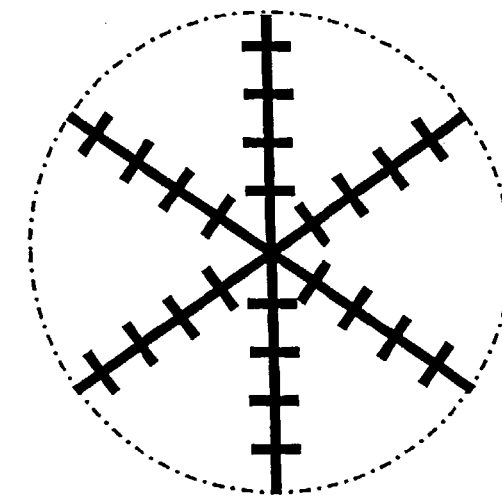
FIG. 27A is a top view of a portion of a twenty-second alternative embodiment in accordance with various aspects of the present invention.

With reference now to FIGS. 27A, B, and C, three additional alternative embodiments of the present invention, according to various aspects of the present invention, are shown. The embodiment of FIG. 27A is similar to that of FIGS. 24A and 24B except that, in the present alternative embodiment, three bars are used. The angle between two adjacent bars is preferably about 60°. The embodiment of FIG. 27B is similar to those of FIGS. 24A and 24B except that four bars are used. The angle between two adjacent bars is preferably about 45°. The embodiment of FIG. 27C is similar to those of FIGS. 24A and 24B except that half of a bar is used. It should be recognized, however, that any number of bars can be used without deviating from the spirit and/or scope of the present invention. Additionally, the adjacent bars can be set at various angles again without deviating from the spirit and/or scope of the present invention.

In the alternative embodiments described thus far, the electropolishing sequence can be started from valves close to the periphery of wafer 31, or started from the center of wafer 31, or started randomly. Starting from the center of wafer 31 is preferred since the non-polished metal layer 121 (FIG. 1A) (with larger diameter) can be used to conduct current for polishing the next portion of metal layer 121 (FIG. 1A) (with smaller diameter).

With reference now to FIGS. 28A and 28B, still another alternative embodiment of the present invention, according to various aspects of the present invention, is shown. The embodiment of FIGS. 28A and 28B is similar to that of FIGS. 24A and 24B except that position fixed valves 202, 204, 206, 208, 210, 212, 214, 216 and 218 have been replaced by two moveable jets 254. Moveable jets 254 are disposed adjacent wafer 31 and apply electrolyte 34 onto specific portions of wafer 34. Moveable jets 254 also sit on guide bar 250, and can move along the X direction as shown in FIGS. 28A and 28B. Additionally, in the present exemplary embodiment, fresh electrolyte is supplied through flexible pipe 258.

Using the present alternative embodiment described above, the following process steps can be suitably employed to selectively electropolish portions of wafer 31:

Step 1: Turn on power supply 200;

Step 2: Turn on pump 33, LMFC 55, and driving mechanism 30. Turn on valves 356, such that electrolyte 34 only contacts the portions of wafer 31 above valves 356. In this manner, metal layer 121 (FIG. 1A) on the portions of wafer 31 above valves 356 are suitably electropolished;

Step 3: When metal layer 121 (FIG. 1A) reaches a set value or thickness, turn off power supply 200, LMFC 55, and valves 356;

Step 4: Move cathode jet 254 to the next position; and

Step 5: Repeat steps 1 to 4 until metal layer 121 (FIG. 1A) has been electropolished from wafer 31.

With reference now to FIGS. 29A and 29B, yet another alternative embodiment of the present invention, according to various aspects of the present invention, is shown. The embodiment of FIGS. 29A and 29B is similar to that of FIGS. 28A and 28B except that two additional moveable cathode jets are added in the Y direction in order to increasing polishing speed. However, the process sequence is similar to that of FIGS. 28A and 28B.

With reference now to FIGS. 30A and 30B, another alternative embodiment of the present invention, according to various aspects of the present invention, is shown. The embodiment of FIGS. 30A and 30B is similar to that of FIGS. 28A and 28B except that wafer 31 is immersed into electrolyte 34. Moveable jets 254 are disposed adjacent to wafer 31 to focus polishing current on a specific portion of wafer 31. In the present alternative embodiment, the gap between moveable jet 254 and wafer 31 can be in the range of about 0.1 millimeters to about 5 millimeters, and preferably about 1 millimeter. Again, the process sequence is similar to that of FIGS. 28A and 28B.

With reference now to FIGS. 31A and 31B, still another alternative embodiment of the present invention, according to various aspects of the present invention, is shown. The embodiment of FIGS. 31A and 31B is similar to that of FIGS. 30A and 30B except that fresh electrolyte 34 can be delivered through pipe 260 instead of moveable jets 252 and 254 through flexible pipe 258. Wafer 31 also can be immersed in electrolyte 34, and moveable jets 252 and 254 can be disposed adjacent to wafer 31 to focus polishing current on a specific portion of wafer 31. In the present alternative embodiment, the gap between moveable jets 252 and 254 and wafer 31 can be in the range of about 0.1 millimeters to about 5 millimeters, and preferably about 1 millimeter. Again the process sequence is similar to that of FIGS. 28A and 28B.

With reference now to FIGS. 32A, 32B, 32C and 32D, four additional alternative embodiments of the present invention, according to various aspects of the present invention, are shown. FIG. 32A shows a moveable jet, which preferably includes cathode 252 and case 262. Case 262 can be suitably formed from an insulator material, such as Teflon, CPVC, PVDF, Polypropylene, and the like. FIG. 32B shows a moveable jet consisting of cathode 266 and case 264. Electrolyte 34 can be delivered through a hole suitably formed at the bottom of case 264. FIG. 32 C shows a moveable jet, which preferably includes cathode 262, electrodes 274 and 270, insulator spacer 272, case 262, and power supplies 276 and 268. Electrode 274 can be suitably connected to the negative output of power supply 276, and electrode 270 can be connected to wafer 31. In accordance with one aspect of the present invention, electrode 276 preferably traps metal ions flowing out of case 262, therefore reducing film buildup in the area outside of case 262. Additionally, electrode 270 preferably prevents electrical field leakage from electrode 276 to minimize etch effect. The embodiment of FIG. 32D is similar to that of FIG. 32C, except that case 264 has a hole at the bottom for electrolyte 34.

Figure 34:
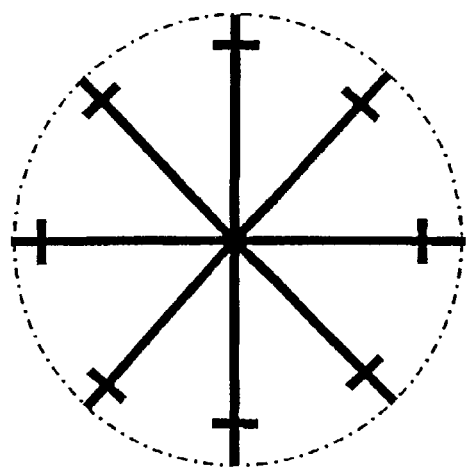
FIG. 34A is a top view of a portion of a thirty-third alternative embodiment in accordance with various aspects of the present invention.
FIG. 34B is a top view of a portion of a thirty-fourth alternative embodiment in accordance with various aspects of the present invention.
FIG. 34C is a top view of a portion of a thirty-fifth alternative embodiment in accordance with various aspects of the present invention.
FIG. 34D is a top view of a portion of a thirty-sixth alternative embodiment in accordance with various aspects of the present invention.
Figure 34:
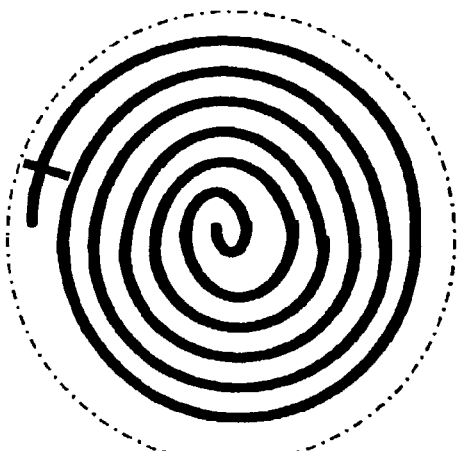
Figure 34:
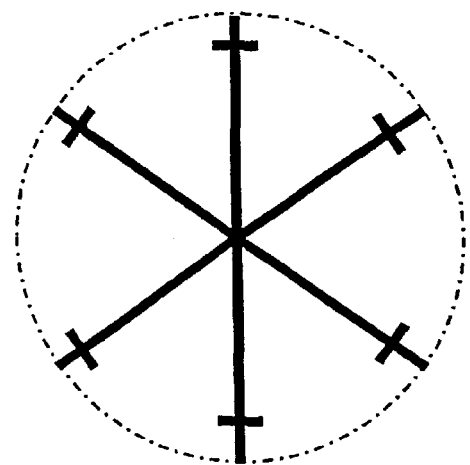
Figure 34:
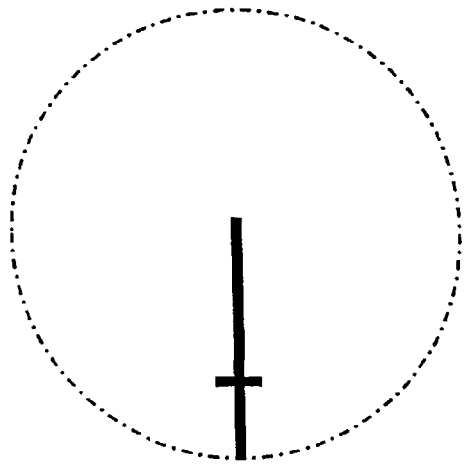

With reference now to FIGS. 34A, 34B, 34C and 34D, four additional alternative embodiments of the present invention, according to various aspects of the present invention, are shown. The embodiment of FIG. 34 A is similar to those of FIGS. 28A and 28B except that three bars are preferably used. The angle between two adjacent bars can be preferably about 60°. The embodiment of FIG. 34B is similar to those of FIGS. 28A and 28B except that four bars are preferably used. The angle between two adjacent bars can be preferably about 45°. The embodiment of FIG. 34 C is similar to those of FIGS. 28A and 28B except that half of a bar is used. Again, it should be recognized that any number of bars can be employed without deviating from the spirit and/or scope of the present invention. Additionally, any two adjacent bars can be separated by any desired angle without deviating from the spirit and/or scope of the present invention. The embodiment of FIG. 34D is similar to those of FIGS. 28A and 28B except that the straight bar is replaced by a spiral bar.

Figure 35:
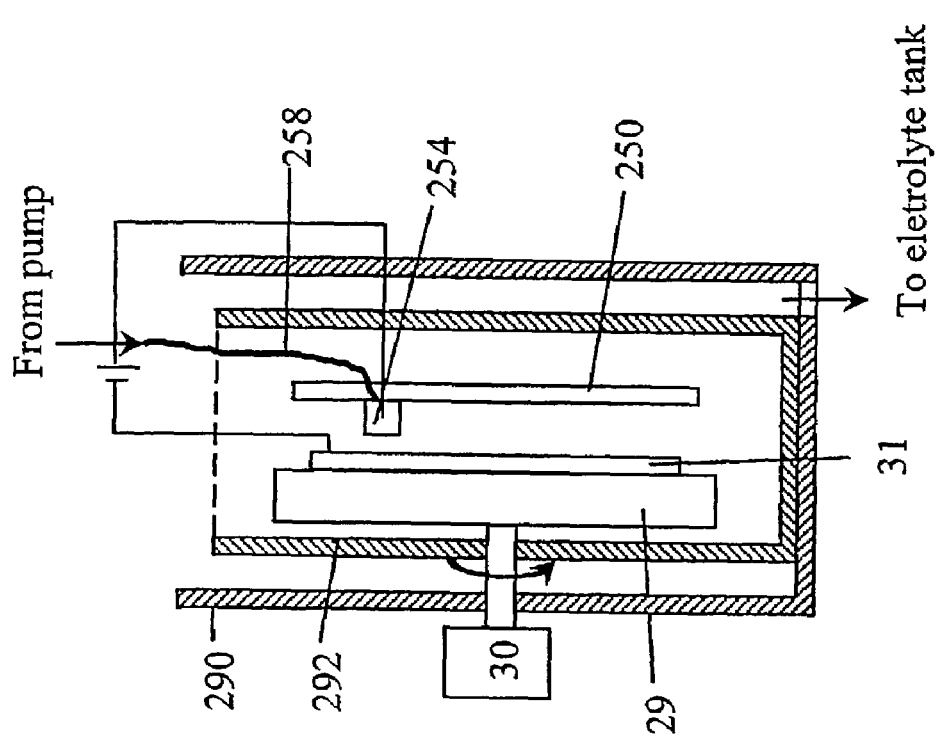
FIG. 35A is a cross section view of a portion of a thirty-seventh alternative embodiment in accordance with various aspects of the present invention.
FIG. 35B is a cross section view of a portion of a thirty-eighth alternative embodiment in accordance with various aspects of the present invention.
Figure 35:
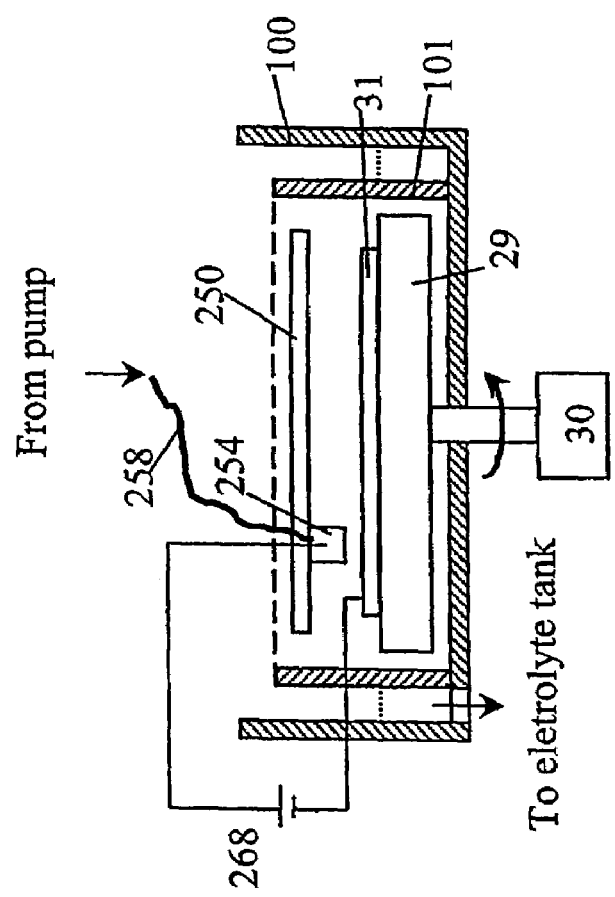

With reference now to FIG. 35, two additional alternative embodiments of the present invention, according to various aspects of the present invention, are shown. The embodiments of FIGS. 35A and 35B are similar to those of FIGS. 28A and 28B except wafer 31 can be positioned upside down and vertically, respectively.

Figure 36:
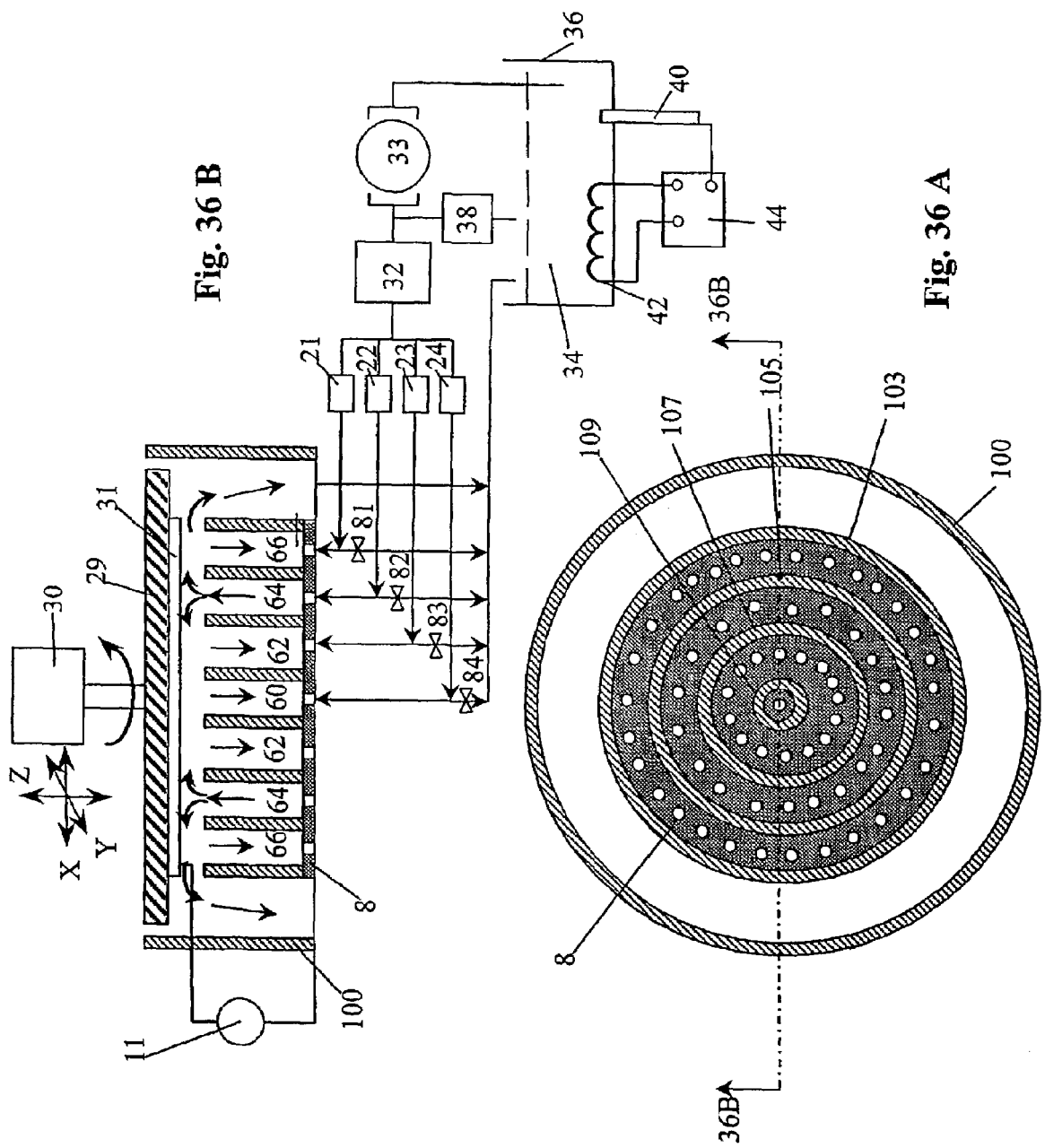
FIG. 36A is a top view of a portion of a thirty-ninth alternative embodiment in accordance with various aspects of the present invention.
FIG. 36B is a view, partly in cross section, taken along the line 36B—36B in FIG. 36A, and partly in block diagram form, of the alternative embodiment shown in FIG. 36A.

With reference now to FIGS. 36A and 36B, another alternative embodiment of the present invention, according to various aspects of the present invention, is shown. The embodiment of FIGS. 36A and 36B is similar to that of FIGS. 14A and 14B except that all cathodes are replaced by a one-piece cathode 8. In the present alternative embodiment, cathode 8 can be suitably connected to single power supply 11.

Using the present alternative embodiment described above, the following process steps can be suitably employed to selectively electropolish portions of wafer 31:

Step 1: Turn on power supply 11;

Step 2: Turn on LMFC 21 and valves 82, 83, and 84, turn off LMFCS 22, 23, 24 and valve 81, such that electrolyte 34 only contacts the portion of wafer 31 above sub-polishing bath 66, and then flows back to electrolyte reservoir 36 through the spaces between section walls 100 and 103, 103 and 105, 105 and 107, 107 and 109. In this manner, metal layer 121 (FIG. 1A) is electropolished from the portion of wafer 31 above sub-polishing bath 66;

Step 3: When metal layer 121 (FIG. 1A) reaches a set value or thickness, turn off power supply 11 and turn off LMFC 21;

Step 4: Repeat steps 1 to 3 for LMFC 22 (turn on LMFC 22, valves 81, 83, 84, and power supply 11, and turn off LMFCs 21, 23, and 24, valve 82);

Step 5: Repeat steps 1 to 3 for LMFC 23 (turn on LMFC 23, valves 81, 82, 84, and power supply 11, and turn off LMFCs 21, 22, and 24, valve 83); and Step 6: Repeat steps 1 to 3 for LMFC 24 (turn on LMFC 24, valves 81, 82, 83, and power supply 11, and turn off LMFCs 21, 22 and 23, and valve 84).

In the above described polishing process, instead of polishing from the periphery of wafer 31 to the center of wafer 31, the polishing also can be performed from center to periphery, or can be performed randomly choosing various cathode sequences.

In addition to selectively electropolishing portions of wafer 31, using the present alternative embodiment described above, the following process steps can be employed to electropolish the entire surface of wafer 31 at one time:

Step 1: Turn on power supply 11;

Step 2: Turn on LMFCs 21, 22, 23 and 24 and turn off valves 81, 82, 83 and 84. The flow rate of electrolyte 34 from each LMFC 21, 22 and 23 can be suitably set proportionate to the surface area of wafer 31 covered by the corresponding cathode; and Step 3: Turn off power supply 11 and LMFCs 21, 22, 23 and 24 until metal layer 121 (FIG. 1A) reaches a set value or thickness. Also, power supplies 11, 12 and 13 can be turned off at different times to adjust the thickness uniformity of metal layer 121 (FIG. 1A).

Figure 37:
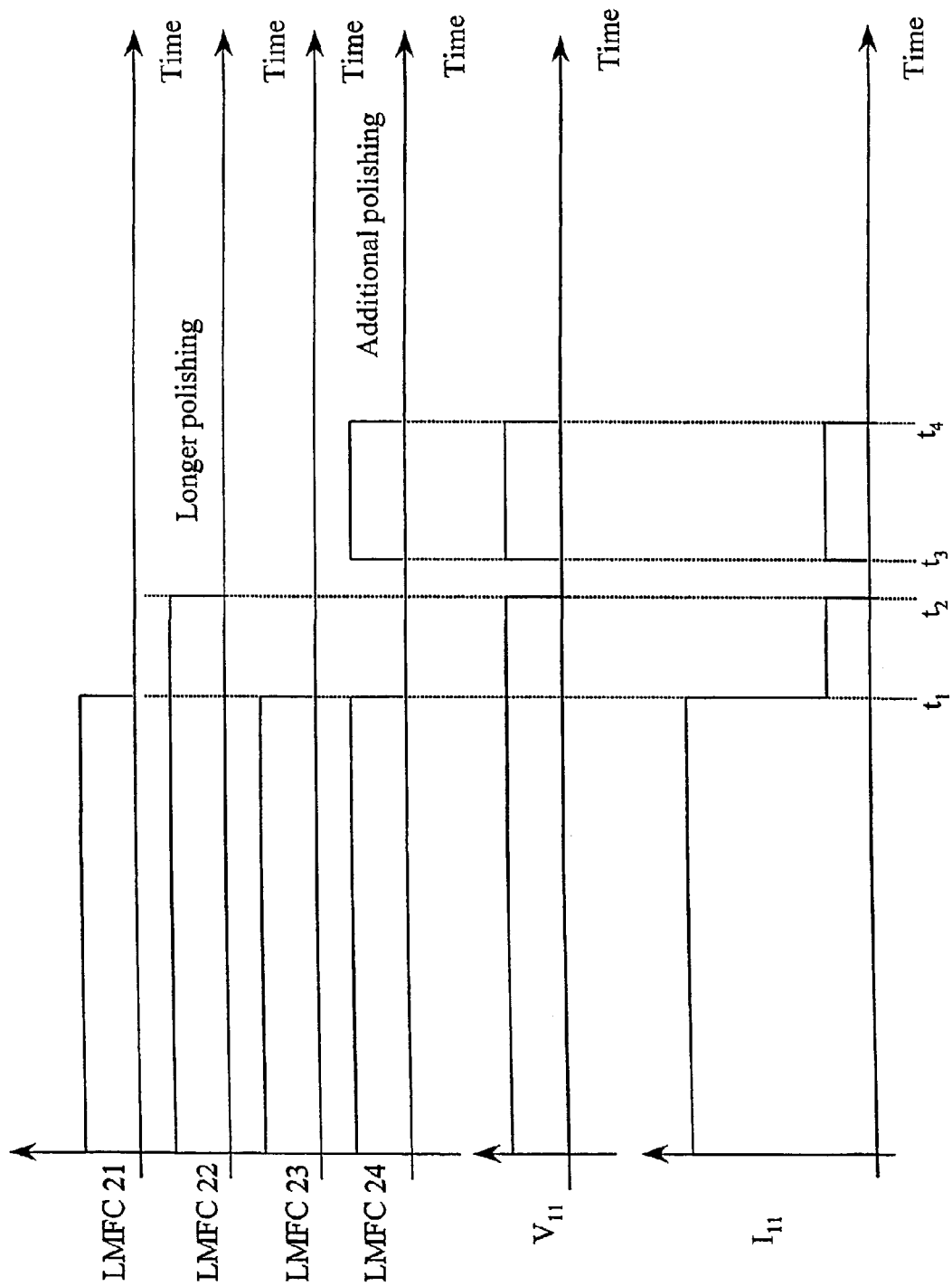
FIG. 37 is a set of waveforms depicting a portion of an electropolishing process in accordance with various aspects of the present invention.

LMFCs can be turned off at different times in order to adjust the electropolishing film thickness uniformity as shown in FIG. 37. At time $t_1$, only LMFCs 21, 23, and 24 are turned off, and valves 81, 83, and 84 are also turned off. Therefore, electrolyte 34 does not contact wafer 31 except for the portion of wafer 31 above sub-polishing bath 64. As the power supply 11 remains turned on, metal layer 121 (FIG. 1A) can be suitably electropolished from the portion of wafer 31 above sub-polishing bath 64. At time $t_2$, LMFC 22 is turned off. Similarly, LMFC 24 is turned on at time $t_3$ and turned off at time $t_4$ to obtain extra polishing of portions of wafer 31 above sub-polishing bath 60. Times $t_2$ and $t_4$ can be fine-tuned by measuring wafer thickness uniformity.

Figure 38:
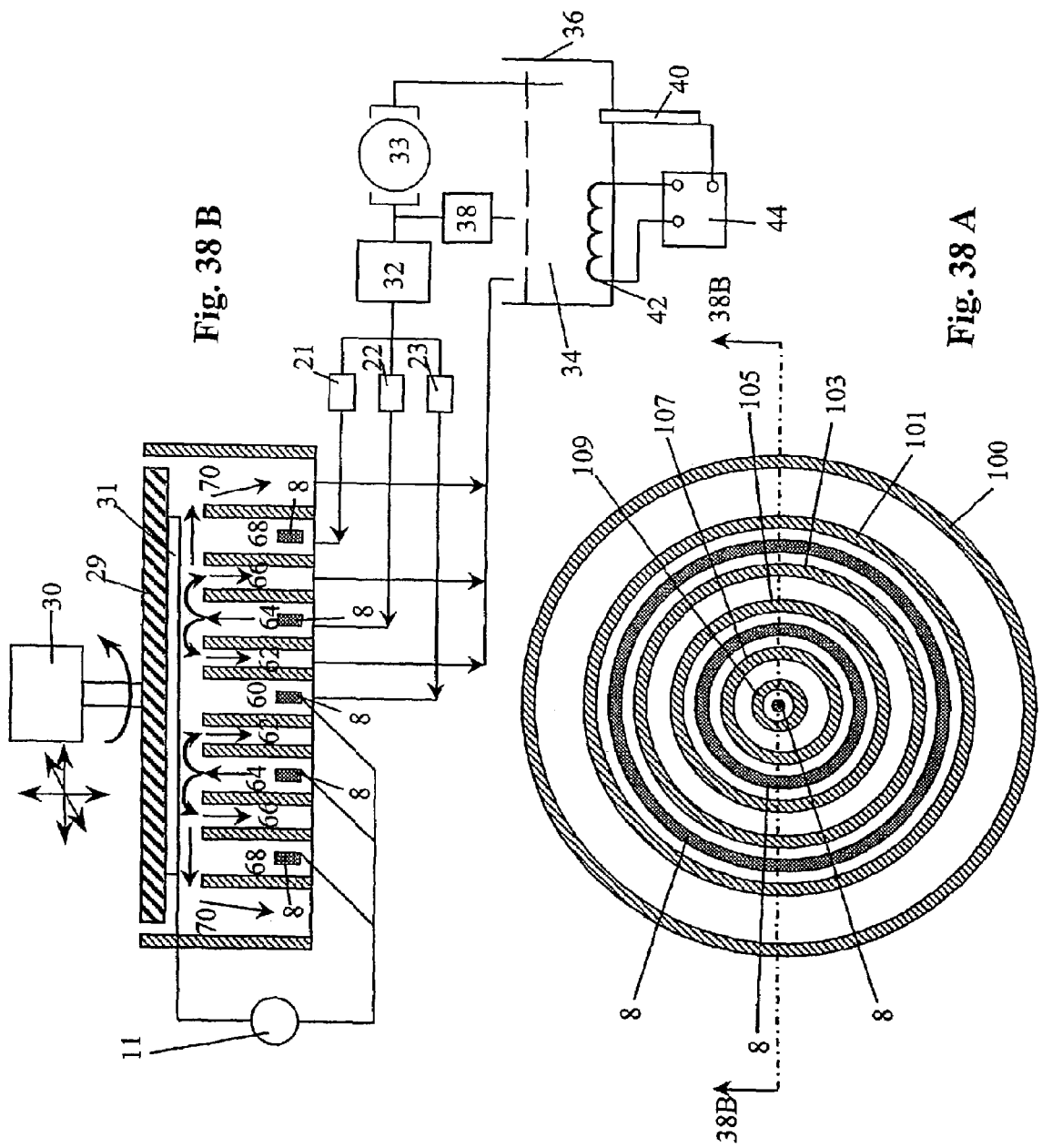
FIG. 38A is a top view of a portion of a fortieth alternative embodiment in accordance with various aspects of the present invention.
FIG. 38B is a view, partly in cross section, taken along the line 38B—38B in FIG. 38A, and partly in block diagram form, of the alternative embodiment shown in FIG. 38A.

With reference now to FIGS. 38A and 38B, still another alternative embodiment of the present invention, according to various aspects of the present invention, is shown. The embodiment of FIGS. 38A and 38B is similar to that of FIGS. 7A and 7B except that all cathodes are connected to single power supply 11. Since the electrolyte only contacts the portion of wafer 31 being selectively electropolished, a majority of the polishing current will come from the cathode and go to that portion of wafer 31. The polishing process steps are similar to those of FIGS. 7A and 7B, with power supply 11 replacing power supplies 12 and 13.

Figure 39:
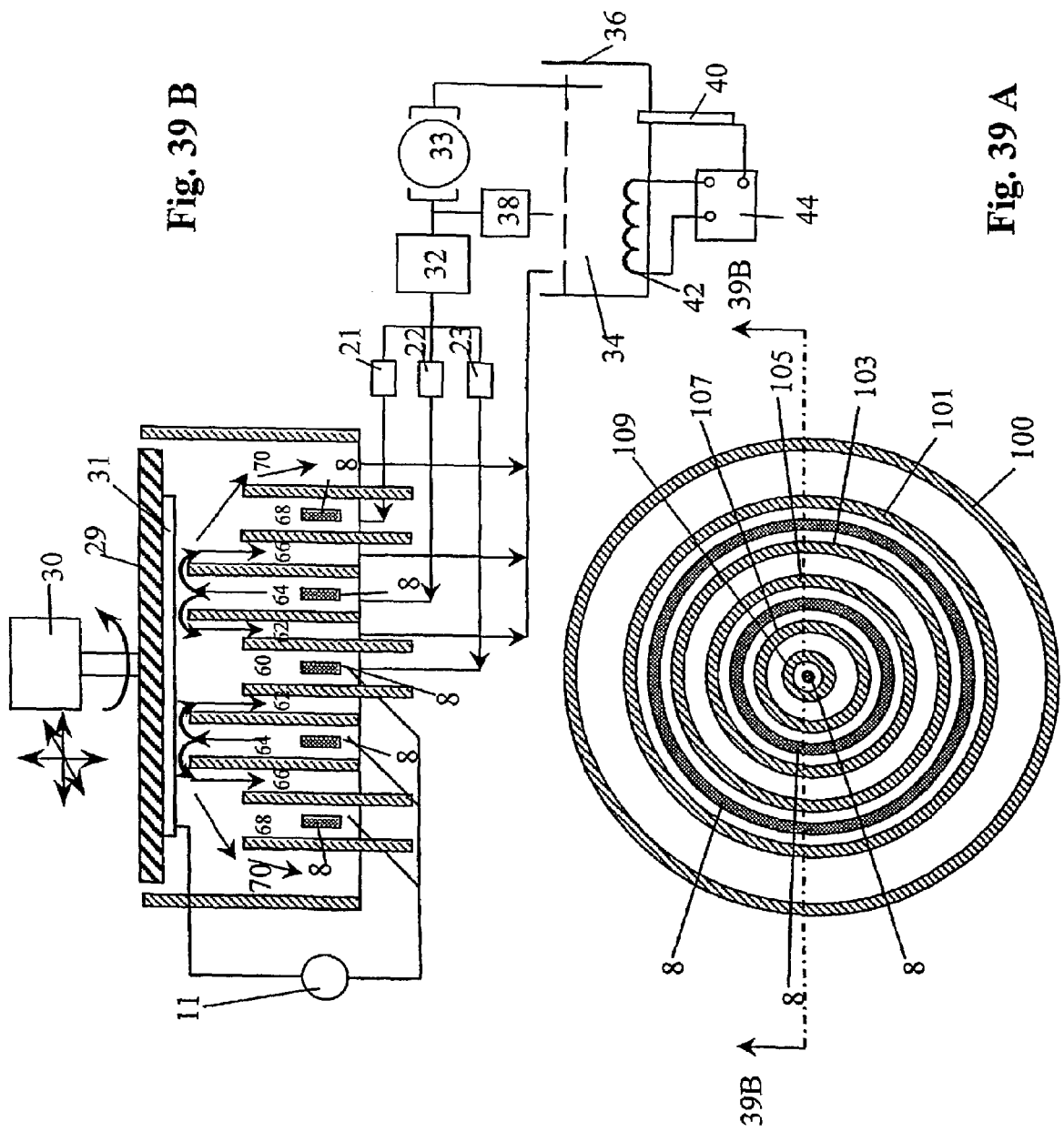
FIG. 39A is a top view of a portion of a forty-first alternative embodiment in accordance with various aspects of the present invention.
FIG. 39B is a view, partly in cross section, taken along the line 39B—39B in FIG. 39A, and partly in block diagram form, of the alternative embodiment shown in FIG. 39A.
Figure 41:
FIG. 41 is a set of waveform diagrams depicting a portion of an electropolishing process in accordance with various aspects of the present invention.

With reference now to FIGS. 39A and 39B, yet another alternative embodiment of the present invention, according to various aspects of the present invention, is shown. The embodiment of FIGS. 39A and 39B is similar to that of FIGS. 38A and 38B except that section walls 101, 103, 105, 107 and 109 can move up and down to adjust the flow pattern. As shown in FIG. 41, section walls 105 and 107 are moved up, so that the electrolyte flows toward the portion of wafer 31 above section walls 105 and 107.

Using the present alternative embodiment described above, the following process steps can be suitably employed to selectively electropolish portions of wafer 31:

Step 1: Turn on power supply 11;

Step 2: Turn on LMFC 21 only and move section walls 101 and 103 close to wafer 31, such that electrolyte 34 only contacts the portion of wafer 31 above section walls 101 and 103. In this manner, metal layer 121 (FIG. 1A) on the portion of wafer 31 above section walls 101 and 103 is suitably electropolished;

Step 3: When metal layer 121 (FIG. 1A) reaches a set value or thickness, turn off power supply 11, turn off LMFC 21, and move section walls 101 and 103 to a lower position;

Step 4: Repeat steps 1 to 3 for section walls 105 and 107, using LMFC 22 and section walls 105 and 107, respectively; and Step 5: Repeat steps 1 to 3 for section wall 109, using LMFC 23 and section wall 109.

In addition to selectively electropolishing portions of wafer 31, using the present alternative embodiment described above, the following process steps can be employed to electropolish the entire surface of wafer 31 at one time:

Step 1: Turn on power supply 11;

Step 2: Turn on LMFCs 21, 22 and 23, and move all section walls 101, 103, 105, and 107 and tube 109 close to wafer 31. The flow rate of electrolyte 34 from LMFCs 21, 22, 23 and 24 can be suitably set proportionate to the surface area of wafer 31 covered by the corresponding cathode; and Step 3: Move all section walls down to a lower position, and turn off all LMFCs at the same time, then turn off power supply 11. Each pair of section walls can also be moved down at a different time, with power supply 11 on, in order adjust thickness uniformity. For example, as shown in FIGS. 39A and 39B, section walls 105 and 107 are being kept at higher positions with LMFC 22 on. Wafer 31 will be selectively electropolished in the area between section walls 105 and 107.

Figure 40:
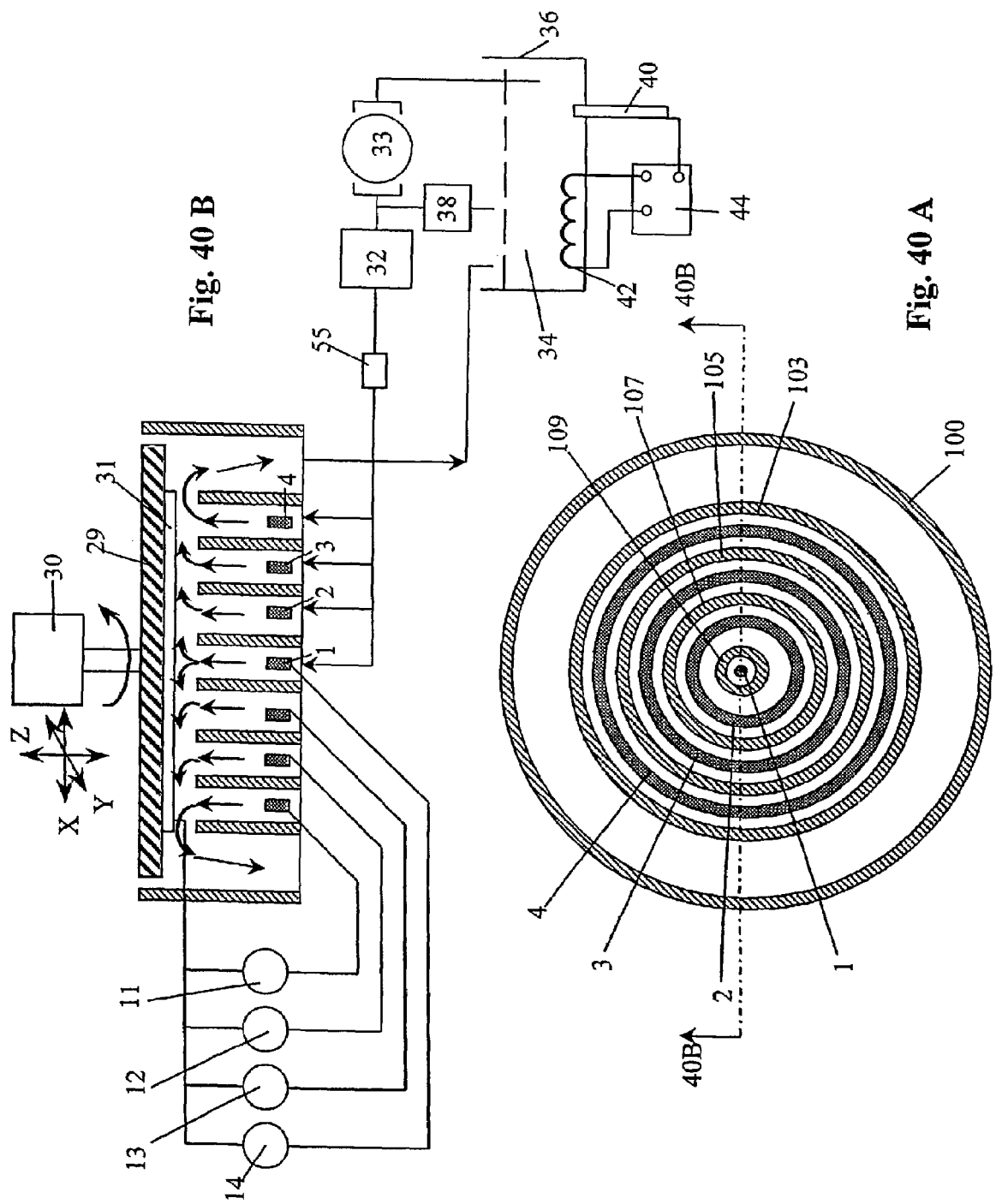
FIG. 40A is a top view of a portion of a forty-second alternative embodiment in accordance with various aspects of the present invention.
FIG. 40B is a view, partly in cross section, taken along the line 40B—40B in FIG. 40A, and partly in block diagram form, of the alternative embodiment shown in FIG. 40A.

With reference now to FIGS. 40A and 40B, another alternative embodiment of the present invention, according to various aspects of the present invention, is shown. FIGS. 40A and 40B illustrate an embodiment with multiple power supplies and a single LMFC for polishing metal layer 121 (FIG. 1A) directly on a substrate with a barrier layer on top. The embodiment of FIGS. 40A and 40B is similar to that of FIGS. 14A and 14B except that LMFCs 21, 22, 23 and 24 are replaced by a single LMFC 55.

Using the present alternative embodiment described above, the following process steps can be suitably employed to selectively electropolish portions of wafer 31:

Step 1: Turn on power supply 11 to output negative potential to electrode 4, and turn on power supplies 12, 13, and 14 to output positive or zero potential to electrodes 3, 2, and 1, respectively;

Step 2: Turn on LMFC 55, thereby immersing the whole wafer into electrolyte 34. In this manner, metal layer 121 (FIG. 1A) will be polished away only from the portion of wafer 31 above cathode 4;

Step 3: When metal layer 121 (FIG. 1A) reaches a set value or thickness, turn off power supply 11;

Step 4: Repeat steps 1 to 3 for cathode 3 (turn on power supply 12 to output positive potential to cathode 3, and power supplies 11, 13 and 14 to output negative potential to cathodes 4, 2 and 1);

Step 5: Repeat steps 1 to 3 for cathode 2 (turn on power supply 13 to output positive potential to cathode 2, and power supplies 11, 12 and 14 to output negative potential to cathodes 4, 3 and 1); and Step 6: Repeat steps 1 to 3 for cathode 1 (turn on power supply 14 to output positive potential to cathode 1, and power supplies 11, 12 and 13 to output negative potential to cathodes 4, 3 and 2).

Figure 42:
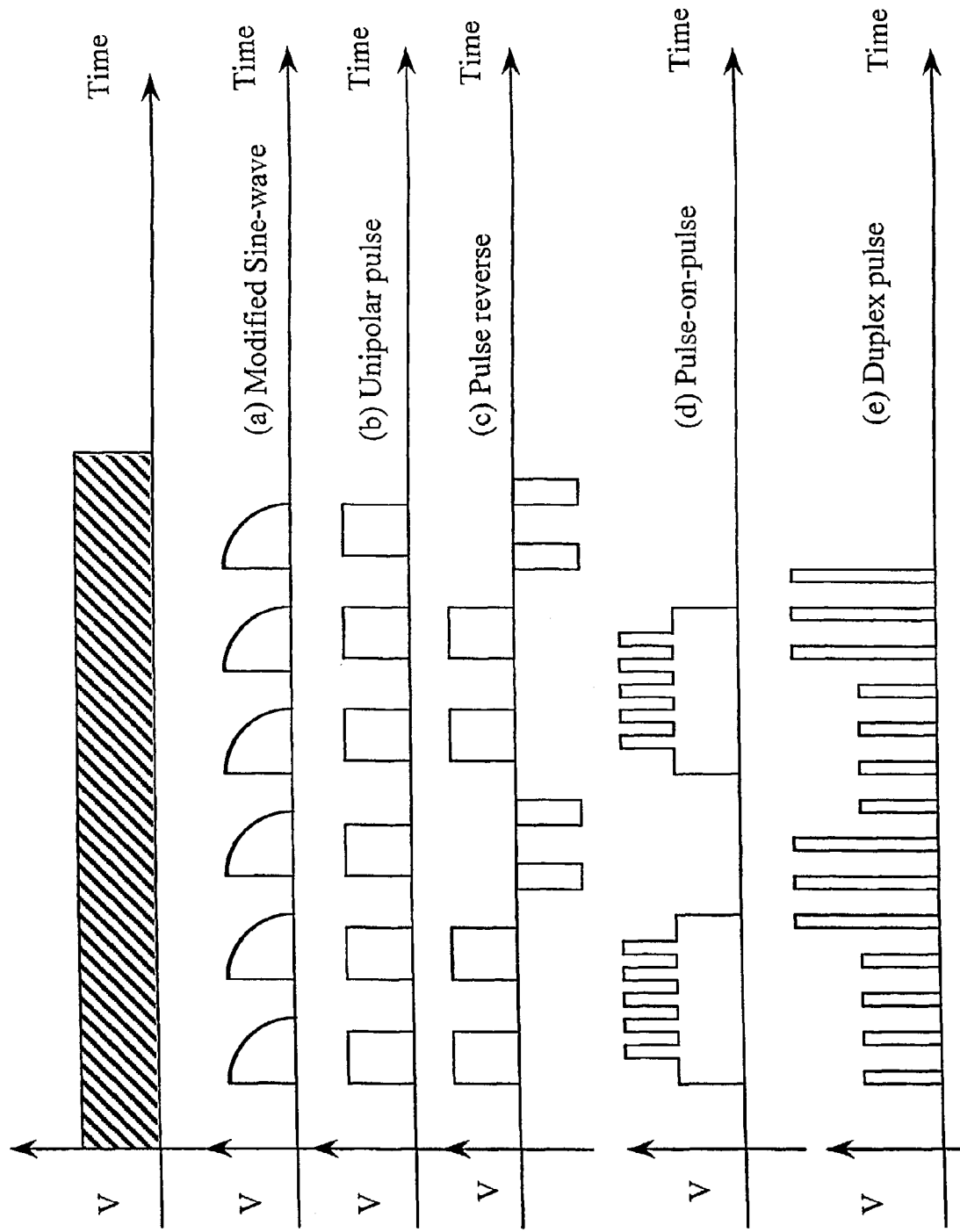
FIG. 42 is additional sets of waveforms, which may be used in conjunction with the present invention.

FIG. 41 shows the power supply turn on/off sequence for polishing wafer areas 4 (above cathode 4), 3, 2, and then 1. The power supply output wave form can be selected from a variety of wave forms such as a modified sine-wave form, a unipolar pulse, a pulse reverse, a pulse-on-pulse, or a duplex pulse, as shown in FIG. 42.

In the above selective electropolishing process, instead of electropolishing from the periphery to the center of the wafer, electropolishing can also be performed from center to periphery, or can be performed randomly by choosing an arbitrary cathode sequence.

In addition to selectively electropolishing portions of wafer 31, using the present alternative embodiment described above, the following process steps can be employed to electropolish the entire surface of wafer 31 at one time:

Step 1: Turn on power supplies 11, 12, 13 and 14. The current of each power supply 11, 12, 13 and 14 can be suitably set proportionate to the surface area of wafer 31 covered by the corresponding cathode.

Step 2: Turn on LMFC 55; and

Step 3: Turn off power supplies 11, 12, 13 and 14 at the same time when metal layer 121 (FIG. 1A) reaches a set value or thickness. Also, power supplies 11, 12, 13 and 14 can be turned off at different times to adjust the thickness uniformity of metal layer 121 (FIG. 1A).

With reference now to FIGS. 43A and 43B, still another alternative embodiment of the present invention, according to various aspects of the present invention, is shown. FIGS. 43A and 43B show an embodiment of the apparatus with multiple power supplies and a single LMFC for polishing metal layer 121 (FIG. 1A) directly on substrate 123 (FIG. 1A) with barrier layer 122 (FIG. 1A) on top. The embodiment of FIGS. 43A and 43B is similar to that of FIGS. 40A and 40B except that section walls can move up and down to adjust the flow pattern. As shown in FIGS. 43A and 43B, section walls 105 and 107 can be moved up, so that the electrolyte flows toward the portion of wafer 31 above walls 105 and 107.

Using the present alternative embodiment described above, the following process steps can be suitably employed to selectively electropolish portions of wafer 31:

Step 1: Turn on power supply 11;

Step 2: Turn on LMFC 55 and move section walls 101 and 103 adjacent to wafer 31, such that electrolyte 34 only contacts the portion of wafer 31 above section walls 101 and 103. In this manner, metal layer 121 (FIG. 1A) on the portion of wafer 31 above section walls 101 and 103 is suitably electropolished;

Step 3: When metal layer 121 (FIG. 1A) reaches a set value or thickness, turn off power supply 11, and move section walls 101 and 103 to a lower position;

Step 4: Repeat steps 1 to 3 for section wall 105 and 107, using section walls 105 and 107 and power supply 12; and Step 5: Repeat steps 1 to 3 for section wall 109, using section wall 109 and power supply 13.

In addition to selectively electropolishing portions of wafer 31, using the present alternative embodiment described above, the following process steps can be employed to electropolish the entire surface of wafer 31 at one time:

Step 1: Turn on power supplies 11, 12, and 13. The current through each power supply 11, 12 and 13 can be suitably set proportionate to the surface area of wafer 31 that is covered by the corresponding cathode;

Step 2: Turn on LMFC 55, and move all section walls 101, 103, 105, 107 and section wall 109 close to wafer 31; and Step 3: Turn off power supplies 11, 12 and 13 at the same time when the thickness uniformity of metal layer 121 (FIG. 1A) reaches a set value or thickness. Also, power supplies 11, 12 and 13 can be turned off at different times to adjust the thickness uniformity of metal layer 121 (FIG. 1A).

Figure 44:
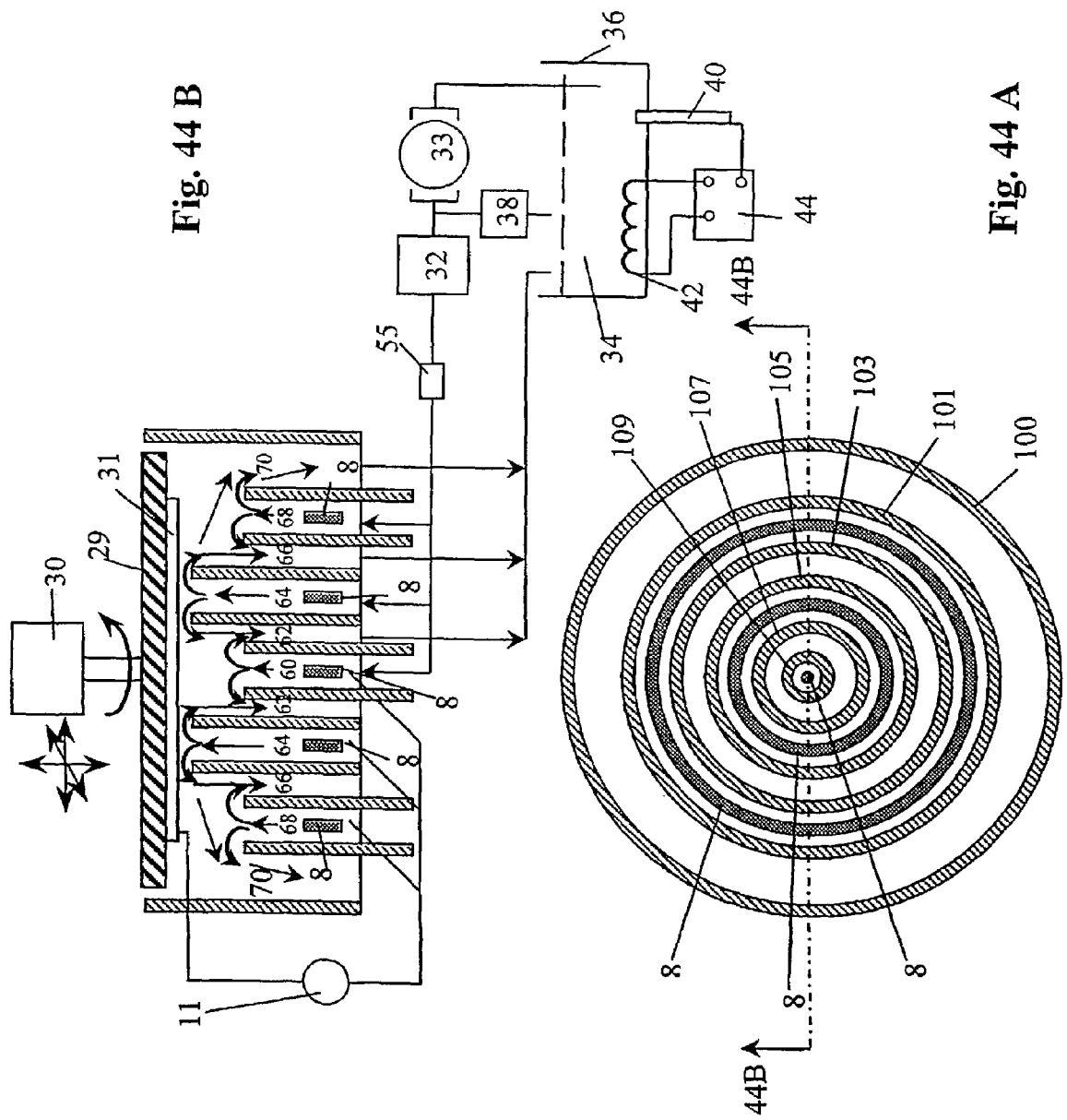
FIG. 44A is a top view of a portion of a forty-fourth alternative embodiment in accordance with various aspects of the present invention.
FIG. 44B is a view, partly in cross section, taken along the line 44B—44B in FIG. 44A, and partly in block diagram form, of the alternative embodiment shown in FIG. 44A.

With reference now to FIGS. 44A and 44B, yet another alternative embodiment of the present invention, according to various aspects of the present invention, is shown. FIGS. 44A and 44B show an embodiment of the apparatus with a single power supply and single LMFC for polishing metal layer 121 (FIG. 1A) directly on substrate 123 (FIG. 1A) with barrier layer 122 (FIG. 1A) on top. The embodiment of FIGS. 44A and 44B is similar to that of FIGS. 43A and 43B except that one power supply 11 is used, and all cathodes are connected to single power supply 11. Similarly, section walls can move up and down to adjust the flow pattern. As shown in FIGS. 44A and 44B, section walls 105 and 107 can be moved up, so that the electrolyte flows toward the portion of wafer above wall 105 and 107.

Using the present alternative embodiment described above, the following process steps can be suitably employed to selectively electropolish portions of wafer 31:

Step 1: Turn on power supply 11;

Step 2: Turn on LMFC 55 and move section walls 101 and 103 close to wafer 31, such that electrolyte 34 only contacts the portion of wafer 31 above section walls 101 and 103. In this manner, metal layer 121 (FIG. 1A) on the portion of wafer 31 above section walls 101 and 103 is suitably electropolished;

Step 3: When metal layer 121 (FIG. 1A) reaches a set value or thickness, turn off power supply 11, and move section walls 101 and 103 to a lower position;

Step 4: Repeat steps 1 to 3 for section walls 105 and 107 (move section walls 105 and 107 up close to wafer 31, and turn on power supply 11); and Step 5: Repeat steps 1 to 3 for section walls 109 (move section wall 109 up close to wafer 31, and turn on power supply 11).

In addition to selectively electropolishing portions of wafer 31, using the present alternative embodiment described above, the following process steps can be employed to electropolish the entire surface of wafer 31 at one time:

Step 1: Turn on power supply 11;

Step 2: Turn on LMFC 55, and move all section walls 101, 103, 105, 107 and 109 up close to wafer 31; and Step 3: Move all section walls down to a lower position at the same time, then turn off power supplies 11. Each pair of section walls can also be moved down at different times, with power supply 11 on, in order adjust thickness uniformity. For example, as shown in FIGS. 44A and 44B, section walls 105 and 107 are being kept at higher position with power supply 11 on. Wafer area above section wall 105 and 107 will have extra polishing film on that portion. The extra polishing time length and location can be determined by analyzing the thickness uniformity of wafer through later film characterization.

Figure 45:
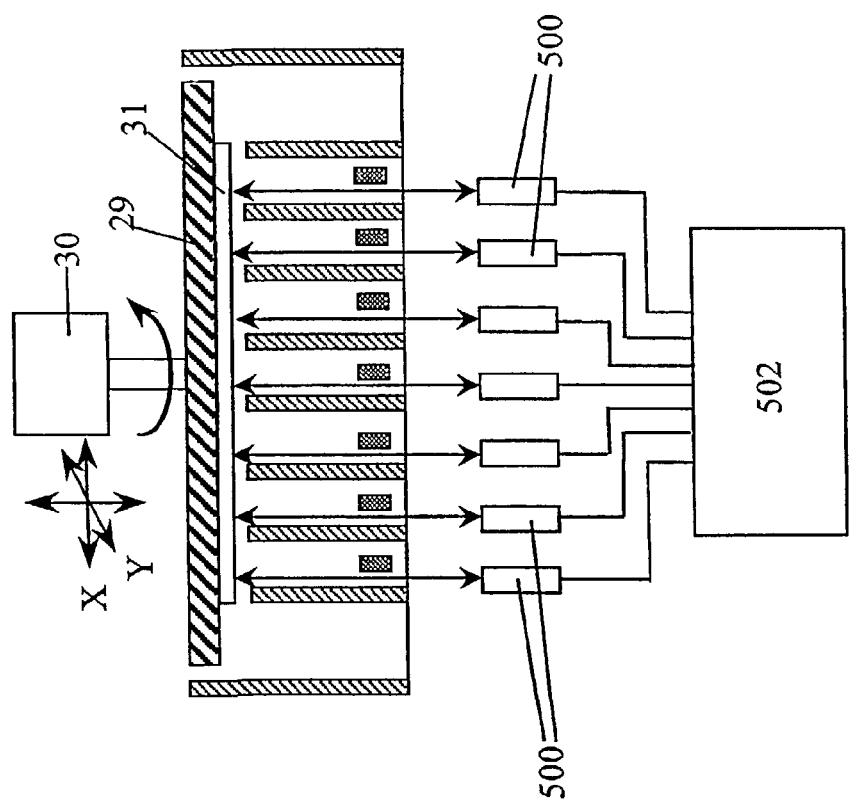
FIG. 45 is a view, partly in cross section, and partly in block diagram form, of a forty-fifth alternative embodiment in accordance with various aspects of the present invention.
Figure 46:
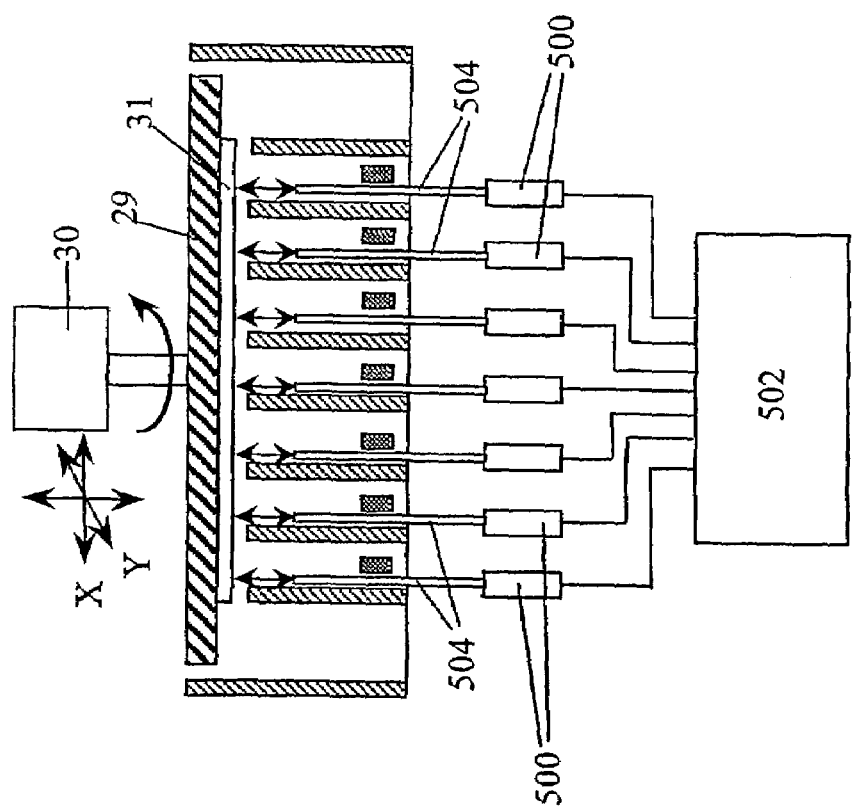
FIG. 46 is a view, partly in cross section, and partly in block diagram form, of a forty-sixth alternative embodiment in accordance with various aspects of the present invention.

With reference now to FIGS. 45 and 46, two additional alternative embodiments of the present invention, according to various aspects of the present invention, are shown. FIGS. 45 and 46 show embodiments configured with an in-situ film thickness uniformity monitor. Sensors 500 can be ultrasonic type thickness measurement sensors. Signal detected from sensors 500 is sent back to computer 502. The in-situ thickness data can be used to adjust or control polishing uniformity and final thickness.

Figure 58:
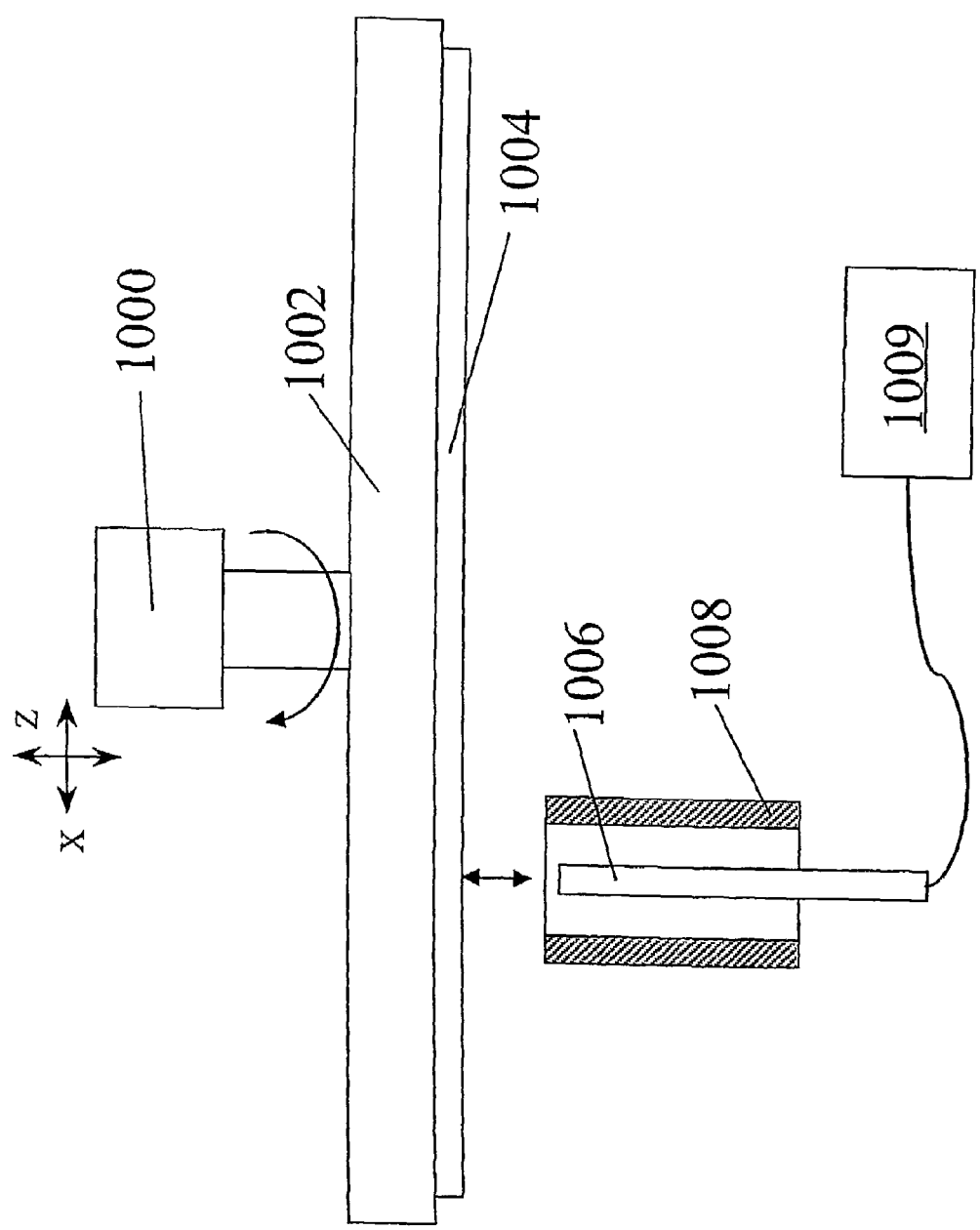
FIG. 58 is a side view of a portion of an end-point detection system.

With reference now to FIG. 58, one embodiment of the present invention includes a drive mechanism 1000, a chuck 1002, a wafer 1004, an injection nozzle 1008, and an end-point detector 1006. During the electropolishing process, drive mechanism 1000 can be configured to rotate wafer 1004 (indicated in FIG. 58 as about the z-axis). Drive mechanism 1000 can also be configured to move wafer 1000 horizontally relative to nozzle 1008 (indicated in FIG. 58 as the x-direction). As alluded to earlier with regard to another embodiment, this movement of the wafer during electropolishing can enhance the uniformity of the electropolished wafer surface.

Additionally, during the electropolishing process, end-point detector 1006 is configured to detect the thickness of the metal layer on wafer 1004. As described above with regard to the embodiments depicted in FIGS. 45 and 46, end-point detector 1006 can include various sensors, such as ultrasonic sensors. In the present embodiment, end-point detector 1006 is configured as an optical reflection sensor. Accordingly, as the metal layer is electropolished, end-point detector 1006 responds to the changing reflectivity of the wafer surface.

Figure 59:
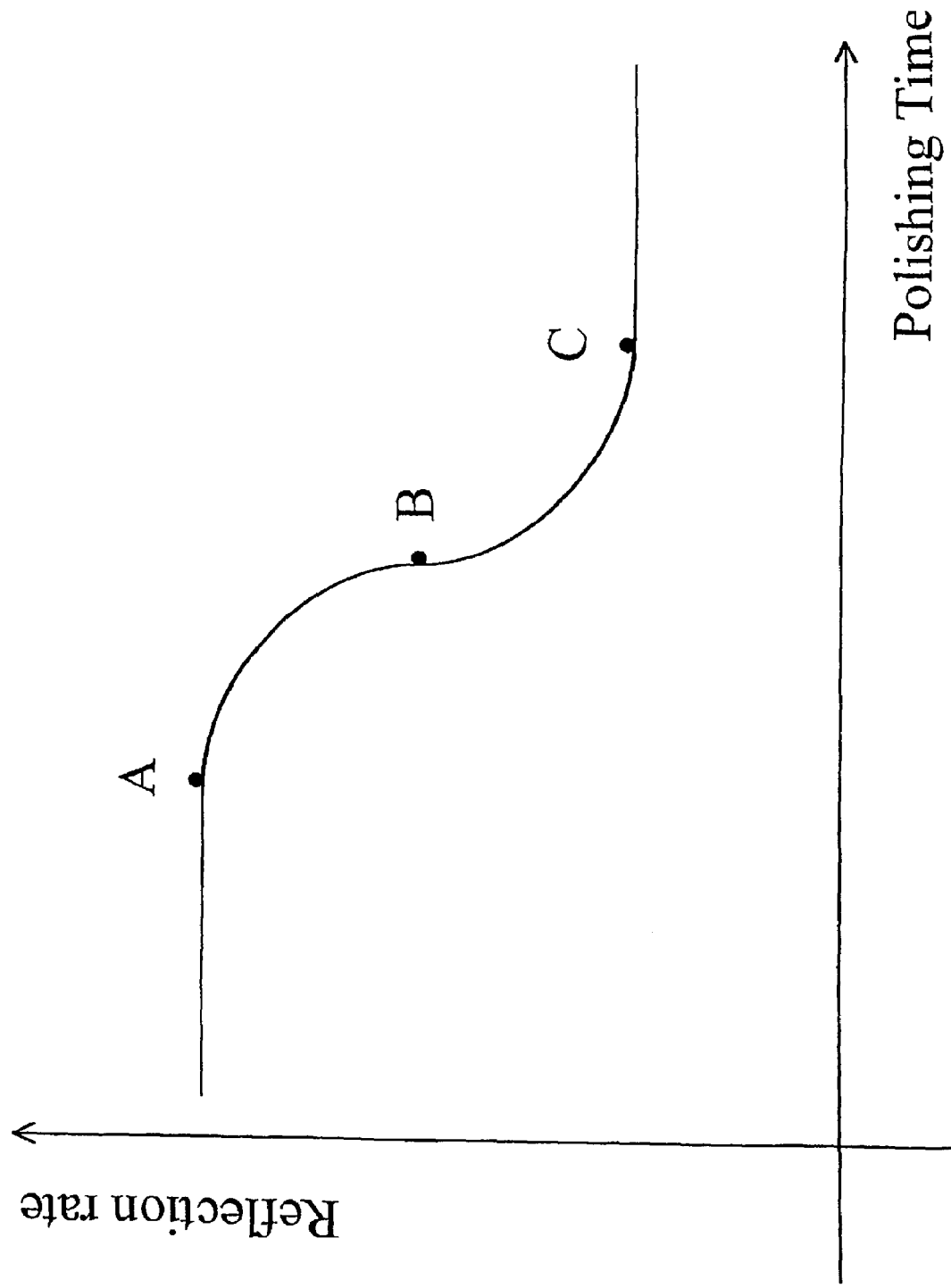
FIG. 59 is a graph depicting the relationship between reflection rate and polishing time.

More particularly, with reference to FIG. 59, for illustrative purpose, a graph depicting the changes in the reflectivity of a wafer surface is shown. It should be recognized, however, that the shape of the curve depicted in FIG. 59 can vary depending on the particular application.

In the graph in FIG. 59, the portion of the line before point A corresponds to the portion of the electropolishing process when the metal layer on the wafer surface is being removed. The reflectivity of the wafer surface does not change significantly during this portion of the electropolishing process because the wafer surface remains covered by the metal layer.

In the graph in FIG. 59, point A corresponds to the portion of the electropolishing process when the metal layer has nearly been removed from the surface of the wafer, but the trenches and/or vias remain filled with the metal layer. At this point, the reflectivity begins to change because the barrier layer and/or dielectric layer typically has a different reflection rate than the metal layer.

In the graph in FIG. 59, point C corresponds to the portion of the electropolishing process when the metal layer has been completely removed from the 30 surface of the wafer. At this point, the reflectivity begins to level off again.

Thus, to facilitate a smooth, planar, and non-recessed wafer surface, the electropolishing process is stopped between points A and C. Toward this end, end-point detector 1006 can be configured to provide the optical reflection rate of an area of the wafer during electropolishing.

More particularly, the local reflection rate of an area of the wafer $R_{light}$ can be expressed as follows:

$$R_{light} = R_{light}(r, \theta)$$

Where, r is the radius of the area being electropolished. $\theta$ is the rotating angle of the area being electropolished.

The electropolishing process can be stopped or ended when $R_{light}$ measured by end-point detector 1006 reaches a predetermined rate $R_{target}$. The value of $R_{target}$ can be determined experimentally. For example, wafers can be processed at various $R_{target}$ settings to determine the value that produces the desired wafer surface profile. Once this value is determined, it can be used to process additional wafers.

Alternatively, $R_{target}$ can be calculated based on the pattern structure on the wafer. More particularly, each area of the wafer includes a portion with metal layers formed within trenches and/or vias and the remaining portion with a barrier layer and/or dielectric layer. Thus, a pattern density PD can be calculated as follows:

$$PD = \frac{SA_{ML}}{SA_T}$$

Where, $SA_{ML}$ is the surface area with trenches and/or vias. $SA_T$ is the total surface area. The values for $SA_{ML}$ and $SA_T$ of any location on the wafer can be obtained from the mask design of the wafer. The target optical reflectivity $R_{target}$ can then be calculated as follows:

$$R_{target} = (R_{ML} \times PD) + [R_{barrier} \times (1 - PD)]$$

Where, $R_{ML}$ is the reflectivity of the metal layer. R barrier is the reflectivity of the barrier layer. It should be recognized that if the wafer does not include a barrier layer, then $R_{barrier}$ would be the reflectivity of the dielectric layer.

Thus, at any location r and $\theta$ on the wafer, end-point detector 1006 provides a measurement of the optical reflectivity $R_{light}$. For that location, the target optical reflectivity $R_{target}$ can be calculated based on the pattern density PD data obtained from the mask design of the wafer. When the measured optical reflectivity $R_{light}$ equals the target optical reflectivity $R_{target}$, then electropolishing can be stopped for that area.

As described earlier with regard to various embodiments, the electropolishing process can be stopped or ended entirely (for example, by turning off the power supply). Alternatively, the electropolishing rate can be reduced to continue to monitor the reflectivity of the metal layer on the wafer surface. If the reflectivity increases (for example, as in unpolished patches or areas of the wafer), then the electropolishing rate can be increased.

As also described earlier with regard to various embodiments, the power supply (not shown) can be operated in DC mode or in a variety of pulse modes. Additionally, it can be operated in constant current mode, constant voltage mode, or combination of these modes. Further, when a pulsed power supply is used, the duty cycle can be constant or varied.

Figure 60:
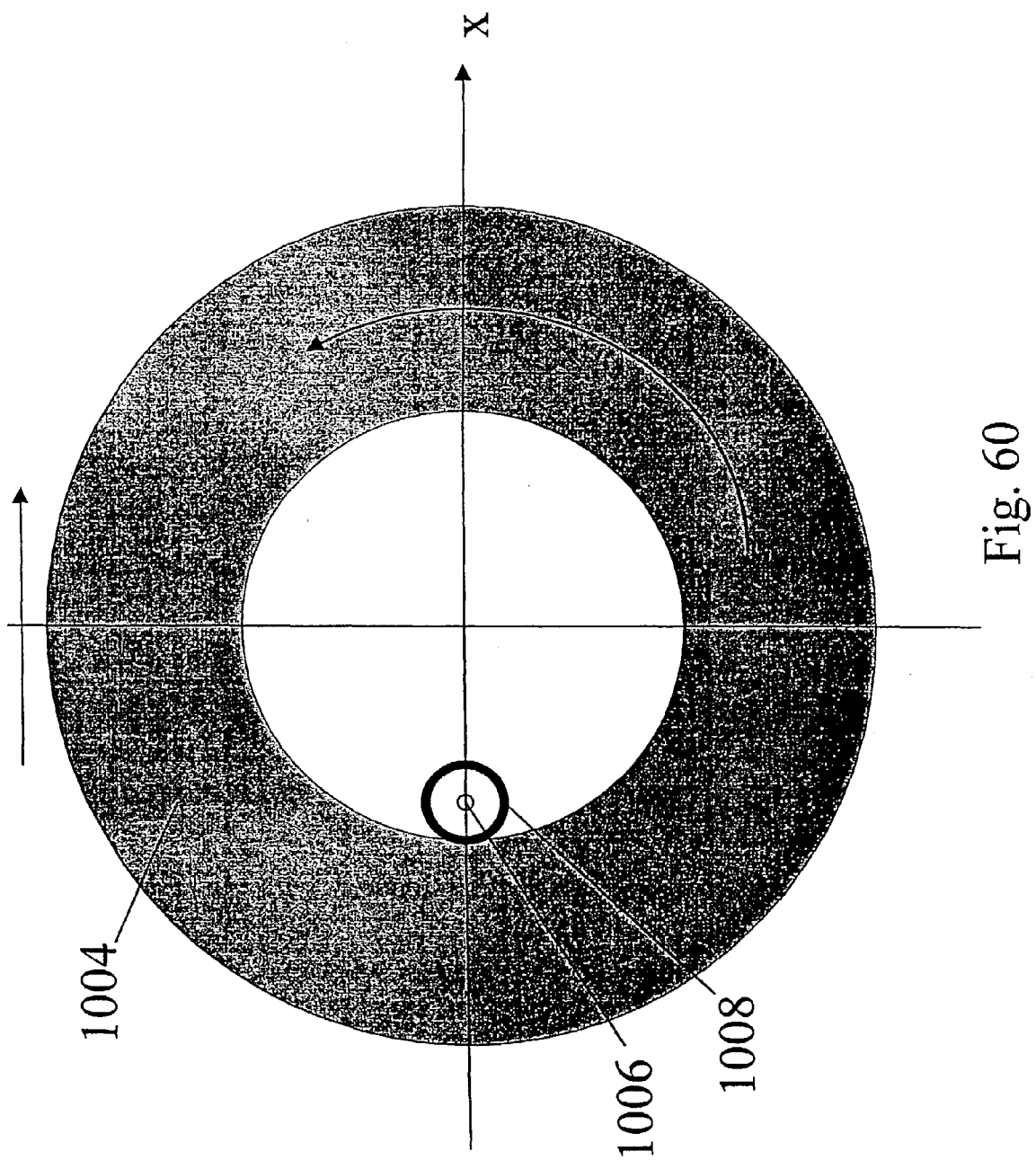
FIG. 60 is a top view of a portion of an end-point detection system.

With reference now to FIG. 60, as wafer 1004 is rotated and moved horizontally, the metal layer on the wafer surface can be electropolished from the center to the edge of wafer 1004 in a spiral pattern. It should be recognized, however, that wafer 1004 can be electropolished in any pattern or order. For example, wafer 1004 can be electropolished beginning from the edge to the center of wafer 1004. Alternatively, wafer 1004 can be electropolished beginning and ending from any points between the edge and the center of wafer 1004.

Additionally, the signals from end-point detectors 1006 can be used to control the speed of the rotation and horizontal movement of wafer 1004. It can also be used to control the polishing power and the polishing rate used. More particularly, the signals from end-point detectors 1006 can be provided to an analyzer 1009. Analyzer 1009 is configured to evaluate and process the signals received from end-point detectors 1006. Based on these signals, analyzer 1009 can then control the rotation and horizontal movement of wafer 1004, the polishing power, and the polishing rate. Analyzer 1009 can include any convenient processing processor, such as an electronic circuit, a computer chip, a computer, and the like. Analyzer 1009 can also include any convenient programming instructions or software needed to carry out the various functions described herein.

When the wafer is translated with constant horizontal speed and the polishing power is constant, the rotation speed can be altered as follows:

$$\omega = C_1 / \{[R_{light}(r, \theta) - R_{target}(r, \theta)]^N r\}$$

where, $\omega$ is the speed of rotation of wafer 1004. r is the distance between nozzle 1008 and the center of wafer 1004. $C_1$ is a constant. N can include any number including integer, rational and irrational fraction. Values for $C_1$ and N can be determined experimentally to tune the electropolishing process to produce the desired wafer surface profile.

When the wafer is translated with constant horizontal speed and the polishing power is varied, the rotation speed can be expressed as follows:

$$\begin{cases} \omega = v_0 / r \\ P_{polishing} = C_2 [R_{light}(r, \theta) - R_{target}(r, \theta)]^N \end{cases}$$

Where, $\omega$ is the speed of rotation of wafer 1004. r is the distance between nozzle 1008 and the center of wafer 1004. $v_0$ is the constant tangent speed of the area of wafer 1004 relative to nozzle 1008. $P_{polishing}$ is the electropolishing power being applied. This can include DC or pulsed power. It can include power provided in constant current mode, constant voltage mode, or combination of these modes. Also, when a pulsed power is used, the duty cycle can be constant or varied. $C_2$ is a constant. N can include any number, such as integer, rational and irrational fractions, and the like. Values for $C_2$ and N can be determined experimentally to tune the electropolishing process to produce the desired wafer surface profile.

When the wafer is translated with constant rotation speed and the polishing power is constant, the horizontal speed can be expressed as follows:

$$v_r = C_3 / \{[R_{light}(r, \theta) - R_{target}(r, \theta)]^N r\}$$

Where, $v_r$ is the horizontal speed of wafer 1004. r is the distance between nozzle 1008 and center of wafer 1004. $C_3$ is a constant. N can include any number, such as integer, rational and irrational fractions, and the like. Values for $C_3$ and N can be determined experimentally to tune the electropolishing process to produce the desired wafer surface profile.

When the wafer is translated with constant rotation speed and the polishing power can be varied, the horizontal speed $$\begin{cases} v_r = C_4 / r \\ P_{polishing} = C_5 [R_{light}(r, \theta) - R_{target}(r, \theta)]^N \end{cases}$$

where, $v_r$ is the horizontal speed of wafer 1004. r the horizontal distance between nozzle 1008 and center of wafer 1004. $P_{polishing}$ is the electropolishing power being applied. This can include DC or pulsed power. It can include power provided in constant current mode, constant voltage mode, or combination of these modes. Also, when a pulsed power is used, the duty cycle can be constant or varied. $C_4$ and $C_5$ are constants. N can include any number, such as integer, rational and irrational fractions, and the like. Values for $C_4$, $C_5$, and N can be determined experimentally to tune the electropolishing process to produce the desired wafer surface profile.

When just the polishing power is constant, then the rotation speed and the horizontal movement speed can be expressed as follows:

$$\begin{cases} \omega = C_6 / [R_{light}(r, \theta) - R_{target}(r, \theta)]^N \\ v_r = C_7 / \{[R_{light}(r, \theta) - R_{target}(r, \theta)]^N r\} \end{cases}$$

or $$\begin{cases} \omega = C_6 / \{[R_{light}(r, \theta) - R_{target}(r, \theta)]^N r\} \\ v_r = C_7 / [R_{light}(r, \theta) - R_{target}(r, \theta)]^N \end{cases}$$

Where, $\omega$ is the speed of rotation of wafer 1004. r is the horizontal distance between nozzle 1008 and the center of wafer 1004. $v_r$ is the horizontal speed of wafer 1004. $C_6$ and $C_7$ are constants. N can include any number, such as integer, rational and irrational fractions, and the like. Values for $C_6$, $C_7$, and N can be determined experimentally to tune the electropolishing process to produce the desired wafer surface profile.

When the polishing power can be varied, then the rotation speed and the horizontal movement speed can be expressed as follows:

$$\omega = C_6 / [R_{light}(r, \theta) - R_{target}(r, \theta)]^N$$

$$\{v_r = C_7 / \{[R_{light}(r, \theta) - R_{target}(r, \theta)]^N r\}$$

$$P_{polishing} = C_5 [R_{light}(r, \theta) - R_{target}(r, \theta)]^N$$

or $$\omega = C_6 / \{[R_{light}(r, \theta) - R_{target}(r, \theta)]^N r\}$$

$$\{v_r = C_7 / [R_{light}(r, \theta) - R_{target}(r, \theta)]^N$$

$$P_{polishing} = C_5 [R_{light}(r, \theta) - R_{target}(r, \theta)]^N$$

Where, $\omega$ is the speed of rotation of wafer 1004. r is the distance between nozzle 1008 and the center of wafer 1004. $v_r$ is the horizontal speed of wafer 1004. $P_{polishing}$ is the electropolishing power being applied. This can include DC or pulsed power. It can include power provided in constant current mode, constant voltage mode, or combination of these modes. Also, when a pulsed power is used, the duty cycle can be constant or varied. $C_5$, $C_6$, and $C_7$ are constants. N can include any number, such as integer, rational and irrational fractions, and the like. Values for $C_5$, $C_6$, $C_7$, and N can be determined experimentally to tune the electropolishing process to produce the desired wafer surface profile.

In one exemplary embodiment, where the electrolyte used for the electropolishing process is 85% (wt.) H2PO4 and for a 300 mm wafer, w can be in the range of about 1 to about 500 revolutions per minute. Vr can be in the range of about 0.01 cm/second to about 1 cm/second. R can be in the range of about 0.1 cm to about 15 cm for a nozzle with an inner diameter of about 0.1 cm. The polishing current density can range between 0 mA/cm$^2$ to about 50 mA/cm$^2$. The polishing voltage density can range between about 0 volts to about 5 volts. It should be recognized, however, that these values are only exemplary and that they can vary depending on the particular application.

Figure 61:
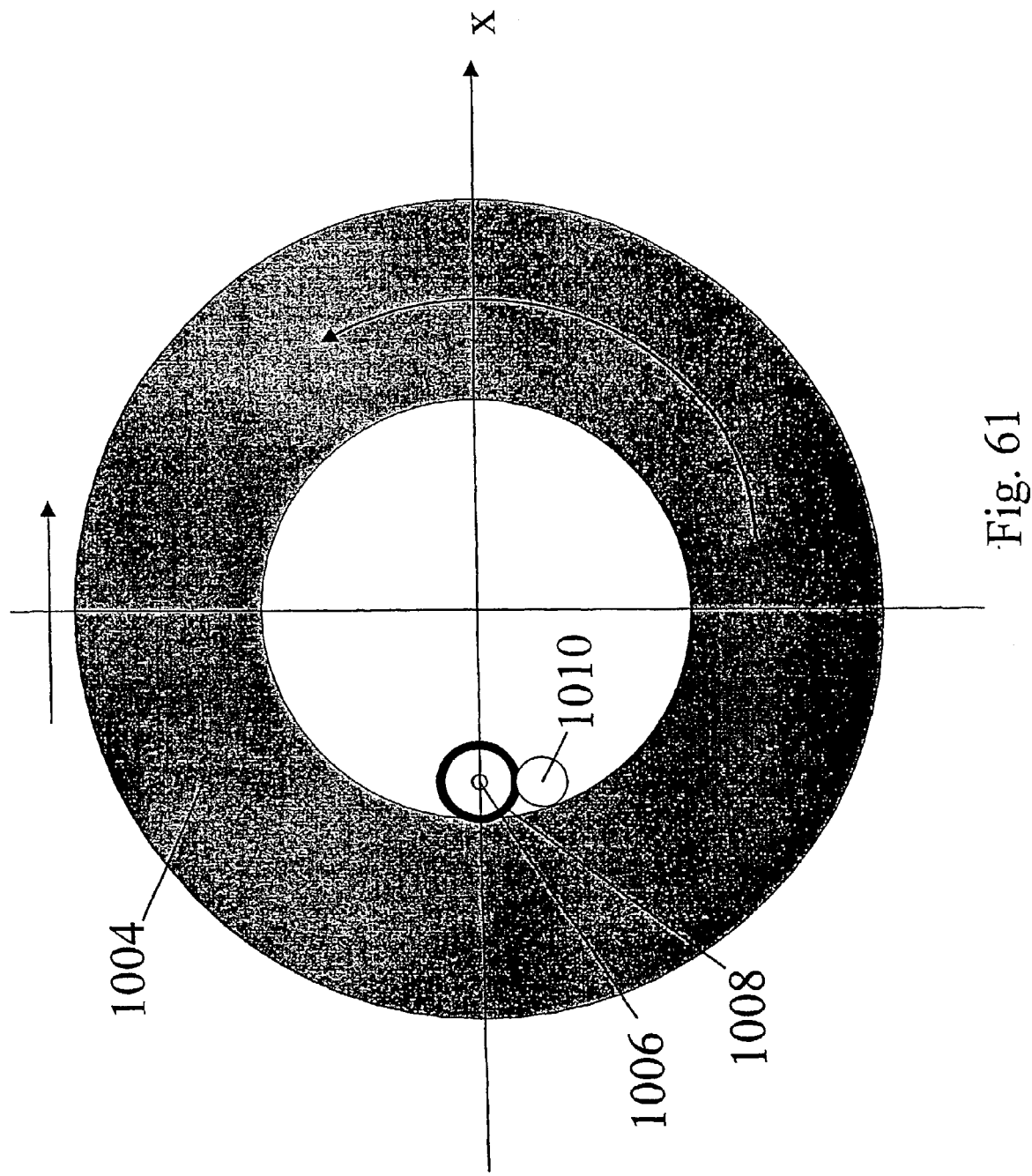
FIG. 61 is a top view of a portion of another end-point detection system.

With reference now to FIG. 61, another embodiment of the present invention includes an additional end-point detector 1010. In the present embodiment, end-point detector 1010 can be configured to provide the optical reflection profile after electropolishing of an area of the wafer surface. Thus, end-point detectors 1006 and 1010 can be configured to provide the optical reflection profile during and after electropolishing of an area on the wafer surface.

Figure 62:
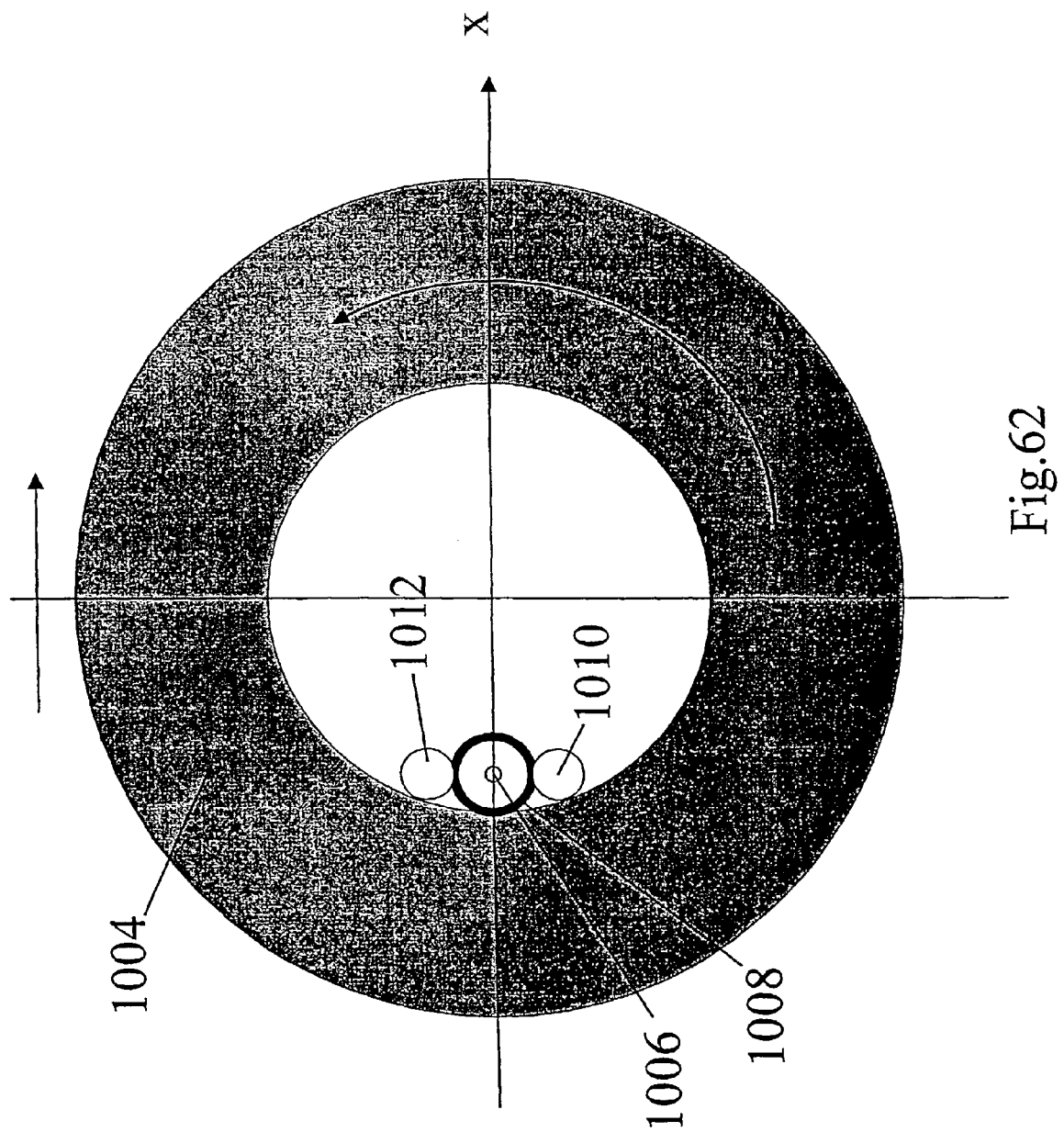
FIG. 62 is a top view of a portion of still another end-point detection system.

With reference now to FIG. 62, another embodiment of the present invention includes a third additional end-point detector 1012. In the present embodiment, end-point detector 1012 can be configured to provide the optical reflection profile before electropolishing of an area of the wafer surface. The difference of reflection rate measured by end-point detectors 1010 and 1012 can be used to determine the electropolishing rate in a single rotation of wafer 1004. This information can be provided to a computer to tune the polishing process. More particularly, adjustments can be made to the polishing power, rotation speed, horizontal speed of wafer 1004, and the like.

With reference now to FIG. 63A, another embodiment of the present invention includes a fourth end-point detector 1014. In the present embodiment, end-point detector 1014 can be configured to provide the electropolishing status after one complete electropolishing cycle (i.e., the nozzle moves relatively from center to edge of the wafer one time). This information can be provided to a computer to tune the polishing process. More particularly, adjustments can be made to the polishing power, rotation speed, horizontal speed of wafer 1004, and the like.

With reference now to FIG. 63B, another embodiment of the present invention includes a fifth end-point detector 1016. In the present embodiment, end-point detector 1016 can be configured to provide the electropolishing status before electropolishing. The difference of reflection rate measured by end-point detectors 1014 and 1016 can be used to determine the electropolishing rate of one electropolishing cycle. This information can be provided to a computer to tune the polishing process. More particularly, adjustments can be made to the polishing power, rotation speed, horizontal speed of wafer 1004, and the like.

With reference now to FIG. 64A, another embodiment of the present invention includes an additional end-point detector 1020 inside of nozzle 1008. In the present embodiment, end-point detector 1020 can be configured to detect the electropolishing uniformity in the area being electropolished. The difference of reflection rate measured by end-point detectors 1010 and 1020 can be used to determine the polishing profile in the area being electropolished on a real-time basis (i.e., at the time of electropolishing). This information can be provided to a computer to tune the polishing process. More particularly, adjustments can be made to the polishing power, rotation speed, horizontal speed of wafer 1004, and the like.

With reference now to FIG. 64B, another embodiment of the present invention includes a third end-point detector 1030 inside of nozzle 1008. In the present embodiment, end-point detector 1030 can be configured to detect the electropolishing uniformity in the area being electropolished. The difference of reflection rate rate measured by end-point detectors 1010, 1020, and 1030 can be used to determine the polishing profile in the area being electropolished. This information can be provided to a computer to tune the polishing process. More particularly, adjustments can be made to the polishing power, rotation speed, horizontal speed of wafer 1004, and the like.

With reference now to FIG. 64C, another embodiment of the present invention includes a fourth end-point detector 1040 inside of nozzle 1008. In the present embodiment, end-point detector 1040 can be configured to detect the electropolishing uniformity in the area being electropolished. The difference of reflection rate measured by end-point detectors 1010 and 120 can be used to determine the electropolishing profile in the x-direction (as depicted in FIG. 15C). The difference of reflection rate measured by end-point detectors 1030 and 1040 can be used to determine the electropolishing profile in the y-direction. This information can be provided to a computer to tune the polishing process. More particularly, adjustments can be made to the polishing power, rotation speed, horizontal speed of wafer 1004, and the like.

With reference to FIG. 64D, another embodiment of the present invention includes a fifth end-point detector 1050 inside of nozzle 1008. It should be recognized that any number of end-point detectors can be disposed within nozzle 1008 to detect the electropolishing uniformity in the area being electropolished.

Thus far, the end-point detectors described above have been depicted as having circular shapes. But it should be recognized that they can also include various alternative shapes. For example, with reference now to FIGS. 65A to E, end-point detector 1006 is depicted as having a circular, a triangular, a square, a trapezoidal, and an elliptical shape.

Additionally, thus far, nozzle 1008 has been depicted as having a circular shape. But it should be recognized that it can also include various alternative shapes. For example, with reference now to FIGS. 66A to E, nozzle 1008 is depicted as having a circular, a triangular, a square, a trapezoidal, and an elliptical shape.

Figure 67A:
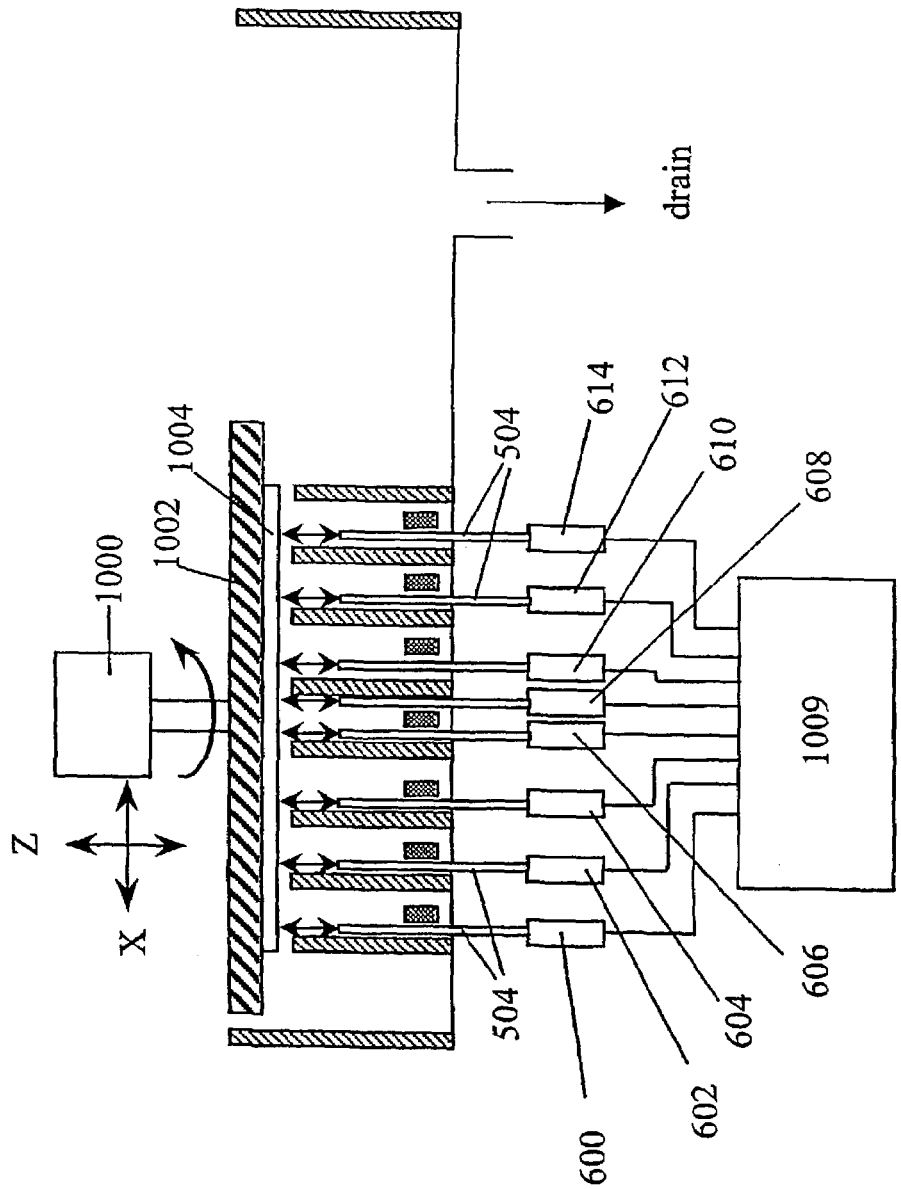
FIGS. 67A and 67B are schematic side and top views, respectively, of a wafer processing tool.
Figure 67B:
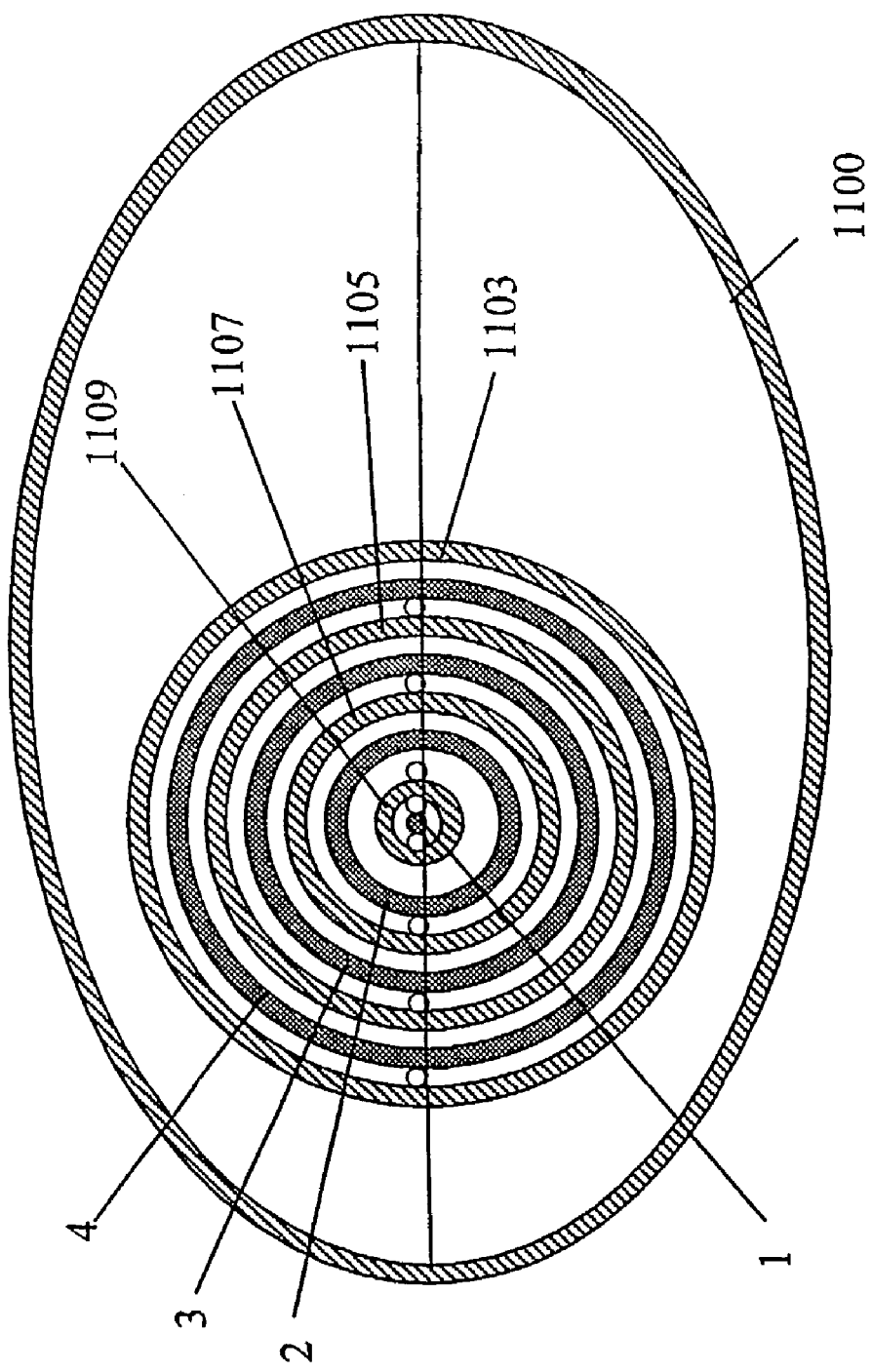

With reference now to FIGS. 67A and B, another embodiment of the present invention includes drive mechanism 1000, chuck 1002, wafer 1004. The present embodiment also includes a polishing receptacle 1100, which is divided into multiple sections by section walls 1103, 1105, 1107, and 1109. Cathodes 1, 2, 3, and 4 are disposed within these sections. Additionally, end-point detectors 600, 602, 604, 606, 608, 610, 612, and 614 are configured measure the electropolishing uniformity of wafer 1004. More particularly, an optical fiber 504 can be connected to each end-point detector 600, 602, 604, 606, 608, 610, 612, and 614. As depicted in FIG. 67A, optical fiber 504 extends into the sections of polishing receptacle 1100. The end-point detectors are also connected to analyzer 1009 that is configured to evaluate and/or process the signals received from the end-point detectors. Analyzer 1009 can be any convenient processor, such as a circuit, a computer chip, a computer, and the like. Analyzer 1009 can also include any convenient programming instructions or software needed to carry out the various functions described herein As described in greater detail with regard to various alternative embodiments, wafer 1004 can be electropolished by delivering an electrolyte into polishing receptacle 1100. More particularly, the electrolyte can be directed to any one or more of the sections of receptacle 1100 defined by section walls 1103, 1105, 1107, and 1109. An electrical charge is then applied to the electrolyte through cathodes 1, 2, 3, and 4. During the electropolishing process, wafer 1004 is held by chuck 1002 and rotated by drive mechanism 1000. In the manner described above, this electropolishing process can be controlled using end-point detectors 600, 602, 604, 606, 608, 610, 612, and 614 to produce the desired wafer surface profile.

After this initial electropolishing process is completed, an additional electropolishing process can be provided by injecting electrolyte through a nozzle disposed within the first section defined by section wall 1109. An electrical charge is applied through cathode 1. Wafer 1004 is then translated horizontally by drive mechanism 1000. In the manner described above, this electropolishing process can be controlled using end-point detectors 606 and 608.

By way of example, the following is an exemplary process for controlling the electropolishing of wafer 1004:

Step 1: Turn on electrolyte flow to all sections of receptacle 1100, and rotate wafer 1004;

Step 2: Apply an electrical charge to the electrolyte through cathodes 1, 2, 3, and 4;

Step 3: When reflectivity measured by each end-point detector 600, 602, 604, 606, 608, 610, 612, and 614 reaches a predetermined value, turn off flow of electrolyte and electrical charge;

Step 4: Turn on electrolyte flow to nozzle disposed within section defined by section wall 1109, apply charge through cathode 1, and move chuck 1004 horizontally such that flow of electrolyte moves across the surface of wafer 1004 from center to edge through a spiral path;

Step 5: Using measurements provided by end-point detectors 606 and 608, control the polishing power, rotating speed, and horizontal movement speed;

Step 6: Repeat steps 4 and 5 until the desired surface is obtained on wafer 1004; and Step 7: Stop process, unload wafer 1004, and load new wafer for electropolishing.

It should be recognized that various modifications can be made to the above steps. For example, in step 3, the electrolyte flow and power can be turned off based on target optical reflectivity calculated from pattern density data rather than a predetermined value for the optical reflectivity. Also, in step 4, wafer 1004 can be moved in various directions to apply the electrolyte moves across wafer 1004 in any desired pattern.

Figure 47:
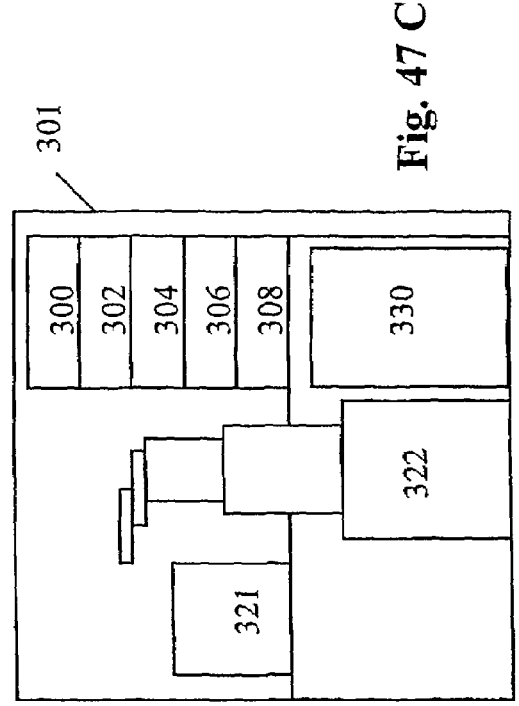
FIGS. 47A–47C are schematic top, cross section, and side views, respectively, of another embodiment of a wafer processing tool in accordance with various aspects of the present invention.
Figure 47:
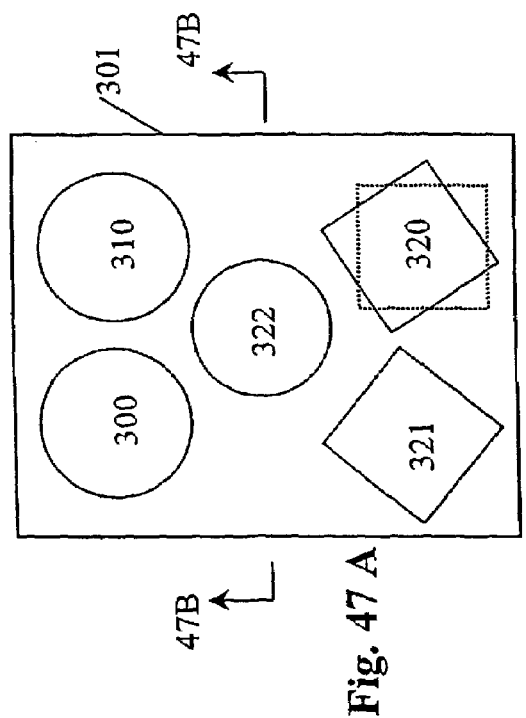
Figure 47:
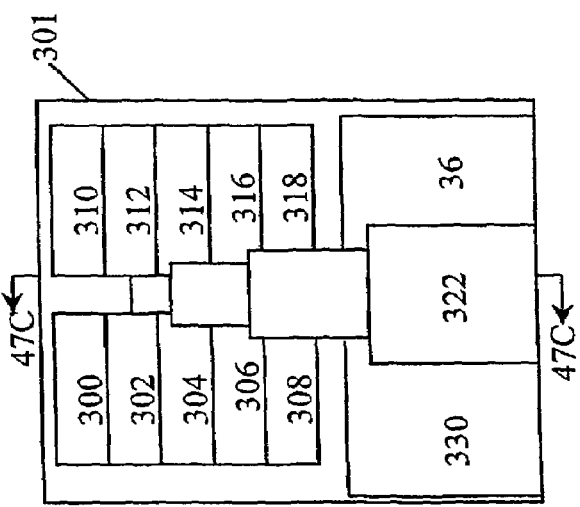

With reference now to FIG. 47, another alternative embodiment of the present invention, according to various aspects of the present invention, is shown. FIG. 47 shows an embodiment configured to be a stand-alone, fully computer-controlled wafer-processing tool with automatic wafer transfer, cleaning module with wafer dry-in and dry-out capability. It preferably includes five stacked polishing receptacles 300, 302, 304, 306 and 308, five stacked cleaning/dry chambers 310, 312, 314, 316 and 318, robot 322, wafer cassettes 320 and 321, electrolyte reservoir 36, and plumbing box 330. As described before, polishing bath 300 preferably includes a plurality of cathodes, a plurality of power supplies, a plurality of section walls or tubes, a wafer chuck, and a driving mechanism, which rotates or oscillates wafer 31 during the electropolishing process. Electrolyte reservoir 36 preferably includes a temperature control sensor. Plumbing box 330 preferably includes of a pump, LMFCs, valves, filters, and plumbing. The polishing system further preferably includes a computer control hardware and an appropriate operating software package. The operation process sequence is described as follows:

Step A: Load wafer cassettes 320 and 321 manually or using robot 322;

Step B: Select recipe and push run button;

Step C: Initialize the system using the control software, including checking any and all system parameters, and monitoring for any alarms existing in the system;

Step D: After completing the initialization, robot 322 picks up a wafer from cassette 320 or 321 and sends the wafer to one of the polishing receptacles 300, 302, 304, 306, or 308

Step E: Metal layer 121 (FIG. 1A) on the wafer is then electropolished;

Step F: After electropolishing, robot 322 picks up the polished wafer from the polishing receptacle, then transports it to one of cleaning/drying chambers 310, 312, 314, 316, or 318;

Step G: The electropolished wafer is then cleaned;

Step H: The electropolished wafer is then dried using any convenient drying process, such as spin-drying and/or $N_2$ purging; and Step I: Finally, the dried wafer is then transported to cassette 320 or 321 manually or by robot 322.

Figure 48:
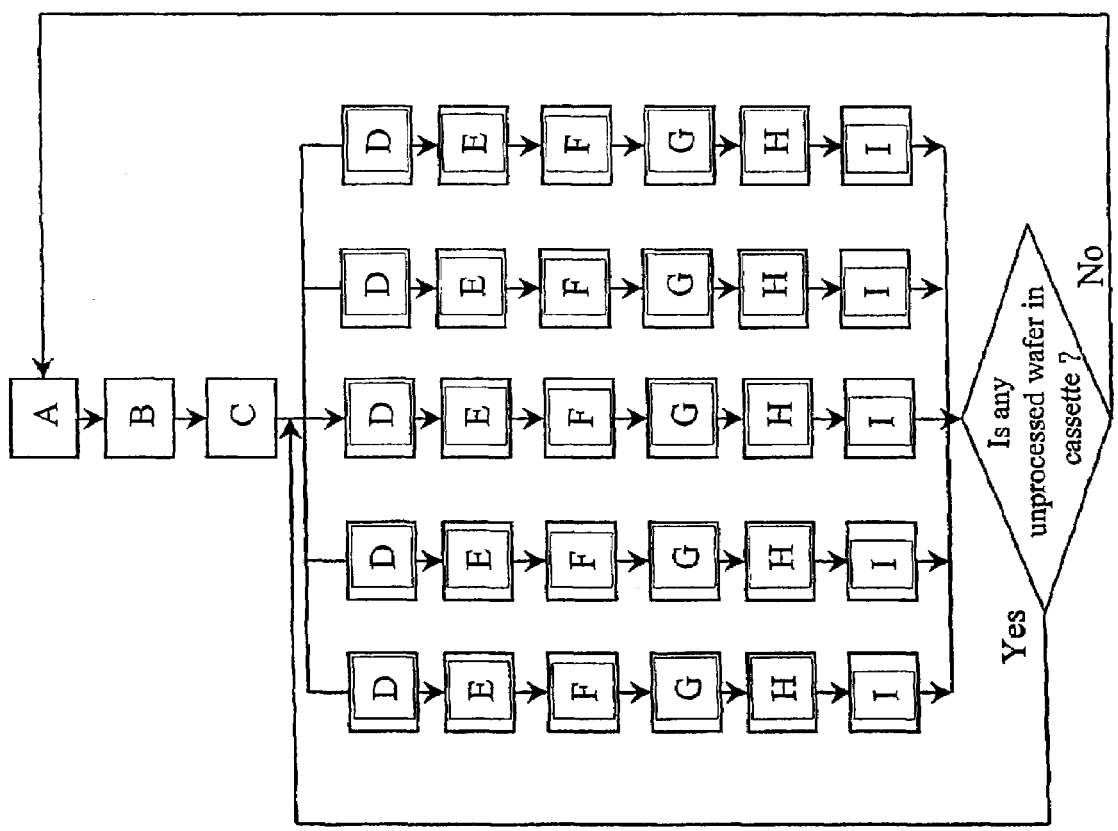
FIG. 48 is a flow chart depicting the operation of a portion of software for controlling a wafer processing tool in accordance with various aspects of the present invention.

FIG. 48 shows the process sequence for polishing multiple wafers simultaneously. The process sequence for polishing multiple wafers is similar to that for electropolishing a single wafer, except that the computer checks for any unprocessed wafers remaining in cassette 320 or 321 after process step I. If there is an unprocessed wafer remaining in cassette 320 or 321, then the system will return to step A (i.e., loading new cassettes or exchanging cassettes). If there is still an unprocessed wafer remaining in cassette 320 and/or 321, the system will return to step D (i.e., robot 322 picks up the unprocessed wafer from the cassette and transports it to one of the polishing receptacles).

Process step E can preferably include a two-process step, the first being to selectively electropolish metal layer 121 (FIG. 1A) on the wafer, and the second being to electropolish metal layer 121 (FIG. 1A) on the whole wafer simultaneously.

Instead of cleaning a wafer in one chamber, the cleaning process can be performed in different chambers. The cleaning process can also consist of several steps, and each step can use different solutions, different concentrations of solutions, or different hardware.

Instead of arranging five polishing receptacles and five-cleaning/drying chambers, the number of polishing receptacles and number of cleaning/drying chambers can be varied from 1 to 10 as shown in the following table:

TABLE 4

| Type | 1 | 2 | 3 | 4 | 5 | 6 | 7 | 8 | 9 |
|---|---|---|---|---|---|---|---|---|---|
| No. of polishing receptacles | 1 | 2 | 3 | 4 | 5 | 6 | 7 | 8 | 9 |
| No. of cleaning/drying chambers | 9 | 8 | 7 | 6 | 5 | 4 | 3 | 2 | 1 |

In accordance with various aspects of the present invention, types 4, 5, 6 and 7 in the above table are preferred.

Figure 49:
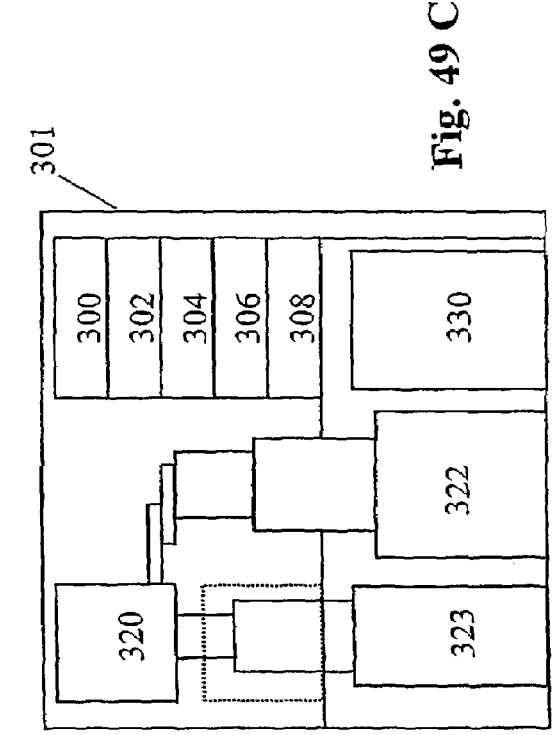
FIGS. 49A–49C are schematic top, cross section, and side views, respectively, of still another embodiment of a wafer processing tool in accordance with various aspects of the present invention.
Figure 49:
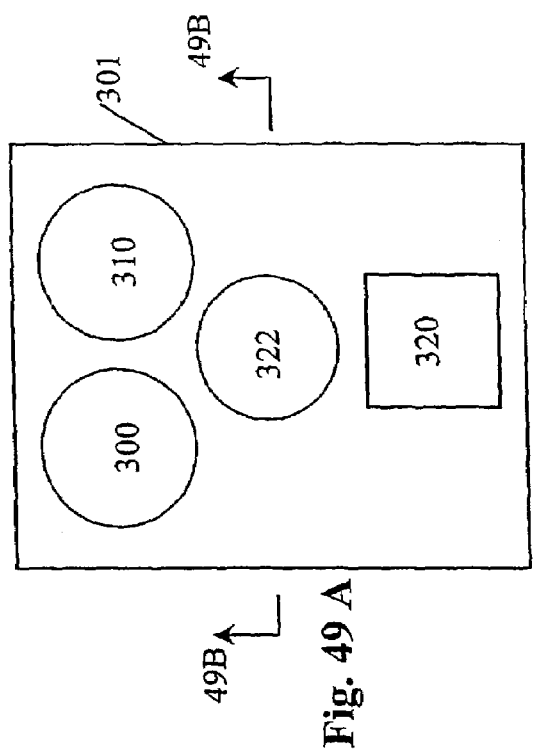
Figure 49:
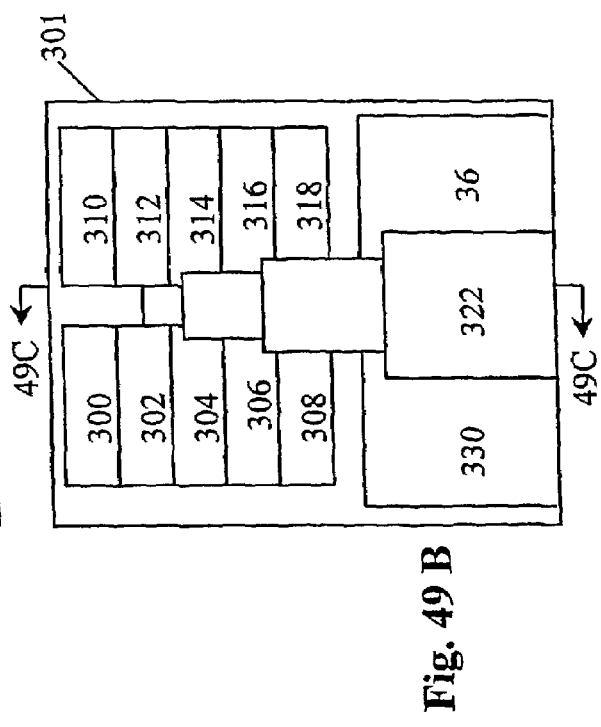

With reference now to FIG. 49, another alternative embodiment of the present invention, according to various aspects of the present invention, is shown. FIG. 49 shows an embodiment configured as a wafer-polishing tool. The embodiment of FIG. 49 is similar to that of FIG. 47, except that cassette 320 can be moved up and down by a robot 323. The position of cassette 320 can be moved up and down to match the position of the polishing receptacle or cleaning/ dry chamber. Accordingly, robot 322 does not need to move in the Z direction when picking up an unprocessed wafer from cassette 320 or putting a polished dry wafer back into cassette 320. In this manner, the operating speed of robot 323 can be suitably increased.

Figure 50:
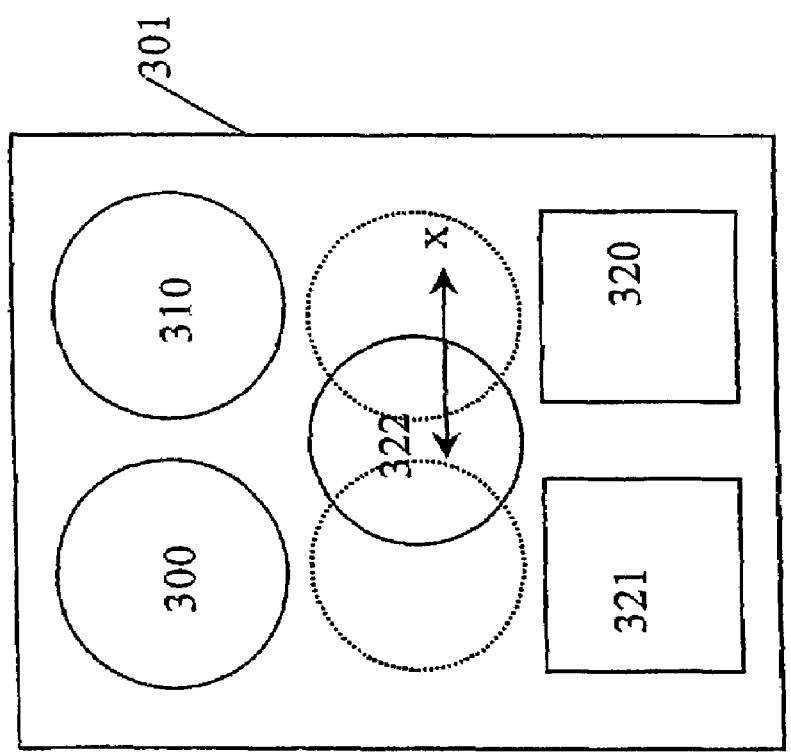
FIG. 50 is a schematic top view of a portion of yet another embodiment of a wafer processing tool in accordance with various aspects of the present invention.

With reference now to FIG. 50, still another alternative embodiment of the present invention, according to various aspects of the present invention, is shown. The embodiment shown in FIG. 50 is similar to that of FIG. 47 except that robot 322 itself can move in the X direction. Accordingly, robot 322 need not rotate about the Z axis.

Figure 51:
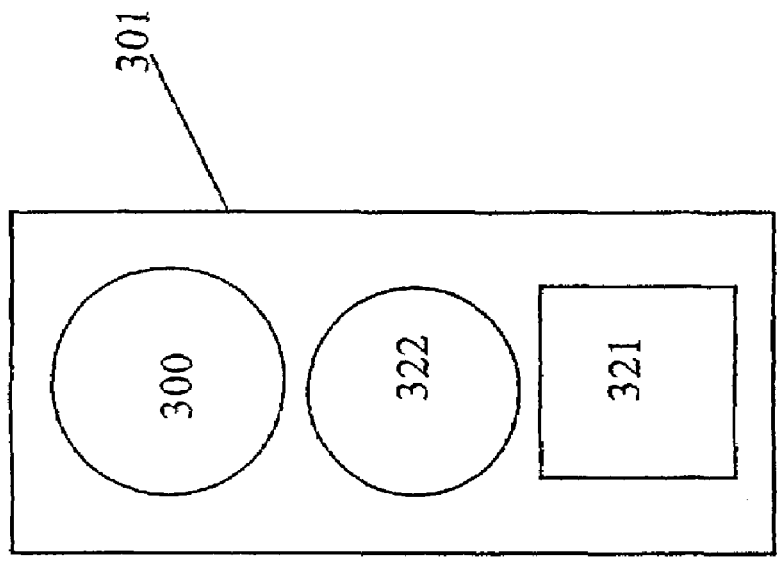
FIG. 51 is a schematic top view of a portion of another embodiment of a wafer-processing tool in accordance with various aspects of the present invention.

With reference now to FIG. 51, yet another alternative embodiment of the present invention, according to various aspects of the present invention, is shown. The embodiment shown in FIG. 51 is similar to that of FIG. 47 except that polishing receptacles and cleaning/drying chambers are put in one column. Compared with the embodiment of FIG. 47, the foot print of the system is reduced, however wafer throughput can be slower.

With reference now to FIG. 52, another alternative embodiment of the present invention, according to various aspects of the present invention, is shown. The embodiment shown in FIG. 52 preferably includes three columns of polishing receptacles and cleaning/drying chambers, linearly moveable robot 322, operation screen 340, two cassettes stacked adjacent to each other, plumbing box 330, and electrolyte reservoir 36. The polishing process steps are similar to those described in FIG. 47.

Figures 54A, 54B:
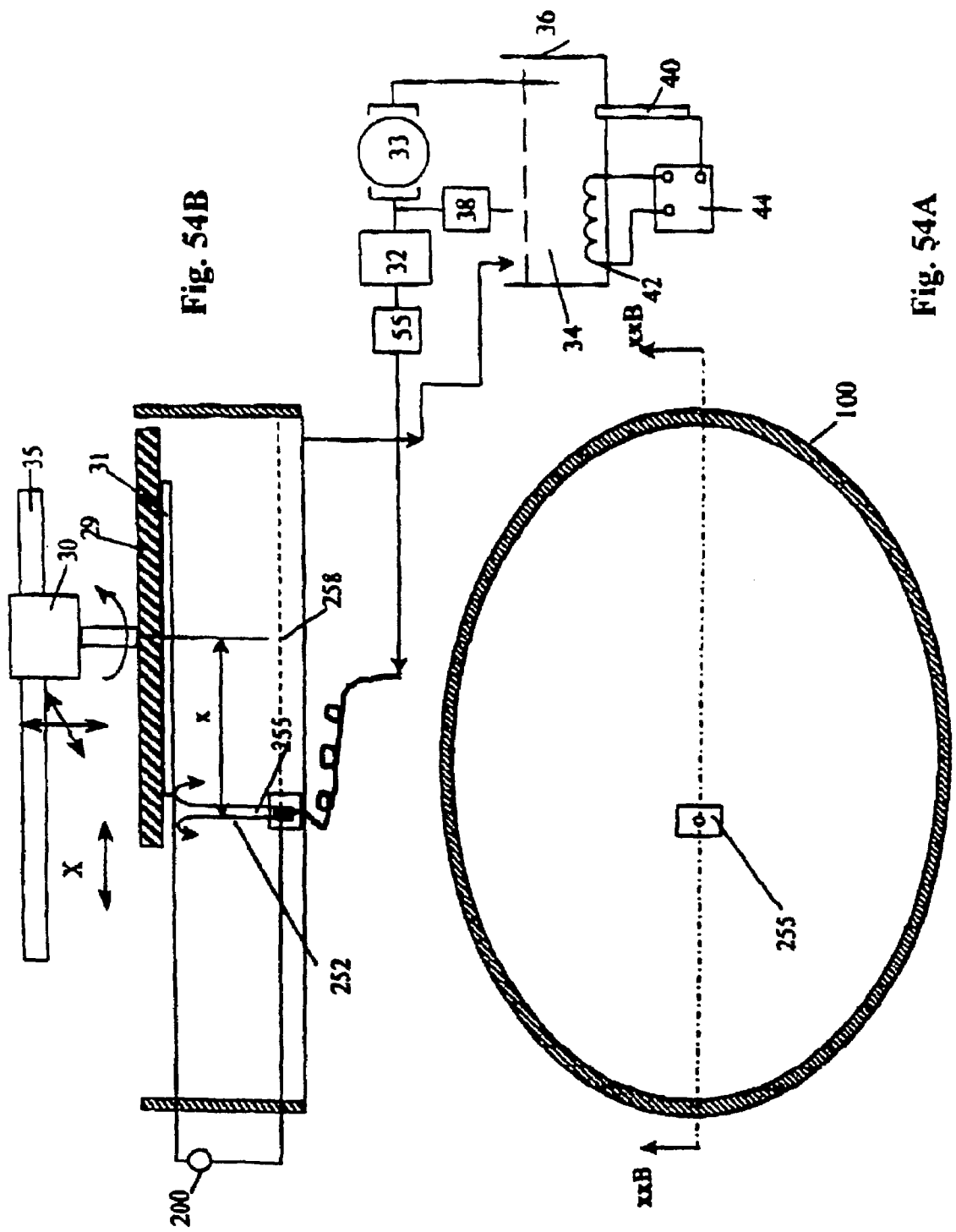
FIG. 54A is a top view of a portion of a forty-seventh alternative embodiment in accordance with various aspects of the present invention.
FIG. 54B is a view, partly in cross section, taken along the line 54B—54B in FIG. 54A, and partly in block diagram form, of the alternative embodiment shown in FIG. 54A.

FIG. 54 shows still another embodiment of apparatus for polishing metal layer 121 (FIG. 1A) in accordance with the present invention. The embodiment of FIG. 54 is similar to that of FIGS. 28A and 28B except that multi-jets are replaced by a single jet 255. Additionally, cathode jet 255 remains stationary while wafer 31 is moved along the X-axis (left and right). More particularly, in the present exemplary embodiment, cathode jet 255 injects electrolyte onto selected portions of wafer 31, while wafer 31 is rotated and moved in the X-axis substantially simultaneously by drive means 30 and guide bar 35. When wafer 31 is moved to the left side, cathode jet 255 injects electrolyte on to the center portion of wafer 31. When wafer 31 is moved to the right side, cathode jet 255 injects electrolyte onto the periphery portion of wafer 31. In accordance with one aspect of the present invention, the rotation speed of wafer 31 can be kept at a constant rate during the polishing process. The speed with which wafer 31 is moved along the x-axis can be varied from large to small as drive means 30 moves the center portion of wafer 31 away from the cathode jet 255. This speed of wafer 31 along the x-axis (Vx) can be expressed as follows:

$$Vx = C/[\pi(x+r)^2] \quad \text{when } x < r$$

$$C/\{\pi[(x+r)^2 - (x-r)^2]\} \quad \text{when } x > r$$

Where C is a constant, x is the distance between center of wafer 31 and cathode jet 255 in the x-axis, and r the radius of liquid column made by cathode jet 255.

It should be recognized, however, that various modifications can be made to the configuration of the wafer polishing cell without deviating from the spirit and/or scope of the present invention. For example, the angle between wafer 31 and cathode jet 255 can be kept at any constant angle, or the angle can be changed during the polishing process. The wafer itself can be placed at any angle relative to polishing receptacle 100. In the embodiment of FIG. 54, jet 255 can be moved instead of moving wafer 31, or both jet 255 and wafer 31 can be moved to achieve the same results. In the embodiment of FIG. 54, wafer 31 can be immersed in the electrolyte, instead of being contacted by the jet stream of the electrolyte.

With reference again to FIG. 1B, after metal layer 121 is electropolished from barrier layer 122 formed on mesas 126, a layer of metal can be replated on wafer 31 to fix recesses 127. As alluded to earlier, this replating process can be performed using any convenient plating process. One such process is an electroless plating process.

In general, electroless plating differs from electroplating in that electrodes are not used in electroless plating. In brief, metal ions are provided in an electroless solution. More particularly the electroless solution typically contains a reducing agent that facilitates plating.

The use of electroless plating is particularly advantageous in this application in that metal layer 121 in trenches 125 will tend to promote plating, while barrier layer 122 will not. Also, electroless plating generally produces a more uniform deposition as it does not suffer from ohmic effects. Thus, recesses 127 can be fixed (i.e., filled in) using an electroless plating process.

Figure 68A:
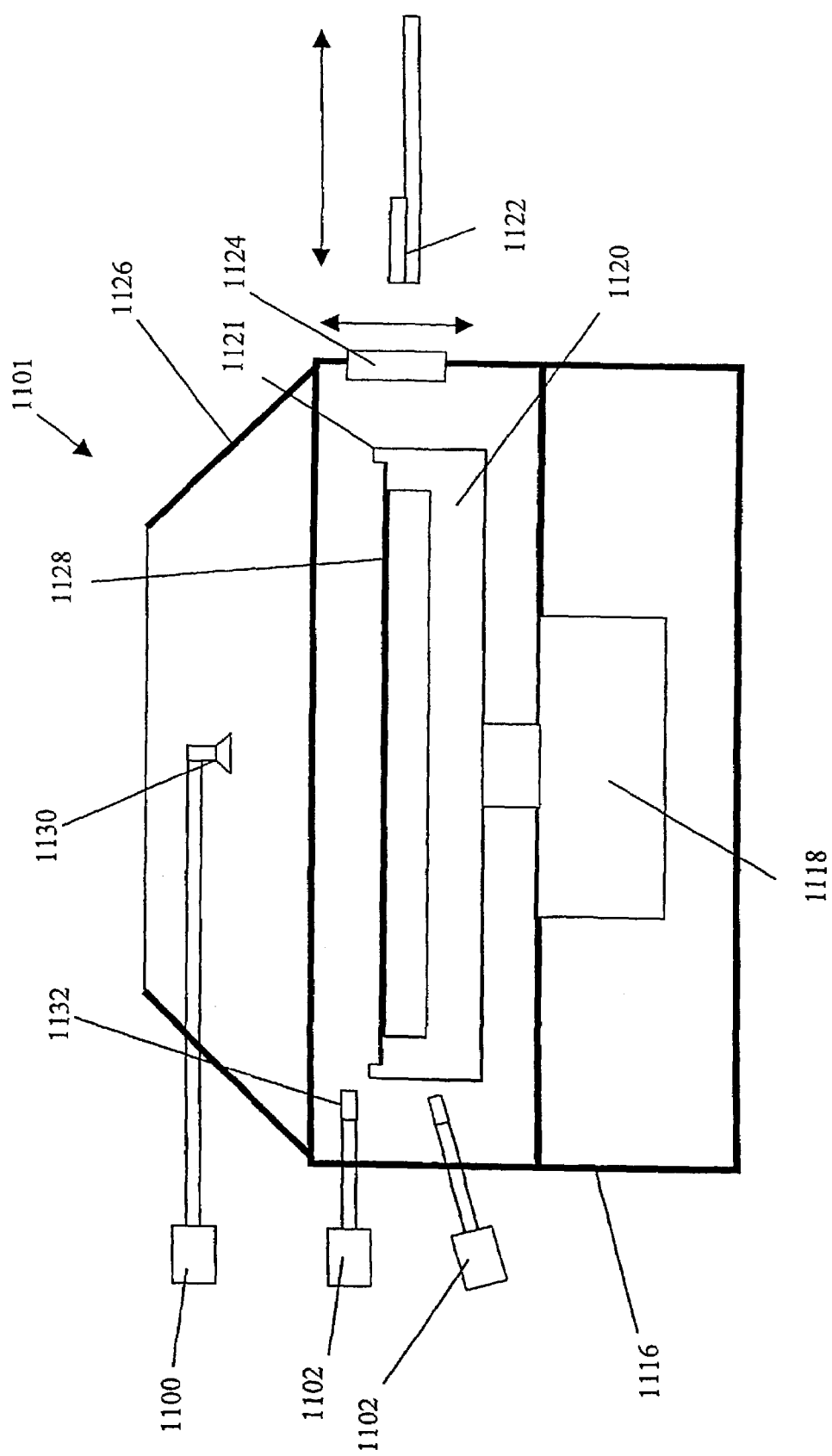
FIG. 68A is a front perspective view of an embodiment of an electroless plating module.
Figure 68B:
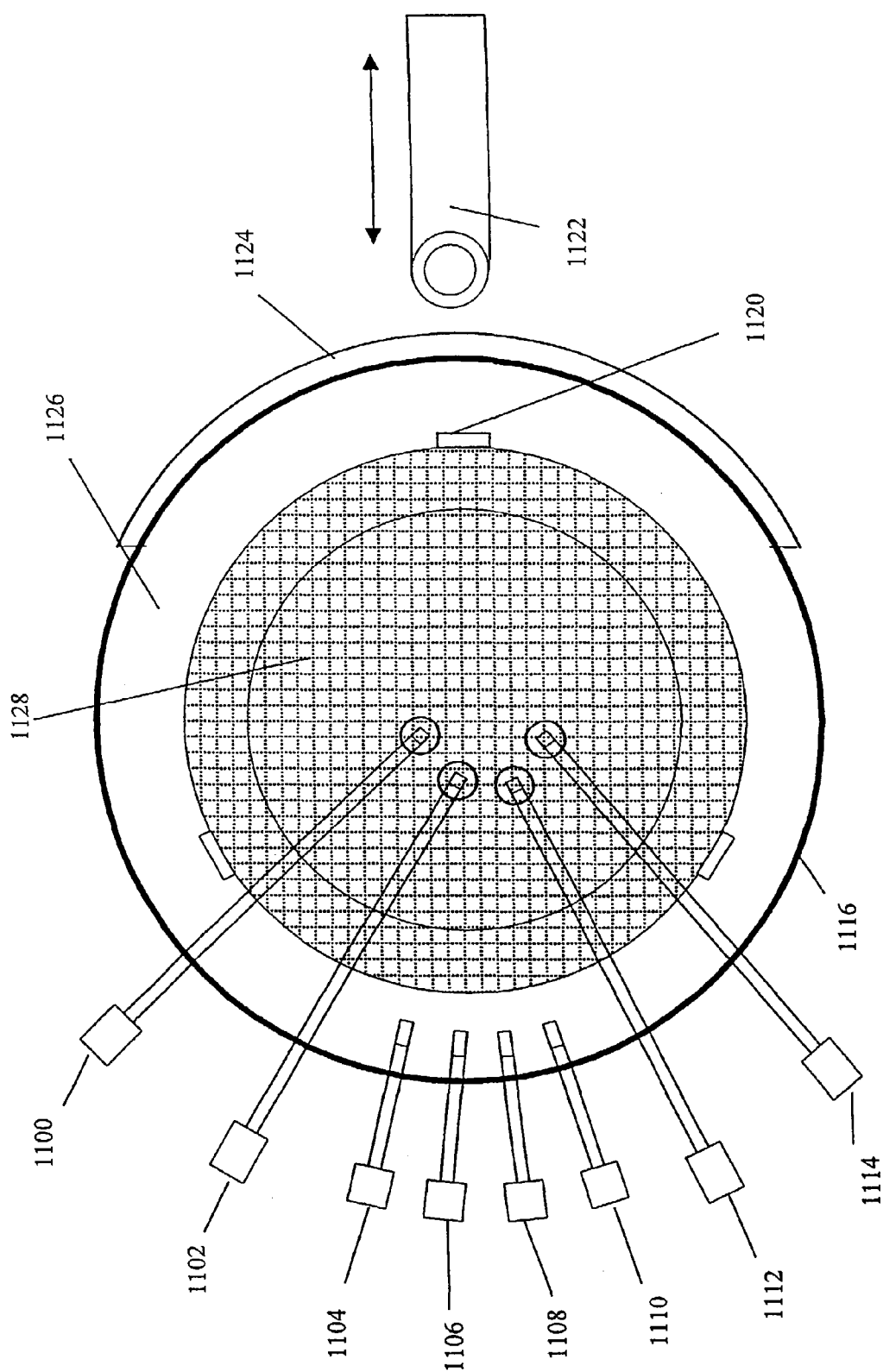
FIG. 68B is a top cross section view of the embodiment shown in FIG. 68A.

With reference now to FIGS. 68A and 68B, an electroless plating module 1101 in accordance with one exemplary embodiment of the present invention is shown. As alluded to above and as will be described in greater detail below, electroless plating module 1101 is configured to replate a metal layer on wafer 31 (FIG. 1B) to fix recesses 127 (FIG. 1B). Additionally, electroless plating module 1101 can be configured to clean and to dry wafer 1128. It should be recognized, however, that electroless plating module 1101 can be configured to perform various processes depending on the particular application. For example, as will be described with reference to various alternative embodiments, electroless plating module 1101 can be configured to perform an etching process.

In one embodiment electroless plating module 1101 is configured to use any electroless solutions suitable for use with copper, such as copper sulfate (CuSiO4-5H2O) at about 8 g/l, EDTA (tetrasodium) at about 14 g/l, formaldehyde (NCOOH) at 20 ml/l, Methyldichlorosilane (CH3Cl2SiH) at 0.25 g/l. It should be recognized, however, that the electroless solution can include various chemistries depending on the application.

Additionally, the electroless solution is maintained at between about 20 degrees Celsius and about 80 degrees Celsius. Accordingly, a deposition rate of about 100 Angstroms per minute to about 1000 Angstroms per minute can be obtained. It should be recognized, however, that the electroless solution can be maintained at various temperatures and that various deposition rates can be used.

Figure 69A:
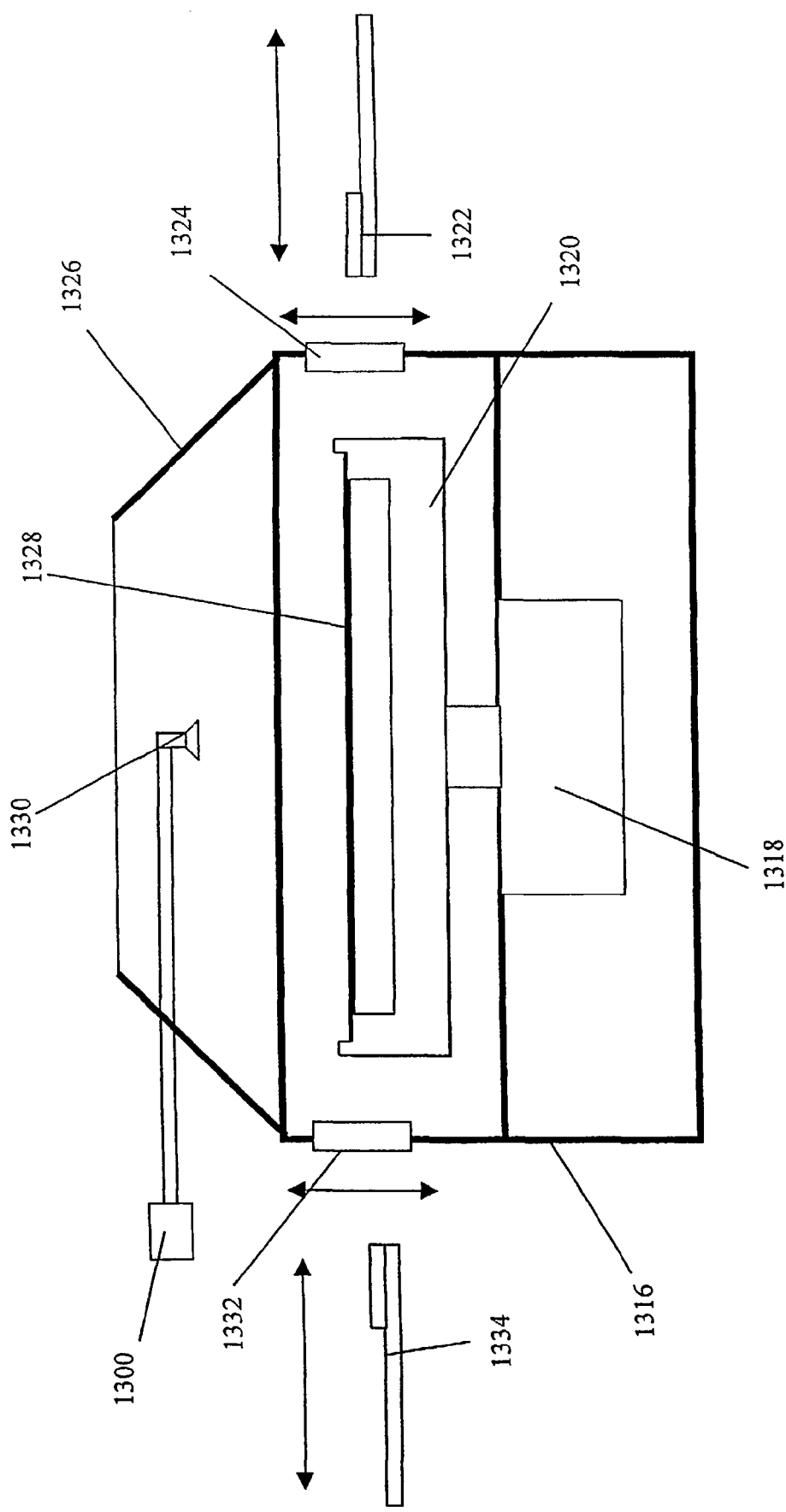
FIG. 69A is a front perspective view of another embodiment of an electroless plating module.
Figure 69B:
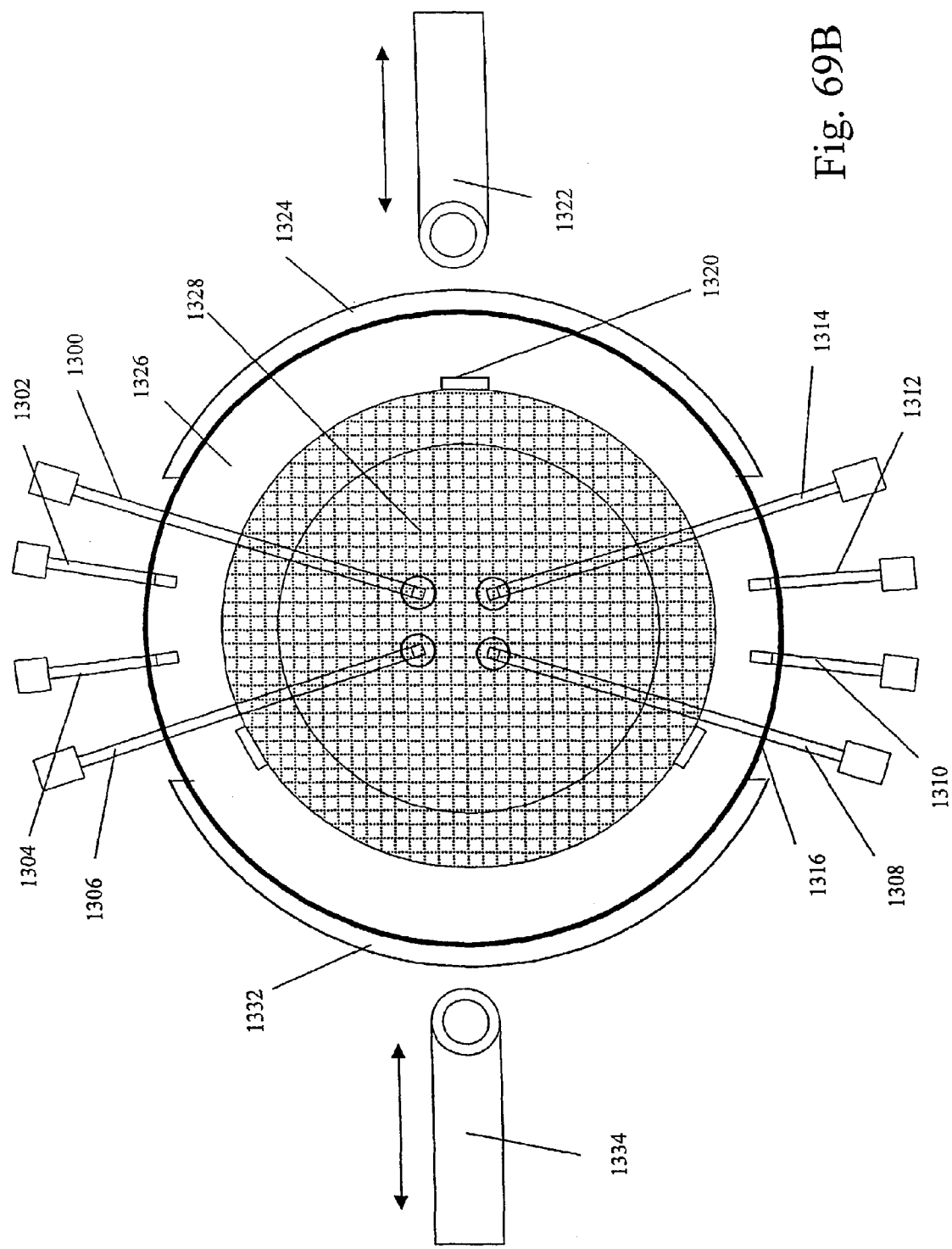
FIG. 69B is a top cross section view of the embodiment shown in FIG. 69A.

As depicted in FIGS. 68A and 68B, electroless plating module 1101 preferably includes a module chamber 1116, a cover 1126, a wafer loading door 1124, a chuck 1120, a motor 1118, and liquid/gas injection pipe 1100, 1102, 1104, 1106, 1108, 1110, and 1112. In the present embodiment, module chamber 1116, cover 1126 and loading door 1126 are configured to seal electroless plating module 1101. In this manner, electroless plating module 1101 can be sealed to isolate the environment within electroless plating module 1101 from the outside environment. This has the advantage of preventing contaminants from the outside environment from entering electroless plating module 1101. It also has the advantage of preventing fluids and/or vapors from escaping from electroless plating module 1101. Accordingly, as will be described below and depicted in various drawing figures, wafer loading door 1124 opens and closes to permit entry into electroless plating module 101. It should be recognized, however, that electroless plating module 1101 can include various alternative configurations. For example, electroless plating module 1101 can be configured without cover 1126 and loading door 1126. Accordingly, in this configuration, direct access can be gained to electroless plating module 1101 without having to open and close wafer loading door 1124. Alternatively, with reference to FIG. 69A, electroless plating module 1101 can include two wafer loading doors 1324 and 1332. Accordingly, wafer 1128 can be loaded from one side and removed from another side.

In the present embodiment depicted in FIGS. 68A and 68B, electroless plating module 1101 includes a cover 1126 and one loading door 1124. As such, loading door 1124 opens to permit access into electroless plating module 1101. More particularly, loading door 1124 opens to permit loading and removal of wafer 1128 from electroless plating module 1101. It should be recognized that loading door 1124 can be opened and closed manually or using any convenient actuator, such as spring, motor, robot, and the like.

In the present embodiment, wafer 1128 is loaded and removed from electroless plating module 1101 using robot 1122. It should be recognized that robot 1122 can be a robot specifically dedicated to loading and unloading electroless plating module 1101. Alternatively, as will be described in greater detail below, electroless plating module 1101 can be a component of a wafer processing tool in which robot 1122 is a multipurpose robot. It should also be recognized that wafer 1128 can be loaded and removed using various wafer transfer systems, such as air tracks, water tracks, and the like. As an additional alternative, wafer 1128 can be manually loaded and removed from electroless plating module 1101.

In the present embodiment, injection pipes 1100, 1102, 1104, 1106, 1108, 1110, and 1112 are configured to deliver various fluids and/or gases to electroless plating module 1101. Although electroless plating module 1101 is depicted having seven injection pipes, it should be recognized that electroless plating module 1101 can include any number of injection pipes. It should also be recognized that injection pipes 1100, 1102, 1104, 1106, 1108, 1110, and 1112 can be formed from any convenient material depending on the nature of the fluids and/or gases to be delivered.

Additionally, any number of injection pipes 1100, 1102, 1104, 1106, 1108, 1110, and 1112 include a nozzle to more uniformly deliver the various fluids and/or gases to electroless plating module 1101. It should be recognized, however, that injection pipes 1100, 1102, 1104, 1106, 1108, 1110, and 1112 can include various shapes and/or attachments to enhance the uniformity of the delivery of fluids and/or gases. For example, injection pipes 1100, 1102, 1104, 1106, 1108, 1110, and 1112 can include a diffuser.

In the present embodiment, wafer chuck 1120 and motor 1118 are configured to hold and to rotate wafer 1128 within electroless plating module 1101. More particularly, wafer chuck 1120 includes a plurality of locks 1121 configured to hold wafer 1128 when rotated and to release wafer 1128 when stopped. In one embodiment, locks 1121 can include any convenient centrifugal-force locks. Motor 1118 can include any convenient motor, such as a step motor, a DC motor, and the like. Additionally, motor 1118 includes rotation speed control and homing function.

In the following and preceding descriptions, various process steps have been described. It should be recognized that each of these steps, and combination of steps, can be implemented as computer program instructions. It should also be recognized that each of these steps, and combination of steps, can be implemented by special purpose hardware-based computer systems that perform the specified functions or steps, or combination of special purpose hardware and computer instructions.

As alluded to above, after wafer 1128 has been electroplated, wafer 1128 can be replated to fix recesses 127 (FIG. 1B). The following is an exemplary process for replating wafer 1128 using electroless plating module 1101:

Step 1. Loading door 1124 moves to an open position.

Step 2. Robot 1122 loads wafer 1128 into electroless plating module 1101.

Step 3. Loading door 1124 moves to a closed position.

Step 4. Chuck 1120 starts rotating wafer 1128. In one embodiment, chuck 1120 rotates wafer 1128 at a speed between about 1 revolutions per minute to about 100 revolutions per minute, and preferably at about 20 revolutions per minute.

Step 5. A cleaning solution is provided through injection pipe 1100. In one embodiment, the cleaning solution is deionized water. The cleaning solution can be provided for any convenient period of time to clean wafer 1128. In one embodiment, wafer 1128 is cleaned for a period of time between about 10 seconds to about 200 seconds, and preferably about 30 seconds.

Step 6. After wafer 1128 has been cleaned, a drying gas is provided through injection pipe 1102. In one embodiment, the drying gas is Nitrogen gas. This process can be performed for any convenient period of time necessary to dry wafer 1128. In one embodiment, wafer 1128 is dried for a period of time between about 20 seconds to about 40 seconds, and preferably about 30 seconds. Additionally, in one embodiment, during this process, wafer chuck 1120 is rotated at about 1500 revolutions per minute to about 3500 revolutions per minute, and preferably about 2500 revolutions per minute.

Step 7. After wafer 1128 has been dried, an electroless-plating solution is provided through injection pipe 1112. This process can be performed for any convenient period of time necessary to replate wafer 1128. In one embodiment, wafer 1128 is electroless plated for a period of time between about a few seconds to about a few hundred seconds. Additionally, in one embodiment, during this process, wafer chuck 1120 is rotated at about 1 revolutions per minute to about 100 revolutions per minute, and preferably about 20 revolutions per minute.

Step 8. After wafer 1128 has been replated, a cleaning solution is provided through injection pipe 1100. In one embodiment, the cleaning solution is deionized water. Additionally, an etching solution is provided on the back side of wafer 1128 (i.e., the side of wafer 1128 that has not been plated) to clean any metal or other contaminants. The cleaning solution can be provided for any convenient period of time to clean wafer 1128. In one embodiment, wafer 1128 is cleaned for a period of time between about 10 seconds to about 200 seconds, and preferably about 30 seconds.

Step 9. After wafer 1128 has been cleaned, a drying gas is provided through injection pipe 1102. In one embodiment, the drying gas is Nitrogen gas. This process can be performed for any convenient period of time necessary to dry wafer 1128. In one embodiment, wafer 1128 is dried for a period of time between about 20 seconds to about 40 seconds, and preferably about 30 seconds. Additionally, in one embodiment, during this process, wafer chuck 1120 is rotated at about 1500 revolutions per minute to about 3500 revolutions per minute, and preferably about 2500 revolutions per minute.

Step 10. After the wafer is dried, wafer chuck 1120 stops. Loading door 1124 is then moved to an unload position, and wafer 1128 is removed from electroless plating module 1101.

As described earlier, after wafer 1128 has been replated, it can be planarized. More particularly, with reference to FIGS. 1C and 1D, metal layer 126 that was replated on trenches 125 is planarized, and barrier layer 122 is removed. In one embodiment described earlier, this process was performed using a CMP process. With reference again to FIGS. 68A and 68B, in the present exemplary embodiment, this process can be performed using electroless plating module 1101:

Step 1. Loading door 1124 moves to an open position.

Step 2. Robot 1122 loads wafer 1128 into electroless plating module 1101.

Step 3. Loading door 1124 moves to a closed position.

Step 4. Chuck 1120 starts rotating wafer 1128. In one embodiment, chuck 1120 rotates wafer 1128 at a speed between about 1 revolutions per minute to about 100 revolutions per minute, and preferably at about 20 revolutions per minute.

Step 5. A cleaning solution is provided through injection pipe 1100. In one embodiment, the cleaning solution is deionized water. The cleaning solution can be provided for any convenient period of time to clean wafer 1128. In one embodiment, wafer 1128 is cleaned for a period of time between about 10 seconds to about 200 seconds, and preferably about 30 seconds.

Step 6. After wafer 1128 has been cleaned, a drying gas is provided through injection pipe 1102. In one embodiment, the drying gas is Nitrogen gas. This process can be performed for any convenient period of time necessary to dry wafer 1128. In one embodiment, wafer 1128 is dried for a period of time between about 20 seconds to about 40 seconds, and preferably about 30 seconds. Additionally, in one embodiment, during this process, wafer chuck 1120 is rotated at about 1500 revolutions per minute to about 3500 revolutions per minute, and preferably about 2500 revolutions per minute.

Step 7. After wafer 1128 has been dried, an electroless-plating solution is provided through injection pipe 1112. This process can be performed for any convenient period of time necessary to replate wafer 1128. In one embodiment, wafer 1128 is electroless plated for a period of time between about a few seconds to about a few hundred seconds. Additionally, in one embodiment, during this process, wafer chuck 1120 is rotated at about 1 revolutions per minute to about 100 revolutions per minute, and preferably about 20 revolutions per minute.

Step 8. After wafer 1128 has been replated, a cleaning solution is provided through injection pipe 100. In one embodiment, the cleaning solution is deionized water. Additionally, an etching solution is provided on the back side of wafer 1128 (i.e., the side of wafer 1128 that has not been plated) through injection pipe 1104. This helps to clean any metal or other contaminants from the back side of wafer 1128. The cleaning solution can be provided for any convenient period of time to clean wafer 1128. In one embodiment, wafer 1128 is cleaned for a period of time between about 10 seconds to about 200 seconds, and preferably about 30 seconds.

Step 9. After the front side of wafer 1128 (i.e., the side of wafer 1128 that has been plated) has been cleaned, etching solution is provided through pipe 1114 to remove barrier layer 1122 (FIG. 1). This etching process can be performed for any convenient period of time necessary to remove barrier layer 1122 (FIG. 1). It should be recognized that this step can be omitted when wafer 1128 does not have a barrier layer 1122.

Step 10. After wafer 1128 has been etched, a cleaning solution is provided through injection pipes 1100 and 1104 to the front and back sides of wafer 1128.

Step 11. After wafer 1128 has been cleaned, a drying gas is provided through injection pipe 1102. In one embodiment, the drying gas is Nitrogen gas. This process can be performed for any convenient period of time necessary to dry wafer 1128. In one embodiment, wafer 1128 is dried for a period of time between about 20 seconds to about 40 seconds, and preferably about 30 seconds. Additionally, in one embodiment, during this process, wafer chuck 1120 is rotated at about 1500 revolutions per minute to about 3500 revolutions per minute, and preferably about 2500 revolutions per minute.

Step 12. After wafer 1128 is dried, wafer chuck 1120 stops. Loading door 1124 is then moved to an unload position, and wafer 1128 is removed from electroless plating module 1101.

As alluded to above, depending on the application, wafer 1128 can include a metal seed layer. When wafer 1128 includes a metal seed layer, it can be advantageous to remove this seed layer from the edges of wafer 1128. In one embodiment of the present invention, electroless plating module 1101 can be used to remove the seed layer from the edges of wafer 1128:

Step 1. Loading door 1124 moves to an open position.

Step 2. Robot 1122 loads wafer 1128 into electroless plating module 1101.

Step 3. Loading door 1124 moves to a closed position.

Step 4. Chuck 1120 starts rotating wafer 1128. In one embodiment, chuck 1120 rotates wafer 1128 at a speed between about 1 revolutions per minute to about 100 revolutions per minute, and preferably at about 20 revolutions per minute.

Step 5. A cleaning solution is provided through injection pipe 1100. In one embodiment, the cleaning solution is deionized water. The cleaning solution can be provided for any convenient period of time to clean wafer 1128. In one embodiment, wafer 1128 is cleaned for a period of time between about 10 seconds to about 200 seconds, and preferably about 30 seconds.

Step 6. After wafer 1128 has been cleaned, a drying gas is provided through injection pipe 1102. In one embodiment, the drying gas is Nitrogen gas. This process can be performed for any convenient period of time necessary to dry wafer 1128. In one embodiment, wafer 1128 is dried for a period of time between about 20 seconds to about 40 seconds, and preferably about 30 seconds. Additionally, in one embodiment, during this process, wafer chuck 1120 is rotated at about 1500 revolutions per minute to about 3500 revolutions per minute, and preferably about 2500 revolutions per minute.

Step 7. After wafer 1128 has been dried, an electroless-plating solution is provided through injection pipe 1112. This process can be performed for any convenient period of time necessary to replate wafer 1128. In one embodiment, wafer 1128 is electroless plated for a period of time between about a few seconds to about a few hundred seconds. Additionally, in one embodiment, during this process, wafer chuck 1120 is rotated at about 1 revolutions per minute to about 100 revolutions per minute, and preferably about 20 revolutions per minute.

Step 8. After wafer 1128 has been replated, a cleaning solution is provided through injection pipe 1100. In one embodiment, the cleaning solution is deionized water. Additionally, an etching solution is provided on the back side of wafer 1128 (i.e., the side of wafer 1128 that has not been plated) to clean any metal or other contaminants. The cleaning solution can be provided for any convenient period of time to clean wafer 1128. In one embodiment, wafer 1128 is cleaned for a period of time between about 10 seconds to about 200 seconds, and preferably about 30 seconds.

Step 9. After wafer 1128 has been cleaned, a drying gas is provided through injection pipe 1102. In one embodiment, the drying gas is Nitrogen gas. This process can be performed for any convenient period of time necessary to dry wafer 1128. In one embodiment, wafer 1128 is dried for a period of time between about 20 seconds to about 40 seconds, and preferably about 30 seconds. Additionally, in one embodiment, during this process, wafer chuck 1120 is rotated at about 1500 revolutions per minute to about 3500 revolutions per minute, and preferably about 2500 revolutions per minute.

Step 10. After wafer 1128 has been dried, an etching solution can be provided through injection pipe 1108 to remove the metal seed layer from the edge of wafer 1128.

Step 11. Cleaning and drying steps 8 and 9 can then be repeated.

Step 12. After the wafer is dried, wafer chuck 1120 stops. Loading door 1124 is then moved to an unload position, and wafer 1128 is removed from electroless plating module 1101.

It should be recognized that the process for removing the metal seed layer from wafer 1128 can be included with the process of planarizing wafer 1128. More particularly, an exemplary process is set forth below:

Step 1. Loading door 1124 moves to an open position.

Step 2. Robot 1122 loads wafer 1128 into electroless plating module 1101.

Step 3. Loading door 1124 moves to a closed position.

Step 4. Chuck 1120 starts rotating wafer 1128. In one embodiment, chuck 1120 rotates wafer 1128 at a speed between about 1 revolutions per minute to about 100 revolutions per minute, and preferably at about 20 revolutions per minute.

Step 5. A cleaning solution is provided through injection pipe 1100. In one embodiment, the cleaning solution is deionized water. The cleaning solution can be provided for any convenient period of time to clean wafer 1128. In one embodiment, wafer 1128 is cleaned for a period of time between about 10 seconds to about 200 seconds, and preferably about 30 seconds.

Step 6. After wafer 1128 has been cleaned, a drying gas is provided through injection pipe 1102. In one embodiment, the drying gas is Nitrogen gas. This process can be performed for any convenient period of time necessary to dry wafer 1128. In one embodiment, wafer 1128 is dried for a period of time between about 20 seconds to about 40 seconds, and preferably about 30 seconds. Additionally, in one embodiment, during this process, wafer chuck 120 is rotated at about 1500 revolutions per minute to about 3500 revolutions per minute, and preferably about 2500 revolutions per minute.

Step 7. After wafer 1128 has been dried, an electroless-plating solution is provided through injection pipe 1112. This process can be performed for any convenient period of time necessary to replate wafer 1128. In one embodiment, wafer 1128 is electroless plated for a period of time between about a few seconds to about a few hundred seconds. Additionally, in one embodiment, during this process, wafer chuck 1120 is rotated at about 1 revolutions per minute to about 100 revolutions per minute, and preferably about 20 revolutions per minute.

Step 8. After wafer 1128 has been replated, a cleaning solution is provided through injection pipe 1100. In one embodiment, the cleaning solution is deionized water. Additionally, an etching solution is provided on the back side of wafer 1128 (i.e., the side of wafer 1128 that has not been plated) through injection pipe 1104. This helps to clean any metal or other contaminants from the back side of wafer 1128. The cleaning solution can be provided for any convenient period of time to clean wafer 1128. In one embodiment, wafer 1128 is cleaned for a period of time between about 10 seconds to about 200 seconds, and preferably about 30 seconds.

Figure 7:
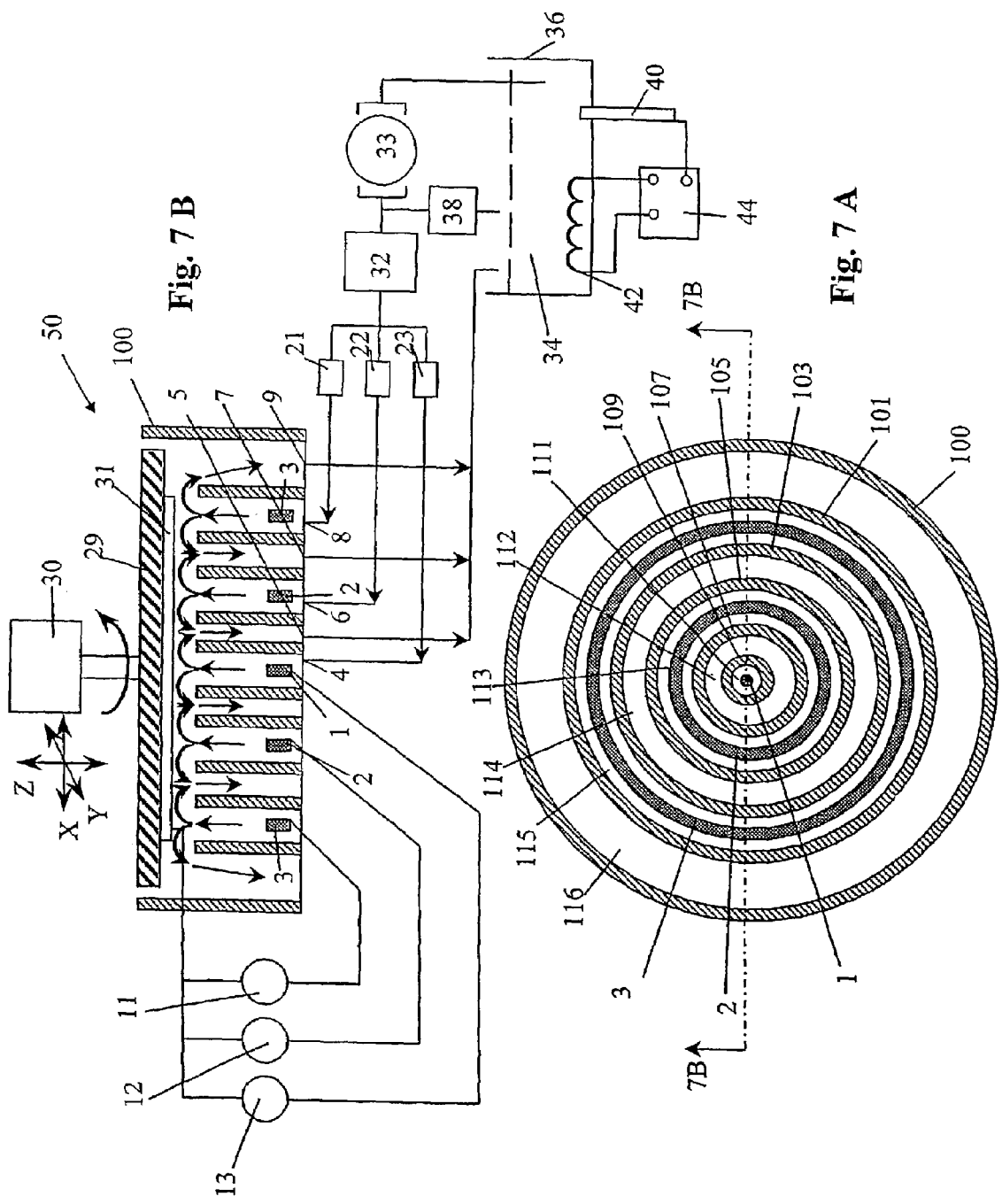
FIG. 7A is a top view of a portion of an electropolishing apparatus in accordance with various aspects of the present invention.
FIG. 7B is a view, partly in cross section, taken along the line 7B—7B in FIG. 7A, and partly in block diagram form, of the electropolishing apparatus shown in FIG. 7A.

Step 9. After the front side of wafer 1128 (i.e., the side of wafer 128 that has been plated) has been cleaned, etching solution is provided through pipe 1114 to remove barrier layer 1122 (FIG. 7). This etching process can be performed for any convenient period of time necessary to remove barrier layer 1122 (FIG. 7). It should be recognized that this step can be omitted when wafer 1128 does not have a barrier layer 1122.

Step 10. Before, during or after wafer 1128 is etched, an etching solution can be provided through injection pipe 1108 to remove the metal seed layer from the edge of wafer 1128.

Step 11. After wafer 1128 has been etched, a cleaning solution is provided through injection pipes 1100 and 1104 to the front and back sides of wafer 1128.

Step 12. After wafer 1128 has been cleaned, a drying gas is provided through injection pipe 1102. In one embodiment, the drying gas is Nitrogen gas. This process can be performed for any convenient period of time necessary to dry wafer 1128. In one embodiment, wafer 1128 is dried for a period of time between about 20 seconds to about 40 seconds, and preferably about 30 seconds. Additionally, in one embodiment, during this process, wafer chuck 1120 is rotated at about 1500 revolutions per minute to about 3500 revolutions per minute, and preferably about 2500 revolutions per minute.

Step 13. After wafer 1128 is dried, wafer chuck 1120 stops. Loading door 1124 is then moved to an unload position, and wafer 1128 is removed from electroless plating module 1101.

As alluded to earlier, electroless plating module 1101 can be integrated into a wafer processing tool. With reference to FIGS. 70A, 70B, and 70C, a wafer processing tool 2010 in accordance with one exemplary embodiment of the present invention is shown. In this embodiment, wafer processing tool 2010 includes an electropolishing station 2000, an electroless plating station 2100, wafer handling stations 2200 and 2210, and a robot 2220.

As depicted in FIG. 70B, electropolishing station 2000 includes five stacked electropolishing receptacles (modules) 2020. Electroless plating station 2100 includes five stacked electroless plating modules 2120. Accordingly, as many as five wafers can be electropolished and/or electroless plated at one time. It should be recognized, however, that electropolishing station 2000 and electroless plating station 2100 can include any number of electropolishing modules and electroless plating modules depending on the particular application. For example, for a low volume application, electropolishing station 2000 and electroless plating station 2100 can be configured with one electropolishing module 2020 and one electroless plating module 2120. Additionally, it should be recognized that the ratio of electropolishing modules 2020 to electroless plating modules 2120 can vary depending on the particular application. For example, in an application where the electropolishing process requires more processing time than the electroless plating process, wafer processing tool 2010 can be configured with more electropolishing modules 2020 than electroless plating modules 2120. Alternatively, in applications where the electroless plating process requires more processing time than the electropolishing process, wafer processing tool 2010 can be configured with more electroless plating modules 2120 than electropolishing modules 2020.

As also depicted in FIG. 70B, electropolishing modules 2020 and electroless plating modules 2120 are configured as vertical stacks. In this manner, the number of wafers processed can be increased without increasing the footprint of (the amount of floor space occupied by) wafer processing tool 2010. In the increasingly competitive semiconductor industry, increasing the ratio of wafers processed per square feet of fabrication spaced occupied by wafer processing tool 2010 can be advantageous.

In the present embodiment, wafer processing tool 2010 includes wafer-handling stations 2200 and 2210. More particularly, wafer-handling stations 2200 and 2210 can include a wafer cassette 2160 for holding wafers. In one embodiment, wafer cassette 2160 can include a standard mechanical interface (SMIF) 2320. It should be recognized that wafer cassette 216 can include any convenient wafer holding and/or carrier apparatus.

In the present embodiment, robot 2220 is configured to remove an unprocessed wafer from wafer cassette 2160 and transport the wafer to any one of the electropolishing modules 2020. After the wafer is electropolished, robot 2220 transports the wafer to any one of the electroless plating modules 2120. After the wafer is plated, etched, cleaned, and tried, robot 2220 then transports the wafer back to wafer cassette 2160. Although a single wafer cassette 2160 is depicted in FIG. 70, it should be recognized that wafer-handling stations 2200 and 2210 can include any number of wafer cassettes 2160.

Additionally, wafer-handling station 2200 and 2210 can include various configurations depending on the particular application. For example, wafer-handling station 2200 and 2210 can each include at least one wafer cassette 2160. In one configuration, a wafer cassette 2160 containing unprocessed wafers is provided at wafer-handling station 2200. The wafers are removed, processed, then returned to the same wafer cassette 2160 at wafer-handling station 2200. Prior to the completion of the processing of wafers from wafer cassette 2160 at wafer-handling station 2200, another wafer cassette 2160 containing unprocessed wafers is provided at wafer-handling station 2210. Once the wafers from wafer cassette 2160 at wafer-handling station 2200 are processed, wafer-processing tool 2010 can begin processing the unprocessed wafers from wafer cassette 2160 at wafer-handling station 2210. The processed wafers in wafer cassette 2160 at wafer-handling station 2200 can then be removed and replaced with yet another wafer cassette 2160 containing unprocessed wafers. In this manner, wafer-processing tool 2010 can be operated continuously without unintended interruption.

In another configuration, a wafer cassette 2160 containing unprocessed wafer can be provided at wafer-handling station 2200. An empty wafer cassette 2160 can be provided at wafer-handling station 2210. The unprocessed wafers from wafer cassette 2160 at wafer-handling station 2200 can be processed then returned to the empty wafer cassette 2160 at wafer-handling station 2210. This configuration also facilitates continuously operation of processing tool 2010. This configuration, however, has the advantage that one of the two handling stations 2200 and 2210 can be designated for unprocessed wafers and the other for processed wafers. In this manner, an operator or a robot is less likely to mistake a wafer cassette 2160 containing processed wafers for one with unprocessed wafers and vice versa.

With reference again to FIGS. 70B and 70C, wafer-processing tool 2010 includes housing unit 2300 for housing the various electrical and mechanical components of wafer-processing tool 2010, such as power supplies, filters, wires, plumbing, chemical containers, pumps, valves, and the like. Wafer-processing tool 2010 can also include a computer 2040 for controlling the operation of wafer-processing tool 2040. More particularly, computer 2040 can be configured with an appropriate software program to implement the processing steps set forth above.

It should be recognized that various modifications can be made to the configuration of wafer-processing tool 2010 without deviating from the spirit and/or scope of the present invention. In this regard, in the following description and associated drawings, various alternative embodiments of the present invention will be described and depicted. It should be recognized, however, that these alternative embodiments are not intended to demonstrate all of the various modifications, which can be made to the present invention. Rather, these alternative embodiments are provided to demonstrate only some of the many possible modifications.

With reference to FIGS. 71A, 71B, and 71C, a wafer processing tool 4010 in accordance with another exemplary embodiment of the present invention is shown. In this embodiment, wafer processing tool 4010 includes an electroplating station 4000, an electroless plating station 4100, an electropolishing station 4500, wafer handling stations 4420, 4440, and 4460, and robots 4220 and 4400.

In the present embodiment, robot 4220 is configured to remove an unprocessed wafer from wafer handling station 4420, 4440, or 4460. Robot 4220 transports the wafer into any one of the electroplating modules 4020 in electroplating station 4000. In electroplating modules 4020, metal layer 121 (FIG. 1A) can be formed on barrier layer 122 (FIG. 1A) or on dielectric layer 123 (FIG. 1A) using an electroplating process. This process is described in greater detail in copending application Ser. No. 09/232,864, entitled PLATING APPARATUS AND METHOD, filed on Jan. 15, 1999, the entire content of which is incorporated herein by reference. It should be recognized that although three electroplating modules 4020 are depicted in FIG. 71, wafer processing tool 4010 can include any number of electroplating modules 4020.

After the wafer is plated, robot 4220 transports the wafer into any one of the electroless plating modules 4120 in electroless plating station 4100. In electroless plating module 4120, the wafer is cleaned, but not replated. Robot 4400 then transports the wafer into any one of the electropolishing modules 4520 in electropolishing station 4500. In electropolishing module 4520, the wafer is electropolished. Robot 4400 then transports the wafer back into electroless plating module 4120. At this point, the wafer is replated, etched, cleaned, and dried. Robot 4220 then returns the wafer to wafer handling station 4420, 4440, or 4460.

Figure 72:
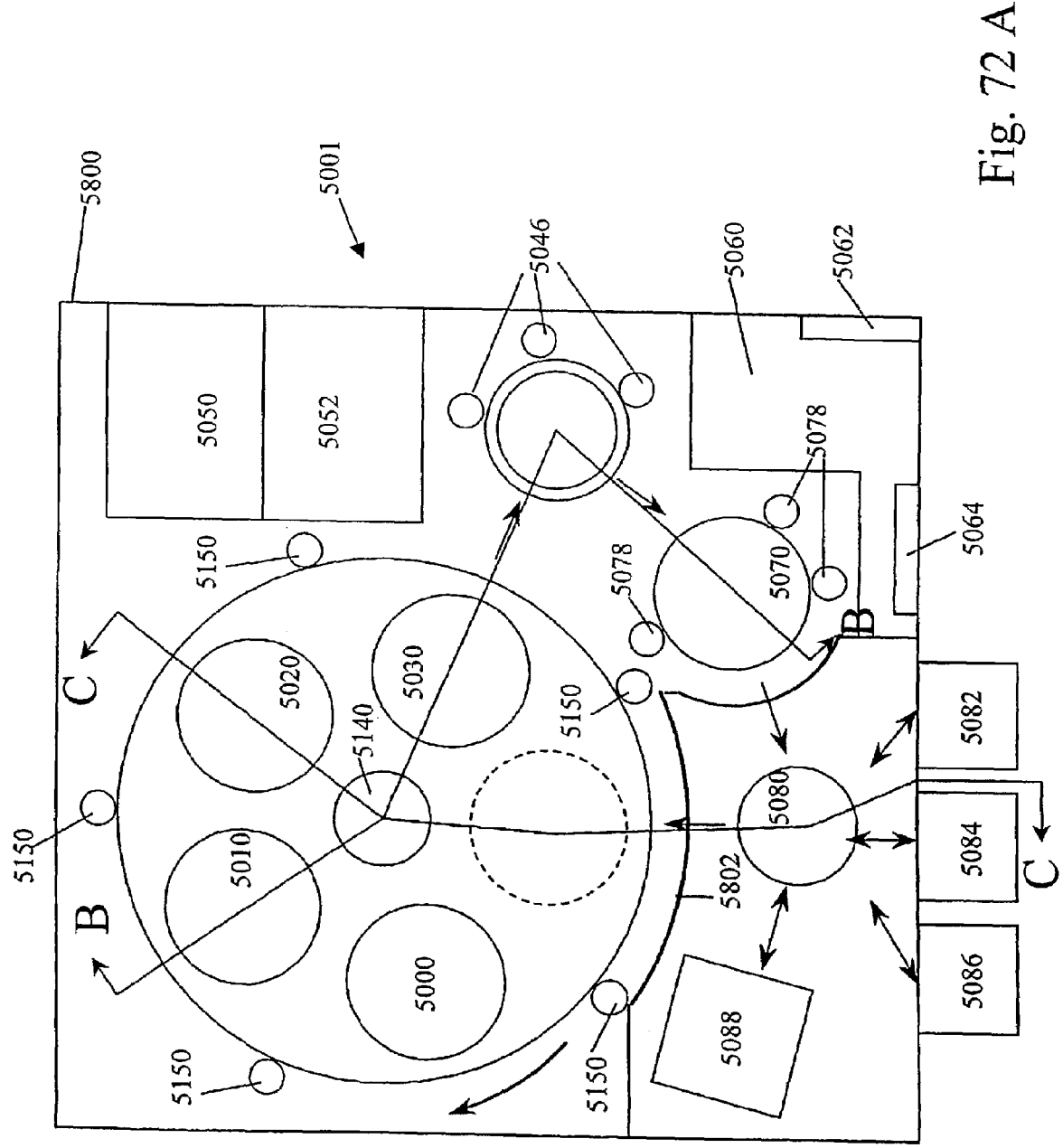
FIGS. 72A through 72C are top and two cross sectional views, respectively, of still another wafer processing tool.
Figure 72:
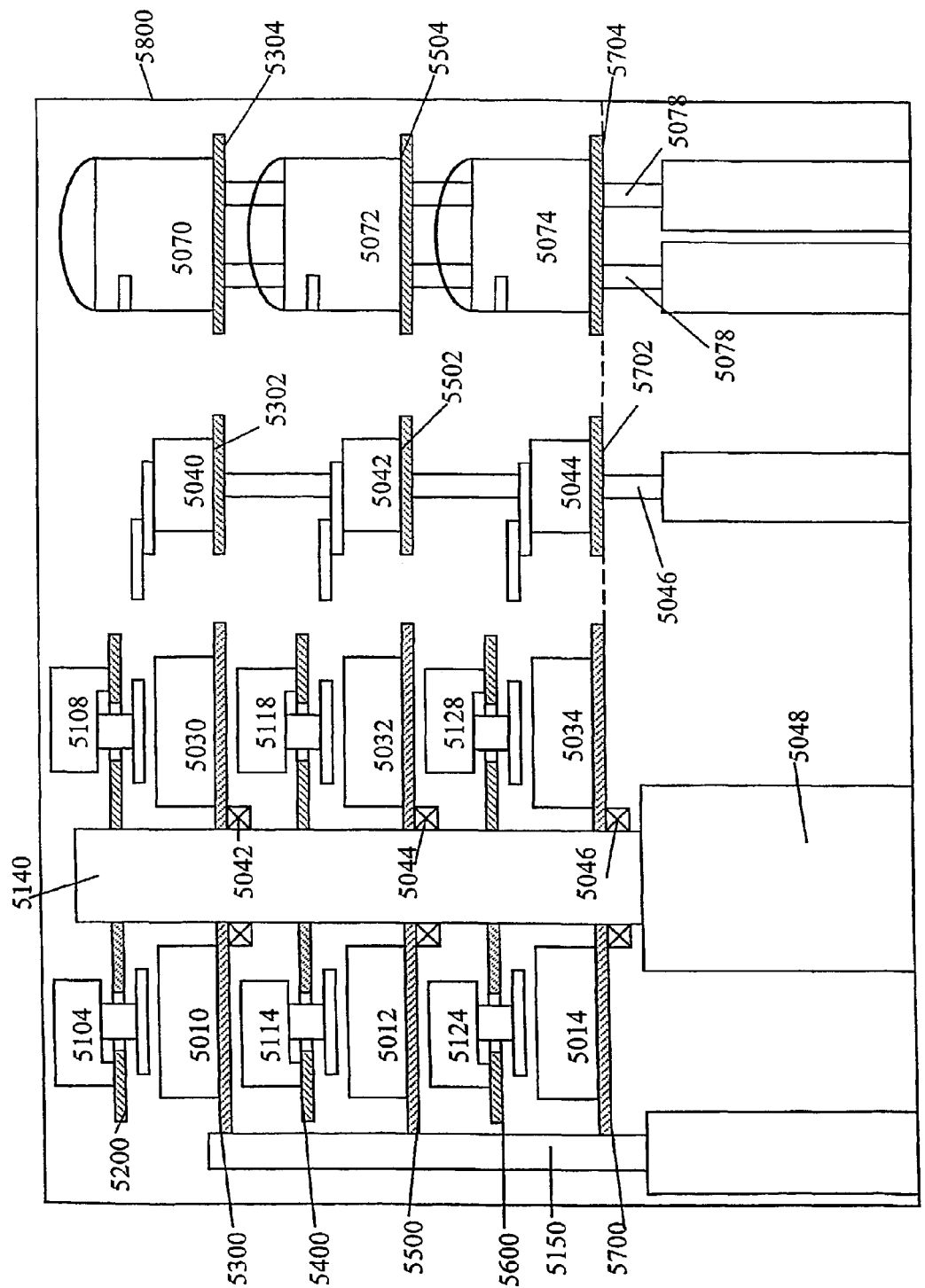
Figure 72:
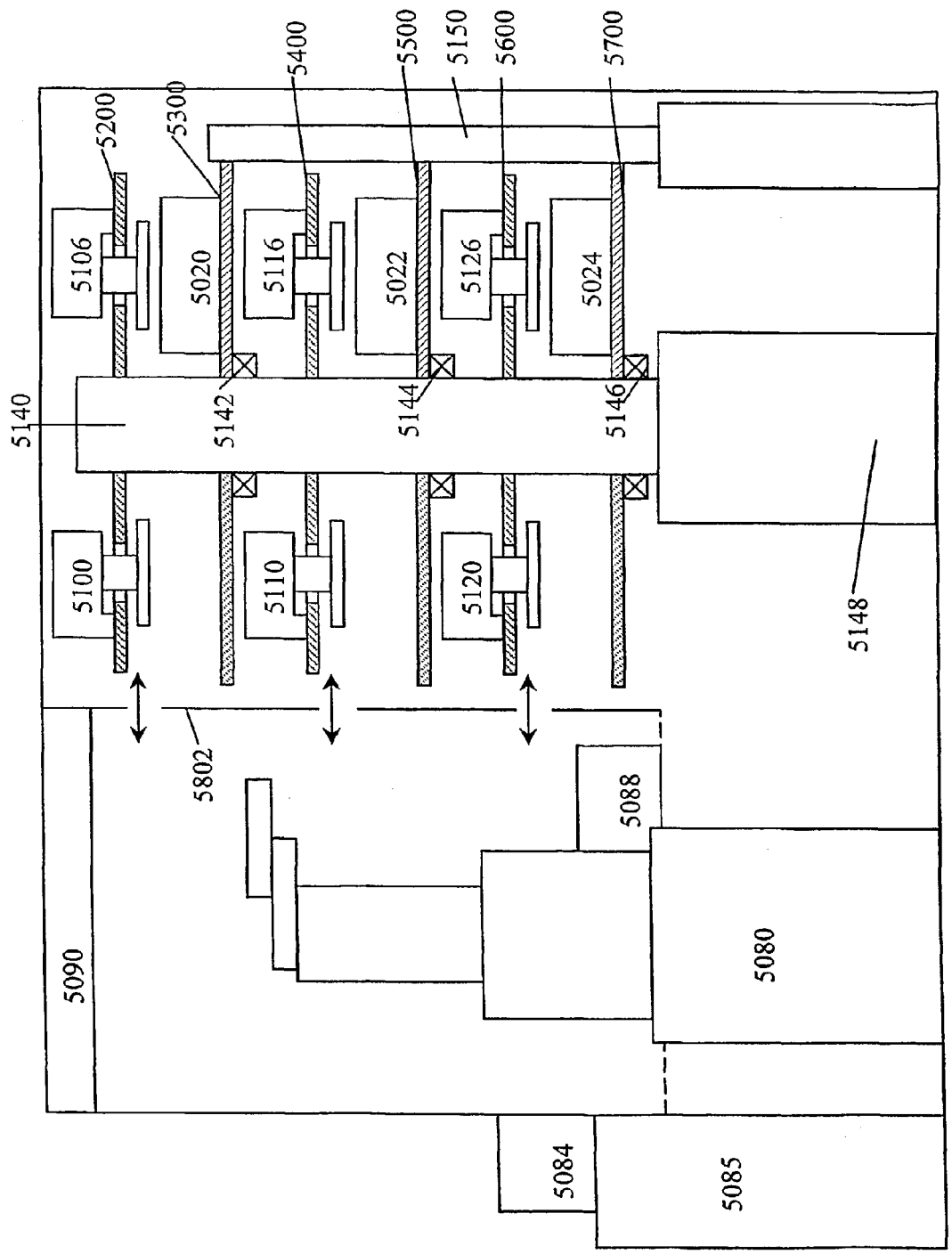

With reference now to FIGS. 72A, 72B, and 72C, a wafer processing tool 5001 in accordance with still another exemplary embodiment of the present invention is shown. In this embodiment, wafer processing tool 5001 includes electroplating modules 5000, 5002, and 5004, cleaning modules 5010, 5012, and 5014, thermal annealing modules 5020, 5022, and 5024, and electropolishing modules 5030, 5032, and 5034.

As depicted in FIGS. 72B and 72C, wafer processing tool 5001 includes support tables 5300, 5500, and 5700, which are supported by support members 5150 and 5150. Each support table includes an electroplating module, a cleaning module, a thermal annealing module, and an electropolishing module. More particularly, support table 5300 includes electroplating module 5000, cleaning module 5010, thermal annealing module 5020, and electropolishing module 5030. Support table 5500 includes electroplating module 5002, cleaning module 5012, thermal annealing module 5022, and electropolishing module 5032. Support table 5700 includes electroplating module 5004, cleaning module 5014, thermal annealing module 5024, and electropolishing module 5034.

As also depicted in FIGS. 72B and 72C, wafer processing tool 5001 includes rotary tables 5200, 5400, and 5600, which are supported by support member 5140. Each rotary table 5200, 5400, and 5600 includes four wafer chuck mechanisms. More particularly, rotary table 5200 includes wafer chuck mechanisms 5100, 5104, 5106, and 5108. Rotary table 5400 includes wafer chuck mechanisms 5110, 5114, 5116, and 5108. Rotary table 5600 includes wafer chuck mechanisms 5120, 5124, 5126, and 5128.

A motor 5048 rotates support member 5140, which then rotates rotary tables 5200, 5400, and 5600. Bearings 5042, 5044, and 5046 allow support tables 5300, 5500, and 5700 to remain stationary. As such, as the rotary tables rotate around the support tables, the wafer held by the wafer chuck mechanisms can be processed in each of the processing modules (i.e., the electroplating module, cleaning module, thermal annealing module, and electropolishing module) on each the support table.

More particularly, with reference to FIG. 72A, a robot 5080 transports wafers from wafer handling station 5082, 5084, or 5086 to pre-aligner (not shown). Robot 5080 then transports the wafers into the three stacked wafer chuck mechanisms (FIGS. 5B and 5C). For example, with reference to FIG. 72C, robot 5080 (FIG. 5A) can transport unprocessed wafers into wafer chuck mechanisms 5100, 5110, and 5120.

With reference to FIGS. 72B and 72C, rotary table 5200, 5400, and 5600 then rotate wafer chuck mechanisms 5100, 5110, and 5120 to electroplating modules 5000, 5002, and 5004. As these wafers are being electroplated, robot 5080 (FIG. 72A) can transport more unprocessed wafers into the wafer chuck mechanisms 5108, 5118, and 5128.

After the wafers are electroplated, rotary table 5200, 5400, and 5600 then rotate wafer chuck mechanisms 5100, 5110, and 5120 to cleaning modules 5010, 5012, and 5014. At the same time wafer chuck mechanisms 5108, 5118, and 5128 rotate to electroplating modules 5000, 5002, and 5004. Also, wafer chuck mechanisms 5106, 5116, and 5126 rotate to receive unprocessed wafers from robot 5080 (FIG. 72A).

After the wafers are cleaned, rotary table 5200, 5400, and 5600 then rotate wafer chuck mechanisms 5100, 5110, and 5120 to thermal annealing modules 5020, 5022, and 5024. At the same time, wafer chuck mechanisms 5108, 5118, and 5128 rotate to cleaning modules 5010, 5012, and 5014. Also, wafer chuck mechanisms 5106, 5116, and 5126 rotate to electroplating modules 5000, 5002, and 5004. Furthermore, wafer chuck mechanisms 5104, 5114, and 5124 rotate to receive unprocessed wafer from robot 5080 (FIG. 72A).

In thermal annealing modules 5020, 5022, and 5024, the metal layer within the trenches and/or vias of the wafer are annealed to produce a more uniform crystal structure. Annealing the wafer in this manner has the advantage that the electrical characteristics of the metal layer within the trenches and/or vias will be more stable. Otherwise, the electrical characteristics of the metal layer within the trenches and/or vias can change as the metal layer naturally anneals over a period of time after processing of the wafer. Additionally, annealing the wafer prior to electropolishing can facilitate a more planar wafer surface. Otherwise, the surface of the metal layer within the trenches and/or vias can change as the metal layer naturally anneals over a period of time after processing of the wafer.

After the wafers are annealed, rotary table 5200, 5400, and 5600 then rotate wafer chuck mechanisms 5100, 5110, and 5120 to electropolishing modules 5030, 5032, and 5034. At the same time, wafer chuck mechanisms 5108, 5118, and 5128 rotate to thermal annealing modules 5020, 5022, and 5024. Also, wafer chuck mechanisms 5106, 5116, and 5126 rotate to cleaning modules 5010, 5012, and 5014. Furthermore, wafer chuck mechanisms 5104, 5114, and 5124 rotate to electroplating modules 5000, 5002, and 5004.

After the wafers are electropolished, robots 5040, 5042, and 5044 transport the wafers from chuck mechanisms 5100, 5110, and 5120 to electroless plating modules 5070, 5072, and 5074. As depicted in FIG. 72B, robots 5040, 5042, and 5044 are supported on support tables 5302, 5502, and 5702, respectively, which are supported by support member 5046. Also, electroless plating modules 5070, 5072, and 5074 are supported on support tables 5304, 5504, and 5704, respectively, which are supported by support members 5078.

After the wafers are removed from chuck mechanisms 5100, 5110, and 5120, rotary table 5200, 5400, and 5600 rotate to repeat the entire process. Also, when the wafers are replated, etched, cleaned, and dried, they are removed from electroless plating modules 5070, 5072, and 5074 and transported to wafer handling station 5082, 5084, or 5086 (FIG. 5A) by robot 5080 (FIG. 72A).

Wafer processing tool 5001 also includes a metrology station 5088, which can include various tools to inspect and examine the wafer during or after processing for quality control and to tune the various wafer processing systems. For example, metrology station 5088 can include four-point probes for measuring resistivity of the metal layer after electroplating. Metrology station 5088 can also include a scanning tunneling microscope (STM) or an atomic force microscope (AFM) for measuring the surface profile of the wafer. Metrology station 5088 can further include an optical microscope for measuring surface defects on the wafer. It should be recognized that metrology station 5088 can include any combination of these tools or various additional tools depending on the application.

Wafer processing tool 5001 can also include various additional processing stations depending on the particular application. For example, wafer processing tool 5001 can include a dry or plasma stripping chamber. As described above, when the wafer includes a barrier layer, it is stripped away from the surface of the wafer. Dry or plasma stripping has the advantage that it does not produce many of the corrosion problems generally associated with wet etching.

As stated earlier, although the present invention has been described in conjunction with a number of alternative embodiments illustrated in the appended drawing figures, various modifications can be made without departing from the spirit and/or scope of the present invention. Therefore, the present invention should not be construed as being limited to the specific forms shown in the drawings and described above.

The invention claimed is:

1. An apparatus for monitoring the end-point of an electroplishing process of a metal layer formed on a wafer, comprising:
   a wafer chuck configured to rotate the wafer;
   a nozzle configured to electroplish the metal layer,
      wherein the nozzle is configured to apply a stream of electrolyte to a portion of the metal layer as the wafer is rotated; and
   an end-point detector disposed adjacent to the nozzle,
      wherein the end-point detector is configured to detect a thickness of the metal layer on a portion of the metal layer as the wafer is rotated.

2. The apparatus of claim 1, wherein the nozzle is stationary, and wherein the wafer chuck is configured to translate the wafer as the wafer is rotated to expose to metal layer to the stationary nozzle and the end-point detector.

3. The apparatus of claim 2, wherein a signal from the end-point detector is used to control the speed of the rotation and movement of the wafer.

4. The apparatus of claim 2, wherein a signal from the end-point detector is used to control the polishing power and polishing rate.

5. The apparatus of claim 1, wherein the nozzle and to end-point detector are moveable to expose the metal layer to the moveable nozzle and the end-point detector.

6. The apparatus of claim 1, wherein an end-point detector comprises:
   a first sensor configured to measure the thickness of the metal layer during electropolishing; and
   a second sensor configured to measure the thickness of the metal layer after electropolishing.

7. The apparatus of claim 6 further comprising:
   a third sensor configured to measure the thickness of the metal layer before electropolishing.

8. The method of claim 1, wherein measuring a thickness comprises:
   measuring the thickness of the metal layer during electropolishing; and
   measuring the thickness of the metal layer after electropolishing.

9. The method of claim 8 further comprising:
   measuring the thickness of the metal layer before electropoishing.

10. An apparatus for monitoring the end-point of an electroplishing process of a metal layer formed on a wafer, comprising:
    a wafer chuck tat rotates and translates the wafer;
    a nozzle that applies a stream of electrolyte to a portion of the metal layer as the wafer is rotated and translated, wherein the nozzle is stationary; and
    an end-point detector adjacent to the nozzle that measures a thickness of the metal layer on a portion of the metal layer as the wafer is rotated and translated.

11. The apparatus of claim 10, wherein a signal from the end-point detector is used to control the speed of the rotation and movement of the wafer.

12. The apparatus of claim 10, wherein a signal from the end-point detector is used to control the polishing power and polishing rate.

13. The apparatus of claim 10, wherein the end-point detector measures the thickness of the metal layer after electropolishing.

14. The apparatus of claim 13, wherein the end-point detector measures the thickness of the metal layer before and during electropolishing.

15. A method for monitoring the end-point of an electroplishing process of a metal layer formed on a wafer, comprising:
    rotating the wafer;
    electropolishing the metal layer using a nozzle to apply a stream of electrolyte to a portion of the metal layer as the wafer is rotated; and
    measuring a thickness of the metal layer on a portion of the metal layer using an end-point detector adjacent to the nozzle.

16. The method of claim 15 further comprising:
    translating the wafer as the wafer is rotated to expose the metal layer to the stationary nozzle and the end-point detector.

17. The method of claim 16, wherein the wafer is rotated and translated while the nozzle is held stationary.

18. The method of claim 16 further comprising:
    controlling the speed of the rotation and movement of the wafer using a signal from the end-point detector.

19. The method of claim 16 further comprising:
    controlling the polishing power and polishing rate of the wafer using a signal from the end-point detector.

20. The method of claim 16 further comprising:
    moving the nozzle and the end-point detector to expose the metal layer to the moveable nozzle and the end-point detector.

* * * * *